(12) United States Patent
Sheng et al.

(10) Patent No.: US 10,647,773 B2
(45) Date of Patent: May 12, 2020

(54) TRISPECIFIC ANTAGONISTS

(71) Applicant: GENSUN BIOPHARMA, INC., Newbury Park, CA (US)

(72) Inventors: Jackie Sheng, Thousand Oaks, CA (US); Bo Liu, Thousand Oaks, CA (US)

(73) Assignee: GENSUN BIOPHARMA, INC., Newbury Park, CA (US)

( * ) Notice: Subject to any disclaimer, the term of this patent is extended or adjusted under 35 U.S.C. 154(b) by 0 days.

(21) Appl. No.: 16/457,343

(22) Filed: Jun. 28, 2019

(65) Prior Publication Data

US 2020/0002439 A1 Jan. 2, 2020

Related U.S. Application Data

(60) Provisional application No. 62/691,658, filed on Jun. 29, 2018, provisional application No. 62/823,989, filed on Mar. 26, 2019.

(51) Int. Cl.
| | | |
|---|---|---|
| C07K 16/00 | (2006.01) | |
| C07K 16/28 | (2006.01) | |
| A61P 35/00 | (2006.01) | |
| C07K 16/22 | (2006.01) | |
| C07K 14/00 | (2006.01) | |

(Continued)

(52) U.S. Cl.
CPC .......... *C07K 16/2863* (2013.01); *A61P 35/00* (2018.01); *C07K 14/00* (2013.01); *C07K 14/71* (2013.01); *C07K 16/22* (2013.01); *C07K 16/2803* (2013.01); *C07K 16/2818* (2013.01); *C07K 16/2827* (2013.01); *C07K 16/468* (2013.01); *A61K 2039/505* (2013.01); *C07K 2317/31* (2013.01); *C07K 2317/565* (2013.01); *C07K 2317/622* (2013.01); *C07K 2317/64* (2013.01); *C07K 2317/76* (2013.01); *C07K 2317/92* (2013.01); *C07K 2318/10* (2013.01);
(Continued)

(58) Field of Classification Search
None
See application file for complete search history.

(56) References Cited

U.S. PATENT DOCUMENTS

| 5,837,243 A | 11/1998 | Deo et al. |
| 5,869,046 A | 2/1999 | Presta et al. |

(Continued)

FOREIGN PATENT DOCUMENTS

| EP | 0090505 | 2/1984 |
| EP | 0 920 505 | 6/2008 |

(Continued)

OTHER PUBLICATIONS

Ahmadzadeh, M. et al., "Tumor antigen-specific CD8 T cells infiltrating the tumor express high levels of PD-1 and are functionally impaired", Blood, Aug. 20, 2009, 114(8):1537.

(Continued)

*Primary Examiner* — Meera Natarajan
(74) *Attorney, Agent, or Firm* — Michael X. Ye; Morris, Manning & Martin, LLP

(57) ABSTRACT

Antitumor antagonists that bind specifically to immune checkpoint regulator and/or components of the angiogenesis pathways and/or components of the TGF pathway are disclosed. Also disclosed is a method of treating proliferative disorders with the antitumor antagonists.

15 Claims, 57 Drawing Sheets

Specification includes a Sequence Listing.

(51) Int. Cl.
*C07K 14/71* (2006.01)
*C07K 16/46* (2006.01)
*A61K 39/00* (2006.01)

(52) U.S. Cl.
CPC ...... *C07K 2319/30* (2013.01); *C07K 2319/32* (2013.01)

(56) References Cited

U.S. PATENT DOCUMENTS

| | | |
|---|---|---|
| 5,922,845 A | 7/1999 | Deo et al. |
| 6,054,297 A | 4/2000 | Carter et al. |
| 6,111,090 A | 8/2000 | Gorman et al. |
| 6,121,022 A | 9/2000 | Presta et al. |
| 6,365,157 B2 | 4/2002 | Rockwell et al. |
| 6,376,653 B1 | 4/2002 | Holmes et al. |
| 6,448,077 B1 | 9/2002 | Rockwell et al. |
| 6,528,959 B2 | 3/2003 | Kitano et al. |
| 6,582,959 B2 | 6/2003 | Kim |
| 6,703,020 B1 | 3/2004 | Thorpe et al. |
| 6,884,879 B1 | 4/2005 | Baca et al. |
| 7,025,962 B1 | 4/2006 | Gorman et al. |
| 7,060,269 B1 | 6/2006 | Baca et al. |
| 7,067,637 B1 | 6/2006 | Hotten et al. |
| 7,138,370 B2 | 11/2006 | Oliner et al. |
| 7,169,901 B2 | 1/2007 | Baca et al. |
| 7,182,135 B2 | 2/2007 | Szarka |
| 7,227,004 B2 | 6/2007 | Kim |
| 7,297,334 B2 | 11/2007 | Baca et al. |
| 7,338,660 B2 | 3/2008 | Bedian et al. |
| 7,365,166 B2 | 4/2008 | Baca et al. |
| 7,494,651 B2 | 2/2009 | Jones et al. |
| 7,498,414 B2 | 3/2009 | Zhu |
| 7,521,053 B2 | 4/2009 | Oliner |
| 7,527,791 B2 | 5/2009 | Adams et al. |
| 7,575,893 B2 | 8/2009 | Simmons |
| 7,579,186 B1 | 8/2009 | Sakamoto et al. |
| 7,618,632 B2 | 11/2009 | Collins et al. |
| 7,619,069 B2 | 11/2009 | Davies et al. |
| 7,658,924 B2 | 2/2010 | Oliner et al. |
| 7,691,977 B2 | 4/2010 | Fuh et al. |
| 7,758,859 B2 | 7/2010 | Fuh et al. |
| 7,811,785 B2 | 10/2010 | Fuh et al. |
| 7,812,135 B2 | 10/2010 | Smith et al. |
| 8,030,025 B2 | 10/2011 | Boone et al. |
| 8,367,805 B2 | 2/2013 | Chamberlain et al. |
| 8,388,967 B2 | 3/2013 | Smith et al. |
| 8,475,798 B2 | 7/2013 | Patti et al. |
| 8,574,577 B2 | 11/2013 | Barbas, III |
| 8,586,023 B2 | 11/2013 | Shiku et al. |
| 8,591,886 B2 | 11/2013 | Ponath et al. |
| 8,992,913 B2 | 3/2015 | Mader et al. |
| 9,079,965 B2 | 7/2015 | Zhou et al. |
| 9,200,079 B2 | 12/2015 | Chamberlain et al. |
| 9,764,038 B2 | 9/2017 | Dennler et al. |
| 9,890,204 B2 | 2/2018 | Brinkmann et al. |
| 9,987,500 B2 | 6/2018 | Papadopoulos et al. |
| 10,112,997 B2 | 10/2018 | Gurney et al. |
| 10,189,902 B2 | 1/2019 | Maurer et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2005/0186208 A1 | 8/2005 | Fyfe et al. |
| 2006/0009360 A1 | 1/2006 | Pifer et al. |
| 2006/0099150 A1 | 5/2006 | Houston et al. |
| 2006/0280747 A1 | 12/2006 | Fuh et al. |
| 2007/0020267 A1 | 1/2007 | Fuh et al. |
| 2007/0059312 A1 | 3/2007 | Baca et al. |
| 2007/0141065 A1 | 6/2007 | Fuh et al. |
| 2011/0217318 A1 | 9/2011 | Takayama et al. |
| 2013/0022601 A1 | 1/2013 | Brinkmann et al. |
| 2013/0078248 A1 | 3/2013 | Gschwind et al. |
| 2013/0259859 A1 | 10/2013 | Ott et al. |
| 2014/0243505 A1 | 8/2014 | Zhou et al. |
| 2014/0308285 A1 | 10/2014 | Yan et al. |
| 2014/0356385 A1 | 12/2014 | Dennler et al. |
| 2015/0197578 A1 | 7/2015 | Thurston |
| 2015/0225483 A1 | 8/2015 | Lo |
| 2015/0337033 A1 | 11/2015 | Kim et al. |
| 2016/0355589 A1 | 12/2016 | Williams et al. |
| 2017/0044256 A1 | 2/2017 | Grogan et al. |
| 2017/0275353 A1 | 9/2017 | Sheng et al. |
| 2018/0185482 A1* | 7/2018 | Sheng ............. A61K 39/39558 |

FOREIGN PATENT DOCUMENTS

| | | |
|---|---|---|
| EP | 1947183 | 7/2008 |
| EP | 1866339 | 5/2013 |
| WO | 98/023289 | 6/1998 |
| WO | 99/20758 | 4/1999 |
| WO | 9920758 | 4/1999 |
| WO | 99/40196 | 8/1999 |
| WO | 9940196 | 8/1999 |
| WO | 2001/03720 | 1/2001 |
| WO | 200103720 | 1/2001 |
| WO | 2005/007190 | 1/2005 |
| WO | 2005007190 | 1/2005 |
| WO | 2005055808 | 6/2005 |
| WO | 2005/115451 | 12/2005 |
| WO | 2006/083289 | 8/2006 |
| WO | 2006083289 | 8/2006 |
| WO | 2007/133822 | 11/2007 |
| WO | 2007133822 | 11/2007 |
| WO | 2010/003118 | 1/2010 |
| WO | 2010003118 | 1/2010 |
| WO | 2011/028683 | 3/2011 |
| WO | 2011028683 | 3/2011 |
| WO | 2011/051726 | 5/2011 |
| WO | 2005115451 | 5/2011 |
| WO | 2011051726 | 5/2011 |
| WO | 2011090754 | 7/2011 |
| WO | 2013/039954 | 3/2013 |
| WO | 2013039954 | 3/2013 |
| WO | 2014062659 | 4/2014 |
| WO | 2016187594 | 11/2016 |
| WO | 2017218707 | 6/2017 |
| WO | 2017161976 | 9/2017 |
| WO | 20181283939 | 7/2018 |

OTHER PUBLICATIONS

Dall'Acqua, et al., "Increasing the Affinity of a Human IgG1 for the Neonatal Fc Receptor: Biological Consequences", The Journal of Immunology, 2002, 169:5171-5180.

Dall'Acqua, et al., "Properties of Human IgG1s Engineered for Enhanced Binding to the Neonatal Fc Receptor (FcRn)", Journal of Biological Chemistry, 2006, 281:23514-23524.

Dranoff, G. et al., "Vaccination with irradiated tumor cells engineered to secrete murine granulocyte-macrophage colony-stimulating factor stimulates potent, specific, and long-lasting antitumor immunity", Proc. Natl. Acad. Sci. U.S.A., Apr. 15, 1993, 90(8):3539-3543.

Greenberg, P.D. et al., "Deficient Cellular Immunit—Finding and Fixing the Defects", Science Jul. 23, 1999, 23:285 (546-551).

Harlow, E. et al., "Antibodies, A Laboratory Manual", (1988), Cold Spring Harbor Publications, New York.

He, Y. et al., "Blocking Programmed Death-1 Ligand-PD-1 Interactions by Local Gene Therapy Results in Enhancement of Antitumor Effect of Secondary Lymphoid Tissue Chemokine", The Journal of Immunology, 2004, 173:4919-4928.

Hinton, et al., "An Engineered Human IgG1 Antibody with Longer Serum Half-Life", Journal of Immunology, 2006, 176:346-356.

Hinton, et al., "Engineered Human IgG Antibodies with Longer Serum Half-lives in Primates", Journal of Biological Chemistry, 2004, 279(8): 6213-6216.

Hutloff, A et al., "ICOS is an inducible T-cell co-stimulator structurally and functionally related to CD28", Nature, Jan. 21, 1999, 397:263-266.

International Search Report and Written Opinion of the International Searching Authority dated May 10, 2018 in PCT Application No. PCT/US17/69072.

(56) References Cited

OTHER PUBLICATIONS

Karyampudi, L. et al., "Accumulation of memory precursor CD8 T cells in regressing tumors following combination therapy with vaccine and anti-PD-1 antibody", Jun. 2014, 74:2974-2985.
Kim, N.W., et al., "Specific Association of Human Telomerase Activity with Immortal Cells and Cancer", Dec. 1994, vol. 266, pp. 2011-2013.
Kugler, A. et al., "Regression of human metastatic renal cell carcinoma after vaccination with tumor cell-dendritic cell hybrids", Nature Medicine, Mar. 6, 2000, 3:332-336.
Kyi, C. et al., "Checkpoint blocking antibodies in cancer immunotherapy", FEBS Letters, 2014, 588:368-376.
Le Mercier, I. et al., "Beyond CTLA-4 and PD-1, the Generation Z of Negative Checkpoint Regulators", Front. Immunol., Aug. 2015, (6), Article 418.
Lo, B.K.C., "Antibody engineering: Methods and Protocols, Methods in molecular biology", (2004) vol. 248. Humana Press, Clifton, N.J.
Melero, I et al., "Monoclonal antibodies against the 4-1BB T-cell activation molecule eradicate established tumors", Nature Medicine, Jun. 1997, 3(6):682-685.
Mokyr, M.B. et al., "Relization of the Therapeutic Potential of CTLA-4 Blockage in Low-Dose Chemotherpahy-treated Tumor-bearing Mice", Cancer Research (1998), 58:5301-5304.
Nestle, F.O. et al., "Vaccination of melanoma patients with peptide- or tumor lysate-pulsed dendritic cells", Nature Medicine, Mar. 1998, 4(3):328-332.
Petkova, S.B. et al., "Enhanced half-life of genetically engineered human IgG1 antibodies in a humanized FcRn mouse model: potential application in humorally mediated autoimmune disease", Int. Immunol., Dec. 2006, 18(12):1759-1769.
Ridge, J.P. et al., "A conditioned dendritic cell can be a temporal bridge between a CD4+ T-helper and a T-killer cell", Nature, Jun. 4, 1998, 393:474-478.
Rosenberg, S.A. et al., "A New Era for Cancer Immunotherapy Based on the Genes that Encode Cancer Antigens", Immunity, Mar. 1999, vol. 10, pp. 281-287.
Shields, et al., "High Resolution Mapping of the Binding Site on Human IgG1 for FcyRI, FcyRII, FcyRIII, and FcRn and Design of IgG1 Variants with Improved Binding to the FcyR", Journal of Biological Chemistry, 2001, 276(9):6591-6604.
Tansey, M.G et al., "The TNF superfamily in 2009: new pathways, new indications, and new drugs", Drug Discovery Today, Dec. 2009, 14(23-24):1082-1088.
Thompson, R.H. et al., "Tumor B7-H1 Is Associated with Poor Prognosis in Renal Cell Carcinoma Patients with Long-term Follow-up", (2006), 66(7):3381.
Weinberg, A.D. et al. "Engagement of the OX-40 receptor in vivo enhances antitumor immunity", Journal of Immunology, Feb. 15, 2000, 15:164(4):2160-2169.
Wranik, et al., "LUZ-Y, a Novel Platform for the Mammalian Cell Production of Full-length IgG-bispecific Antibodies", Journal of Biological Chemistry, 2012, 287(52):43331-43339.
Yeung, et al., "Engineering Human IgG1 Affinity to Human Neonatal Fc Receptor: Impact of Affinity Improvement of Pharmacokinetics in Primates", The Journal of Immunology, 2009, 182:7663.
Zalevsky, J. et al., "Enhanced antibody half-life improves in vivo activity", Nat. Biotechnol., Feb. 2010, 28(2):157-159.
U.S. Appl. No. 16/457,399, filed Jun. 28, 2019, pending.
U.S. Appl. No. 16/457,421, filed Jun. 28, 2019, pending.
PCT/US19/39982, Jun. 28, 2019, pending.
PCT/US19/39979, Jun. 28, 2019, pending
PCT/US19/39994, Jun. 28, 2019, pending.
Hinton, P.R., "Engineerd human IgG antibodies with longer serum half-lives in primates"et al., Feb. 20, 2004, J. Biol. Chem., vol. 279(8), pp. 6213-6216.
Hinton, P.R., et al., "An Engineered Human IgG1 Antibody with Longer Serum Half-Life", Jan. 1, 2006, The Journal of Immunology, vol. 176(1), pp. 346-356.

Shields, R.L., et al., "High resolution mapping of the binding site on human IgF1 for Fc gamma RI, Fc gamma RII, Fc gamma RIII, and FcRn and design of IgG1 variants with improved binding to the Fc gamma R", Mar. 2, 2001, J. Biol. Chem., vol. 276(9) pp. 6591-6604.
Dall'Acqua, W.F., et al., "Increasing the Affinity of a Human IgG1 for the Neonatal Fc Receptor: Biological Consequences", Nov. 1, 2002, The Journal of Immunology, vol. 169, pp. 5171-5180.
Dall'Acqua, W.F., et al., Properties of human IgG1s engineered for enhanced binding to the neonatal Fc recptor (FcRn), Aug. 18, 2006, J. Biol. Chem., vol. 281(33), pp. 23514-23524.
Yeung, Y.A., et al., Engineering human IgG1 affinity to human neonatal Fc receptor: impact of affinity improvement on pharmacokinetics in primates, Jun. 15, 2009, J. Immunol., vol. 182(12) pp. 7663-7671.
Zalevsky, J., et al., "Enhanced antibody half-life improves in vivo activity", Feb. 2010, Nat. Biotechnol., vol. 28(2), pp. 157-159.
Petkova, S.B., et al., "Enhanced half-life of genetically engineered human IgG1 antibodies in a humanized FcRn mouse model: potential application in humorally mediated autoimmune disease", Dec. 2006, Int. Immunol. vol. 18(12), pp. 1759-1769.
Joller, N., et al., "Treg cells expressing the coinhibitory molecule TIGIT selectively inhibity proinflammatory Th1 and Th17 cell responses", Immunity, Apr. 17, 2014, vol. 40(4), pp. 569-581.
Johnston, R.J., et al., "The immunoreceptor TIGIT regulates antitumor and antiviral CD8(+) T cell effector function", Dec. 8, 2014, Cancer Cell, vol. 26(6), pp. 923-937.
He, Y.F., et al., "Blocking Programmed Death-1 Ligand-PD-1 Interactions by Local Gene Therapy Results in Enhancement of Antitumor Effect of Secondary Lymphoid Tissue Chemokine", Mar. 31, 2004, The Journal of Immunology, vol. 173, pp. 4919-4928.
Dranoff, G., et al., "Vaccination with irradiated tumor cells engineered to secrete murine granulocyte-macrophage colony-stimulating factor stimulates potent, specific, and long-lasting antitumor immunity", Apr. 15, 1993, Proc. Natl. Acad. Sci. U.S.A., vol. 90(8), pp. 3539-3543.
Rosenberg, S. A., et al.,"A New Era for Cancer Immunotherapy Based on the Genes that Encode Cancer Antigens", Mar. 1999, Immunity, vol. 10(3), pp. 281-287.
Kim, N.W., et al., "Specific association of human telomerase activity with immortal cells and cancer", Dec. 23, 1994, Science Mag, vol. 266(5193), pp. 2011-2013.
Karyampudi, L. et al., "Acculation of memory precursor CD8 T cells in regressing tumors following combination therapy with vaccine and anti-PD-1 antibody", Jun. 1, 2014, Cancer Research, vol. 74(11), pp. 2974-2985.
Nestle, F.O., et al., Vaccination of melanoma patients with peptide- or tumor lysate-pulsed dendritic cells, Mar. 1998, Nature Medicine, vol. 4(3), pp. 328-332.
Kulger, A., et al., Retraction Note to: Regression of human metastatic renal cell carcinoma after vaccination with tumor cell-dendritic cell hybrids, (2000) Nature Medicine 6:332-336.
Mokyr, M.B., et al., Realization of the Therapeutic Potential of CTLA-4 Blockade in Low-Dose Chemotherapy-treated Tumor-bearing Mice, Dec. 1, 1998, Cancer Research, vol. 58, pp. 5301-5304.
Weinberg, A.D., et al., "Engagement of the OX-40 Receptor In Vivo Enhances Antitumor Immunity", 2000 The Journal of Immunology, 164: 2160-2169.
Melero, I., et al., "Monoclonal antibodies against the 4-1BB T-cell activation molecule eradicate established tumors", (1997) Nature Medicine, vol. 3, pp. 682-685.
Hutloff,A., et al., "ICOS is an inducible T-cell co-stimulator structurally and functionally related to CD28", Jan. 21, 1999, Nature, vol. 397, pp. 262-266.
Greenberg & Riddell (1999) Science 285: 546-51.
Thompson R H et al., Cancer Res 2006, 66(7):3381.
Blood 2009 114(8):1537.
Le Mercier et al. (2015) Front. Immunol., (6), Article 418.
Kyi et al., FEBS Letters, 588:368-376 (2014.
Tansey, M.G. et al. (2009) Drug Discovery Today, 14(23-24):1082-1088. Abstract.
Wranik et al., J. Biol. Chem., 287(5):43331-43339, 2012.

(56) References Cited

OTHER PUBLICATIONS

Ridge, J.P., et al., "A conditioned dendritic cell can be a temporal bridge between a CD4+ T-helper and a T-killer cell", Nature, vol. 393(4), Jun. 4, 1998, pp. 474-478.

International Search Report and the Written Opinion of the International Searching Authority issued in International Application No. PCT/US19/39982, dated Dec. 3, 2019.

International Search Report and the Written Opinion of the International Searching Authority issued in International Application No. PCT/US19/39979, dated Nov. 12, 2019.

International Search Report and the Written Opinion of the International Searching Authority issued in International Application No. PCT/US19/39994, dated Nov. 21, 2019.

* cited by examiner

Exemplary Functional Checkpoint Sequences

| VH/VL or Fusion Protein Domain | Amino Acid Sequences of Functional Domains |
|---|---|
| Anti-PD-L1 HCVR (PL-08) | QVQLVQSGAEVKKPGASVKVSCKASGYTFTSYWMHWVRQAPGQGLEWMGMIHPNSGGNNYNEKFKSRVTMTRDTSISTAYMELSRLRSDDTAVYYCARSWYGSSPYYFDYWGQGTLVTVSS (SEQ ID NO: 153) |
| Anti-PD-L1 LCVR (PL-08) | DIQMTQSPSSLSASVGDRVTISCRASQDIDNYLNWYQQKPGKAPKLLIKYTSRLHSGVPSRFSGSGSGTDFTLTISSLQPEDFATYFCQQGYTLPWTFGGGTKVEIK (SEQ ID NO: 154) |
| Anti-PD-1 HCVR (nivolumab) | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS(SEQ ID: 245) |
| Anti-PD-2 LCVR (nivolumab) | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK(SEQ ID NO: 246) |
| Anti-PD-1 HCVR (2P17 or PD-06) | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSS (SEQ ID NO: 137) |
| Anti-PD-1 LCVR (2P17 or PD-06) | DIQMTQSPSFLSASVGDRVTITCKASQNVGTNVAWYQQKPGKAPKALIYSASYRYSGVPSRFSGSGSGTEFTLTISSLQPEDFATYYCQQYYSYPYTFGQGTKLEIK (SEQ ID NO: 138) |
| Anti-PD1 HCVR (2P16 or PD-05) | QVQLVQSGAEVKKPGASVKVSCKASGYTFTTYYIYWVRQAPGQGLEWMGGINPGNGGTNFNEKFKIRVTMTRDTSISTAYMELSSLRSEDTAVYYCARRYHGYDGGLDYWGQGTLVTVSS (SEQ ID NO: 135) |
| Anti-PD1 LCVR (2P16 or PD-05) | DIVLTQSPASLAVSPGQRATITCRASKSVSTSGFSYIHWYQQKPGQPPKLLIYLASNLESGVPARFSGSGSGTDFTLTINPVEANDTANYYCQHTWELPNTFGGGTKVEIK(SEQ ID NO: 136) |
| Anti-TIGIT HCVR (B21-35 or T-10) | QVQLVQSGAEVKKPGASVKVSCKASGYTFTSYYMHWVRQAPGQGLEWMGIINPSGGRTSYAQMFQGRVTMTRDTSTSTVYMELSSLRSEDTAVYYCARDREEQWPVGGFDYWGQGTLVTVSS (SEQ ID NO: 125) |
| Anti-TIGIT LCVR (B21-35 or T-10) | DIQMTQSPSSLSASVGDRVTITCRASQSIRRYLNWYQQKPGKAPKLLIYSASNLQSGVPSRFSGSGSGTDFTLTISSLQPEDFATYYCQQSYIPPTFGQGTKVEIK (SEQ ID NO: 126) |
| Anti-Lag-3 HCVR (2L2A.1) | QVQLVQSGAEVKKPGASVKVSCKASGYTLTDYYMNWMRQAPGQGLEWMGVINPYNGDTSYNQKFKGRVTMTRDTSTSTVYMELSSLRSEDTAVYYCVRDDGYYVHYFDYWGQGTLVTVSS(SEQ ID NO: 171) |
| Anti-Lag-3 LCVR (2L2A.1) | DIQMTQSPSSLSASVGDRVTITCRASQDISSRLTWLQQEPEKAPKRLIYATSSLDSGVPKRFSGSGSGTDFTLTISSLQPEDFATYYCLQYASSPLTFGGGTKVEIK(SEQ ID NO: 175) |

*FIG. 1*

Functional Domain Sequences

| VH/VL or Fusion Protein Domain | Amino Acid Sequences of Functional Domains |
|---|---|
| Trebananib long peptide | AQQEECEWDPWTCEHMGSGSATGGSGSTASSGSGSATHQEECEWDPWTCEHM (SEQ ID NO: 182) |
| Trebananib-short peptide | QEECEWDPWTCEHM (SEQ ID NO: 194) |
| Bevacizumab (Avastin) HCVR (wt) | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS (SEQ ID NO: 233) |
| Bevacizumab (Avastin) HCVR (mt) | EVQLVQSGGGVVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS (SEQ ID NO: 235) |
| Bevacizumab (Avastin) LVCR | DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK (SEQ ID NO: 234) |
| Ranibizumab (Lucentis) HCVR | EVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSS (SEQ ID NO: 305) |
| Ranibizumab (Lucentis) LCVR | DIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK (SEQ ID NO: 306) |
| Aflibercept VEGF binding domain | GRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK (SEQ ID NO: 185) |
| TGF-β RII-ECD | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD (SEQ ID NO: 186) |

*FIG. 2*

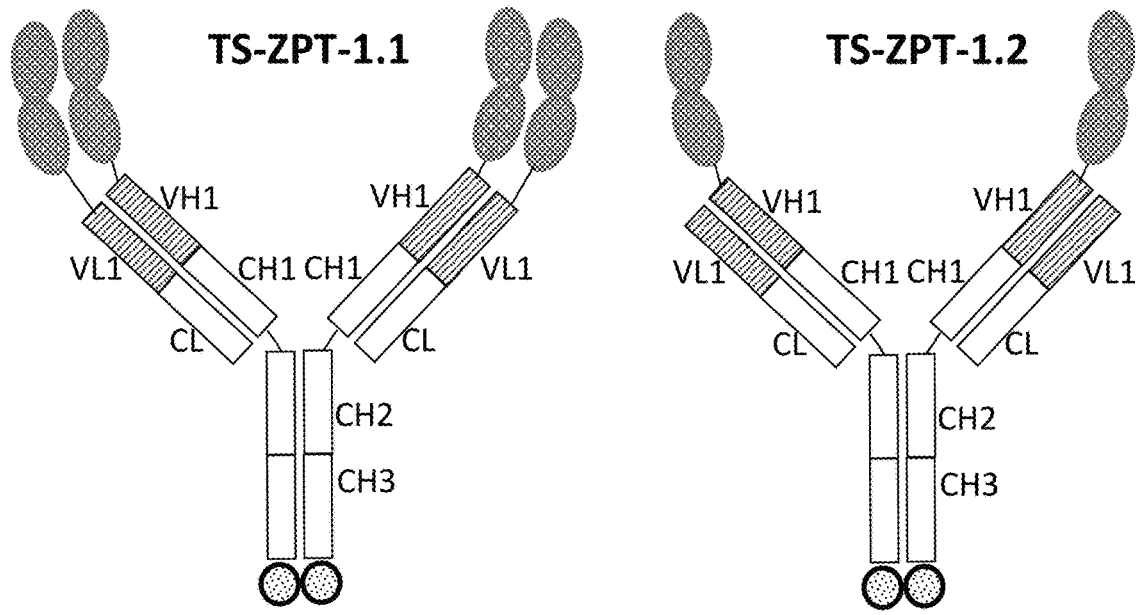
FIG. 3A
FIG. 3B
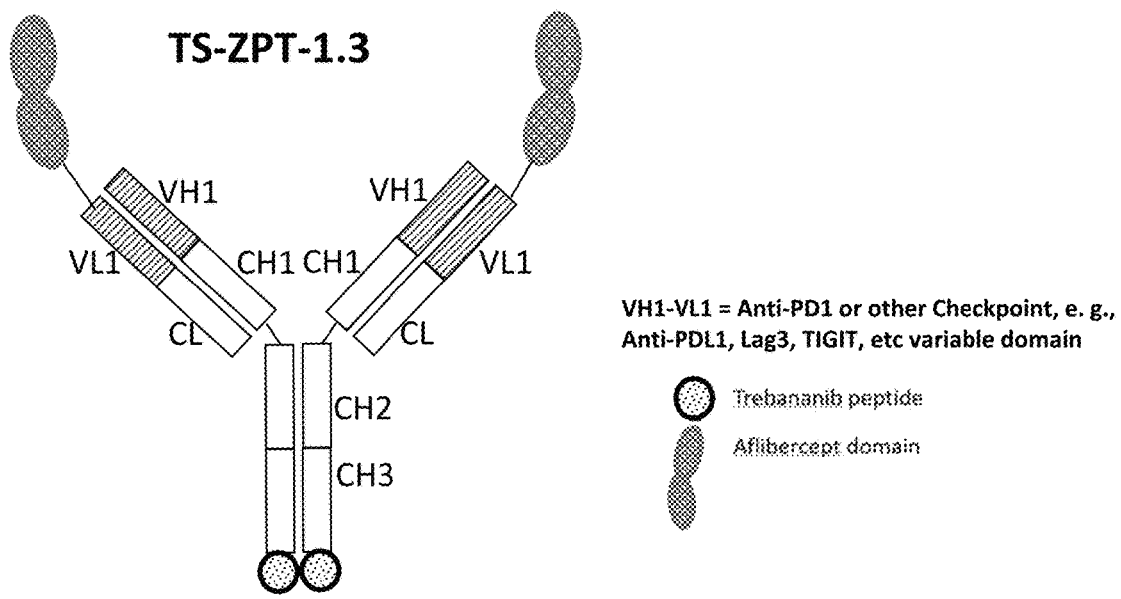
FIG. 3C

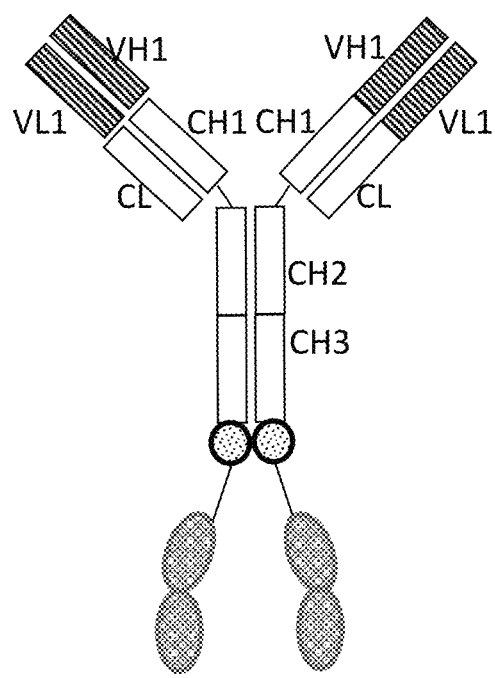 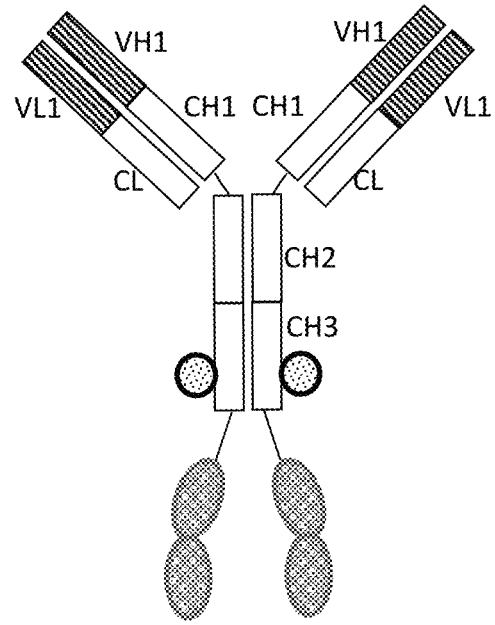
FIG. 3D  FIG. 3E
VH1-VL1 = Anti-PD1 or other Checkpoint Ab, e. g., Anti-PDL1, Lag3, TIGIT, etc variable domain
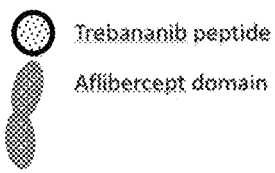

TS-ZPT-7
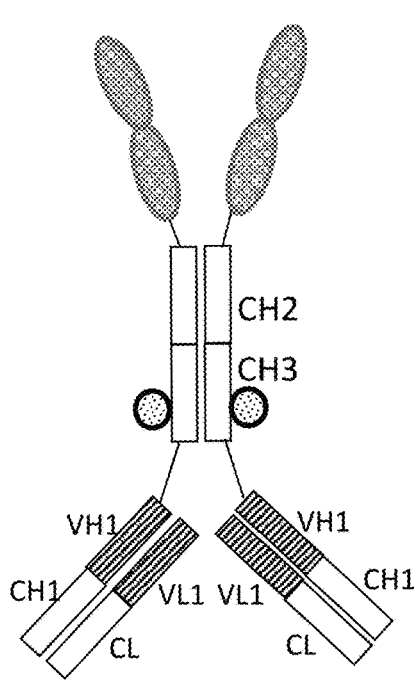
FIG. 4A
TS-ZPT-8
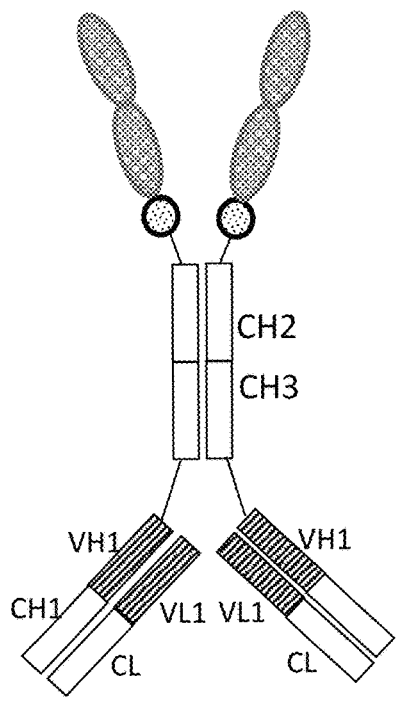
FIG. 4B
TS-ZPT-9
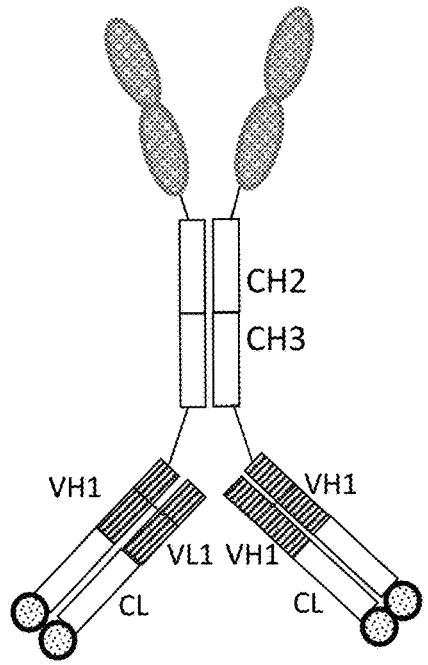
FIG. 4C
VH1-VL1 = Anti-PD1 or other Checkpoint Ab, e.g., Anti-PDL1, Lag3, TIGIT, etc variable domain
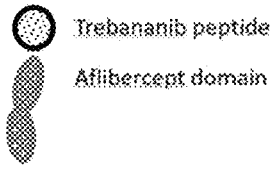

TS-LPT-1                    TS-LPT-2
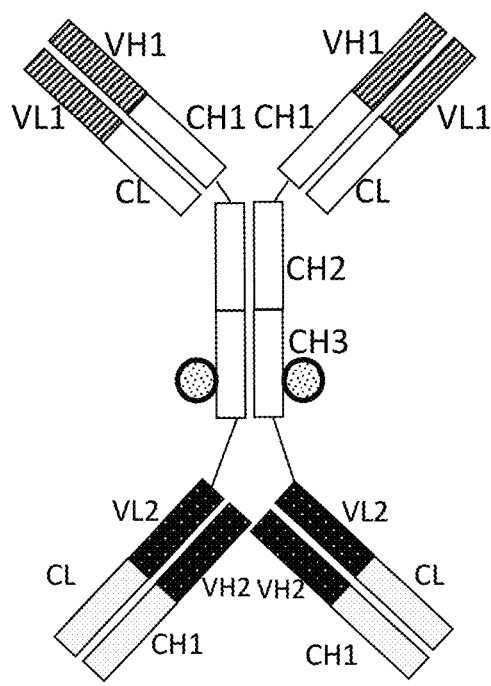        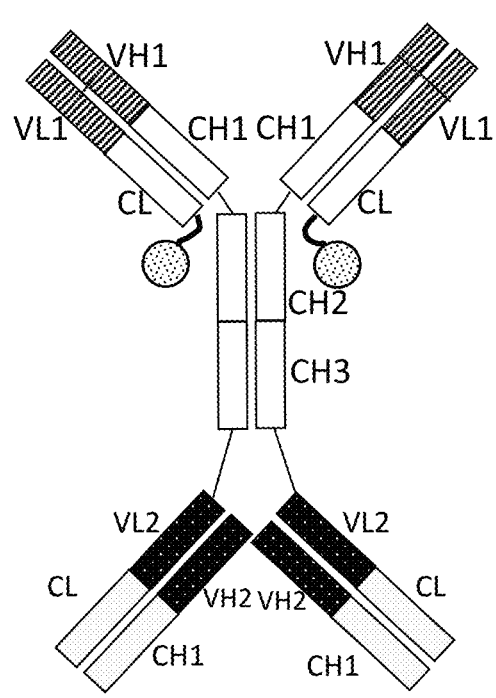
FIG. 5A                 FIG. 5B
VH1-VL1 = Anti-PD1 or other Checkpoint Ab, e. g.,
Anti-PDL1, Lag3, TIGIT, etc variable domain
VH2-VL2 = Lucentis, Avastin, or other anti-VEGF
● Trebananib peptide

TS-LPT-3

TS-LPT-4

TS-LPT-5

VH1-VL1 = Anti-PD1 or other Checkpoint Ab, e. g., Anti-PDL1, Lag3, TIGIT, etc variable domain VH2-VL2 = Lucentis, Avastin, or other anti-VEGF ◯ Trebananib peptide TS-M3                                         TS-M4
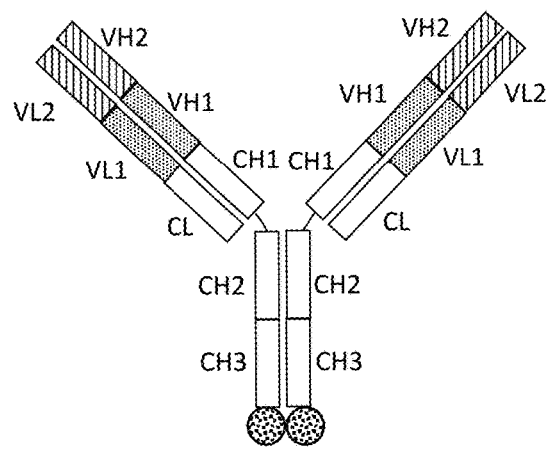
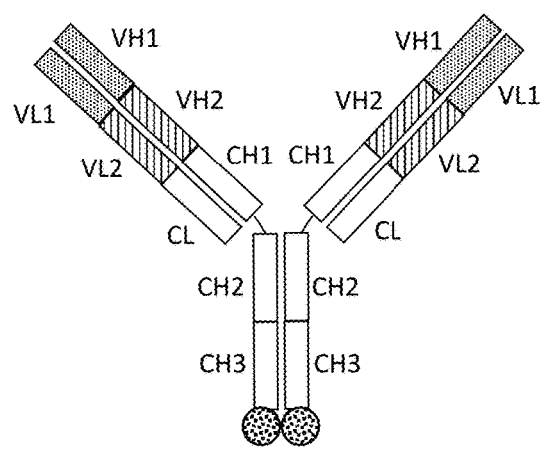
FIG. 5F                                        FIG. 5G
VH1-VL1 = Anti-PD1 or other Checkpoint Ab, e. g.,
Anti-PDL1, Lag3, TIGIT, etc variable domain
VH2-VL2 = Lucentis, Avastin, or other anti-VEGF
 Trebananib peptide

Trispecific Antitumor Antagonists Block Interaction of PD-1 and PD-L1

| Antagonist | IC50 (nM) |
|---|---|
| Benchmark | 2.89 |
| TS-ZPT-1.1(2P16) | 139.70 |
| TS-ZPT-1.2(2P16) | 14.77 |
| TS-ZPT-1.3(2P16) | 32.97 |
| TS-ZPT-2(2P16) | 4.62 |
| TS-ZPT-3(2P16) | 3.55 |
| anti-PD-1 mAb | 2.48 |

*FIG. 7A*

| Antagonist | IC50 (nM) |
|---|---|
| Benchmark | 0.64 |
| TS-ZPT-5(2P16) | 1.30 |
| TS-ZPT-6(2P16) | 1.16 |

*FIG. 7B*

**Trispecific Antitumer Antagonists
Block Interaction of VEGF and VEGFR-2**

| Antagonist | IC50 (nM) |
|---|---|
| TS-ZPT-2(2P16) | 0.11 |
| TS-ZPT-3(2P16) | 0.50 |
| TS-ZPT-5(2P16) | 0.26 |
| Aflibercept | 0.20 |
| Bevacizumab | 1.57 |

*FIG. 8A*

| Antagonist | IC50 (nM) |
|---|---|
| TS-ZPT-2(2P16) | 0.17 |
| TS-ZPT-5(2P16) | 1.78 |
| TS-ZPT-6(2P16) | 0.66 |
| Aflibercept | 0.29 |
| BVZ | 1.36 |

*FIG. 8B*

**Trispecific Antitumer Antagonists Block
Interaction of Ang2 and Tie2**

| Antagonist | IC50 (nM) |
|---|---|
| TS-ZPT-1.2 | 0.95 |
| TS-ZPT-2 | 0.65 |
| TS-ZPT-5 | 0.40 |
| TS-ZPT-6 | 0.55 |
| TS-LPT-1 | 1.26 |
| BVZ-Trebananib | 0.57 |

*FIG. 9*

Size Exclusion Chromatography of HEK293 transiently produced molecules

| Construct | HMW% | Dimer% | LMW% |
|---|---|---|---|
| 2P17 | 1.0 | 97.3 | 1.7 |
| TS-ZPT-2(2P17) | 0.0 | 81.5 | 18.5 |
| TS-ZPT-3L(2P17) | 0.0 | 95.1 | 4.9 |
| TS-ZPT-5(2P17) | 0.6 | 65.3 | 34.1 |

*FIG. 10*

Size Exclusion Chromatography of stable CHO cell produced molecules

| Construct | HMW% | Dimer% | LMW% |
|---|---|---|---|
| TS-ZPT-2(2P17) | 0.6 | 89.9 | 9.7 |
| TS-ZPT-5(2P17) | 0.7 | 92.4 | 6.9 |
| TS-ZPT-3L(2P17) Pool 1 | 0.5 | 97.7 | 1.8 |
| TS-ZPT-3L(2P17) Pool 2 | 0.9 | 97.4 | 1.7 |

*FIG. 11*

Size Exclusion Chromatography of 4 degree stability sample

| Day | HMW% | Dimer% | LMW% |
|---|---|---|---|
| 0 | 1.3 | 97.2 | 1.5 |
| 112 | 0.8 | 97.1 | 2.1 |

Exemplary Amino acid sequences of TS-ZPT-3L

Heavy Chain with peptide and fusion protein

<u>QVQLVQSGAEVKKPGASVKVSCKASGYTFTSYYIHWVRQAPGQGLEWMGWIFPGSGNS</u>  Anti-PD-1
<u>KYNENFKGRVTLTADTSTSTVYMELSSLRSEDTAVYYCASETYDYGDYWGQGTLVTVSS</u>AST  2P17 HCVR
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLPP
KPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMGG<u>AQQE</u>
<u>ECEWDPWTCEHMGSGSATGGSGSTASSGSGSATHQEECEWDPWTCEHMGGTKNQVS</u>  Trebananib peptide
LTCLVKGFYPSDIAVEWESNGQPENNYKTTPPVLDSDGSFFLYSKLTVDKSRWQQGNVFSC
SVMHEALHNHYTQKSLSLSPGKGGGGSGGGGSGGGGSS<u>DTGRPFVEMYSEIPEIIHMTE</u>
<u>GRELVIPCRVTSPNITVTLKKFPLDTLIPDGKRIIWDSRKGFIISNATYKEIGLLTCEATVNGHLY</u>
<u>KTNYLTHRQTNTIIDVVLSPSHGIELSVGEKLVLNCTARTELNVGIDFNWEYPSSKHQHKKLV</u>  Aflibercept
<u>NRDLKTQSGSEMKKFLSTLTIDGVTRSDQGLYTCAASSGLMTKKNSTFVRVHEK</u> (SEQ ID  domain
NO: 202)

Light Chain

<u>DIQMTQSPSFLSASVGDRVTITCKASQNVGTNVAWYQQKPGKAPKALIYSASYRYSGVPS</u>  Anti-PD-1
<u>RFSGSGSGTEFTLTISSLQPEDFATYYCQQYYSYPYTFGQGTKLEIK</u>RTVAAPSVFIFPPSDEQ  2P17 LCVR
LKSGTASVVCLLNNFYPREAKVQWKVDNALQSGNSQESVTEQDSKDSTYSLSSTLTLSKAD
YEKHKVYACEVTHQGLSSPVTKSFNRGEC (SEQ ID NO: 201)

*FIG. 13A*

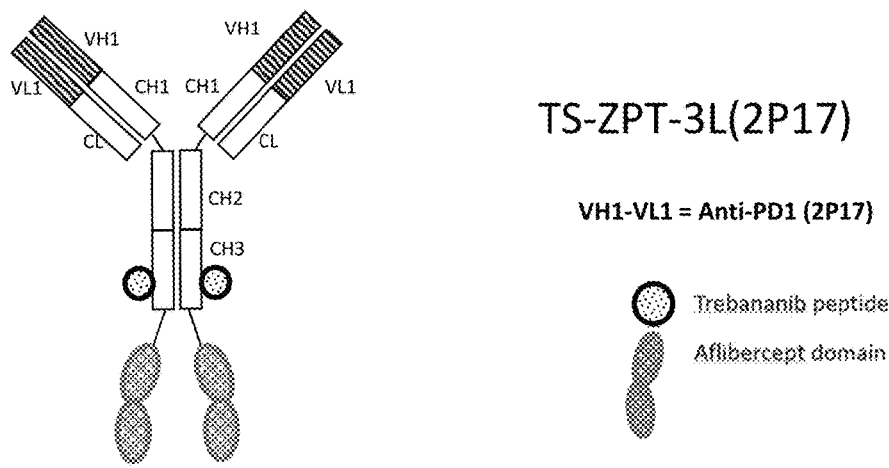

*FIG. 13B*

Exemplary Amino acid sequences of TS-ZPT-3S

Heavy Chain with peptide and fusion protein

<u>QVQLVQSGAEVKKPGASVKVSCKASGYTFTSYYIHWVRQAPGQGLEWMGWIFPGSGNS</u> Anti-PD-1
<u>KYNENFKGRVTLTADTSTSTVYMELSSLRSEDTAVYYCASETYDYGDYWGQGTLVTVSS</u>AST 2P17 HCVR
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMGG<u>QEECE</u> Trebananib
<u>WDPWTCEHMGGTKNQVSLTCLVKGFYPSDIAVEWESNGQPENNYKTTPPVLDSDGSFFL</u> short peptide
YSKLTVDKSRWQQGNVFSCSVMHEALHNHYTQKSLSLSPGKGGGGSGGGGSGGGGSS<u>D</u>
<u>TGRPFVEMYSEIPEIIHMTEGRELVIPCRVTSPNITVTLKKFPLDTLIPDGKRIIWDSRKGFIIS</u>
<u>NATYKEIGLLTCEATVNGHLYKTNYLTHRQTNTIIDVVLSPSHGIELSVGEKLVLNCTARTELN</u> Aflibercept
<u>VGIDFNWEYPSSKHQHKKLVNRDLKTQSGSEMKKFLSTLTIDGVTRSDQGLYTCAASSGL</u> domain
<u>MTKKNSTFVRVHEK</u> (SEQ ID NO: 200)

Light Chain

<u>DIQMTQSPSFLSASVGDRVTITCKASQNVGTNVAWYQQKPGKAPKALIYSASYRYSGVPS</u> Anti-PD-1
<u>RFSGSGSGTEFTLTISSLQPEDFATYYCQQYYSYPYTFGQGTKLEIK</u>RTVAAPSVFIFPPSDEQ 2P17 LCVR
LKSGTASVVCLLNNFYPREAKVQWKVDNALQSGNSQESVTEQDSKDSTYSLSSTLTLSKAD
YEKHKVYACEVTHQGLSSPVTKSFNRGEC (SEQ ID NO: 201)

*FIG. 14A*

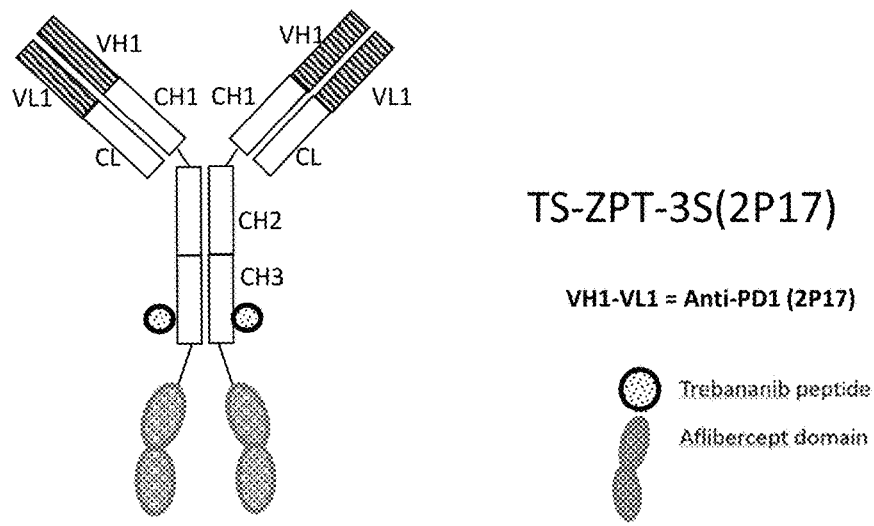

*FIG. 14B*

1: TS-M3 (Nivolumab)
2: TS-M4 (Nivolumab)
3: TS-M3(2P16)
4: TS-M3(2P17)
5: TS-ZPT-3S(2P17)
6: TS-ZPT-3L(2P17)

| Day | TS-ZPT-3L(2P17) | | | TS-ZPT-3S(2P17) | | |
|---|---|---|---|---|---|---|
| | HMW % | Dimer % | LMW % | HMW % | Dimer % | LMW % |
| 0 | 3.0 | 93.7 | 3.4 | 0.5 | 97.9 | 1.6 |
| 7 | 3.2 | 93.8 | 3.0 | 0.8 | 97.9 | 1.4 |
| 14 | 3.2 | 93.7 | 3.0 | 0.8 | 97.9 | 1.3 |
| 20 | 3.3 | 93.6 | 3.1 | 0.6 | 07.7 | 1.7 |
| 28 | 3.3 | 93.6 | 3.1 | 0.7 | 07.6 | 1.6 |
| 35 | 3.5 | 93.2 | 3.3 | 0.6 | 97.6 | 1.8 |
| 42 | 3.4 | 93.2 | 3.4 | 0.6 | 97.7 | 1.7 |
| 48 | 3.2 | 93.2 | 3.6 | 0.8 | 97.5 | 1.7 |

*FIG. 17*

| PD-1/PDL-1 | IC50 (nM) |
|---|---|
| Anti-PD1 Benchmark Ab | 0.44 |
| TS-ZPT-3S(2P16) | 0.43 |
| TS-ZPT-3L(2P16) | 0.64 |
| TS-ZPT-3S(2P17) | 0.37 |
| TS-ZPT-3(2P17) | 0.65 |
| 2P17 | 0.37 |
| Control Ab | N/A |

| VEGF/VEGFR2 | IC50 (pM) |
|---|---|
| TS-ZPT-3S(2P16) | 123 |
| TS-ZPT-3L(2P16) | 142 |
| TS-ZPT-3S(2P17) | 129 |
| TS-ZPT-3L(2P17) | 63 |
| Bevacizumab | 202 |
| Control | No blocking |

| Ang2/Tie2 | IC50 (nM) |
|---|---|
| TS-ZPT-3S(2P16) | 6.71 |
| TS-ZPT-3L (2P16) | 0.73 |
| TS-ZPT-3S(2P17) | 9.34 |
| TS-ZPT-3L(2P17) | 0.60 |
| Control Ab | N/A |
| Trebananib | 0.50 |

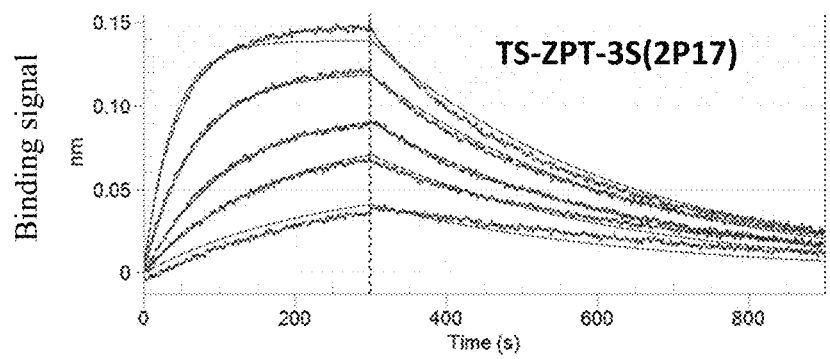
FIG. 21D
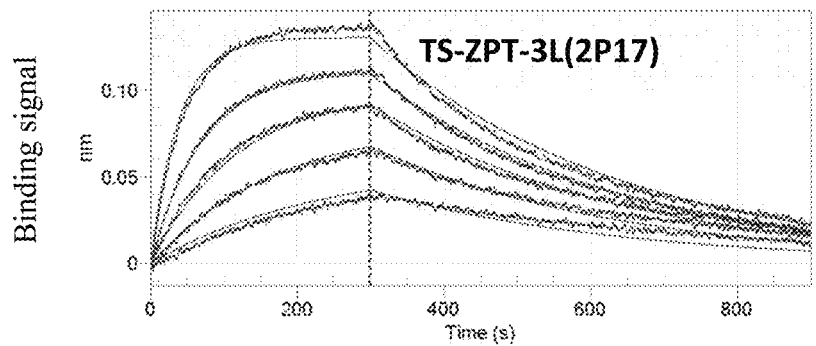
FIG. 21E
| | PD-1-His (R&D) | | |
|---|---|---|---|
| Ab name | $K_D$ (nM) | $K_a$ (M$^{-1}$s$^{-1}$) | $K_d$ (s$^{-1}$) |
| Anti-PD1 Benchmark | 7.32E-09 | 1.98E+05 | 1.45E-03 |
| TS-ZPT-3S(2P16) | 4.76E-09 | 3.35E+05 | 1.59E-03 |
| TS-ZPT-3L(2P16) | 4.67E-09 | 3.33E+05 | 1.55E-03 |
| TS-ZPT-3S(2P17) | 3.71E-09 | 3.94E+05 | 1.46E-03 |
| TS-ZPT-3L(2P17) | 3.84E-09 | 3.82E+05 | 1.47E-03 |
FIG. 21F

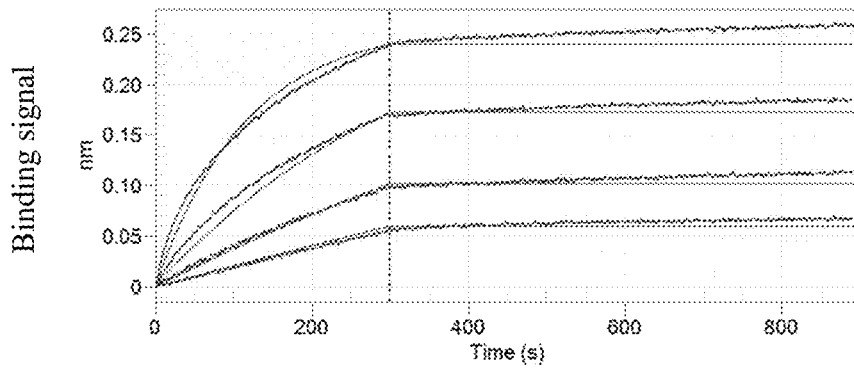
FIG. 22D
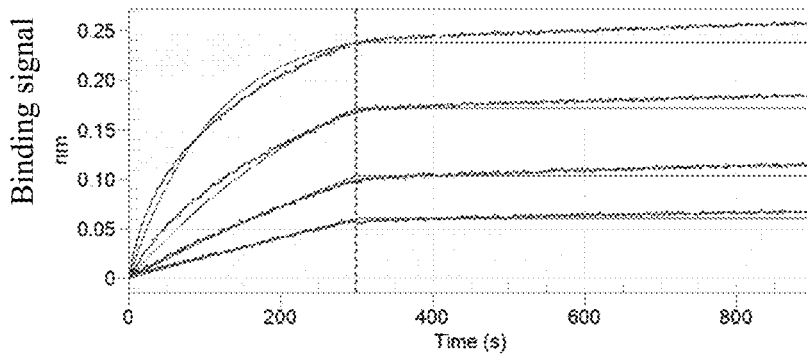
FIG. 22E
| | rhVEGF165 | | |
|---|---|---|---|
| Ab name | $K_D$ (pM) | $K_a$ (M$^{-1}$s$^{-1}$) | $K_d$ (s$^{-1}$) |
| Bevacizumab | 20.4 | 1.97E+05 | 4.00E-06 |
| TS-ZPT-3S(2P16) | 6.3 | 6.83E+05 | 4.31E-06 |
| TS-ZPT-3L(2P16) | 5.3 | 8.45E+05 | 4.47E-06 |
| TS-ZPT-3S(2P17) | 5.2 | 9.74E+05 | 5.03E-06 |
| TS-ZPT-3L(2P17) | 4.9 | 1.02E+06 | 5.00E-06 |
FIG. 22F

Trebananib

TS-ZPT-3S(2P16)

TS-ZPT-3L(2P16)

TS-ZPT-3S(2P17)
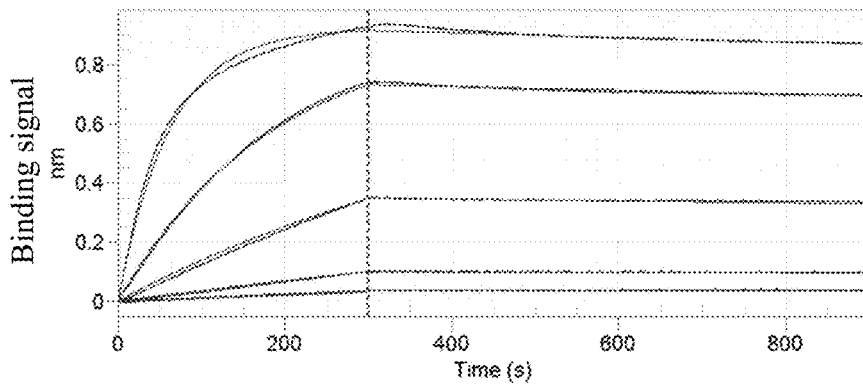
FIG. 23D
TS-ZPT-3L(2P17)
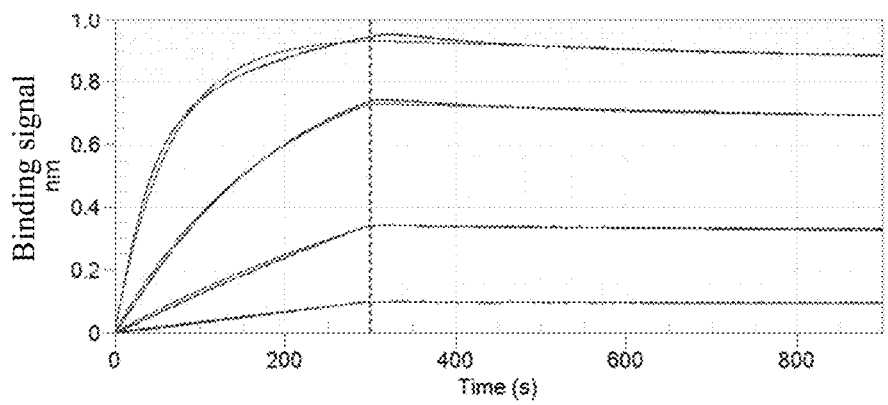
FIG. 23E
| Ab name | rhAng2-His | | |
|---|---|---|---|
| | $K_D$ (nM) | $K_a$ (M$^{-1}$s$^{-1}$) | $K_d$ (s$^{-1}$) |
| Trebananib | 1.23 | 1.19E+05 | 1.46E-04 |
| TS-ZPT-3S(2P16) | 0.87 | 1.26E+05 | 1.10E-04 |
| TS-ZPT-3L(2P16) | 0.76 | 1.24E+05 | 9.39E-05 |
| TS-ZPT-3S(2P17) | 0.65 | 1.34E+05 | 8.66E-05 |
| TS-ZPT-3L(2P17) | 0.70 | 1.30E+05 | 9.05E-05 |
FIG. 23F

VH1 VL1 = Checkpoint #1 e.g. Anti-PD-1, anti-PD-L1 or any other mAb variable domain
VH2 VL2 = Checkpoint #2 Anti-LAG3, anti-TIGIT or any other mAb variable domain
● = trebananib or other biological peptide

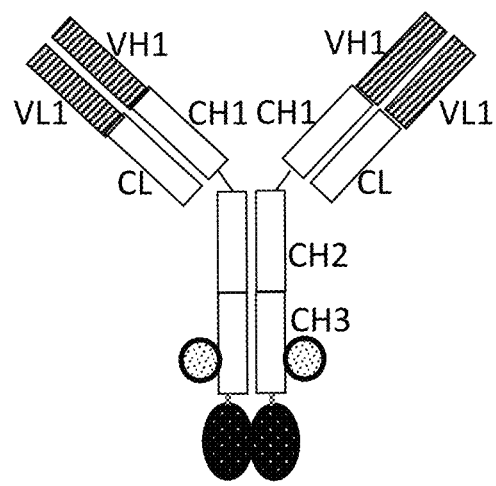
TS-A1BT-1
VH1-VL1 = Avastin (m), Avastin (WT), Lucentis, or other anti-VEGF Ab
 TGFRβR II ECD
 Trebananib peptide
*FIG. 27*

TS-ZPB-1

TS-ZPB-2

TS-ZPB-3

VH1-VL1 = Anti-PD1 or other Checkpoint, e. g., Anti-PDL1, Lag3, TIGIT, etc variable domain

TGFRβR-II ECD

Aflibercept VEFG binding domain

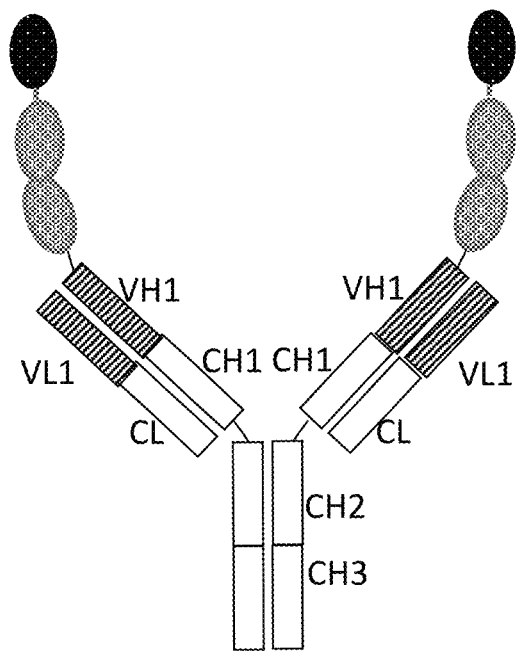
FIG. 30D
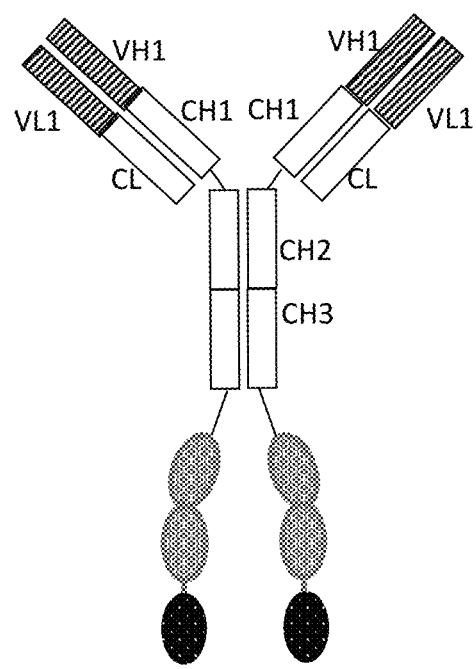
FIG. 30E
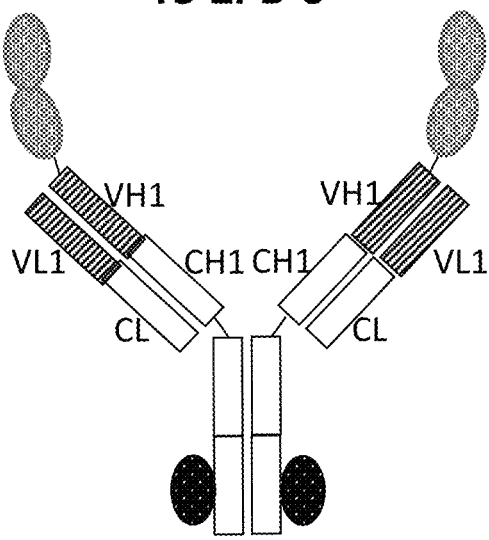
FIG. 30F
VH1-VL1 = Anti-PD1 or other Checkpoint, e. g., Anti-PDL1, Lag3, TIGIT, etc variable domain
 TGFRβR-II ECD
 Aflibercept VEFG binding domain

| Construct | HMW% | Dimer% | LMW% |
|---|---|---|---|
| TS-ZPB-1(2P17) | 4.5 | 89.5 | 6.0 |
| TS-ZPB-2(2P17) | 6.5 | 92.3 | 1.2 |
| TS-ZPB-3(2P17) | 7.1 | 91.3 | 1.5 |
| TS-ZPB-5(2P17) | 4.7 | 95.0 | 0.3 |
| TS-ZPLB-1 | 4.8 | 94.0 | 1.3 |
| TGFβR II-Fc | 15.5 | 84.3 | 0.2 |

| Antagonist | IC50 (nM) |
|---|---|
| TS-ZPB-1(2P17) | 9.29 |
| TS-ZPB-2(2P17) | 11.05 |
| TS-ZPB-3(2P17) | 2.39 |
| TS-ZPB-5(2P17) | 2.72 |

| Antagonist | IC50 (nM) |
| --- | --- |
| TGFβ RII-Fc | 2.02 |
| TS-ZPB-1(2P17) | 0.07 |
| TS-ZPB-2(2P17) | 0.24 |
| TS-ZPB-3(2P17) | 2.95 |
| TS-ZPB-5(2P17) | 0.17 |
| TS-ZPLB-1 | 0.11 |

| Antagonist | IC50 (nM) |
|---|---|
| Bevacizumab | 3.11 |
| TS-ZPB-1 | 1.32 |
| TS-ZPB-2 | 1.92 |
| TS-ZPB-3 | 7.71 |
| TS-ZPB-5 | 6.58 |
| TS-ZPLB-1 | 1.57 |

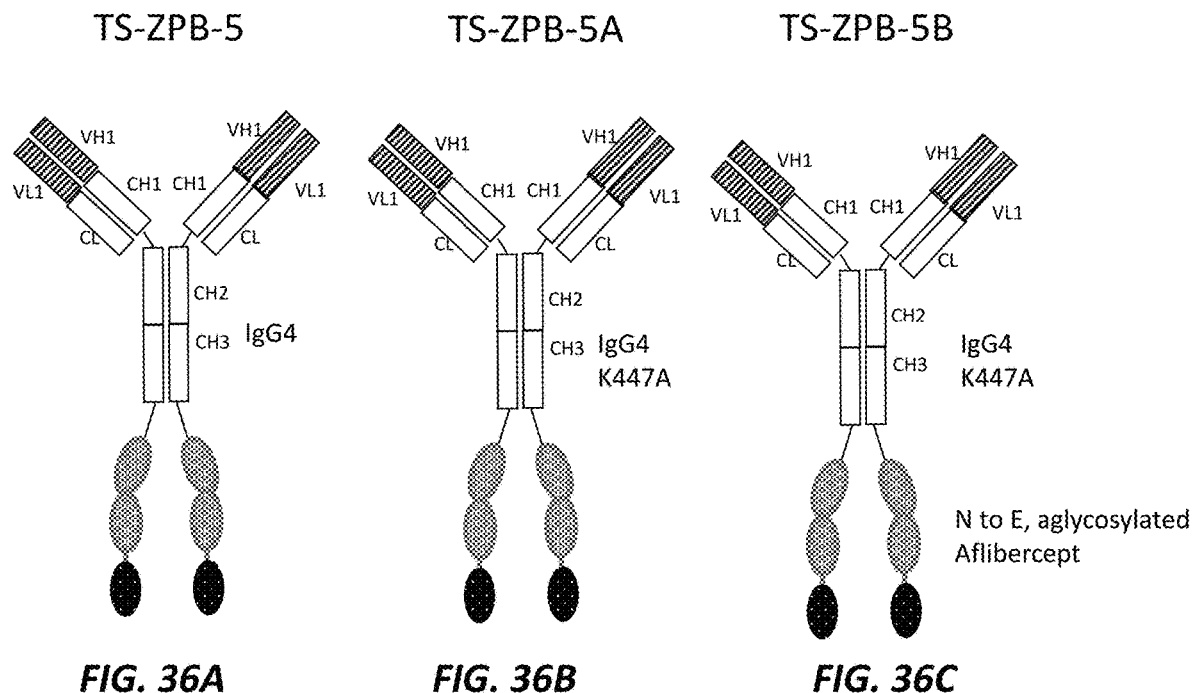
TS-ZPB-5　　TS-ZPB-5A　　TS-ZPB-5B
FIG. 36A　　FIG. 36B　　FIG. 36C
VH1-VL1 = Anti-PD1 or other Checkpoint, e. g.,
Anti-PDL1, Lag3, TIGIT, etc variable domain
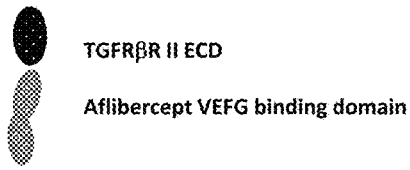
TGFRβR II ECD
Aflibercept VEFG binding domain

**Bi-ZPL-1
(or Bi-ZP-1)**

**Bi-ZPL-2
(or Bi-ZP-2)**

**Bi-ZPL-3
(or Bi-ZP-3)**

VH1-VL1 = Anti-PDL1, anti-PD1 or other Checkpoint, e. g., anti-Lag3, anti-TIGIT, etc variable domain aflibercept

| Antagonist | IC50 (nM) |
|---|---|
| BM | 2.14 |
| Bi-ZPL-1 | 3.30 |

| | IC50 (nM) |
|---|---|
| Bevacizumab | 0.29 |
| Bi-ZP-2 | 0.14 |
| Bi-ZPL-3 | 0.18 |

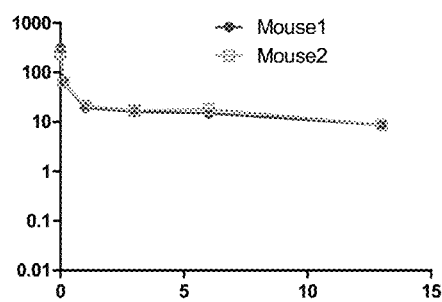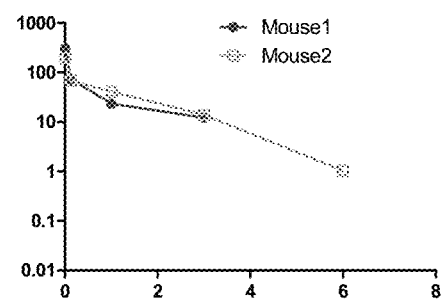
FIG. 45

| SEQ ID No. | Description | Sequence |
|---|---|---|
| 299 | T-01 HFR1 | QVQLQESGPGLVKPSQTLSLTCTVSGYSIT |
| 300 | T-01, 02, 06, 07 HFR2 | WIRQPPGKGLEWIG |
| 301 | T-01, 06 HFR3 | RVTISVDTSKNQFSLKLSSVTAADTAVYYCAR |
| 302 | T-01 HFR4 | WGQGTSVTVSS |
| 303 | T-01, 03, 04, 05, 06, 07, 10 LFR1 | DIQMTQSPSSLSASVGDRVTITC |
| 304 | T-01 LFR2 | WHQQKPGKAPKLLIY |
| 305 | T-01, 02 LFR3 | GVPSRFSGSGSGTDFTLTISSLQPEDFATYYCQQSYSTP |
| 306 | T-01, 06 LFR4 | FGGGTKLEIKR |
| 307 | T-02 HFR1 | QVKLQESGPGLVKPSQTLSLTCTVTGYSIT |
| 308 | T-02 HFR3 | RVTISVDTSKNQFSLKLSSVTAADTAVYSCAR |
| 309 | T-02, 06, 07 HFR4 | WGQGTLVTVSA |
| 310 | T-02 LFR1 | DIQMTQSPSSLSASVGDRVTIPC |
| 311 | T-02, 03, 04, 05, 06, 07, 10 LFR2 | WYQQKPGKAPKLLIY |
| 312 | T-02 LFR4 | FGEGTKLEIK |
| 313 | T-03, 04 HFR1 | EVQLVQSGAEVKKPGATVKISCKVSGYTFT |
| 314 | T-03, 04, 05 HFR2 | WVQQAPGKGLEWMG |
| 315 | T-03, 04 HFR3 | RVTITADTSTDTAYMELSSLRSEDTAVYYCAT |
| 316 | T-03 HFR4 | WGQGTLITVSVA |
| 317 | T-03, 05, 06, 10 LFR3 | GVPSRFSGSGSGTDFTLTISSLQPEDFATYYC |
| 318 | T-03, 05 LFR4 | FGAGTKLELK |
| 319 | T-04, 05, 08, 09, 10 HFR4 | WGQGTLVTVSS |
| 320 | T-04 LFR3 | GVPSRFSGSGSGTDFTFTISSLQPEDIATYYC |
| 321 | T-04 LFR4 | FGAGTKLEIK |
| 322 | T-05 HFR1 | EVQLKQSGAEVKKPGATVKISCKVSGYTFT |
| 323 | T-05 HFR3 | RVTITADTSTDTAYMELSSLRSEDTAVYFCAR |
| 324 | T-06 HFR1 | QVQLQESGPGLVKPSQTLSLTCTVSGGSVS |
| 325 | T-07 HFR1 | EVQLQESGPGLVKPSDTLSLTCAVSGYSIT |
| 326 | T-07 HFR3 | RVTMSVDTSKNQFSLKLSSVTAVDTAVYYCTR |
| 327 | T-07 LFR3 | GAPSRFSGSGSGTDFTLTISSLQPEDFGIYYC |
| 328 | T-07 LFR4 | FGGGTKLEFK |
| 329 | T-08 HFR1 | QVQLVQSGSELKKPGASVKVSCKASGYTFT |
| 330 | T-08, 10 HFR2 | WVRQAPGQGLEWMG |
| 331 | T-08 HFR3 | RFVFSLDTSVSTAYLQISSLKAEDTAVYYCAR |
| 332 | T-08 LFR1 | DVVMTQSPLSLPVTLGQPASISC |
| 333 | T-08 LFR2 | WFQQRPGQSPRVLIY |
| 334 | T-08 LFR3 | GVPDRFSGSGSGTDFTLKISRVEAEDVGVYYC |
| 335 | T-08 LFR4 | FGRGTKLEIK |
| 336 | T-09 HFR1 | QVTLKESGPTLVKPTQTLTLTCTFSGFSLS |
| 337 | T-09 HFR2 | WIRQPPGKALEWLA |
| 338 | T-09 HFR3 | RLTITKDTSKNQVVLTMTNMDPVDTATYYCAR |
| 339 | T-09 LFR1 | QAVVTQEPSLTVSPGGTVTLTC |
| 340 | T-09 LFR2 | WVQQKPGQLFRGLIG |
| 341 | T-09 LFR3 | WVPARFSGSLIGDKAALTLSGVQPEDEAEYFC |
| 342 | T-09 LFR4 | FGGGTKLTVL |
| 343 | T-10 HFR1 | QVQLVQSGAEVKKPGASVKVSCKASGYTFT |
| 344 | T-10 HFR3 | RVTMTRDTSTSTVYMELSSLRSEDTAVYYCAR |
| 345 | T-10 LFR4 | FGQGTKVEIK |

*FIG. 46A*

| SEQ ID NO. | Description | Sequence |
|---|---|---|
| 346 | PD-01 HFR1 | EVQLVESGGGLVQPGGSLRLSCAASGFTFS |
| 347 | PD-01 HFR2 | WVRQAPGKGLEWVS |
| 348 | PD-01 HFR3 | RFTISRDNSKNTLYLQMNSLRAEDTAVYYCAK |
| 349 | PD-01 HFR4 | WGQGTSVTVSS |
| 350 | PD-01 LFR1 | DIQMTQSPSSVSASVGDRVTITC |
| 351 | PD-01, 02, 03, 04; PL-02, 03 LFR2 | WYQQKPGKAPKLLIY |
| 352 | PD-01, 02, 03, 04 LFR3 | GVPSRFSGSGSGTDFTLTISSLQPEDFATYYC |
| 353 | PD-01; PL-05 LFR4 | FGGGTKLEIK |
| 354 | PD-02, 03, 04 HFR1 | QVQLVQSGAEVKKPGASVKVSCKASDYTFT |
| 355 | PD-02 HFR2 | WLRQAPGQGLEWMG |
| 356 | PD-02 HFR3 | RTTSTRDTSISTAYMELSRLRSDDTVVYYCTR |
| 357 | PD-02, 04, 05, 06; PL-01, 02, 03, 04, 06, 07, 08 HFR4 | WGQGTLVTVSS |
| 358 | PD-02, 04 LFR1 | DIQMTQSPSSLSASVGDRVTFTC |
| 359 | PD-02, 04, 05; PL-01, 04, 06, 07, 08 LFR4 | FGGGTKVEIK |
| 360 | PD-03, 04, 05, 06; PL-02, 03, 04, 08 HFR2 | WVRQAPGQGLEWMG |
| 361 | PD-03, 04; PL-01 HFR3 | RVTSTRDTSISTAYMELSRLRSDDTVVYYCA |
| 362 | PD-03; PL-05 HFR4 | WGQGTTLTVSS |
| 363 | PD-03 LFR1 | DIQMTQSPSSLSASVGDRVTITC |
| 364 | PD-03 LFR4 | FGAGTKLDLK |
| 365 | PD-04, 05; PL-01, 04, 06, 07, 08 LFR4 | FGGGTKVEIK |
| 366 | PD-05, 06; PL-01, 02, 03, 04, 06, 07, 08 HFR1 | QVQLVQSGAEVKKPGASVKVSCKASGYTFT |
| 367 | PD-05 HFR3 | RVTMTRDTSISTAYMELSSLRSEDTAVYYCAR |
| 368 | PD-05 LFR1 | DIVLTQSPASLAVSPGQRATITC |
| 369 | PD-05 LFR2 | WYQQKPGQPPKLLIY |
| 370 | PD-05 LFR3 | GVPARFSGSGSGTDFTLTINPVEANDTANYYC |
| 371 | PD-06 HFR3 | RVTLTADTSTSTVYMELSSLRSEDTAVYYCA |
| 372 | PD-06 LFR1 | DIQMTQSPSFLSASVGDRVTITC |
| 373 | PD-06 LFR2 | WYQQKPGKAPKALIY |
| 374 | PD-06 LFR3 | GVPSRFSGSGSGTEFTLTISSLQPEDFATYYC |
| 375 | PD-06 LFR4 | FGQGTKLEIK |
| 376 | PL-01 HFR2 | WMKQAPGQGLEWMG |
| 377 | PL-01, 02, 03, 04, 08 LFR1 | DIQMTQSPSSLSASVGDRVTISC |
| 378 | PL-01, 04, 08 LFR2 | WYQQKPGKAPKLLIK |
| 379 | PL-01, 04, 08 LFR3 | GVPSRFSGSGSGTDFTLTISSLQPEDFATYFC |
| 380 | PL-02 HFR3 | KATMTRDKSSSTVYMELSSLRSEDTAVYYCAR |
| 381 | PL-02, 03 LFR3 | GVPSRFSGSGSGTDFTFTISSLQPEDIATYFC |
| 382 | PL-02, 03 LFR4 | FGQGTKVEIK |
| 383 | PL-03, 08 HFR3 | RVTMTRDTSISTAYMELSRLRSDDTAVYYCAR |
| 384 | PL-04 HFR3 | RVTMTRDTSTSTVYMELSRLRSEDTAVYYCAR |
| 385 | PL-05 HFR1 | DVQLQESGPGLVKPSQSLSLTCTVTGYSIT |
| 386 | PL-05 HFR2 | WIRQFPGNKLEWMG |
| 387 | PL-05 HFR3 | RISITRDTSKNQFFLQLNSVTTEDTATYYCAN |
| 388 | PL-05 LFR1 | DIVMTQSHKFMSTSVGDRVSITC |
| 389 | PL-05 LFR2 | WYQQKPGQSPKLLIF |
| 390 | PL-05 LFR3 | GVPDRFTGSGSGTDYTLTISSVQAEDLALYYC |
| 391 | PL-06, 07 HFR2 | WVRQAPGQRLEWMGW |
| 392 | PL-06, 07 HFR3 | RVTITRDTSASTAYMELSSLRSEDTAVYYCAR |
| 393 | PL-06 LFR1 | DIQMTQSPSSLSAFVGDRVTITC |
| 394 | PL-06 LFR2 | WYQQKPGKAPKLLIH |
| 395 | PL-06 LFR3 | GVPSRFSGSGSGRDFTFTISSLQPEDIATYYC |
| 396 | PL-07 LFR1 | EIVLTQSPVTLSLSPGERATLSC |
| 397 | PL-07 LFR2 | WYLQKPGQAPRLLIK |
| 398 | PL-07 LFR3 | IPARFSGSGSGSDFTLTISSLEPEDFAVYYC |

*FIG. 46B*

| SEQ ID NO. | Description | Sequence |
|---|---|---|
| 399 | 2L2A.1 HFR1 | QVQLVQSGAEVKKPGASVKVSCKASGYTLT |
| 400 | 2L2A.1 HFR2 | WMRQAPGQGLEWMG |
| 401 | 2L2A.1 HFR3 | RVTMTRDTSTSTVYMELSSLRSEDTAVYYCVR |
| 402 | 2L2A.1, 2L2A.6, 3L1A HFR4 | WGQGTLVTVSS |
| 403 | 2L2A.1, 2L2A.6, 2L27B LFR1 | DIQMTQSPSSLSASVGDRVTITC |
| 404 | 2L2A.1 LFR2 | WLQQKPEKAPKRLIY |
| 405 | 2L2A.1, 2L2A.6, 2L27B LFR3 | GVPSRFSGSGSGTDFTLTISSLQPEDFATYYC |
| 406 | 2L2A.1, 2L2A.6, 2L27B LFR4 | FGGGTKVEIK |
| 407 | 2L2A.6 HFR1 | QVQLVQSGAEVKKPGASVKVSCKASGYTFT |
| 408 | 2L2A.6 HFR2 | WVRQAPGQGLEWMG |
| 409 | 2L2A.6 3L1A HFR3 | RVTMTRDTSTSTVYMELSSLRSEDTAVYYCAR |
| 410 | 2L2A.6, 3L1A LFR2 | WLQQKPGKAPKRLIY |
| 411 | 2L27B HFR1 | QVQLVQSGAEVKKPGASVKVSCKASGFTFS |
| 412 | 2L27B HFR2 | WVRQAPGQGLEWMGL |
| 413 | 2L27B HFR3 | RVTMTRDTSTSTVYMELSSLRSEDTAVYFC |
| 414 | 2L27B HFR4 | FDYWDDGYYVEHFDYWGQGTLVTVSS |
| 415 | 2L27B LFR2 | WYQQKPGKAPKRLIY |
| 416 | 3L1A HFR1 | QVQLVQSGAEVKKPGASVKVSCKASGYTF |
| 417 | 3L1A LFR1 | DIQMTQSPSTLSASVGDRVTITC |
| 418 | 3L1A LFR2 | WLAWYQQKPGKAPKLLIY |
| 419 | 3L1A LFR3 | GVPSRFSGSGSGTEFTLTISSLQPDDFATYYC |
| 420 | 3L1A LFR4 | FGQGTKLEIK |

*FIG. 46C*

TRISPECIFIC ANTAGONISTS

This application claims priority to U.S. Provisional Patent Application Ser. No. 62/691,658, filed on Jun. 29, 2018, and U.S. Provisional Patent Application Ser. No. 62/823,989, filed on Mar. 26, 2019, the contents of which are expressly incorporated herein by reference for all purposes.

FIELD

The present application relates generally to cancer treatment and in particular, to bispecific and trispecific antagonists capable of modulating pathways associated with tumorigenesis, tumor immunity, and angiogenesis.

BACKGROUND

The inability of the host to eliminate cancer cells remains a major problem. Although an increasing number of therapeutic monoclonal antibodies have been approved for treatment of various cancers, emergence of resistance to these antibodies is frequently observed, given the many different molecular pathways underlying cancer growth and progression to metastasis. Although the immune system is the principal mechanism of cancer prevention, cancer cells counteract immune surveillance. Therefore, there exists a need for improved therapeutic binding antagonists or antibodies and methods of treating cancer and chronic viral infections with such reagents.

SUMMARY

One aspect of the present application relates to a trispecific antagonist, comprising: an immunoglobulin scaffold comprising a CH1 domain, a CH2 domain and a CH3 domain; a first targeting domain comprising one or more variable domains selected from the group consisting of anti-PD-1 variable domains, anti-PD-L1 variable domains, anti-TIGIT variable domains and anti-LAG-3 variable domains; a second targeting domain that binds specifically to VEGF and comprises one or more peptide domains derived from VEGFR; and a third targeting domain that comprises a peptide inhibitor of the angiopoietin/Tie-2 signaling pathway; wherein the second targeting domain is structurally linked to a carboxy-terminal of the CH3 domain and wherein the third targeting domain is inserted within the CH3 domain.

Another aspect of the present application relates to a trispecific antagonist, comprising: an immunoglobulin scaffold comprising a CH1 domain, a CH2 domain and a CH3 domain; a first targeting domain comprising one or more variable domains selected from the group consisting of anti-PD-1 variable domains, anti-PD-L1 variable domains, anti-TIGIT variable domains and anti-LAG-3 variable domains; a second targeting domain of anti-PD-1 variable domains, anti-PD-L1 variable domains, anti-TIGIT variable domains and anti-LAG-3 variable domains; and a third targeting domain that comprises a peptide inhibitor of the angiopoietin/Tie-2 signaling pathway; wherein the second targeting domain is structurally linked to a carboxy-terminal of the CH3 domain and wherein the third targeting domain is inserted within the CH3 domain.

Another aspect of the present application relates to a trispecific antagonist, comprising: an immunoglobulin scaffold comprising a CH1 domain, a CH2 domain and a CH3 domain; a first targeting domain comprising one or more variable domains selected from the group consisting of anti-VEGF variable domains; a second targeting domain comprising a TGF-β pathway inhibitor; and a third targeting domain that comprises a peptide inhibitor of the angiopoietin/Tie-2 signaling pathway; wherein the second targeting domain is structurally linked to a carboxy-terminal of the CH3 domain and wherein the third targeting domain is inserted within the CH3 domain.

Another aspect of the present application relates to a trispecific antagonist that comprises an immunoglobulin scaffold comprising a CH1 domain, a CH2 domain and a CH3 domain, a first targeting domain comprising one or more variable domains selected from the group consisting of anti-PD-1 variable domains, anti-PD-L1 variable domains, anti-TIGIT variable domains and anti-LAG-3 variable domains; a second targeting domain comprising a component of VEGFR; and a third targeting domain comprising a TGF-β pathway inhibitor, wherein the second targeting domain is structurally linked to a carboxy-terminal of the CH3 domain, and wherein the third targeting domain is structurally linked to a carboxy-terminal of the second targeting domain.

Another aspect of the present application relates to a bispecific antagonist that comprises an immunoglobulin scaffold comprising a CH1 domain, a CH2 domain and a CH3 domain, a first targeting domain comprising one or more variable domains selected from the group consisting of anti-PD-1 variable domains, anti-PD-L1 variable domains, anti-TIGIT variable domains and anti-LAG-3 variable domains; and a second targeting domain comprising a component of VEGFR, and wherein the third targeting domain is structurally linked to a carboxy-terminal of the second targeting domain.

Another aspect of the present application relates to a method for treating a cell proliferative disorder. The method comprises the step of administering to a subject in need thereof an effective amount of the trispecific antagonists of the present application.

BRIEF DESCRIPTION OF THE DRAWINGS

FIG. 1 shows HCVR and LCVR sequences of certain checkpoint antagonists, anti-PD-1, anti-PD-L1, anti-TIGIT, anti-LAG-3, monoclonal antibodies (Mabs).

FIG. 2 shows HCVR and LCVR and other domain sequences for trebananib, bevacizumab, ranibizumab, Tie2, VEGF, and TGF-B antagonists.

FIGS. 3A-3H show eight trispecific antitumor antagonists, TS-ZPT-1.1, TS-ZPT-1.2, TS-ZPT-1.3, TS-ZPT-2, TS-ZPT-3, TS-ZPT-4, TS-ZPT-5 and TS-ZPT-6, respectively, with IgG1 or IgG4 backbones comprising: (1) anti-PD-1 variable region (VH1, VL1) domains or other checkpoint antibody variable domains; (2) an aflibercept fusion protein domain: (i) at the amino-terminal end of one or both IgG arms (FIGS. 3A-3C, 3F); (ii) at the carboxy-terminal end of each antagonist (FIGS. 3D, 3E, 3H); or (iii) between the carboxy-terminal end of the CH3 domain and a trebananib peptide (or other biological peptide) (FIG. 3G) (3) a trebananib peptide (or other biological peptide): (i) fused to the carboxy-terminal end of each CH3 region (FIGS. 3A-3D); (ii) inserted within each of the two CH3 regions (FIG. 3E); (iii) fused to the carboxy-terminal end of each CH1 region (FIG. 3F); (iv) fused to the carboxy-terminal end of each aflibercept fusion protein domain (FIG. 3G); or (v) fused to the carboxy-terminal end of each CL region (FIG. 3H). The aflibercept fusion protein domain comprises vascular endothelial growth factor (VEGF)-binding portions from the extracellular domains of human VEGF receptors 1 and 2, while the trebananib peptide targets and binds to Ang1 and Ang2, thereby preventing the interaction of Ang1 and/or Ang2 with their cognate Tie2 receptors.

FIGS. 4A-4C show three different trispecific antitumor antagonists, TS-ZPT-7, TS-ZPT-8 and TS-ZPT-9, respectively, comprising (1) an aflibercept fusion protein domain at each carboxy-terminal end; (2) anti-PD-1 or other checkpoint antagonist antibody variable domain (VH1, VL1); and (3) a trebananib peptide (or other biological peptide): (i) inserted within each of the two CH3 regions (FIG. 4A); (ii) inserted between the carboxy-terminal end of each CH2 region and an aflibercept fusion protein domain at the carboxy-terminal end of each polypeptide chain in the antagonist (FIG. 4B); or (iii) fused to the amino terminal end of each IgG1 arm (FIG. 4C).

FIGS. 5A-5G show seven different trispecific antitumor antagonists, TS-LPT-1, TS-LPT-2, TS-LPT-3, TS-LPT-4, TS-LPT-5, TS-M3, and TS-M4, respectively, comprising: (1) VH2 and VL2 regions corresponding to ranibizumab (Lucentis), bevacizumab (Avastin) or other anti-VEGF variable domains; (2) VH1 and VL1 regions corresponding to anti-PD-1 or other checkpoint antagonist antibody variable domains; and (3) a trebananib peptide (or other biological peptide): (i) inserted within each of the two CH3 regions (FIG. 5A); (ii) fused to the carboxy-terminal end of each CL1 region (FIG. 5B) (iii) fused to the carboxy-terminal end of the CH1 region in each of the two polypeptide chains (FIG. 5C); (iv) fused to the carboxy-terminal end of the CL region in each of the two polypeptide chains (FIG. 5D); (v) fused to the carboxy-terminal end of the CH1 region in each of the two polypeptide chains and fused to the carboxy-terminal end of the CL region in each of the two polypeptide chains (FIG. 5E) (vi and vii fused to the carboxy-terminus of the CH3 (FIGS. 5F and 5G). The ranibizumab variable domains are derived from bevacizumab and both are known to block binding of human VEGF-A to VEGFR 1 and 2. Exemplary sequences of TS-LPT-1, TS-LPT-2, TS-LPT-3, TS-LPT-4, TS-LPT-5 TS-M3, and TS-M4 are shown in SEQ ID NOS:247-269.

FIGS. 7A and 7B show IC50 values (nM) calculated from a cell-based binding assay reflecting the ability of the trispecific antitumor antagonists depicted in FIGS. 3A-3H to block the interaction between human PD-1 and human PD-L1.

FIGS. 8A and 8B show IC50 values (nM) calculated from a binding assay reflecting the ability of the trispecific antitumor antagonists depicted in FIGS. 3D, 3E and 3G to block the interaction between VEGF and VEGFR-2.

FIG. 9 shows IC50 values (nM) calculated from a binding assay reflecting the ability of the trispecific antitumor antagonists depicted in FIGS. 3B, 3D, 3G, 3H and 5A to block the interaction between Ang2 and Tie2, compared to a bevacizumab-trebananib fusion control molecule.

FIG. 10 shows the results of a size exclusion chromatography analysis (SEC) of purified trispecific antitumor antagonists TS-ZPT-2(2P17), TS-ZPT-3L(2P17) and TS-ZPT-5(2P17) and anti-PD-1 monospecific antibody 2P17, produced by transient transfection of HEK293 cells. The percentage of high molecular weight (HWM %) species, low molecular weight (LMW %) species and dimerized molecule (Dimer %) are shown. The amino acid sequences of the HCVR and LCVR of these trispecific antitumor antagonists are shown in SEQ ID NOS:201-204.

FIG. 11 shows the results of a size exclusion chromatography analysis (SEC) of purified trispecific antitumor antagonists TS-ZPT-2(2P17), TS-ZPT-3L(2P17) and TS-ZPT-5(2P17) expressed by CHO stable pools. Two transfection pools were assessed for TS-ZPT-3L(2P17). The percentage of high molecular weight (HWM %) species, low molecular weight (LMW %) species and dimerized molecule (Dimer %) are shown.

FIG. 13A shows the heavy chain (SEQ ID NO:202) and light chain amino acid sequences (SEQ ID NO:201) for an exemplary trispecific antitumor antagonist with the trebananib long peptide, i.e., TS-ZPT-3L (2P17), comprising (1) anti-PD-1 of another checkpoint antagonist antibody 2P17 variable domain (VH1, VL1), aflibercept VEFG binding domain fused to the carboxyl-terminal end of each antagonist, and connected to the CH3 domain with a 3×G4S linker; and (3) a trebananib peptide (or other biological peptide) inserted within each of the two CH3 regions. FIG. 13B depicts an exemplary molecule derived from these sequences.

FIG. 14A shows the heavy chain (SEQ ID NO:200) and light chains amino acid sequences (SEQ ID NO:201) for an exemplary trispecific antitumor antagonist with the trebananib short peptide, i.e., TS-ZPT-3S(2P17), comprising (1) anti-PD-1 of another checkpoint antagonist antibody 2P17 variable domain (VH1, VL1), aflibercept VEFG binding domain fused to the carboxyl-terminal end of each antagonist, and connected to the CH3 domain with a 3×G4S linker; and (3) a trebananib peptide (or other biological peptide) inserted within each of the two CH3 regions; (i) a single copy of the trebananib blocking peptide. FIG. 14B depicts an exemplary molecule derived from these sequences.

FIG. 17 shows the size exclusion chromatography analysis of TS-ZPT-3L(2P17) and TS-ZPT-3 S(2P17) over time with storage at 4 degrees C.

FIGS. 21A-21E show the results of PD-1 binding to TS-ZPT-3 S(2P16 and 2P17) and TS-ZPT-3L(2P16 and 2P17) trispecific antitumor antagonists compared to the benchmark anti-PD-1 antibody as determined by bio-layer interferometry, along with their resultant binding affinity constants (FIG. 21F).

FIGS. 22A-22E show the results of VEGF 165 binding to TS-ZPT-3 S(2P16 and 2P17) and TS-ZPT-3L(2P16 and 2P17) trispecific antitumor antagonists compared to the benchmark antibody bevacizumab as determined by bio-layer interferometry, along with their resultant binding affinity constants (FIG. 22F).

FIGS. 23A-23E show the results of Ang2 binding to TS-ZPT-3 S(2P16 and 2P17) and TS-ZPT-3L(2P16 and 2P17) trispecific antitumor antagonists compared to the benchmark molecule trebananib as determined by bio-layer interferometry, along with their resultant binding affinity constants (FIG. 23F).

FIG. 27 depicts a trispecific antitumor antagonist, TS-A1BT-1, having amino-terminal anti-VEGF variable regions (VH1, VL1) containing two amino acid substitutions in the VH region (E6Q, L11V) from Avastin/bevacizumab in a mutant IgG1 (K447A) scaffold; Trebananib short peptide inserted within the IgG1 CH3 domain; and a carboxy-terminal TGF-β1 RII ECD connected to the CH3 domain with a 4×G4S linker. The amino acid sequences of the HC and LC of this trispecific antitumor antagonist is listed in SEQ ID NOS:229 and 230.

FIGS. 30A-30F show six trispecific antitumor antagonist configurations comprising a TGF-βRII extracellular domain (ECD): TS-ZPB-1, TS-ZPB-2, TS-ZPB-3, TS-ZPB-4, TS-ZPB-5, and TS-ZPB-6, respectively.

FIGS. 36A-36C show three trispecific antagonists: TS-ZPB-5, and variants TS-ZPB-5A, with K447A mutation in the CH3 domain, and TS-ZPB-5B, additionally with mutations to eliminate N-linked glycosylation of the aflibercept VEGF binding domain.

FIG. 45 shows the pharmacokinetic assessment in mice of Bi-ZP-2 and Bi-ZPL-3.

FIGS. 46A-46C show the sequences of the exemplary framework regions. FIG. 46A shows the exemplary framework regions of anti-TIGIT mAbs. FIG. 46B shows exemplary framework regions of anti-PD-1 and anti-PD-L1 mAbs. FIG. 46C shows the exemplary framework regions of anti-LAG3 mAbs.

DETAILED DESCRIPTION

Definitions

Figure 3F:
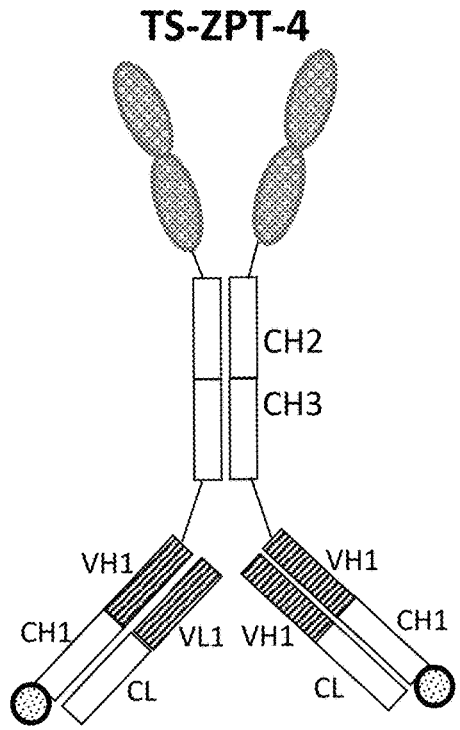
Figure 3G:
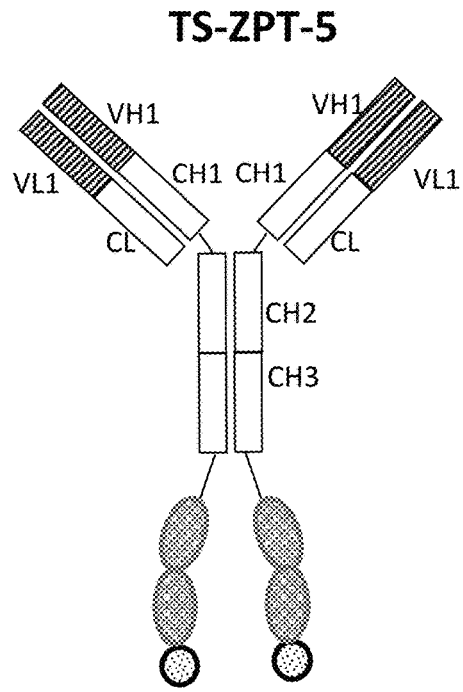

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine. An exemplary human PD-1 amino acid sequence is listed below:

(SEQ ID NO: 180)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.

As used herein, the term "PD-L1" refers to any form of PD-L1 and variants thereof that retain at least part of the activity of PD-L1. Unless indicated differently, such as by specific reference to human PD-L1, PD-L1 includes all mammalian species of native sequence PD-L1, e.g., human, canine, feline, equine, and bovine. An exemplary human PD-L1 amino acid sequence is listed below:

(SEQ ID NO: 181)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

As used herein, the term "TIGIT" refers to any form of TIGIT and variants thereof that retain at least part of the activity of TIGIT. Unless indicated differently, such as by specific reference to human TIGIT, TIGIT includes all mammalian species of native sequence TIGIT, e.g., human, canine, feline, equine, and bovine. The following is an exemplary human TIGIT amino acid sequence:

(SEQ ID NO: 179)
MTGTIETTGNISAEKGGSIILQCHLSSTTAQVTQVNWEQQDQLLAICNAD

LGWHISPSFKDRVAPGPGLGLTLQSLTVNDTGEYFCIYHTYPDGTYTGRI

FLEVLESSVAEHGARFQIPLLGAMAATLVVICTAVIVVVALTRKKKALRI

HSVEGDLRRKSAGQEEWSPSAPSPPGSCVQAEAAPAGLCGEQRGEDCAEL

HDYFNVLSYRSLGNCSFFTETG.

As used herein, the term "LAG-3" refers to any form of LAG-3 and variants thereof that retain at least part of the activity of lymphocyte-activation gene 3 (LAG-3). Unless indicated differently, such as by specific reference to human LAG-3, LAG-3 includes all mammalian species of native sequence LAG-3, e.g., human, canine, feline, equine, and bovine. The following is an exemplary human LAG-3 amino acid sequence:

(SEQ ID NO: 293)
MWEAQFLGLLFLQPLWVAPVKPLQPGAEVPVVWAQEGAPAQLPCSPTIPL

QDLSLLRRAGVTWQHQPDSGPPAAAPGHPLAPGPHPAAPSSWGPRPRRYT

VLSVGPGGLRSGRLPLQPRVQLDERGRQRGDFSLWLRPARRADAGEYRAA

VHLRDRALSCRLRLRLGQASMTASPPGSLRASDWVILNCSFSRPDRPASV

HWFRNRGQGRVPVRESPHHHLAESFLFLPQVSPMDSGPWGCILTYRDGFN

VSIMYNLTVLGLEPPTPLTVYAGAGSRVGLPCRLPAGVGTRSFLTAKWTP

PGGGPDLLVTGDNGDFTLRLEDVSQAQAGTYTCHIHLQEQQLNATVTLAI

ITVTPKSFGSPGSLGKLLCEVTPVSGQERFVWSSLDTPSQRSFSGPWLEA

QEAQLLSQPWQCQLYQGERLLGAAVYFTELSSPGAQRSGRAPGALPAGHL

PAGHLLLFLILGVLSLLLLVTGAFGEHLWRRQWRPRRFSALEQGIHPPQA

QSKIEELEQEPEPEPEPEPEPEPEPEPEQL.

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antagonist" or "inhibitor" refers to a substance that prevents, blocks, inhibits, neutralizes, or reduces a biological activity or effect of another molecule, such as a receptor or ligand. An antagonist can be a mono-specific antibody, a bispecific antibody or a trispecific antibody.

As used herein, the term "antibody" refers to a polypeptide or a polypeptide complex that specifically recognizes and binds to an antigen through one or more immunoglobulin variable regions. An antibody can be a whole antibody, an antigen binding fragment or a single chain thereof. The term "antibody" encompasses various broad classes of polypeptides that can be distinguished biochemically. Those skilled in the art will appreciate that heavy chains are classified as alpha, delta, epsilon, gamma, and mu, or α, δ, ε, γ and μ) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules.

Antibodies or antibody antagonists of the present application may include, but are not limited to, polyclonal, monoclonal, monospecific, multispecific, bispecific, trispecific, human, humanized, primatized, chimeric and single chain antibodies. Antibodies disclosed herein may be from any animal origin, including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

The terms "antibody fragment" or "antigen-binding fragment" are used with reference to a portion of an antibody, such as F(ab')$_2$, F(ab)$_2$, Fab', Fab, Fv, single-chain Fvs (scFv), single-chain antibodies, disulfide-linked Fvs (sdFv), fragments comprising either a VL or VH domain, fragments produced by a Fab expression library and anti-idiotypic (anti-Id) antibodies. Regardless of structure, an antibody fragment binds with the same antigen that is recognized by the intact antibody. The term "antibody fragment" includes DARTs and diabodies. The term "antibody fragment" also includes any synthetic or genetically engineered proteins comprising immunoglobulin variable regions that act like an antibody by binding to a specific antigen to form a complex. A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. With regard to IgGs, a standard immunoglobulin molecule comprises two identical light chain polypeptides of molecular weight approximately 23,000 Daltons, and two identical heavy chain polypeptides of molecular weight 53,000-70, 000. The four chains are typically joined by disulfide bonds in a "Y" configuration where the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the carboxy-terminal portion is a constant region; the CH3 and CL domains actually comprise the carboxy-terminus of the heavy and light chain, respectively. Exemplary CHI-CH2-CH3 sequences described in the current application include the following wild type IgG1 (SEQ ID NO:274), IgG1 with a K447A mutation (SEQ ID NO:275), IgG1 with the N297A mutation (SEQ ID NO:276), wild type IgG2 (SEQ ID NO:278), IgG2 with carboxy terminal lysine deleted (SEQ ID NO:279), IgG4 with the hinge S231P mutation (SEQ ID NO:280), IgG4 with S23P and K447A mutation (SEQ ID NO:281), and IgG4 S231P and the carboxy-terminal lysine deleted (SEQ ID NO:282). Exemplary CL sequence is SEQ ID NO:292.

The term "Fc fragment" or "Fc" are used with reference to a portion of an antibody contains no antigen-binding activity but was originally observed to crystallize readily, and for this reason was named the Fc fragment, for Fragment crystallizable. This fragment corresponds to the paired CH2 and CH3 domains and is the part of the antibody molecule that interacts with effector molecules and cells. The Fc fragments described herein may be derived from human IgG1, IgG2 and IgG4 antibodies with the modifications of a-glycosylation, hinge mutation and deletion of carboxy-terminal lysine. Exemplary Fc sequences described in the current application include the following: wild type IgG1 Fc (SEQ ID NO:210), a-glycosylated IgG1 Fc (SEQ ID NO:211), IgG4 Fc with hinge mutation (SEQ ID NO:212), wild type IgG2 Fc (SEQ ID NO:213), IgG1 Fc with deletion of carboxy-terminal lysine (SEQ ID NO:214), a-glycosylated IgG1 Fc with deletion of carboxy-terminal lysine (SEQ ID NO:215), IgG4 Fc with hinge mutation and deletion of carboxy-terminal lysine (SEQ ID NO:216), and IgG2 Fc with deletion of carboxy-terminal lysine (SEQ ID NO:217).

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e., HCDR1, HCDR2, HCDR3, LCDR1, LCDR 2 and LCDR 3). In some instances, e.g., certain immunoglobulin molecules are derived from camelid species or engineered based on camelid immunoglobulins. Alternatively, an immunoglobulin molecule may consist of heavy chains only with no light chains or light chains only with no heavy chains.

In naturally occurring antibodies, the six CDRs present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined.

As used herein, the terms "VH1" and "VH2" refer to immunoglobulin heavy chain variable domains corresponding to two different binding specificities. Likewise, the terms "VL1" and "VL2" refer to light chain variable domains corresponding to two different binding specificities. When used together, it is to be understood that VH1 and VL1 regions define a common binding specificity and that VH2 and VL2 domains define a second binding specificity.

The term "framework region (FR)" as used herein refers to variable domain residues other than the CDR residues. Each variable domain typically has four FRs flanking the corresponding CDRs. For example, a VH domain typically has four HFRs, HFR1, HFR2, HFR3 and HFR4, flanking the three HCDRs in the configuration of HFR1-HCDR1-HFR2-HCDR2-HFR3-HCDR3-HFR4. Similarly, an LH domain typically has four LFR, LFR1, LFR2, LFR3 and LFR4, flanking the three LCDRs in the configuration of: LFR1-LCDR1-LFR2-LCDR2-LFR3-LCDR3-LFR4. Exemplary FRs are summarized in FIGS. 46A-46C.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

As used herein, the term "light chain constant region (CL)" includes amino acid sequences derived from antibody light chain CL (SEQ ID NO:292). Preferably, the light chain constant region comprises at least one of a constant kappa domain or constant lambda domain.

As used herein, the term "heavy chain constant region (CH)" includes amino acid sequences derived from an immunoglobulin heavy chain. A polypeptide comprising a heavy chain constant region comprises at least one of: a CH1 domain (SEQ ID NOS:290-291), a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

For example, as reflected in the disclosure herein below, Applicant has found that the CH3 domain can tolerate or accommodate significant insertions (e.g., greater than 100 aa) in the Fc loop of the CH3 domain (see, e.g., FIG. 3E). Therefore, in the present application, any of the disclosed inhibitor domains may be similarly inserted in the Fc loop in a manner analogous to the insertion of trebananib or the TGFβ1 RII ECD domain in the Fc loop.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

A "light chain-heavy chain pair" refers to the collection of a light chain and heavy chain that can form a dimer through a disulfide bond between the CL domain of the light chain and the CH1 domain of the heavy chain.

The subunit structures and three dimensional configurations of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the carboxy-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are structurally linked by a disulfide bond and the two heavy chains are structurally linked by two disulfide bonds at positions corresponding to 239 and 242 using the Kabat numbering system (position 226 or 229, EU numbering system).

As used herein, a "variant" of antibody, antibody fragment or antibody domain refers to antibody, antibody fragment or antibody domain that (1) shares a sequence identity of at least 80%, 85%, 90%, 95%, 96%, 97%, 98% or 99% with the original antibody, antibody fragment or antibody domain, and (2) binds specifically to the same target that the original antibody, antibody fragment or antibody domain binds specifically. It should be understood that where a measure of sequence identity is presented in the form of the phrase "at least x % identical" or "at least x % identity", such an embodiment includes any and all whole number percentages equal to or above the lower limit. Further it should be understood that where an amino acid sequence is presented in the present application, it should be construed as additionally disclosing or embracing amino acid sequences having a sequence identity of at least 80%, at least 85%, at least 90%, at least 95%, at least 96%, at least 97%, at least 98% or at least 99% identity to that amino acid sequence.

It should be understood that where a sequence homology range is presented herein, as in e.g., the phrase "about 80% to about 100%", such an embodiment includes any and all sub-ranges defined by any whole numbers within, wherein the lower number can be any whole number between 80 and 100.

As used herein, the phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

Included within the scope of the multispecific antibodies of the present application are various compositions and methodologies, including asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; Biolonic, Merus); Fab-exchanged antibodies (Genmab); symmetric IgG-like antibodies (e.g. dual targeting (DT)-Ig (GSK/Domantis); two-in-one antibody (Genentech); crosslinked MAbs (Karmanos Cancer Center); mAb$^2$ (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec, TvAb, Roche); scFv/Fc fusions; SCORPION (Emergent BioSolutions/Trubion, ZymoGenetics/BMS); dual affinity retargeting technology (Fc-DART); MacroGenics; dual (scFv)$_2$-Fabs (National Research Center for Antibody Medicine); F(ab)$_2$ fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D". In some embodiments, an antibody or antibody fragment "has specificity to" an antigen if the antibody or antibody fragment forms a complex with the antigen with a dissociation constant ($K_d$) of $10^{-6}$M or less, $10^{-7}$M or less, $10^{-8}$M or less, $10^{-9}$M or less, or $10^{-10}$M or less.

The term "antagonist antibody" refers to an antibody that binds to a target and prevents or reduces the biological effect of that target. In some embodiments, the term can denote an antibody that prevents the target, e.g., TIGIT, to which it is bound from performing a biological function.

As used herein, an "anti-PD-1 antagonist antibody" refers to an antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including downstream events mediated by PD-1, such as PD-1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present application, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, an anti-PD-1 antagonist antibody binds PD-1 and upregulates an anti-tumor immune response.

As used herein, an "anti-PD-L1 antagonist antibody" refers to an antibody that is able to inhibit PD-L1 biological activity and/or downstream event(s) mediated by PD-L1. Anti-PD-L1 antagonist antibodies encompass antibodies that block, antagonize, suppress or reduce (to any degree including significantly) PD-L1 biological activity, including downstream events mediated by PD-L1, such as PD-L1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present application, it will be explicitly understood that the term "anti-PD-L1 antagonist antibody" (interchangeably termed "antagonist PD-L1 antibody", "antagonist anti-PD-L1 antibody" or "PD-L1 antagonist antibody") encompasses all the previously identified terms, titles, and functional states and characteristics whereby PD-L1 itself, a PD-L1 biological activity, or the consequences of the biological activity, are substantially nullified, decreased, or neutralized in any meaningful degree. In some embodiments, an anti-PD-L1 antagonist antibody binds PD-L1 and upregulates an anti-tumor immune response.

The phrase "immune checkpoint regulator" refers to a functional class of agents, which inhibit or stimulate signaling through an immune checkpoint. An "immune checkpoint regulator" includes cell surface receptors and their associated ligands, which together provide a means for inhibiting or stimulating signaling pathways associated with T-cell activation. Exemplary immune checkpoint regulators include, but are not limited to PD-1 and its ligands, PD-L1 and PD-L2; TIGIT and its CD155 ligand, PVR; CTLA-4 and its ligands, B7-1 and B7-2; TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA.

The phrases "checkpoint regulator antagonist", "immune checkpoint binding antagonist" and "immune checkpoint antagonist" are used interchangeably herein with reference to a class of agents that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Immune checkpoint regulator antagonists include antibody fragments, peptide inhibitors, dominant negative peptides and small molecule drugs, either in isolated forms or as part of a fusion protein or conjugate.

The phrases "immune checkpoint binding agonist" and "immune checkpoint agonist" are used interchangeably herein with reference to a class of agents that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Exemplary immune checkpoint regulator agonists include, but are not limited to members of the tumor necrosis factor (TNF) receptor superfamily, such as CD27, CD40, OX40 (CD 134), glucocorticoid-induced TNFR family-related protein (GITR), and 4-1BB (CD137) and their ligands. Additional checkpoint regulator agonists belong to the B7-CD28 superfamily, including CD28 and ICOS.

The phrases "dominant-negative protein" or "dominant-negative peptide" refer to a protein or peptide derived from a wild type protein that has been genetically modified by mutation and/or deletion so that the modified protein or peptide interferes with the function of the endogenous wild-type protein from which it is derived.

The phrase "VEGF binding antagonist" refers to a functional class of agents that bind to VEGF-A or its receptor, VEGFR-2, so that, as a result of the binding, activation of VEGFR-2 by VEGF-A is blocked or inhibited. As used herein, the term "VEGF binding antagonists" include antibody fragments, peptide inhibitors, dominant negative peptides and small molecule drugs, either in isolated forms or as part of a fusion protein or conjugate.

The phrase "Tie2 tyrosine kinase receptor binding antagonist" refers to a functional class of agents that bind to a Tie2 tyrosine kinase receptor or one of its ligands so that, as a result of the binding, activation of the Tie2 tyrosine kinase receptor by one or more of its ligands (i.e., Ang1, Ang2, Ang3 and Ang4) is blocked or inhibited. As used herein, the term "Tie2 tyrosine kinase receptor binding antagonist" include antibody fragments, peptide inhibitors, dominant negative peptides and small molecule drugs, either in isolated forms or as part of a fusion protein or conjugate.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

When describing polypeptide domain arrangements with hyphens between individual domains (e.g., CH2-CH3), it should be understood that the order of the listed domains is from the amino terminal end to the carboxy terminal end.

The term "immunoconjugate" refers to an antibody which is fused by covalent linkage to an inhibitory peptide or small molecule drug. The peptide or small molecule drug can be chemically linked to the C-terminus of a constant heavy chain or to the N-terminus of a variable light and/or heavy chain.

A "linker" may be used to link the peptide or small molecule drug, such as a maytansinoid, to the antitumor antagonists in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. The immunoconjugate may further include a flexible 3-15 amino acid linker, for example, GGG (SEQ ID NO:283) or GGGGS (G4S) repetitive peptide linker (SEQ ID NOS:284-289), between an antitumor antagonist and the peptide and/or small molecule drug.

As used herein, the term "scaffold" refers to any polymer of amino acids that exhibits properties desired to support the function of an antagonist, including addition of antibody specificity, enhancement of antibody function or support of antibody structure and stability. A scaffold can be grafted with binding domains of a donor polypeptide to confer the binding specificity of the donor polypeptide onto the scaffold.

As used herein, the phrase "multispecific inhibitor" refers to a molecule comprising at least two targeting domains with different binding specificities. In some embodiments, the multispecific inhibitor is a polypeptide comprising a scaffold and two or more immunoglobulin antigen binding domains targeting different antigens or epitopes. In certain embodiments, the multispecific inhibitor is a bispecific antibody or antagonist. In other embodiments, the multispecific inhibitor is a trispecific antibody or antagonist.

As used herein, the phrase "bispecific" refers to a molecule comprising at least two targeting domains with different binding specificities. Each targeting domain is capable of binding specifically to a target molecule and inhibiting a biological function of the target molecule upon binding to the target molecule. In some embodiments, the bispecific checkpoint regulator antagonist is a polymeric molecule having two or more peptides. In some embodiments, the targeting domain comprises an antigen binding domain or a CDR of an antibody. In some embodiments, the bispecific inhibitor is a bispecific antibody.

The terms "bispecific antibody," and "bispecific antagonist" are used interchangeably herein with reference to an antibody that can specifically bind two different antigens (or epitopes). In some embodiments, the bispecific antibody is a full-length antibody that binds one antigen (or epitope) on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences), and is monovalent for each antigen it binds to.

In other embodiments, the bispecific antibody is a full-length antibody that can bind two different antigens (or epitopes) in each of its two binding arms (two pairs of HC/LC) In these embodiments, the bispecific antibody has two identical antigen binding arms, with identical specificity and identical CDR sequences, and is bivalent for each antigen it binds to.

The terms "trispecific antibody" and "trispecific antagonist" are used interchangeably herein with reference to a molecule comprising three targeting domains with three different binding specificities. Each targeting domain is capable of binding specifically to a target molecule and inhibiting a biological function of the target molecule upon binding to the target molecule. In some embodiments, the trispecific antagonist is a polymeric molecule having two or more peptides. In some embodiments, the targeting domain comprises an antigen binding domain or a CDR of an antibody. In some embodiments, the trispecific antagonist is a trispecific antibody.

Exemplary bispecific and trispecific antibodies may include asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb2 (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (Zymo-Genetics); HERCULES (Biogen Idec, TvAb, Roche); scFv/Fc fusions; SCORPION (Emergent BioSolutions/Trubion, ZymoGenetics/BMS); dual affinity retargeting technology (Fc-DART), MacroGenics; dual (scFv)2-Fabs (National Research Center for Antibody Medicine); F(ab)2 fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

The terms "treat" and "treatment" refer to the amelioration of one or more symptoms associated with a cell proliferative disorder; prevention or delay of the onset of one or more symptoms of a cell proliferative disorder; and/or lessening of the severity or frequency of one or more symptoms of cell proliferative disorder.

The phrases "to a patient in need thereof", "to a patient in need of treatment" or "a subject in need of treatment" includes subjects, such as mammalian subjects, that would benefit from administration of the antitumor antagonist of the present disclosure for treatment of a cell proliferative disorder.

The terms "therapeutically effective amount", "pharmacologically effective amount", and "physiologically effective amount" are used interchangeably to mean the amount of an antitumor antagonist that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm, cancer or tumor.

The term "cancer" or "tumor" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma in situ, invasive ductal carcinoma, lobular carcinoma, invasive lobular carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

I. Trispecific Antitumor Antagonists

One aspect of the present application relates to trispecific antitumor antagonists that comprise: a protein scaffold, a first targeting domain that binds specifically to an immune checkpoint regulator; a second targeting domain that binds specifically to VEGF and comprises one or more peptide domains derived from VEGFR, a third targeting domain comprising an inhibitor of the angiopoietin/Tie-2 signaling pathway, wherein the first targeting domain is located at an amino terminal of the protein scaffold and the second targeting domain is located at a carboxyl terminal of the protein scaffold. In some embodiments, the third targeting domain is inserted into a CH3 domain in a Fc loop of the protein scaffold.

Fusion proteins (e.g., Fc-fusion proteins) produced by recombinant DNA technology often face a serious problem of fully or partially degradation in cell culture (clipping) because of the host-cell derived proteases. Clipping generates low molecular weight (LMW) species of the target protein and leads to inactive polypeptides. While not wishing to be bound by any particular theory, it has been hypothesized that the location of the biological peptide affects the degree of degradation in the resulting fusion protein. The inventors of the present application found that insertion of the second targeting domain into the CH3 region of the Fc loop significantly reduces clipping of the resulting trispecific antagonist.

Another aspect of the present application relates to trispecific antitumor antagonists that comprise: a protein scaffold, a first targeting domain that binds specifically to an immune checkpoint regulator; a second targeting domain that binds specifically to VEGF and comprises one or more peptide domains derived from VEGFR, and a third targeting domain comprising a TGF pathway inhibitor.

In some embodiments, the second targeting domain is located at the carboxy-terminal of a CH3 domain of the protein scaffold, and the third targeting domain is located at the carboxy-terminal of the second targeting domain. In some embodiments, the second targeting domain is structurally linked to the carboxy-terminal of the CH3 domain of the protein scaffold through a first linker. In some embodiments, the third targeting domain is structurally linked to the carboxy-terminal of the second targeting domain through a second linker. In some embodiments, the second targeting domain is structurally linked to the carboxy-terminal of the CH3 domain of the protein scaffold through a first linker and the third targeting domain is structurally linked to the carboxy-terminal of the second targeting domain through a second linker. The inventors of the present application unexpected found that such configurations confer improved pharmacokinetics to the corresponding antagonists.

In some embodiments, the second targeting domain comprises a VEGFR component with amino acid sequence of SEQ ID NO:185 (aflibercept). In further embodiments, the VEGFR component is a-glycosylated by replacing asparagine residues with glutamic acid residues. An exemplary amino acid sequence of a-glycosylated VEGFR component is demonstrated in SEQ ID NO:207. The trispecific antitumor antagonist variants with a-glycosylated VEGFR component retain the VEGFR bioactivity while demonstrating improved pharmacokinetics compared to the wild type aflibercept.

Another aspect of the present application relates to a trispecific antitumor antagonist that comprises a protein scaffold, a first targeting domain that binds specifically to an immune checkpoint regulator; a second targeting domain comprising a TGF-β pathway inhibitor; and a third targeting domain comprising a peptide inhibitor of the angiopoietin/Tie-2 signaling pathway.

In some embodiments, the first targeting domain comprises bevacizumab or a variant thereof and the third targeting domain is inserted within each of the two CH3 regions of the Fc loop of the protein scaffold. In some embodiments, the first targeting domain comprising one or more anti-PD-1 variable domains and the third targeting domain is inserted within each of the two CH3 regions of the Fc loop of the protein scaffold. In some embodiments, the first targeting domain comprising one or more anti-PD-L1 variable domains and the third targeting domain is inserted within each of the two CH3 regions of the Fc loop of the protein scaffold.

In some embodiments, the trebananib peptide comprises the sequence: AQQEECEWDPWTCEHMGSGSATGGSGSTAS SGSGSATHQEECEWDPWTCEHMLE (SEQ ID NO: 182). Unless otherwise noted, the "trebananib peptide" and the designation "-long" or "-L" correspond to the sequence of SEQ ID NO:182, which comprises two copies of the Ang-1/2 blocking peptide sequence, QEECEWDPWTCEHM (SEQ ID NO:194). In certain embodiments, the trispecific antagonists of the present application comprise modified version of the trebananib peptide containing a single copy of the sequence corresponding to SEQ ID NO:194 with the designation "-short" or "-S".

II. Bispecific Antitumor Antagonists

Another aspect of the present application relates to a bispecific antitumor antagonist that comprises a protein scaffold, a first targeting domain that binds specifically to an immune checkpoint regulator; and a second targeting domain comprising a peptide inhibitor of the angiopoietin/Tie-2 signaling pathway.

In some embodiments, the first targeting domain comprises one or more anti-PD-1 or anti-PD-L1 variable domains, and the second targeting domain is inserted within each of the two CH3 regions of the Fc loop of the protein scaffold.

Another aspect of the present application relates to a bispecific antitumor antagonist that comprises a protein scaffold, a first targeting domain that binds specifically to an immune checkpoint regulator; and a second targeting domain comprising a VEGFR component.

Figure 40:
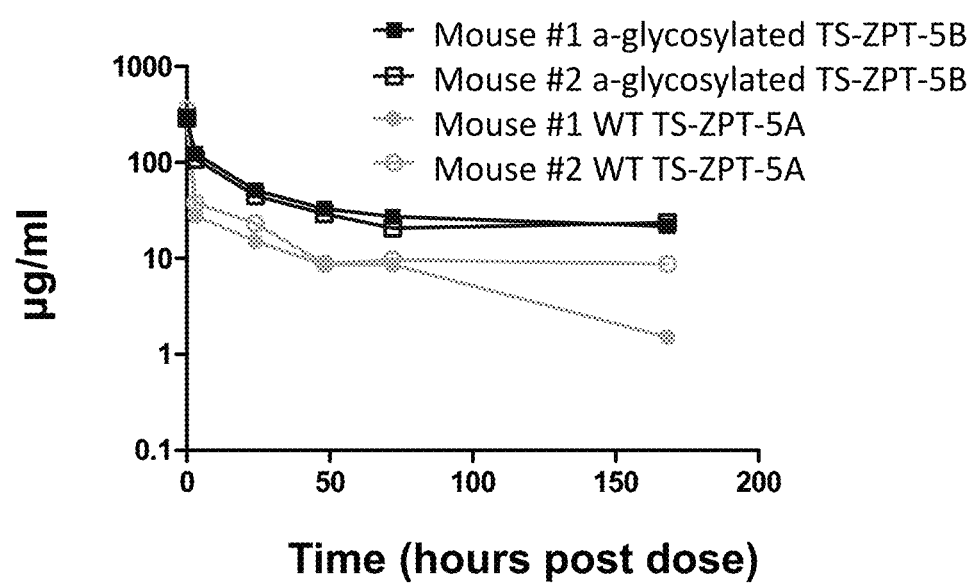
FIG. 40 shows the pharmacokinetic profiles of TS-ZPT-5A and the TS-ZPT-5B in two mice each.
Figure 41A:
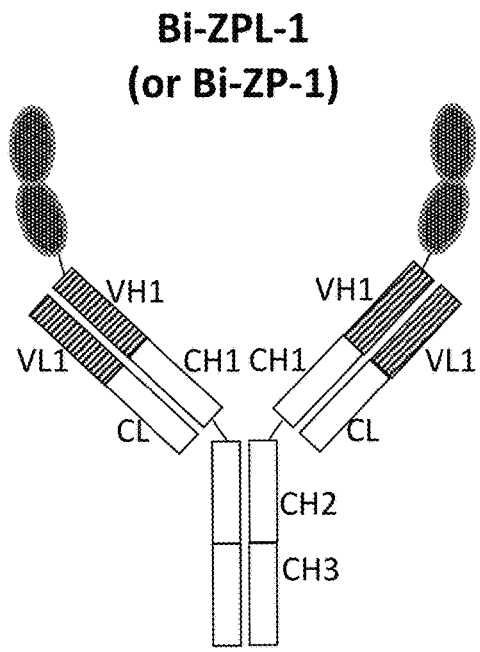
FIGS. 41A-41C show three different bispecific antitumor antagonist configurations, Bi-ZPL-1 (or Bi-ZP-1) and Bi-ZPL-2 (or Bi-ZP-2) and Bi-ZPL-3 (or Bi-ZP-3) each comprising (1) anti-PD-1 or anti-PD-L1 variable regions and (2) an aflibercept VEGF binding domain (i) fused to the amino-terminus of the VH1; (ii) mutated to eliminate the N-linked glycosylation sites and fused to the amino-terminus of the VH1; (iii) mutated to eliminate the N-Linked glycosylation sites and fused to the carboxy-terminus of the CH3 with a 3×G4S linker.
Figure 41B:
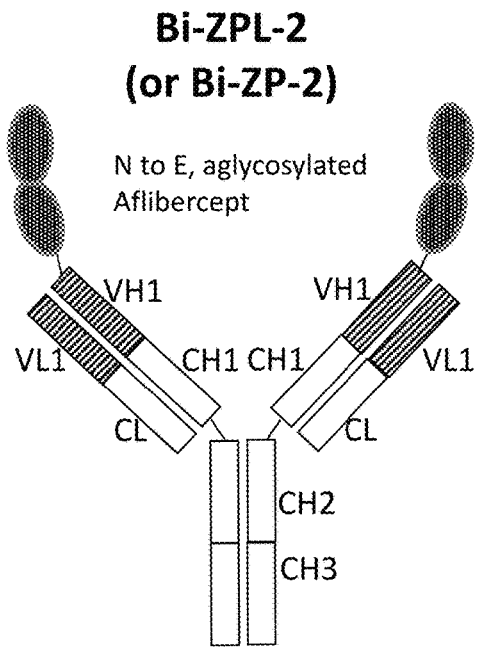
Figure 41C:
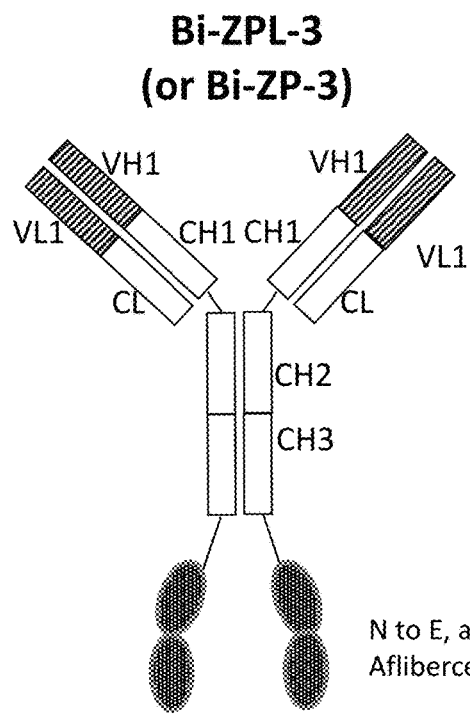

FIGS. 41A-40C depict exemplary bispecific anti-PD-1/VEGFR component and anti-PD-L1/VEGFR component molecules, Bi-ZPL-1 and Bi-ZPL-2, and Bi-ZPL-3, respectively that contain an aflibercept at the N-terminal end (FIG. 41A) or the carboxy-terminal end (FIG. 41B-C). In one embodiment, Bi-ZPL-1 has an immunoglobulin heavy chain containing the sequence set forth in SEQ ID NO:218 and/or an immunoglobulin light chain containing the sequence set forth in SEQ ID NO:219. In another embodiment, Bi-ZP-1 has an immunoglobulin heavy chain containing the sequence set forth in SEQ ID NO:220 and/or an immunoglobulin light chain containing the sequence set forth in SEQ ID NO:221.

In another embodiment, Bi-ZP-2 has an immunoglobulin heavy chain containing the sequence set forth in SEQ ID NO:222 and/or an immunoglobulin light chain containing the sequence set forth in SEQ ID NO:223. In another embodiment, Bi-ZPL-2 has an immunoglobulin heavy chain containing the sequence set forth in SEQ ID NO:224 and/or an immunoglobulin light chain containing the sequence set forth in SEQ ID NO:225.

In another embodiment, Bi-ZPL-3 has an immunoglobulin heavy chain containing the sequence set forth in SEQ ID NO:296 and/or an immunoglobulin light chain containing the sequence set forth in SEQ ID NO:297.

Another aspect of the present application relates to bispecific antitumor antagonists that comprise a protein scaffold, a first targeting domain comprising bevacizumab; and a second targeting domain comprising a peptide inhibitor of the angiopoietin/Tie-2 signaling pathway. In some embodiments, the second targeting domain is inserted within the CH3 domain in the Fc loop of the protein scaffold.

Another aspect of the present application relates to bispecific antitumor antagonists that comprise a protein scaffold comprising an Fc fragment, a first targeting domain comprising a VEGFR component, and a second targeting domain comprising a peptide inhibitor of the angiopoietin/Tie-2 signaling pathway. In some embodiments, the second targeting domain is inserted within the CH3 domain in the Fc loop of the protein scaffold. In some embodiments, the Fc fragment of protein scaffold comprises an amino acid sequence selected from the group consisting of SEQ ID NOS:210-217 prior to the insertion of the second targeting domain.

Another aspect of the present application relates to bispecific antitumor antagonists that comprise a protein scaffold comprising an Fc fragment, a first targeting domain comprising a TGFBR2 ECD, and a second targeting domain comprising a peptide inhibitor of the angiopoietin/Tie-2 signaling pathway. In some embodiments, the second targeting domain is inserted within the CH3 domain in the Fc loop of the protein scaffold. In some embodiments, the Fc fragment of protein scaffold comprises an amino acid sequence selected from the group consisting of SEQ ID NOS:210-217 prior to the insertion of the second targeting domain.

The bispecific antitumor antagonists of the present application may be constructed with an IgG backbone. More specifically, any of the bispecific antagonists of the present application may be constructed with an IgG1 or IgG4 backbone. Use of an IgG1 backbone is preferable for cancer treatment where a target is present on antigen presenting cells that can mediate antibody-dependent cell-mediated cytotoxicity (ADCC). Use of an IgG4 backbone allows targeting of antigen where antigen binding alone is sufficient to generate the desired therapeutic benefits. IgG4-based antagonists preclude undesirable effector functions associated with e.g., IgG1 antibodies, including FcγR binding and complement activation.

III. Targeting Domains

A. Targeting Domains that Bind Specifically to Immune Checkpoint Regulators

Targeting Domains that bind specifically to immune checkpoint regulators include, but are not limited to, (1) anti-PD-1 antibody and anti-PD-1 antibody fragments, (2) anti-PD-L1 antibody and anti-PD-L1 antibody fragments, (3) Anti-TIGIT antibody and anti-TIGIT antibody fragments, and (4) Anti-LAG-3 antibody and anti-LAG-3 antibody fragments.

1. Anti-PD-1 Antibody and Anti-PD-1 Antibody Fragments

In some embodiments, the checkpoint regulator antagonist is an anti-PD-1 antibody or antibody fragment. In a particular embodiment, the PD-1 inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% identity to an amino acid sequence selected from the group consisting of SEQ ID NOS:48, 51, 54, 56 and 59, wherein HCDR2 has an amino acid sequence that is about 80% to about 100% identity to an amino acid sequence selected from the group consisting of SEQ ID NOS:49, 52, 57 and 60, and wherein HCDR3 has an amino acid sequence that is about 80% to about 100% identity to an amino acid sequence selected from the group consisting of SEQ ID NOS:50, 53, 55, 58 and 61; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% identity to an amino acid sequence selected from the group consisting of SEQ ID NOS:62, 65, 68, 69, 70 and 73, wherein LCDR2 has an amino acid sequence that is about 80% to about 100% identity to an amino acid sequence selected from the group consisting of SEQ ID NOS:63, 66, 71 and 74, and wherein LCDR3 has an amino acid sequence that is about 80% to about 100% identity to an amino acid sequence selected from the group consisting of SEQ ID NOS:64, 67, 72 and 75, wherein the antibody, or the antigen-binding portion thereof, binds specifically to human PD-1.

In some embodiments, the PD-1 inhibitor of the present application is an antibody, or an antigen-binding portion thereof, comprising: (1) a heavy chain variable region having an amino acid sequence that is about 80% to about 100% identity to an amino acid sequence selected from the group consisting of SEQ ID NOS:127, 129, 131, 133, 135 and 137; and (2) a light chain variable region having an amino acid sequence that is about 80% to about 100% identity to an amino acid sequence selected from the group consisting of SEQ ID NOS:128, 130, 132, 134, 136 and 138, wherein the antibody, or the antigen-binding portion thereof, binds specifically to human PD-1.

In some embodiments, the anti-PD-1 antibody or antibody fragment comprises a heavy chain variable region that comprises (1) an HCDR1 of SEQ ID NO:59, an HCDR2 of SEQ ID NO:60 and an HCDR 3 of SEQ ID NO:61 and (2) an HFR1 having at least 80%, 85% or 90% identity to the amino acid sequence of SEQ ID NO:366, an HFR2 having at least 80%, 85% or 90% identity to the amino acid sequence of SEQ ID NO:360, an HFR3 having at least 80%, 85% or 90% identity to the amino acid sequence of SEQ ID NO:371, an HFR4 having at least 80%, 85% or 90% identity to the amino acid sequence of SEQ ID NO:357, and an immunoglobulin heavy chain variable region that comprises (1) an LCDR1 of SEQ ID NO:73, an LCDR2 of SEQ ID NO:74 and an LCDR 3 of SEQ ID NO:75 and (2) an LFR1 having at least 80%, 85% or 90% identity to the amino acid sequence of SEQ ID NO:372, an LFR2 having at least 80%, 85% or 90% identity to the amino acid sequence of SEQ ID NO:373, an LFR3 having at least 80%, 85% or 90% identity to the amino acid sequence of SEQ ID NO:374, an LFR4 having at least 80%, 85% or 90% identity to the amino acid sequence of SEQ ID NO:375.

In some embodiments, the anti-PD-L1 antibody or antibody fragment comprises a heavy chain variable region that comprises (1) an HCDR1 of SEQ ID NO:56, an HCDR2 of SEQ ID NO:57 and an HCDR 3 of SEQ ID NO:58 and (2) an HFR1 having at least 80%, 85% or 90% identity to the amino acid sequence of SEQ ID NO:366, an HFR2 having at least 80%, 85% or 90% identity to the amino acid sequence of SEQ ID NO:360, an HFR3 having at least 80%, 85% or 90% identity to the amino acid sequence of SEQ ID NO:367, an HFR4 having at least 80%, 85% or 90% identity to the amino acid sequence of SEQ ID NO:357, and an immunoglobulin heavy chain variable region that comprises (1) an LCDR1 of SEQ ID NO:70, an LCDR2 of SEQ ID NO:71 and an LCDR 3 of SEQ ID NO:72 and (2) an LFR1 having at least 80%, 85% or 90% identity to the amino acid sequence of SEQ ID NO:368, an LFR2 having at least 80%, 85% or 90% identity to the amino acid sequence of SEQ ID NO:369, an LFR3 having at least 80%, 85% or 90% identity to the amino acid sequence of SEQ ID NO:370, an LFR4 having at least 80%, 85% or 90% identity to the amino acid sequence of SEQ ID NO:365.

The term "2P17" or "PD-06" refers to the PD-1 inhibitor of the present application, comprising: (1) a heavy chain variable region having an amino acid sequence of SEQ ID NO:137, and (2) a light chain variable region having an amino acid sequence of SEQ ID NO:138. The CDR and FR regions of 2P17 (or PD-06) are listed as SEQ ID NOS:59-61, 73-75, 357, 360, 366 and 371-375.

The term "2P16" or "PD-05" refers to the PD-1 inhibitor of the present application, comprising: (1) a heavy chain variable region having an amino acid sequence of SEQ ID NO:135, and (2) a light chain variable region having an amino acid sequence of SEQ ID NO:136. The CDR and FR regions of 2P16 (or PD-05) are listed as SEQ ID NOS:56-58, 70-72, 357, 360, 366 and 365-370.

2. Anti-PD-L1 Antibody and Anti-PD-L1 Antibody Fragments

In one embodiment, the checkpoint regulator antagonist is an anti-PD-L1 antibody or antibody fragment. In a particular embodiment, the PD-L1 inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% identity to an amino acid sequence selected from the group consisting of SEQ ID NOS:76, 79, 85 and 88, wherein HCDR2 has an amino acid sequence that is about 80% to about 100% identity to an amino acid sequence selected from the group consisting of SEQ ID NOS:77, 80, 82, 84, 86 and 89, and wherein HCDR3 has an amino acid sequence that is about 80% to about 100% identity to an amino acid sequence selected from the group consisting of SEQ ID NOS:78, 81, 83, 87 and 90; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% identity to an amino acid sequence selected from the group consisting of SEQ ID NOS:91, 94, 98, 101 and 104, wherein LCDR2 has an amino acid sequence that is about 80% to about 100% identity to an amino acid sequence selected from the group consisting of SEQ ID NOS:92, 95, 99, 102 and 105, and wherein LCDR3 has an amino acid sequence that is about 80% to about 100% identity to an amino acid sequence selected from the group consisting of SEQ ID NOS:93, 96, 97, 100 and 106, wherein the antibody, or the antigen-binding portion thereof, binds specifically to human PD-L1.

In some embodiments, the anti-PD-L1 antibody or antibody fragment comprises a heavy chain variable region that comprises (1) an HCDR1 of SEQ ID NO:79, an HCDR2 of SEQ ID NO:82 and an HCDR 3 of SEQ ID NO:83 and (2) an HFR1 having at least 80%, 85% or 90% identity to the amino acid sequence of SEQ ID NO:366, an HFR2 having at least 80%, 85% or 90% identity to the amino acid sequence of SEQ ID NO:360, an HFR3 having at least 80%, 85% or 90% identity to the amino acid sequence of SEQ ID NO:383, an HFR4 having at least 80%, 85% or 90% identity to the amino acid sequence of SEQ ID NO:357, and an immunoglobulin heavy chain variable region that comprises (1) an LCDR1 of SEQ ID NO:91, an LCDR2 of SEQ ID NO:92 and an LCDR 3 of SEQ ID NO:93 and (2) an LFR1 having at least 80%, 85% or 90% identity to the amino acid sequence of SEQ ID NO:377, an LFR2 having at least 80%, 85% or 90% identity to the amino acid sequence of SEQ ID NO:378, an LFR3 having at least 80%, 85% or 90% identity to the amino acid sequence of SEQ ID NO:379, an LFR4 having at least 80%, 85% or 90% identity to the amino acid sequence of SEQ ID NO:365.

In some embodiments, the PD-L1 inhibitor of the present application is an antibody, or an antigen-binding portion thereof, comprising: (1) a heavy chain variable region having an amino acid sequence that is about 80% to about 100% identity to an amino acid sequence selected from the group consisting of SEQ ID NOS:139, 141, 143, 145, 147, 149, 151 and 153; and (2) a light chain variable region having an amino acid sequence that is about 80% to about 100% identity to an amino acid sequence selected from the group consisting of SEQ ID NOS:140, 142, 144, 146, 148, 150, 152 and 154, wherein the antibody, or the antigen-binding portion thereof, binds specifically to human PD-L1. In the preferred embodiment the anti-PD-L1 antibody heavy and light chains consist of SEQ ID NOs: 153-154.

The term "PL-08" refers to the PD-L1 inhibitor of the present application, comprising: (1) a heavy chain variable region having an amino acid sequence of SEQ ID NO: 153, and (2) a light chain variable region having an amino acid sequence of SEQ ID NO:154. The CDR and FR regions of PL-08 are listed as SEQ ID NOS:79, 82, 83, 91-93, 357, 360, 365, 366, 377-379 and 383.

3. Anti-TIGIT Antibody and Anti-TIGIT Antibody Fragments

In some embodiments, the checkpoint regulator antagonist is an anti-TIGIT antibody or antibody fragment. In a particular embodiment, the TIGIT inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% identity to an amino acid sequence selected from the group consisting of SEQ ID NOS:1, 6, 11, 15, 17, 20 and 23, wherein HCDR2 has an amino acid sequence that is about 80% to about 100% identity to an amino acid sequence selected from the group consisting of SEQ ID NOS:2, 4, 7, 9, 12, 13, 16, 18, 21 and 24, and wherein HCDR3 has an amino acid sequence that is about 80% to about 100% identity to an amino acid sequence selected from the group consisting of SEQ ID NOS:3, 5, 8, 10, 14, 19, 22 and 25; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% identity to an amino acid sequence selected from the group consisting of SEQ ID NOS:26, 29, 31, 33, 35, 39, 42 and 45, wherein LCDR2 has an amino acid sequence that is about 80% to about 100% identity to an amino acid sequence selected from the group consisting of SEQ ID NOS:27, 30, 36, 37, 40, 43 and 46, and wherein LCDR3 has an amino acid sequence that is about 80% to about 100% identity to an amino acid sequence selected from the group consisting of SEQ ID NOS:28, 32, 34, 38, 41, 44 and 47, wherein the antibody, or the antigen-binding portion thereof, binds specifically to human TIGIT.

In some embodiments, the anti-TIGIT antibody or antibody fragment comprises a heavy chain variable region that comprises (1) an HCDR1 of SEQ ID NO:23, an HCDR2 of SEQ ID NO:24 and an HCDR 3 of SEQ ID NO:25 and (2) an HFR1 having at least 80%, 85% or 90% identity to the amino acid sequence of SEQ ID NO:343, an HFR2 having at least 80%, 85% or 90% identity to the amino acid sequence of SEQ ID NO:330, an HFR3 having at least 80%, 85% or 90% identity to the amino acid sequence of SEQ ID NO:344, an HFR4 having at least 80%, 85% or 90% identity to the amino acid sequence of SEQ ID NO:319, and an immunoglobulin heavy chain variable region that comprises (1) an LCDR1 of SEQ ID NO:45, an LCDR2 of SEQ ID NO:46 and an LCDR 3 of SEQ ID NO:47 and (2) an LFR1 having at least 80%, 85% or 90% identity to the amino acid sequence of SEQ ID NO:303, an LFR2 having at least 80%, 85% or 90% identity to the amino acid sequence of SEQ ID NO:311, an LFR3 having at least 80%, 85% or 90% identity to the amino acid sequence of SEQ ID NO:317, an LFR4 having at least 80%, 85% or 90% identity to the amino acid sequence of SEQ ID NO:345.

In another embodiment, the TIGIT inhibitor of the present application is an antibody, or an antigen-binding portion thereof, comprising: (1) a heavy chain variable region having an amino acid sequence that is about 80% to about 100% identity to an amino acid sequence selected from the group consisting of SEQ ID NOS:107, 109, 111, 113, 115, 117, 119, 121, 123 and 125; and (2) a light chain variable region having an amino acid sequence that is about 80% to about 100% identity to an amino acid sequence selected from the group consisting of SEQ ID NOS:108, 110, 112, 114, 116, 118, 120, 122, 124 and 126, wherein the antibody, or the antigen-binding portion thereof, binds specifically to human TIGIT. In the preferred embodiment the anti-TIGIT antibody has heavy and light chain sequences consisting of SEQ ID NOs: 125 and 126.

The term "B21-35" or "T-10" refers to the TIGIT inhibitor of the present application, comprising: (1) a heavy chain variable region having an amino acid sequence of SEQ ID NO:125, and (2) a light chain variable region having an amino acid sequence of SEQ ID NO:126. The CDR and FR regions of B21-35 (or T-10) are listed as SEQ ID NOS:23-25, 45-47, 303, 311, 317, 319, 330 and 343-345.

4. Anti-LAG-3 Antibody and Anti-LAG-3 Antibody Fragments

In one embodiment, the checkpoint regulator antagonist is an anti-LAG-3 antibody or antibody fragment. In a particular embodiment, the LAG-3 inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% identity to an amino acid sequence selected from the group consisting of SEQ ID NOS:155-157, wherein HCDR2 has an amino acid sequence that is about 80% to about 100% identity to an amino acid sequence selected from the group consisting of SEQ ID NOS:158-160, and wherein HCDR3 has an amino acid sequence that is about 80% to about 100% identity to an amino acid sequence selected from the group consisting of SEQ ID NOS: 161-163; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% identity to an amino acid sequence selected from the group consisting of SEQ ID NOS:164-166, wherein LCDR2 has an amino acid sequence that is about 80% to about 100% identity to an amino acid sequence selected from the group consisting of SEQ ID NOS: 167 and 168, and wherein LCDR3 has an amino acid sequence that is about 80% to about 100% identity to an amino acid sequence selected from the group consisting of SEQ ID NOS: 169 and 170, wherein the antibody, or the antigen-binding portion thereof, binds specifically to human LAG-3.

In some embodiments, the anti-LAG-3 antibody or antibody fragment comprises a heavy chain variable region that comprises (1) an HCDR1 of SEQ ID NO:156, an HCDR2 of SEQ ID NO:158 and an HCDR 3 of SEQ ID NO:161 and (2) an HFR1 having at least 80%, 85% or 90% identity to the amino acid sequence of SEQ ID NO:399, an HFR2 having at least 80%, 85% or 90% identity to the amino acid sequence of SEQ ID NO:400, an HFR3 having at least 80%, 85% or 90% identity to the amino acid sequence of SEQ ID NO:401, an HFR4 having at least 80%, 85% or 90% identity to the amino acid sequence of SEQ ID NO:402, and an immunoglobulin heavy chain variable region that comprises (1) an LCDR1 of SEQ ID NO:164, an LCDR2 of SEQ ID NO:167 and an LCDR 3 of SEQ ID NO:169 and (2) an LFR1 having at least 80%, 85% or 90% identity to the amino acid sequence of SEQ ID NO:403, an LFR2 having at least 80%, 85% or 90% identity to the amino acid sequence of SEQ ID NO:404, an LFR3 having at least 80%, 85% or 90% identity to the amino acid sequence of SEQ ID NO:405, an LFR4 having at least 80%, 85% or 90% identity to the amino acid sequence of SEQ ID NO:406.

In other embodiments, the LAG-3 inhibitor of the present application is an antibody, or an antigen-binding portion thereof, comprising: (1) a heavy chain variable region having an amino acid sequence that is about 80% to about 100% identity to an amino acid sequence selected from the group consisting of SEQ ID NOS:171-174; and (2) a light chain variable region having an amino acid sequence that is about 80% to about 100% identity to an amino acid sequence selected from the group consisting of SEQ ID NOS: 175-178, wherein the antibody, or the antigen-binding portion thereof, binds specifically to human LAG-3. In the preferred embodiment, the anti-LAG-3 antibody has heavy and light chain sequences consisting of SEQ ID NOS:171 and 175.

The term "2L2A. 1" refers to the LAG-3 inhibitor of the present application, comprising: (1) a heavy chain variable region having an amino acid sequence of SEQ ID NO: 171, and (2) a light chain variable region having an amino acid sequence of SEQ ID NO:175. The CDR and FR regions of 2L2A. 1 are listed as SEQ ID NOS:156, 158, 161, 164, 167, 169 and 399-406.

B. Targeting Domains that Bind Specifically to Angiogenesis Pathway Components

Angiogenesis, the development of new blood vessels from pre-existing vessels, is essential for tumor growth and metastasis. Angiogenesis inhibition presents a potentially valuable strategy for treating diseases, such as cancer, in which progression (e.g., metastasis) is dependent on neovascularization. Inhibition of angiogenesis leads to tumor cell death, which may feed tumor antigen into host antigen presentation pathways.

Two important angiogenesis pathways include the vascular endothelial growth factor (VEGF) pathway and the Tie2 pathway.

1. VEGF Pathway Antagonists and Inhibitors

The principal VEGF pathway is mediated by the transmembrane tyrosine kinase VEGF-R2. Various isoforms of VEGF, particularly VEGF-A, bind to VEGF-R1 and VEGFF-R2, resulting in dimerization and activation through phosphorylation of various downstream tyrosine kinases.

In some embodiments, the VEGF pathway antagonist binds to VEGF-A or its receptors VEGFR-1 and VEGFR-2 so that, as a result of the binding, activation of VEGFR-1 and VEGFR-2 by VEGF-A is blocked or inhibited. Angiogenesis inhibitors may be in the form of e.g., antibodies, variable domain fragments, or dominant negative fusion protein fragments.

An exemplary dominant negative anti-VEGFR antagonist is a protein fragment corresponding to the extracellular domain (ECD) of human VEGF receptor 1 or 2. In a preferred embodiment, the dominant negative anti-VEGFR antagonist is aflibercept (Zaltrap®), a recombinant fusion protein containing VEGF-A binding portions from the extracellular domains of human VEGF receptors 1 and 2 fused to the human IgG1 or IgG4 Fc fragment. VEGFR ECDs, such as aflibercept act as soluble receptor decoys for VEGF-A.

Aflibercept (also known as Zaltrap®) is a recombinant VEGF fusion protein consisting of vascular endothelial growth factor (VEGF)-binding portions from the extracellular domains of human VEGF receptors 1 and 2 that are fused to the Fc portion of the human IgG1 immunoglobulin. Aflibercept binds multiple ligands involved in angiogenesis, including VEGF-A, VEGF-B, anti-placental growth factor (PIGF)-1 and PIGF-2, including soluble ligands in circulation.

In a preferred embodiment, the aflibercept domain of the trispecific antitumor antagonists described herein is a-glycosylated by replacing asparagine (Asn, N) residues with glutamic acid (Glu, E) residues. N-linked glycosylation is the attachment of a glycan, to a nitrogen atom (the amide nitrogen) of an Asn residue of a protein. The Asn residue to be glycosylated must be located in a specific consensus sequence in the primary structure (Asn-X-Ser or Asn-X-Thr, where X refers to any amino acid except proline). By replacing the Asn residues with Glu residues (or any other amino acid residues), no glycosylation occurs on these sites. One or more Asn residues locate in the specific consensus sequence described above may be replaced.

Asialoglycoprotein receptor 1 and 2 (ASGR1 and ASGR2) is transmembrane proteins that play a critical role in serum glycoprotein homeostasis by mediating the endocytosis and lysosomal degradation of glycoproteins with exposed terminal galactose or N-acetylgalactosamine residues. In some cases, glycosylation of proteins can lead to increased clearance by ASGR1 and ASGR2. To improve the pharmacokinetics (i.e., achieve longer half-life) of the trispecific antitumor antagonists with VEGFR component domains, the inventors of the present application created a-glycosylated variant of the VEGFR component for limiting protein clearance by ASGR1 and ASGR2. The trispecific antitumor antagonist variant with a-glycosylated VEGFR component retains the VEGFR bioactivity while improves the alpha phase of pharmacokinetics by about five fold compared to the glycosylated VEGFR component. See FIG. 37. An exemplary amino acid sequence of aflibercept VEGF binding domain is demonstrated in SEQ ID NO:185, i.e., SDTGRPFVEMYSEIPEIIHMTEGRELVIPCRVTSP NITVTLKKFPLDTLIPDGKRIIWDSRKG FIIS NATYKEIGLLTCEATVNGHLYKTNYLTHRQTNTIIDV VLSPSHGIELSVGEKLVLNC TARTELNVGIDFN- WEYPSSKHQHKKLVNRDLKTQSGSEMKKFLSTLTI- DGVTRSDQGLY TCAASSGLMTKKNSTFVRVHEK, and an exemplary amino acid sequence of a-glycosylated aflibercept VEGF binding domain is demonstrated in SEQ ID NO:207, i.e., SDTGRPFVEMYSEIPEIIHMTEGREL- VIPCRVTSPEITVTLKKFPLDTLIPDGKRIIWD SRKG FIISEATYKEIGLLTCEATVNGHLYKTNYLTHR QTNTI- IDVVLSPSHGIELSVGEKLVLECT ARTELNVGIDFN- WEYPSSKHQHKKLVNRDLKTQSGSEMKKFLSTLTI- DGVTRSDQGLYT CAASSGLMTKKESTFVRVHEK. The replacement sites are underlined.

An exemplary VEGF antibody antagonist is bevacizumab (AVASTIN™), a humanized antibody. Bevacizumab comprises mutated human IgG1 framework regions (FRs) and antigen-binding complementarity-determining regions from the murine anti-hVEGF monoclonal antibody A4.6.1 that blocks binding of human VEGF-A to VEGFR-2. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated. In certain embodiments, amino acid substitutions may be included in a bevacizumab/AVASTIN antibody as described in U.S. Pat. No. 7,575,893 (SEQ ID NOS:226-227). Exemplary amino acid substitutions include, but are not limited to E1Q, E6Q, L11V, Q13K, L18V, R19K, A23K, or combinations thereof.

Additional anti-VEGF antibodies include ranibizumab (trade name Lucentis™)(SEQ ID NOS:294-295), a monoclonal antibody fragment derived from the same parent murine antibody as bevacizumab; the G6 or B20 series antibodies (e.g., G6-23, G6-31, B20-4.1) described in U.S. Publication No. 2006/0280747, 2007/0141065 and/or 2007/ 0020267, as well as the antibodies described in U.S. Pat. Nos. 7,297,334, 7,060,269, 6,884,879, 6,582,959, 6,703, 020, 6,054,297; U.S. Patent Application Publication Nos. U.S. 2007/059312, U.S. 2006/009360, U.S. 2005/0186208, U.S. 2003/0206899, U.S. 2003/0190317, and U.S. 2003/ 0203409.

An exemplary anti-VEGFR-2 antibody antagonist is the humanized IgG1 monoclonal antibody, ramucirumab, which binds to the extracellular domain of VEGFR-2, thereby blocking its interaction with VEGF-A. Additional anti-VEGFR-2 antibodies are described in U.S. Pat. Nos. 7,498, 414, 6,448,077 and 6,365,157.

Exemplary small molecule antagonists of the VEGF pathway include multikinase inhibitors of VEGFR-2, including sunitinib, sorafenib, cediranib, pazonpanib and nintedanib.

2. Tie2 Pathway Antagonists and Inhibitors

The Tie2 pathway is another angiogenesis pathway for which therapeutic antibodies and small molecule drugs have been developed. The Tie2 tyrosine kinase receptor activates angiogenesis in response to binding by its angiopoietin (Ang) ligands (i.e., Ang1, Ang2, Ang3 (mouse) and Ang4). A Tie2 pathway antagonist binds to the Tie2 tyrosine kinase receptor or one of its angiopoietin (Ang) ligands (i.e., Ang-1, Ang-2, Ang-3 and Ang-4) so that, as a result of the binding, activation of the Tie2 receptor by one or more of its ligands is blocked or inhibited.

In one embodiment, the Tie2 receptor binding antagonist is an inhibitory peptide. In another embodiment, the inhibitory peptide comprises the amino acid sequence in SEQ ID NO:182, i.e., AQQEECEWDPWTCEH- MGSGSATGGSGSTASSGSGSATHQEECEWDPWTCE- HMLE. In another embodiment, the Tie2 receptor binding antagonist comprises the peptide of SEQ ID NO:182 fused to the C-terminus of an Fc fragment, i.e., DKTHTCPPC- PAPELLGGPSVFLFPPKPKDTLMISRTPEVTCVVVD- VSHEDPEVKFNWYVD GVEVHNAKTKPREEQYN- STYRVVSVLTVLHQDWLNGKEYKCKVSNKALPAPIE KTISK AKGQPREPQVYTLPPSRDELTKNQVSLT- CLVKGFYPSDIAVEWESNGQPENNYKTTPPVL DSDGSFFLYSKLTVDKSRWQQGNVFSCSVMHEALH- NHYTQKSLSLSPGKGGGGGAQQE ECEWDPWTCEH- MGSGSATGGSGSTASSGSGSATHQEECEWDPWTCE- HMLE (SEQ ID NO:183). In another embodiment, the inhibitory peptide comprises a single copy of the amino acid sequence of QEECEWDPWTCEHM (SEQ ID NO:194).

In another embodiment, the inhibitory peptide is incorporated within each of the two CH3 regions in the Fc loops. The loop region is an irregular secondary structure in proteins that is not α-helix or β-sheet, while it connects together β-sheets to β-sheets, β-sheets to α-helices, or α-helices to α-helices. The inhibitory peptide may be added by insertion (i.e., between amino acids in the previously existing Fc loop) or by replacement of amino acids in the previously existing Fc loop (i.e., removing amino acids in the previously existing Fc loop and adding peptide amino acids).

An exemplary Fc fragment comprises the amino acid sequence in SEQ ID NO:208, i.e., DKTHTCPPCPAPELLG- GPSVFLFPPKPKDTLMISRTPEVTCVVVDV SHEDPEVKFNWYV DGVEVHNAKTKPREEQ YNSTYRVVSVLTVLHQDWLNGKEYKCKVS NKALPAPIEKT ISKAKGQPREPQVYTLPPSRE EMTKNQVSLTCLVKGFYPSDIAVEWESNGQP ENNYKT TPPVLDSDGSFFLYSKLTVDKSRWQ QGNVFSCSVMHEALHNHYTQKSLSLSPGK. The predicated loop regions are in bold. Any or all of the sites shown in bold may be suitable for full or partial replacement by or insertion of the inhibitory peptide sequences. Specifically preferred replacement and insertion sites are underlined.

In another embodiment, the inhibitory peptide is inserted into the Fc loop defined as the sequence EEMTK, between Fc residues Met and Lys and includes two Gly residues as linkers flanking either side of the inserted peptide, as shown in SEQ ID NO: 209, i.e.,
SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMGGAQQEECEW

DPWTCEHMGSGSATGGSGSTASSGSGSATHQEECEWDPWTCEHMLEGGTK

-continued

NQVSLTCLVKGFYPSDIAVEWESNGQPENNYKTTPPVLDSDGSFFLYSKL

TVDKSRWQQGNVFSCSVMHEALHNHYTQKSLSLSPGK.

The Gly linkers are in italics, and the inhibitory peptide insertion is underlined. The insertion site is also demonstrated in FIGS. 13A-14B of TS-ZPT-3. In the heavy chain, the first underlined section corresponds to the anti-PD-1 variable domain, the second underlined section corresponds to the trebananib peptide inserted in the Fc loop, and the third underlined section corresponds to the aflibercept domain fused to the carboxy-terminal end.

Other peptide inhibitors of Tie2 activation (including Ang-2 inhibitors) include A-11 (Compugen), which comprises the amino acid sequence ETFLSTNKLENQ (SEQ ID NO:184); a peptide having the amino acid sequence NSL-SNASEFRAPY (SEQ ID NO:195); a peptide having the amino acid sequence NLLMAAS (SEQ ID NO:196); the CVX-060 peptide (Pfizer); the CVX-037 peptide (Pfizer); and CGEN-25017 (Compugen). Additional peptide inhibitors of Tie2 activation are described in U.S. Pat. No. 7,138,370. Exemplary peptide inhibitors of angiopoietin-1 or -2 are described in U.S. Pat. Nos. 7,138,370, 7,521,053, 7,658,924, and 8,030,025.

Antibody inhibitors of Tie2 activation (and/or angiopoietin-2) include AMG-780 (Amgen), MEDI-3617 (Medlmmune/AstraZeneca), DX-2240 (Dyax/Sanofi-Aventis), REGN-910 (Sanofi/Regeneron), RG7594 (Roche), LC06 (Roche), TAvi6 (Roche), AT-006 (Roche/Affitech). Additional Tie2 receptor binding antibody antagonists and antibody binding sequences therefrom are described in U.S. Pat. Nos. 6,376,653, 7,521,053, 7,658,924, 8,030,025, as well as U.S. Patent Application Publication Nos. 2013/0078248, 2013/0259859, and 2015/0197578.

Tie2 binding antagonists also include the small molecule inhibitors, CGI-1842 (CGI Pharmaceuticals), LP-590 (Locus Pharmaceuticals), ACTB-1003 (Act Biotech/Bayer AG), CEP-11981 (Cephalon/Teva), MGCD265 (Methylgene), Regorafenib (Bayer), Cabozantinib/XL-184/BMS-907351 (Exelixis), Foretnib (Exelixis), MGCD-265 (MethylGene Inc.).

C. TGF Pathway Inhibitors

TGF-β includes a multifunctional set of peptides that control cell proliferation and differentiation, migration and adhesion, extracellular matrix modification including tumor stroma and immunosuppression, angiogenesis and desmoplasia, apoptosis, and other functions in many cell types. TGF-β is a potent inducer of angiogenesis, which provides a critical support system for solid tumors, as well as a mechanism for tumor cell dissemination. Many cells synthesize TGF-β and almost all of them have specific receptors for these peptides. TGF-β1, TGF-β2, and TGF-β3 all function through the same receptor signaling systems. The active form of TGF-β is a dimer that signals through the formation of a membrane bound heterotetramer composed of the serine threonine type 1 and type 2 receptors, TGF-β RI and TGFβ RII, respectively.

Recently, TGF-β pathway inhibitors have been developed in the form of e.g., antibodies or binding fragments directed against TGF-β1 or TGF-β1 RII, such as dominant negative fusion protein fragments containing the extracellular domain (ECD) of TGF-β1 RII. As further described herein, the TGFβ1 RII ECD has been further combined with additional binding agents targeting additional checkpoint regulator pathways or angiogenesis pathways, which are central to tumor growth and dissemination. An exemplary human TGF-β1 RII ECD (wild-type) has the amino acid sequence set forth in SEQ ID NO:186.

A TGF-β pathway inhibitor may be in the form of e.g., antibodies or variable domain fragments directed against TGF-β1 or a TGF-β1 RII, a TGF binding peptide, or dominant negative fusion protein fragment, such as the extracellular domain (ECD) of TGF-β1 RII. In certain embodiments, a bispecific or trispecific antitumor antagonist comprises a TGF-β1 RII ECD. In certain embodiments, a bispecific or trispecific antitumor antagonist comprises a TGF-β1 RII ECD. In some embodiments, the TGF-β1 RII ECD is fused to the carboxy-terminus of an IgG in a bispecific or trispecific antitumor antagonist, as depicted in e.g., FIGS. 30A and 30E. In other embodiments, the TGF-β1 RII ECD is fused to the amino-terminus of an IgG in a bispecific or trispecific antitumor antagonist, as depicted in e.g., FIGS. 30B and 30D. In yet other embodiments, the TGF-β1 RII ECD is inserted within the IgG Fc fragments (i.e., CH2 or CH3 regions) of an IgG in a bispecific or trispecific antitumor antagonist, as depicted in e.g., FIGS. 30C and 30F.

Exemplary anti-TGF-β1 antibodies are described in U.S. Pat. Nos. 7,067,637, 7,494,651, 7,527,791, and 7,619,069. Exemplary anti-TGF-β1 RII antibodies are described in U.S. Pat. No. 7,579,186. An exemplary peptide inhibitor of TGF-β1 is KRIWFIPRSSWYERA (SEQ ID NO:197).

D. Overall Configurations of the Targeting Domains

Any one of the anti-PD-1, anti-PD-L1, anti-TIGIT, anti-LAG-3, anti-VEGF, anti-VEGFR, anti-angiopoietin-1/2, and/or anti-Tie2 receptor antagonists can be in the form of a monoclonal antibody, chimeric antibody, humanized antibody, scFv or multi-specific antagonists, such as bispecific and trispecific antagonists. In addition, any of the antagonists described herein may include multiple binding specificities targeting PD-1, PD-L1, TIGIT, LAG-3, VEGF, VEGFR, angiopoietin, and/or Tie2 receptor. Moreover, any of the antibody antagonists may be engineered to target multiple epitopes in a given target. Furthermore, in some embodiments, the checkpoint antagonist and/or angiogenesis specificity may be included in the form of a dominant negative fusion protein, such as an extracellular domain (ECD) from a corresponding receptor.

The HCVRs and LCVRs described herein may be structurally linked to a naturally-occurring CH1-CH2-CH3 region or a non-naturally occurring or mutated Fc (CH2-CH3) region, e.g., an effectorless or mostly effectorless Fc (e.g., human IgG2 or IgG4) or, alternatively, an Fc with enhanced binding to one or more activating Fc receptors (FcγRI, FcγRIIa or FcγRIIIa) so as to enhance Treg depletion in the tumor environment. Accordingly, in certain embodiments the anti-PD-1, anti-PD-L1, anti-TIGIT, anti-LAG-3, anti-VEGF, anti-VEGFR HCVRs and LCVRs described herein may be structurally linked to an CH1-CH2-CH3 comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. More specifically, in certain embodiments, the antibodies in the present application may include modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for Clq and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

For uses where effector function is to be avoided altogether, e.g., when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) may be generated that is devoid of effector function, lacking the ability to bind FcγRs (like IgG2) and activate complement (like IgG4). When using an IgG4 constant domain, it is usually preferable to include the substitution S228P, which mimics the hinge sequence in IgG1 and thereby stabilizes IgG4 molecules, reducing Fab-arm exchange between the therapeutic antibody and endogenous IgG4 in the patient being treated.

In certain embodiments, the anti-PD-1, anti-PD-L1, anti-TIGIT, anti-LAG-3, anti-VEGF, anti-VEGFR, anti-angiopoietin, and anti-Tie2R antibodies or fragments thereof may be modified to increase its biological half-life. Various approaches may be employed, including e.g., that increase the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022. The numbering of residues in the Fc region is that of the EU index. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g., if sequences differ between naturally occurring isotypes, or if multiple mutations may be substituted at the position, they are separated by slashes (e.g., "X/Y/Z").

Exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 31 IA, 312A, 378Q, 380A, 382A, 434A (Shields et al. (2001) J. Biol. Chem., 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) J. Immunol., 169:5171-5180, Dall'Acqua et al. (2006) J. Biol. Chem., 281:23514-23524, and U.S. Pat. No. 8,367,805.

Modification of certain conserved residues in IgG Fc (I253, H310, Q311, H433, N434), such as the N434A variant (Yeung et al. (2009) J. Immunol. 182:7663), have been proposed as a way to increase FcRn affinity, thus increasing the half-life of the antibody in circulation (WO 98/023289). The combination Fc variant comprising M428L and N434S has been shown to increase FcRn binding and increase serum half-life up to five-fold (Zalevsky et al. (2010) Nat. Biotechnol. 28:157). The combination Fc variant comprising T307A, E380A and N434A modifications also extends half-life of IgG1 antibodies (Petkova et al. (2006) Int. Immunol. 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life (U.S. 2006/173170). Further, a combination Fc variant comprising M252Y, S254T and T256E was reported to increase half-life-nearly 4-fold. Dall'Acqua et al. (2006) J. Biol. Chem. 281:23514.

IV. Preferred Embodiments of Trispecific Antagonists

In one embodiment, the trispecific antitumor antagonist comprises: (1) a first targeting domain comprises: (a) a heavy chain variable region having an amino acid sequence that is about 80% to about 100% identity to an amino acid sequence selected from the group consisting of SEQ ID NOS:127, 129, 131, 133, 135 and 137; and (b) a light chain variable region having an amino acid sequence that is about 80% to about 100% identity to an amino acid sequence selected from the group consisting of SEQ ID NOS: 128, 130, 132, 134, 136 and 138; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid sequence selected from the group consisting of SEQ ID NOS:48, 51, 54, 56 and 59, wherein HCDR2 has an amino acid sequence that is about 80%, about 85%, about 90%, about 95% or about 100% identity to an amino acid sequence selected from the group consisting of SEQ ID NOS:49, 52, 57 and 60, and wherein HCDR3 has an amino acid sequence that is about 80%, about 90% or about 100% identity to an amino acid sequence selected from the group consisting of SEQ ID NOS:50, 53, 55, 58 and 61, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence selected from the group consisting of SEQ ID NOS:62, 65, 68, 69, 70 and 73, wherein HCDR2 has an amino acid sequence that is about 80%, about 90% or about 100% identity to an amino acid sequence selected from the group consisting of SEQ ID NOS:63, 66, 71 and 74, and wherein HCDR3 has an amino acid sequence that is about 80%, about 90% or about 100% identity to an amino acid sequence selected from the group consisting of SEQ ID NOS:64, 67, 72 and 75; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In a preferred embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid of SEQ ID NO:59, wherein HCDR2 has an amino acid sequence that is about 80%, about 85%, about 90%, about 95% or about 100% identity to an amino acid sequence of SEQ ID NO:60, and wherein HCDR3 has an amino acid sequence that is about 80%, about 90% or about 100% identity to an amino acid sequence of SEQ ID NO:61, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence of SEQ ID NO:73, wherein HCDR2 has an amino acid sequence that is about 80%, about 90% or about 100% identity to an amino acid sequence of SEQ ID NO:74, and wherein HCDR3 has an amino acid sequence that is about 80%, about 90% or about 100% identity to an amino acid sequence of SEQ ID NO:75; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid of SEQ ID NO:56, wherein HCDR2 has an amino acid sequence that is about 80%, about 85%, about 90%, about 95% or about 100% identity to an amino acid sequence of SEQ ID NO:57, and wherein HCDR3 has an amino acid sequence that is about 80%, about 90% or about 100% identity to an amino acid sequence of SEQ ID NO:58, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence of SEQ ID NO:70, wherein HCDR2 has an amino acid sequence that is about 80%, about 90% or about 100% identity to an amino acid sequence of SEQ ID NO:71, and wherein HCDR3 has an amino acid sequence that is about 80%, about 90% or about 100% identity to an amino acid sequence of SEQ ID NO:72; (2) a second targeting domain conferred by one or more anti-VEGF antagonist and/or one or more anti-VEGFR antagonist as further described herein and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain conferred by one or more variable regions comprising one or more anti-PD-1 variable domains or one or more anti-PD-L1 variable domains; (2) a second targeting domain conferred by an aflibercept (or Zaltrap®) domain with amino acid sequence of SEQ ID NO:185; and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an aflibercept (or Zaltrap®) domain with amino acid sequence of SEQ ID NO: 185; and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an aflibercept (or Zaltrap®) domain with amino acid sequence of SEQ ID NO: 185; and (3) a third targeting domain comprising a biological peptide that binds specifically to Tie2 tyrosine kinase receptor, Ang-1, Ang-2, Ang-3 or Ang-4 as further described herein. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an aflibercept (or Zaltrap®) domain with amino acid sequence of SEQ ID NO: 185; and (3) a third targeting domain comprises only one of the amino acid sequence of SEQ ID NO: 194. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an aflibercept (or Zaltrap®) domain with amino acid sequence of SEQ ID NO: 185; and (3) a third targeting domain comprises only one of the amino acid sequence of SEQ ID NO: 194. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an aflibercept (or Zaltrap®) domain with amino acid sequence of SEQ ID NO: 185; and (3) a third targeting domain comprises the amino acid sequence of SEQ ID NO: 182. In another embodiment, the second targeting domain is inserted downstream of the CH3 domain at the carboxy-terminal end of the antagonist, and the third targeting domain is inserted within the CH3 domain.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an aflibercept (or Zaltrap®) domain with amino acid sequence of SEQ ID NO: 185; and (3) a third targeting domain comprises the amino acid sequence of SEQ ID NO: 182. In another embodiment, the second targeting domain is inserted downstream of the CH3 domain at the carboxy-terminal end of the antagonist, and the third targeting domain is inserted within the CH3 domain.

In other embodiments, the trispecific antitumor antagonists comprises: a heavy chain having an amino acid sequence that is about 80% to about 100% identity to an amino acid sequence selected from the group consisting of SEQ ID NOS:198, 200, 202, 203 and 204; and a light chain having an amino acid sequence that is about 80% to about 100% identity to an amino acid sequence selected from the group consisting of SEQ ID NOS:199 and 201.

In other embodiments, the trispecific antitumor antagonists comprises: a heavy chain having an amino acid sequence that is about 80% to about 100% identity to an amino acid sequence of SEQ ID NO:198; and a light chain having an amino acid sequence that is about 80% to about 100% identity to an amino acid sequence of SEQ ID NO:199.

In other embodiments, the trispecific antitumor antagonists comprises: a heavy chain having an amino acid sequence that is about 80% to about 100% identity to an amino acid sequence of SEQ ID NO:200; and a light chain having an amino acid sequence that is about 80% to about 100% identity to an amino acid sequence of SEQ ID NO:201.

In other embodiments, the trispecific antitumor antagonists comprises: a heavy chain having an amino acid sequence that is about 80% to about 100% identity to an amino acid sequence of SEQ ID NO:202; and a light chain having an amino acid sequence that is about 80% to about 100% identity to an amino acid sequence of SEQ ID NO:201.

Figure 5C:
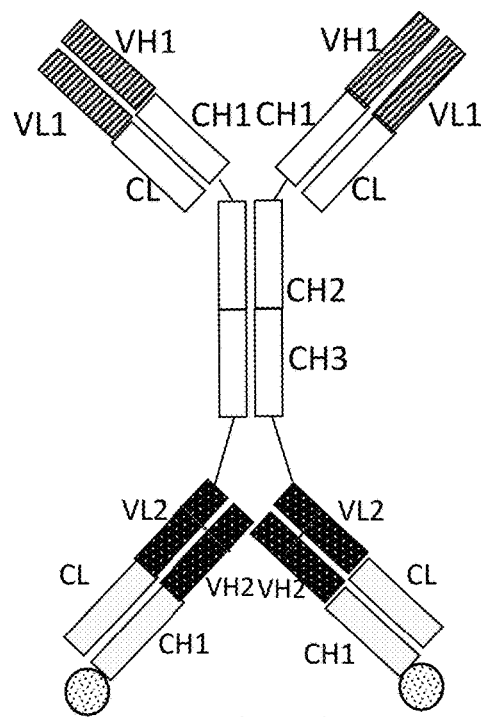

FIGS. 3A-FIG. 4C show a variety of different trispecific antitumor antagonists, where: (1) the VH1 and VL1 regions correspond to anti-PD-1 variable domains or other checkpoint antibodies; (2) the double ovals correspond to aflibercept fusion protein domains; and (3) the circles correspond to trebananib peptide. FIGS. 5A-5E show a variety of different trispecific antagonists where (1) the VH1 and VL1 regions correspond to anti-PD-1 variable domains or another checkpoint antibody; (2) VH and VL of bevacizumab or another anti-VEGF-A antibody (3) the circles correspond to trebananib peptide. As shown in these figures, these components can be rearranged in multiple configurations. For example, the trebananib peptides are arranged in the following locations: (i) fused to the carboxy-terminal end of each IgG4 CH3 region (FIGS. 3A-3D); (ii) inserted within each of the two CH3 regions (FIG. 3E, FIG. 4A, and FIG. 5A); (iii) fused to the carboxy-terminal end of each CH1 region (FIG. 3F, FIG. 4C, FIG. 5C-5E); (iv) fused to the carboxy-terminal end of each aflibercept fusion protein domain (FIG. 3G); (v) fused to the carboxy-terminal end of each CL region (FIG. 3H, FIG. 5B); or (vi) fused to the amino-terminal end of the CH2 domain (FIG. 4B).

In other embodiments, the trispecific antitumor antagonist comprises: (1) a first targeting domain comprises: (a) a heavy chain variable region having an amino acid sequence that is about 80% to about 100% identity to an amino acid sequence selected from the group consisting of SEQ ID NOS:127, 129, 131, 133, 135 and 137; and (b) a light chain variable region having an amino acid sequence that is about 80% to about 100% identity to an amino acid sequence selected from the group consisting of SEQ ID NOS: 128, 130, 132, 134, 136 and 138; (2) a second targeting domain comprising an anti-VEGF antagonist or an anti-VEGFR antagonist; and (3) a third targeting domain comprising a TGF-β pathway inhibitor. In one embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain comprising an anti-VEGF antagonist or an anti-VEGFR antagonist; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain comprising an anti-VEGF antagonist or an anti-VEGFR antagonist; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid sequence selected from the group consisting of SEQ ID NOS:48, 51, 54, 56 and 59, wherein HCDR2 has an amino acid sequence that is about 80%, about 85%, about 90%, about 95% or about 100% identity to an amino acid sequence selected from the group consisting of SEQ ID NOS:49, 52, 57 and 60, and wherein HCDR3 has an amino acid sequence that is about 80%, about 90% or about 100% identity to an amino acid sequence selected from the group consisting of SEQ ID NOS:50, 53, 55, 58 and 61, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence selected from the group consisting of SEQ ID NOS:62, 65, 68, 69, 70 and 73, wherein HCDR2 has an amino acid sequence that is about 80%, about 90% or about 100% identity to an amino acid sequence selected from the group consisting of SEQ ID NOS:63, 66, 71 and 74, and wherein HCDR3 has an amino acid sequence that is about 80%, about 90% or about 100% identity to an amino acid sequence selected from the group consisting of SEQ ID NOS:64, 67, 72 and 75; (2) a second targeting domain comprising an anti-VEGF antagonist or an anti-VEGFR antagonist; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid of SEQ ID NO:59, wherein HCDR2 has an amino acid sequence that is about 80%, about 85%, about 90%, about 95% or about 100% identity to an amino acid sequence of SEQ ID NO:60, and wherein HCDR3 has an amino acid sequence that is about 80%, about 90% or about 100% identity to an amino acid sequence of SEQ ID NO:61, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence of SEQ ID NO:73, wherein HCDR2 has an amino acid sequence that is about 80%, about 90% or about 100% identity to an amino acid sequence of SEQ ID NO:74, and wherein HCDR3 has an amino acid sequence that is about 80%, about 90% or about 100% identity to an amino acid sequence of SEQ ID NO:75; (2) a second targeting domain conferred by one or more anti-VEGF antagonist and/or one or more anti-VEGFR antagonist as further described herein and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region, wherein the heavy chain variable region comprises three complementarity determining regions (HCDRs): HCDR1, HCDR2 and HCDR3, wherein HCDR1 has an amino acid sequence that is about 80% or about 100% identity to an amino acid of SEQ ID NO:56, wherein HCDR2 has an amino acid sequence that is about 80%, about 85%, about 90%, about 95% or about 100% identity to an amino acid sequence of SEQ ID NO:57, and wherein HCDR3 has an amino acid sequence that is about 80%, about 90% or about 100% identity to an amino acid sequence of SEQ ID NO:58, and (b) a light chain variable region, wherein the light chain variable region comprises three complementarity determining regions (LCDRs): LCDR1, LCDR2 and LCDR3, wherein LCDR1 has an amino acid sequence that is about 80%, about 90% or about 100% identity to an amino acid sequence of SEQ ID NO:70, wherein HCDR2 has an amino acid sequence that is about 80%, about 90% or about 100% identity to an amino acid sequence of SEQ ID NO:71, and wherein HCDR3 has an amino acid sequence that is about 80%, about 90% or about 100% identity to an amino acid sequence of SEQ ID NO:72; (2) a second targeting domain conferred by one or more anti-VEGF antagonist and/or one or more anti-VEGFR antagonist as further described herein and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an aflibercept (or Zaltrap®) domain with amino acid sequence of SEQ ID NO: 185; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an aflibercept (or Zaltrap®) domain with amino acid sequence of SEQ ID NO: 185; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an a-glycosylated aflibercept (or Zaltrap®) domain with amino acid sequence of SEQ ID NO: 185; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an a-glycosylated aflibercept (or Zaltrap®) domain with amino acid sequence of SEQ ID NO: 185; and (3) a third targeting domain comprising a TGF-β pathway inhibitor. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an aflibercept (or Zaltrap®) domain with amino acid sequence of SEQ ID NO: 185; and (3) a third targeting domain comprises a TGFβ1 RII extracellular domain (EAD) with amino acid sequence of SEQ ID NO: 186. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an aflibercept (or Zaltrap®) domain with amino acid sequence of SEQ ID NO: 185; and (3) a third targeting domain comprises a TGFβ1 RII extracellular domain (ECD) with amino acid sequence of SEQ ID NO: 186. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:137, and (b) a light chain variable region having an amino acid sequence that is about 80% to about 100% identity to an amino acid sequence of SEQ ID NO: 138; (2) a second targeting domain conferred by an a-glycosylated aflibercept (or Zaltrap®) domain with amino acid sequence of SEQ ID NO: 185; and (3) a third targeting domain comprises a TGFβ1 RII extracellular domain (EAD) with amino acid sequence of SEQ ID NO:186. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonist comprises: (1) a first targeting domain comprises: (a) a heavy chain variable region having an amino acid sequence that is about 80% to about 100% identity to an amino acid sequence of SEQ ID NO:135, and (b) a light chain variable region having an amino acid sequence that is about 80% to about 100% identity to an amino acid sequence of SEQ ID NO: 136; (2) a second targeting domain conferred by an a-glycosylated aflibercept (or Zaltrap®) domain with amino acid sequence of SEQ ID NO:185; and (3) a third targeting domain comprises a TGFβ1 RII extracellular domain (ECD) with amino acid sequence of SEQ ID NO:186. In another embodiment, the second targeting domain is inserted downstream of the CH3 domain at the carboxy-terminal end of the antagonist, and the third targeting domain is inserted downstream of the second targeting domain at the carboxy-terminal end.

In other embodiments, the trispecific antitumor antagonists comprise: a heavy chain having an amino acid sequence that is about 80% to about 100% identity to an amino acid sequence selected from the group consisting of SEQ ID NOS:187, 189, 190, 192, 205 and 206; and a light chain having an amino acid sequence that is about 80% to about 100% identity to an amino acid sequence selected from the group consisting of SEQ ID NOS:188, 191 and 193.

In other embodiments, the trispecific antitumor antagonists comprise: a heavy chain having an amino acid sequence that is about 80% to about 100% identity to an amino acid sequence of SEQ ID NO:192; and a light chain having an amino acid sequence that is about 80% to about 100% identity to an amino acid sequence of SEQ ID NO:193.

In other embodiments, the trispecific antitumor antagonists comprise: a heavy chain having an amino acid sequence that is about 80% to about 100% identity to an amino acid sequence of SEQ ID NO:205; and a light chain having an amino acid sequence that is about 80% to about 100% identity to an amino acid sequence of SEQ ID NO:193.

In other embodiments, the trispecific antitumor antagonists comprise: a heavy chain having an amino acid sequence that is about 80% to about 100% identity to an amino acid sequence of SEQ ID NO:206; and a light chain having an amino acid sequence that is about 80% to about 100% identity to an amino acid sequence of SEQ ID NO:193.

The trispecific antitumor antagonists of the present application may be constructed with an IgG backbone. More specifically, any of the trispecific antagonists of the present application may be constructed with an IgG1 or IgG4 backbone. Use of an IgG1 backbone is preferable for cancer treatment where a target is present on antigen presenting cells that can mediate antibody-dependent cell-mediated cytotoxicity (ADCC). Use of an IgG4 backbone allows targeting of antigen where antigen binding alone is sufficient to generate the desired therapeutic benefits. IgG4-based antagonists preclude undesirable effector functions associated with e.g., IgG1 antibodies, including FcγR binding and complement activation.

V. Methods of Using the Antitumor Antagonists

The antitumor antagonists of the present application, such as anti-PD-1 antagonists, anti-PD-1 antibody fragments, anti-PD-L1 antibodies, anti-PD-L1 antibody fragments, anti-TIGIT antibodies, anti-TIGIT antibody fragments, anti-LAG-3 antibodies, anti-LAG-3 antibody fragments, angiogenesis pathway inhibitors, TGFβ pathway inhibitors, as well as bispecific antitumor antagonists and trispecific antitumor antagonists that bind specifically to PD-1, PD-L1, TIGIT, LAG-3, VEGF/VEGFR, TGFβ/TGFβ receptor, have numerous in vitro and in vivo utilities including, for example, enhancement of immune responses and treatment of cancers, infectious diseases or autoimmune diseases.

A. Antitumor Therapy

In some embodiments, the antitumor antagonists of the present application are administered to cells in culture, in vitro or ex vivo, or to human subjects, e.g., in vivo, to enhance immunity in a variety of diseases. Accordingly, provided herein are methods of modifying an immune response in a subject comprising administering to the subject an antibody or antigen-binding fragment thereof as described herein such that the immune response in the subject is enhanced, stimulated or up-regulated. Preferred subjects include human patients in whom enhancement of an immune response would be desirable. The methods are particularly suitable for treating human patients having a disorder that can be treated by augmenting an immune response (e.g., the T-cell mediated immune response). The methods are particularly suitable for treatment of cancer or chronic infections in vivo. For example, the anti-PD-1, anti-PD-L1, anti-TIGIT or anti-LAG-3 compositions may be administered together with an antigen of interest or the antigen may already be present in the subject to be treated (e.g., a tumor-bearing or virus-bearing subject) to enhance antigen-specific immunity. When anti-TIGIT antibodies are administered together with another agent, the two can be administered separately or simultaneously.

In some embodiments, the checkpoint regulator antagonist used in the above-described method is an anti-PD-1 antibody, anti-PD-L1 antibody, anti-TIGIT antibody, anti-LAG-3 antibody, a fragment thereof, or combination thereof. In some embodiments, the checkpoint regulator antagonist is a bispecific or trispecific antibody of the present application.

In some embodiments, the checkpoint regulator antagonist or antitumor antagonist is in the form of an antibody or antibody fragment. In some embodiments, the antibodies described herein are human or humanized antibodies.

Also encompassed are methods for detecting and/or measuring the presence of human PD-1, human PD-L1, human TIGIT or human LAG-3, in a sample comprising contacting the sample and a control sample, with a human monoclonal antibody thereof, or an antigen binding fragment thereof, which specifically binds to human PD-1, human PD-L1, human TIGIT or human LAG-3 under conditions that allow for formation of a complex between the antibody or fragment thereof and human PD-1, human PD-L1, human TIGIT or human LAG-3. The formation of a complex is then detected, wherein a difference in complex formation between the sample compared to the control sample is indicative the presence of human PD-1, human PD-L1, human TIGIT or human LAG-3 antigen in the sample.

Given the ability of anti-PD-1, anti-PD-L1, anti-TIGIT and anti-LAG-3 antibodies to block inhibition or co-inhibition of T cell responses, provided herein are in vitro and in vivo methods of using the antibodies described herein to stimulate, enhance or upregulate antigen-specific T cell responses, e.g., anti-tumor T cell responses. In certain embodiments, CD3 stimulation is also provided (e.g., by co-incubation with a cell expressing membrane CD3), which stimulation can be provided at the same time, before, or after treatment with an anti-PD-1, anti-PD-L1, anti-TIGIT or anti-LAG-3 antibody. For example, provided herein are methods of enhancing an antigen-specific T cell response comprising contacting said T cell with an anti-PD-1, anti-PD-L1, anti-TIGIT or anti-LAG-3 antibody described herein, and optionally with CD3, such that an antigen-specific T cell response is enhanced, e.g., by removal of a PD-1, PD-L1, TIGIT or LAG-3 mediated inhibitory effect. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-gamma production by the antigen-specific T cell is enhanced.

Further encompassed are methods for enhancing an immune response (e.g., an antigen-specific T cell response) in a subject comprising administering an anti-PD-1 antibody, an anti-PD-L1 antibody, an anti-TIGIT antibody, an anti-LAG-3 antibody, or a bispecific or trispecific antitumor antagonist described herein to the subject such that an immune response (e.g., an antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In other embodiments, a tumor is non-immunogenic. In certain embodiments, a tumor is PD-L1 positive. In other embodiments a tumor is PD-L1 negative. A subject may also be a virus-bearing subject in whom an immune response against the virus is enhanced as a consequence of administering an anti-PD-1 antibody, anti-PD-L1 antibody, anti-TIGIT antibody, anti-LAG-3 antibody, bispecific antitumor antagonist or trispecific antitumor antagonist as described herein.

In one embodiment, a method for inhibiting the growth of tumor cells in a subject comprises administering to the subject an anti-PD-1 antibody, anti-PD-L1 antibody, anti-TIGIT antibody, anti-LAG-3 antibody, bispecific antitumor antagonist or trispecific antitumor antagonist described herein such that growth of the tumor is inhibited in the subject. Also provided are methods of treating chronic viral infection in a subject comprising administering to the subject an anti-PD-1 antibody, anti-PD-L1 antibody, anti-TIGIT antibody, anti-LAG-3 antibody, bispecific antitumor antagonist or trispecific antitumor antagonist as described herein such that the chronic viral infection is treated in the subject.

Also encompassed herein are methods for depleting Treg cells from the tumor microenvironment of a subject with a tumor, e.g., cancerous tumor, comprising administering to the subject a therapeutically effective amount of an anti-PD-1 antibody, anti-PD-L1 antibody, anti-TIGIT antibody, anti-LAG-3 antibody, bispecific antitumor antagonist or trispecific antitumor antagonist described herein that comprises an Fc that stimulates depletion of Treg cells in the tumor microenvironment. An Fc may, e.g., be an Fc with effector function or enhanced effector function, such as binding or having enhanced binding to one or more activating Fc receptors.

In a preferred embodiment, Treg depletion occurs without significant depletion or inhibition of Teff in the tumor microenvironment, and without significant depletion or inhibition of Teff cells and Treg cells outside of the tumor microenvironment. In certain embodiments, the subject has higher levels of TIGIT on Treg cells than on Teff cells, e.g., in the tumor microenvironment. In certain embodiments, anti-TIGIT antibodies or antagonists may deplete Tregs in tumors and/or Tregs in tumor infiltrating lymphocytes (TILs). For example, in the CT26 tumor model, an anti-mouse TIGIT antibody formatted as a mouse IgG2a (which exhibits effector function) partially depleted both Treg and CD8+ T cells, but did not deplete CD4+ T cells. An effectorless counterpart anti-TIGIT antibody, formatted as a mouse IgG1 D265A, did not deplete T cells.

When considering whether or not to employ Fc effector function or an effectorless anti-TIGIT antibody, due consideration must be given to the tradeoff between depletion of Tregs, which may enhance anti-tumor immune response, and depletion of CD8+ T cells, which would eliminate some of the cells needed to actually kill tumor cells. Although depletion of Tregs might be expected to enhance anti-tumor activity, recent studies have demonstrated that ligation of TIGIT on TIGIT+ Tregs promotes Treg cell-mediated suppression of Teff cell proliferation (Joller et al. (2014) Immunity 40:569), suggesting that blocking of TIGIT signaling (e.g., using an antagonist anti-TIGIT antibody of the present invention) might also enhance anti-tumor activity. Accordingly, it may be most efficacious to use an antagonist anti-TIGIT antibody lacking effector function, which: i) blocks TIGIT signaling in Tregs thus reducing their immunesuppresive activity; ii) activates anti-tumor CD8+ T cells by blocking TIGIT's inhibitory effects, while at the same time avoiding their effector-function-mediated depletion; and iii) enhances DNAM-mediated activation by allowing DNAM to bind to PVR (CD155, the TIGIT ligand) that would otherwise have been bound by TIGIT (and by reducing direct TIGIT-DNAM interactions) (Johnston et al. (2014) Cancer Cell 26:923). The same is applicable to use of anti-PD-1 antibodies, anti-PD-L1 antibodies, bispecific antitumor antagonists, or trispecific antitumor antagonists.

In certain embodiments, an anti-PD-1 antibody, anti-PD-L1 antibody, anti-TIGIT antibody, anti-LAG-3 antibody, bispecific antitumor antagonist or trispecific antitumor antagonist described herein is given to a subject as an adjunctive therapy. Treatment of cancer patient with an anti-PD-1 antibody, anti-PD-L1 antibody, anti-TIGIT antibody, anti-LAG-3 antibody, bispecific antitumor antagonist or trispecific antitumor antagonist according to the present application may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a cancer patient with an anti-PD-1 antibody, anti-PD-L1 antibody, anti-TIGIT antibody, anti-LAG-3 antibody, bispecific antitumor antagonist or trispecific antitumor antagonist prevents recurrence of cancer or delays recurrence of cancer by, e.g., 1, 2, 3, 4, 5, or 10 or more years. An anti-PD-1, anti-PD-L1, anti-TIGIT, and/or anti-LAG-3 treatment can be used as a primary or secondary line of treatment.

In certain preferred embodiments, the subject has a cell proliferative disease or cancer. Blocking of PVR/Nectin-2 signaling through TIGIT by anti-TIGIT antibodies can enhance the immune response to cancerous cells in the patient. Similarly, blocking of Provided herein are methods for treating a subject having cancer, comprising administering to the subject an anti-PD-1, anti-PD-L1, anti-TIGIT, anti-LAG-3, bispecific antitumor antagonist or trispecific antitumor antagonist thereof as described herein, such that the subject is treated, e.g., such that growth of cancerous tumors is inhibited or reduced and/or that the tumors regress. An anti-PD-1, anti-PD-L1, anti-TIGIT, anti-LAG-3, bispecific antitumor antagonist or trispecific antitumor antagonist thereof as described herein can be used alone to inhibit the growth of cancerous tumors. Alternatively, any of these antitumor antagonists can be used in conjunction with another agent, e.g., other anti-cancer targets, immunogenic agents, standard cancer treatments, or other antibodies, as described below.

Accordingly, provided herein are methods of treating cancer, e.g., by inhibiting growth of tumor cells, in a subject, comprising administering to the subject a therapeutically effective amount of an anti-PD-1, anti-PD-L1, anti-TIGIT, anti-LAG-3, bispecific antitumor antagonist or trispecific antitumor antagonist as described herein. Preferably, the antibody is a human anti-PD-1, anti-PD-L1, anti-TIGIT or anti-LAG-3 antibody comprising the anti-PD-1, anti-PD-L1, anti-TIGIT or anti-LAG-3 HCVRs and LCVR described herein, or it may be a chimeric or humanized non-human anti-hu PD-1, anti-PD-L1 antibody, anti-hu TIGIT or anti-LAG-3 antibody, e.g., a chimeric or humanized anti-PD-1, anti-PD-L1, anti-TIGIT or anti-LAG-3 antibody that competes for binding with, or binds to the same epitope as, at least one of the anti-PD-1, anti-PD-L1, anti-TIGIT or anti-LAG-3 antibodies described herein.

Cancers whose growth may be inhibited using the antibodies of the application include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

An anti-PD-1 antibody, anti-PD-L1 antibody, anti-TIGIT, anti-LAG-3 antibody, bispecific antitumor antagonist or trispecific antitumor antagonist can be administered alone, in combination with another antitumor antagonist, or concurrently with another antitumor antagonist. An anti-PD-1 antibody, anti-TIGIT, anti-LAG-3 antibody, bispecific antitumor antagonist or trispecific antitumor antagonist can also be administered in combination, or concurrently with, an immunogenic agent, such as cancerous cells, tumor vaccines, purified tumor antigens (including recombinant proteins, peptides, and carbohydrate molecules), cells transfected with genes encoding immune stimulating cytokines, in a cancer vaccine strategy (He et al. (2004) J. Immunol. 173:4919-28), or an oncolytic virus.

Many experimental strategies for vaccination against tumors have been devised. In one of these strategies, a vaccine is prepared using autologous or allogeneic tumor cells. Some of these cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). Cancer vaccines have been shown to enhance effector T-cell infiltration into the tumors in preclinical models. The major types of cancer vaccines include peptide vaccines, vector-based antigen specific vaccines, whole-cell vaccines, and dendritic cell vaccines. All vaccine-based therapies are designed to deliver either single or multiple antigenic epitopes or antigens from the whole cells to the patients and induce tumor-specific effector T cells. Thus, a vaccine-based therapy may be the most efficient way to induce T-cell infiltration into the tumor.

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host.

PD-1, PD-L1, TIGIT and/or LAG-3 inhibition may be used in conjunction with a collection of recombinant proteins and/or peptides expressed in a tumor in order to generate an immune response to these proteins. Such proteins may be viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). Tumor antigens can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Non-limiting examples of tumor vaccines include sipuleucel-T (Provenge®), an FDA-approved tumor vaccine for metastatic prostate cancer; tumor cells transfected to express the cytokine granulocyte macrophage colony-stimulating factor (GM-CSF), such as the whole cell GM-CSF-secreting irradiated, allogeneic pancreatic cancer vaccine (GVAX; Johns Hopkins); a multi-peptide vaccine consisting of immunogenic peptides derived from breast cancer antigens, neu, legumain, and 3-catenin, which prolonged the vaccine-induced progression-free survival of breast tumor-bearing mice when administered in combination with anti-PD-1 antibody (Karyampudi L. et al. (2014) Cancer Res 74:2974-2985); peptides of melanoma antigens, such as peptides of gp100, MAGE antigens, Trp-2, MARTI and/or tyrosinase. Other tumor vaccines include proteins from viruses implicated in human cancers such as human papilloma viruses (HPV)(e.g., Gardasil®, Gardasil 9®, and Cervarix®; hepatitis B virus (e.g., Engerix-B and Recombivax HB); hepatitis C virus (HCV), Kaposi's sarcoma associated herpes sarcoma virus (KSHV). Another form of tumor specific antigen that can be used in conjunction with TIGIT inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity. Talimogene laherparepvec (T-VEC, or Imlygic®) is an FDA-approved oncolytic virus for the treatment of some patients with metastatic melanoma that cannot be surgically removed.

Dendritic cells (DC) are potent antigen presenting cells that can be used to prime antigen-specific responses. DC's can be produced ex vivo and loaded with various protein and peptide antigens, as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization may be effectively combined with TIGIT blocking to activate (unleash) more potent anti-tumor responses.

PD-1, PD-L1, TIGIT and/or LAG-3 inhibition can also be combined with standard cancer treatments (e.g., surgery, radiation, and chemotherapy). In particular, PD-1, PD-L1, TIGIT and/or LAG-3 inhibition can be effectively combined with chemotherapeutic regimes. In these instances, it may be possible to reduce the dose of chemotherapeutic reagent administered (Mokyr et al. (1998) Cancer Research 58: 5301-5304). An example of such a combination is an anti-tumor antagonist in combination with decarbazine for the treatment of melanoma. Another example of such a combination is a checkpoint regulator antagonist or antitumor antagonist in combination with interleukin-2 (IL-2) for the treatment of melanoma. For example, the scientific rationale behind the combined use of PD-1, PD-L1, TIGIT and/or LAG-3 inhibition and chemotherapy to promote cell death is a consequence of the cytotoxic action of most chemotherapeutic compounds, should result in increased levels of tumor antigen in the antigen presentation pathway. Other combination therapies that may result in synergy with TIGIT, PD-1, PD-L1 and/or LAG-3 inhibition through cell death are radiation, surgery, and hormone deprivation. Each of these protocols creates a source of tumor antigen in the host. Angiogenesis inhibitors can also be combined with TIGIT, PD-1, PD-L1 and/or LAG-3 inhibition. Inhibition of angiogenesis leads to tumor cell death, which may feed tumor antigen into host antigen presentation pathways.

The anti-TIGIT antibodies, anti-PD-1 antibodies, anti-PD-L1 antibodies, bispecific antitumor antagonists and trispecific antitumor antagonists described herein may also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/antitumor antigen (e.g., Her-2/neu) bispecific antibodies have been used to target macrophages to sites of tumor. This targeting may more effectively activate tumor specific responses. The T cell arm of these responses would be augmented by the inhibition of TIGIT, PD-1, PD-L1 and/or LAG-3. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity (Ridge et al. (1998) Nature 393: 474-478) and can be used in conjunction with anti-TIGIT antibodies. Activating antibodies to T cell costimulatory molecules, such as OX-40 (Weinberg et al.

(2000) Immunol 164: 2160-2169), CD137/4-1BB (Melero et al. (1997) Nature Medicine 3: 682-685 (1997), and ICOS (Hutloff et al. (1999) Nature 397: 262-266) may also provide for increased levels of T cell activation. In addition, inhibitors of other immune checkpoint regulators may also be used in conjunction with other antitumor antagonists described herein, as further described below.

Bone marrow transplantation is currently being used to treat a variety of tumors of hematopoietic origin. While graft versus host disease is a consequence of this treatment, TIGIT inhibition may be used to increase the effectiveness of the donor engrafted tumor specific T cells by reducing graft vs. tumor responses.

Ex vivo activation and expansion of antigen specific T cells and adoptive transfer of these cells into recipients in order to stimulate antigen-specific T cells against cancers or viral infections in the presence of anti-TIGIT antibodies can increase the frequency and activity of the adoptively transferred T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) Science 285: 546-51). These methods can also be used to activate T cell responses to infectious agents such as CMV. Ex vivo activation in the presence of anti-TIGIT antibodies can increase the frequency and activity of the adoptively transferred T cells.

In certain embodiments, an antitumor antagonist described herein may be administered to a subject with an infectious disease, especially chronic infections. In this case, similar to its application to cancer, antibody-mediated PD-1, PD-L1, TIGIT and/or LAG-3 inhibition can be used alone, or as an adjuvant, in combination with vaccines, to enhance immune responsiveness to pathogens, toxins, and self-antigens. Exemplary pathogens for which this therapeutic approach can be applied include, but are not limited to, HIV, Hepatitis (A, B, & C), Influenza, Herpes, *Giardia*, Malaria, *Leishmania, Staphylococcus aureus*, and *Pseudomonas aeruginosa*. PD-1, PD-L1, TIGIT and/or LAG-3 inhibition is particularly useful against established infections by agents such as HIV that present novel or altered antigens over the course of the infections. Administration of the anti-PD-1 antibodies, anti-PD-L1 antibodies, anti-TIGIT antibodies, bispecific antitumor antagonists and trispecific antitumor antagonists can allow for recognition of these antigens as foreign so as to provoke an appropriate T cell response.

Other pathogenic viruses causing infections treatable by the methods described herein include HIV, hepatitis (A, B, or C), herpesvirus infections (e.g., VZV, HSV-1, HAV-6, HSV-II, and CMV, Epstein Barr virus), and infections caused by an adenovirus, influenza virus, flavivirus, echoviruses, rhinoviruses, coxsackie viruses, coronaviruses, respiratory syncytial viruses, mumps viruses, rotavirus, measles virus, rubella virus, parvovirus, vaccinia virus, HTLV virus, dengue virus, papillomavirus, molluscum virus, poliovirus, rabies virus, JC virus, arboviral encephalitis virus, or combination thereof.

Exemplary pathogenic bacteria or diseases caused therefrom which may be treatable by the methods described herein include *Chlamydia, Rickettsia*, Mycobacteria, Staphylococci, Streptococci, Pneumonococci, Meningococci and Gonococci, *Klebsiella, Proteus, Serratia, Pseudomonas, Legionella, Diphtheria, Salmonella*, Bacilli, Cholera, Leptospirosis tetanus, botulism, anthrax, plague, and Lyme disease.

Exemplary pathogenic fungi causing infections treatable by the methods described herein include *Candida* (e.g., *albicans, krusei, glabrata, tropicalis*, etc.), *Cryptococcus neoformans, Aspergillus* (e.g., *fumigatus, niger*, etc.), Mucorales (e.g., *mucor, absidia, rhizopus*), *Sporothrix schenkii, Blastomyces dermatitidis, Paracoccidioides brasiliensis, Coccidioides immitis* and *Histoplasma capsulatum*.

Exemplary pathogenic parasites causing infections treatable by the methods described herein include *Entamoeba histolytica, Balantidium coli, Naegleria fowleri, Acanthamoeba* sp., *Giardia* Zambia, *Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*.

In all of the above methods, PD-1, PD-L1, TIGIT and/or LAG-3 inhibition can be combined with other forms of immunotherapy such as cytokine treatment (e.g., interferons, GM-CSF, G-CSF, IL-2), or bispecific antibody therapy using two different binding specificities to provide enhanced presentation of tumor antigens.

Anti-PD-1 antibodies, anti-PD-L1 antibodies, anti-TIGIT antibodies, anti-LAG-3 antibodies, bispecific antitumor antagonists and trispecific antitumor antagonists described herein can be used to enhance antigen-specific immune responses by co-administration of one or more of any of these antibodies with an antigen of interest (e.g., a vaccine). Accordingly, provided herein are methods of enhancing an immune response to an antigen in a subject, comprising administering to the subject: (i) the antigen; and (ii) anti-PD-1 antibody, anti-PD-L1 antibody, an anti-TIGIT antibody, anti-LAG-3 antibody, bispecific antitumor antagonists, trispecific antitumor antagonist, or combination thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which an anti-PD-1 antibody, anti-PD-L1 antibody, anti-TIGIT antibody, LAG-3 antibody, bispecific antitumor antagonists, trispecific antitumor antagonist binds may be used as a vaccine instead of, or in addition to, the antitumor antagonist(s).

Suitable routes of administering the antibody compositions (e.g., human monoclonal antibodies, multi-specific antibodies or antagonists and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

B. Pharmaceutical Compositions and Methods of Treatment

Another aspect of the present application relates to pharmaceutical compositions and methods for treating a cell proliferative disorder, such as cancer, chronic infections, or immunologically compromised disease states. In one embodiment, the pharmaceutical composition comprises one or more antitumor antagonists of the present application. In some embodiments, the antitumor antagonist(s) comprise one or more checkpoint regulator antagonists, such as PD-1 inhibitors, PD-L1 inhibitors, anti-TIGIT inhibitors, LAG-3 inhibitors; one or more angiogenesis inhibitors, such as VEGF inhibitors, VEGFR2 inhibitors, angiopoietin-1/2 inhibitors, and Tie2R inhibitors; one or more antitumor inhibitors, such as TGF-β inhibitors and TGF-31 RII inhibitors; or bispecific and trispecific antitumor antagonists thereof. The antagonist(s) are formulated together with a pharmaceutically acceptable carrier. Pharmaceutical composition of the present application may include one or more different antibodies, one or more multispecific antibodies, one or more immunoconjugates, or a combination thereof as described herein.

As described above, methods for using the pharmaceutical compositions described herein comprise administering to a subject in need thereof an effective amount of the pharmaceutical composition according to the present disclosure.

Any suitable route or mode of administration can be employed for providing the patient with a therapeutically or prophylactically effective dose of the antibody or antagonist. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising an antibody or antagonist in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The antitumor antagonist can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic antitumor antagonist preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the antitumor antagonist to elicit a desired response in the individual, previous therapy, the age, weight and sex of the patient, the patient's clinical history and response to the antibody, the type of the antitumor antagonist used, discretion of the attending physician, etc. A therapeutically effective amount is also one in which any toxic or detrimental effect of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the antitumor antagonist are derived from the same host in which they are to be administered in order to reduce inflammatory responses against the administered therapeutic agents.

The antitumor antagonist is suitably administered to the patent at one time or over a series of treatments and may be administered to the patient at any time from diagnosis onwards. The antitumor antagonist may be administered as the sole treatment or in conjunction with other drugs or therapies useful in treating the condition in question.

As a general proposition, a therapeutically effective amount or prophylactically effective amount of the antitumor antagonist will be administered in a range from about 1 ng/kg body weight/day to about 100 mg/kg body weight/day whether by one or more administrations. In a particular embodiment, each antitumor antagonist is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 g/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the antitumor antagonist is administered at a dose of 500 g to 20 g every three days, or 25 mg/kg body weight every three days.

In other embodiments, each antitumor antagonist is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The antitumor antagonist may be administered daily, every 2, 3, 4, 5, 6 or 7 days, or every 1, 2, 3 or 4 weeks.

In other particular embodiments, the amount of the antitumor antagonist may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for an antitumor antagonist are incorporated into a suitable expression vector (e.g., viral or non-viral vector) for expressing an effective amount of the antitumor antagonist in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least 1010, at least 1011, at least 1012, at least 1013, at least 1014, at least 1015 genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

C. Combination Therapies

In another aspect, the present application provides combination therapies for enhancing an antigen-specific T cell response in a subject. In one embodiment, the method includes contacting a T cell with an anti-PD-1 antibody, anti-PD-L1 antibody, anti-TIGIT antibody, anti-LAG-3 antibody, antibody fragment thereof, bispecific antitumor antagonist or trispecific antitumor antagonist in combination with a second antibody, antibody fragment, antagonist or drug such that an antigen-specific T cell response or apoptotic pathway is enhanced.

In a related aspect, a method of reducing or depleting regulatory T cells in a tumor of a subject in need thereof includes administering an effective amount of an antibody or antibody fragment in combination with a second antibody, antibody fragment, antagonist or drug such that the number of regulatory T cells in the subject is reduced.

In some embodiments, the subject has a cell proliferative disease or cancer as described herein.

In other embodiments, the subject has a chronic viral infection, inflammatory disease or autoimmune disease as described herein.

The provision of two distinct signals to T-cells is a widely accepted model for lymphocyte activation of resting T lymphocytes by antigen-presenting cells (APCs). This model further provides for the discrimination of self from non-self and immune tolerance. The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs). This induces T-cells to promote clonal expansion, cytokine secretion and effector function. In the absence of co-stimulation, T-cells can become refractory to antigen stimulation, which results in a tolerogenic response to either foreign or endogenous antigens.

In the two-signal model, T-cells receive both positive co-stimulatory and negative co-inhibitory signals. The regulation of such positive and negative signals is critical to maximize the host's protective immune responses, while maintaining immune tolerance and preventing autoimmunity. Negative signals seem necessary for induction of T-cell tolerance, while positive signals promote T-cell activation. Both co-stimulatory and co-inhibitory signals are provided to antigen-exposed T cells, and the interplay between co-stimulatory and co-inhibitory signals is essential to controlling the magnitude of an immune response. Further, the signals provided to the T cells change as an infection or immune provocation is cleared, worsens, or persists, and these changes powerfully affect the responding T cells and re-shape the immune response.

The mechanism of co-stimulation is of therapeutic interest because the manipulation of co-stimulatory signals has shown to provide a means to either enhance or terminate cell-based immune response. Recently, it has been discovered that T cell dysfunction or energy can occur concurrently with an induced and sustained expression of immune checkpoint regulators, such as PD-1 and its ligands, PD-L1 and PD-L2. PD-L1 is overexpressed in many cancers and is often associated with poor prognosis (Thompson R H et al., Cancer Res 2006, 66(7):3381). Further, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8): 1537). This may be due to exploitation of PD-L1 signaling mediated by PD-L1 expressing tumor cells interacting with PD-1 expressing T cells to result in attenuation of T cell activation and evasion of immune surveillance. Inhibition of the PD-L1/PD-1 interaction provides a means to enhance T cell immunity, including CD8+ T cell-mediated killing of cancer cells and tumors. Similar enhancements to T cell immunity have been observed by inhibiting the binding of PD-L1 to the binding partner B7-1. Consequently, therapeutic targeting of PD-1 and other immune checkpoint regulators are an area of intense interest.

Combining inhibition of PD-1, PD-L1, TIGIT and/or LAG-3 signaling with other signaling pathways deregulated in tumor cells can provide a means for enhance treatment efficacy. In recent years, a number of immune checkpoint regulators in the form of receptors and their ligands have been identified. One important family of membrane-bound ligands that bind to co-stimulatory or co-inhibitory receptors is the B7 family, which includes CTLA-4 and its ligands, B7-1 and B7-2; PD-1 and its ligands, PD-L1 (B7-H1) and PD-L2 (B7-DC); B7-H2 (ICOS-L), B7-H3, B7-H4, B7-H5 (VISTA), and B7-H6. Additional immune checkpoint antagonists include, but are not limited to TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA (Le Mercier et al. (2015) Front. Immunol., (6), Article 418). In addition, a number of checkpoint regulator antagonists have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated by virtue of e.g., the FDA approval of the PD-1 inhibitors, nivolumab and pembrolizumab, as well as the anti-CTLA-4 antibody, ipilimumab for metastatic melanoma.

An immune checkpoint antagonist modulates or interferes with the activity of the immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. In contrast, an immune checkpoint agonist (of e.g., a costimulatory molecule) stimulates the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced.

Accordingly, in one embodiment, a method for stimulating an immune response in a subject comprises administering to the subject an anti-PD-1 antibody, anti-PD-L1 antibody, anti-TIGIT antibody, anti-LAG-3 antibody, antibody fragment(s) thereof (e.g., anti-TIGIT HCVR and/LCVRs), bispecific antitumor antagonist or trispecific antitumor antagonist described herein in combination with another immune checkpoint regulator described herein above, such that an immune response is stimulated in the subject, for example to inhibit tumor growth or to stimulate an anti-viral response.

In one embodiment, an anti-PD-1 antibody, anti-PD-L1 antibody, anti-TIGIT antibody, anti-LAG-3 antibody, antibody fragment(s) thereof, bispecific antitumor antagonist or trispecific antitumor antagonist according to the present application is administered in combination with another immune checkpoint regulator, either as separate antibodies or in multi-specific antibody comprising binding specificities to multiple products. Generally, an anti-PD-1 antibody, anti-PD-L1 antibody, anti-TIGIT antibody, anti-LAG-3 antibody, bispecific antitumor antagonist or trispecific antitumor antagonist described herein can be combined to stimulate an immune response with (i) an antagonist of the IgSF family protein, B7 family or TNF family that inhibit T cell activation, or antagonist of a cytokine that inhibits T cell activation (e.g., IL-6, IL-10, TGF-β, VEGF, or other immunosuppressive cytokines) and/or (ii) an agonist of a stimulatory receptors of the IgSF family, B7 family or TNF family or of cytokines to stimulate T cell activation, for stimulating an immune response.

In certain embodiments, only subjects with a cancer exhibiting high expression of a ligand for an immune checkpoint regulator are selected for combination treatment with the anti-PD-1, anti-PD-L1, anti-TIGIT, and/or anti-LAG-3 antibody, fragment thereof, or any of the bispecific or trispecific antagonists of the present application. By way of example, in one embodiment, a subject with a cancer exhibiting high expression of PVR (CD155) and/or Nectin-2 (CD112) and/or low expression PD-L1 may be selected for monotherapy with anti-TIGIT antibodies, fragments thereof, or TIGIT antagonists of the present application, or combination therapy with a PD-1 antagonist or other immune checkpoint regulator.

The anti-PD-1 antibody, anti-PD-L1 antibody, anti-TIGIT antibody may be administered separately from the second antibody, antibody fragment or antagonist, or a multispecific antibody or antagonist may be administered comprising at least one binding specificity for TIGIT and a second binding specificity for the other targeted product. Further, the anti-PD-1 antibody, anti-PD-L1 antibody, anti-TIGIT or bispecific or trispecific antagonists in accordance with the present application may be co-administered with one or more additional agents, e.g., antibodies, antagonists, or drugs in amount(s) effective in stimulating an immune response and/or apoptosis so as to further enhance, stimulate or up-regulate an immune response and/or apoptosis in a subject.

In some embodiments, the anti-PD-1, anti-PD-L1, anti-TIGIT or anti-LAG-3 antibody or fragment(s) thereof is administered subsequent to treatment with a different anti-tumor antagonist. For example, in one embodiment, anti-PD-1, anti-PD-L1, anti-TIGIT or anti-LAG-3 antibodies may be administered only after treatment with a PD-1/PD-L1 antagonist has failed, has led to incomplete therapeutic response, or there has been recurrence of the tumor or relapse (or "PD-1 failure"). In some embodiments, cancers exhibiting such failures may be screened for expression of e.g., PVR and/or Nectin-2 and only those having high level expression are treated with an anti-PD-1, anti-PD-L1, anti-TIGIT or anti-LAG-3 antibody, fragment or antagonist of the present application.

Other anti-PD-1 antibodies include, but are not limited to, nivolumab (BMS-936558, MDX-1106, OPDIVO™), a humanized immunoglobulin G4 (IgG4) mAb (Bristol-Myers Squibb); pembrolizumab (MK-3475, lambrolizumab, Keytruda™)(Merck); pidilizumab (CT-011)(Medivation); and AMP-224 (Merck). Anti-PD-1 antibodies are commercially available, for example from ABCAM (AB137132), BIOLEGEND™ (EH12.2H7, RMPi-14) and AFFYMETRIX EBIOSCIENCE (J105, J116, MIH4).

Other anti-PD-L1 antibodies include atezolizumab (MPDL3280A, RG7446), a fully human IgG4 mAb Genentech/Roche); BMS-936559 (MDX-1105), a fully humanized IgG4 mAb (Bristol-Myers Squibb); MEDI4736, a humanized IgG antibody (Medimmune/AstraZeneca); and MSB0010718C, a fully human IgG4 monoclonal antibody (Merck, EMD Serono).

Exemplary anti-CTLA-4 antibodies for use in accordance with the present methods include ipilimumab, trevilizumab and tremelimumab.

In certain embodiments, the antitumor antagonist is a dominant negative protein of the immune checkpoint regulator. In particular embodiments, the dominant negative protein comprises an extracellular domain derived from a member selected from the group consisting of PD-L1, PD-L2, PD-1, B7-1, B7-2, B7H3, CTLA-4, LAG-3, TIM-3, TIGIT, BTLA, VISTA, CD70, and combinations thereof. In certain particular embodiments, these extracellular domains are fused to an immunoglobulin constant region or Fc receptor in the presently described antibodies. Such mutants can bind to the endogenous receptor so as to form a complex that is deficient in signaling. In certain embodiments, the extracellular domain is fused to an immunoglobulin constant region or Fc fragment or to a monomer in the oligomeric protein complex.

In certain embodiments, a dominant negative PD-L1 antagonist comprises the extracellular domain of PD-L1, PD-L2 or PD-1. In another embodiment, a dominant-negative PD-1 antagonist is employed, which has a mutation so that it is no longer able to bind PD-L1. An exemplary dominant negative protein is AMP-224 (co-developed by Glaxo Smith Kline and Amplimmune), a recombinant fusion protein comprising the extracellular domain of PD-L2 and the Fc region of human IgG.

Exemplary immune checkpoint regulator agonists include, but are not limited to members of the tumor necrosis factor (TNF) receptor superfamily, such as CD27, CD40, OX40, GITR and 4-1BB (CD137) and their ligands, or members of the B7-CD28 superfamily, including CD28 and ICOS (CD278). Additional checkpoint regulator agonists include CD2, CDS, ICAM-1, LFA-1 (CD 11a/CD18), CD30, BAFFR, HVEM, CD7, LIGHT, NKG2C, SLAMF7, NKp80, CD160, B7-H3, CD83 ligand. Immune checkpoint antagonists can include antibodies or soluble fusion protein agonists comprising one or more co-stimulatory domains. Agonist antibodies include, but are not limited to anti-CD40 mAbs, such as CP-870,893, lucatumumab, and dacetuzumab; anti-CD137 mAbs, such as BMS-663513 urelumab, and PF-05082566; anti-OX40 mAbs; anti-GITR mAbs, such as TRX518; anti-CD27 mAbs, such as CDX-1127; and anti-ICOS mAbs.

Exemplary GITR agonists include, e.g., GITR fusion proteins and anti-GITR antibodies (e.g., bivalent anti-GITR antibodies) such as, e.g., a GITR fusion protein described in U.S. Pat. Nos. 6,111,090 and 8,586,023; European Patent No.: 090505B1, U.S. Patent No. PCT Publication Nos.: WO 2010/003118 and 2011/090754. Anti-GITR antibodies are described in, e.g., in U.S. Pat. Nos. 7,025,962, 7,618,632, 7,812,135, 8,388,967, and 8,591,886; European Patent Nos.: 1947183B1 and 1866339; PCT Publication Nos.: WO 2011/028683, WO 2013/039954, WO2005/007190, WO 2007/133822, WO2005/055808, WO 99/40196, WO 2001/03720, WO99/20758, WO2006/083289, WO 2005/115451, WO 2011/051726. An exemplary anti-GITR antibody is TRX518.

Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNF γ, TNFR2, TNFα, LTβR, Lymphotoxin α1(32, FAS, FASL, RELT, DR6, TROY, NGFR (see, e.g., Tansey, M. G. et al. (2009) Drug Discovery Today, 14(23-24):1082-1088).

Immune checkpoint agonists or co-stimulatory molecules include cell surface molecules other than antigen receptors or their ligands that are required for an efficient immune response, and include, but are not limited to MHC class I molecules, MHC class II molecules, TNF receptor proteins, immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF 1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one aspect, T cell responses can be stimulated by a combination of the anti-PD-1, anti-PD-L1, anti-TIGIT or anti-LAG-3 mAbs of the present application and one or more of (i) an antagonist of a protein that inhibits T cell activation (e.g., immune checkpoint inhibitors), such as CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD-1H, LAIR1, TIM-1, CD96 and TIM-4, and (ii) an agonist of a protein that stimulates T cell activation such as B7-1, B7-2, CD28, 4-1BB (CD137), 4-1BBL, ICOS, CD40, ICOS-L, OX40, OX40L, GITR, GITRL, CD70, CD27, CD40, DR3 and CD28H.

Exemplary agents that modulate one of the above proteins and may be combined with the anti-PD-1 antibodies, anti-PD-L1 antibodies, anti-TIGIT antibodies and/or anti-LAG-3 antibodies of the present application for treating cancer, include: YERVOY™/ipilimumab or tremelimumab (to CTLA-4), galiximab (to B7.1), OPDIVO™/nivolumab/BMS-936558 (to PD-1), pidilizumab/CT-011 (to PD-1), KEYTRUDA™/pembrolizumab/MK-3475 (to PD-1), AMP224 (to B7-DC/PD-L2), BMS-936559 (to B7-H1), MPDL3280A (to B7-H1), MEDI-570 (to ICOS), AMG557 (to B7H2), MGA271 (to B7H3), IMP321 (to LAG-3), urelumab/BMS-663513 and PF-05082566 (to CD137/4-1BB), CDX-1127 (to CD27), MEDI-6383 and MEDI-6469 (to OX40), RG-7888 (to OX40L), Atacicept (to TACI), CP-870893 (to CD40), lucatumumab (to CD40), dacetuzumab (to CD40), and muromonab-CD3 (to CD3).

Other molecules that can be combined with the antitumor antagonists described herein for the treatment of cancer include antagonists of inhibitory receptors on NK cells or agonists of activating receptors on NK cells. For example, antagonist anti-PD-1, anti-PD-L1 and/or anti-TIGIT antibodies can be combined with antagonists of KIR (e.g., lirilumab), CSF-1R antagonists, such as RG7155.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity and can be used in conjunction with the antitumor antagonists described herein. Activating antibodies to T cell costimulatory molecules such as OX-40, CD137/4-1BB, and ICOS may also provide for increased levels of T cell activation.

In certain embodiments, the antitumor antagonists described herein can be co-administered with one or other more therapeutic agents, e.g., anti-cancer agents, radiotoxic agents or an immunosuppressive agent. Such co-administration can solve problems due to development of resistance to drugs, changes in the antigenicity of the tumor cells that would render them unreactive to the antibody, and toxicities (by administering lower doses of one or more agents).

The antitumor antagonists described herein can be chemically linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. The antitumor antagonists described herein may be co-administered with one or more anti-cancer agents so as to provide two anti-cancer agents operating synergistically via different mechanisms to yield a cytotoxic effect in human cancer cells.

The antitumor antagonists described herein may be combined with an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3Kα,δ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torinl, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, R04987655, R05068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof, CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-PI31; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In certain embodiments, the antitumor antagonists described herein are administered at a subtherapeutic dose, another anti-immune checkpoint regulator antibody or antagonist is administered at a subtherapeutic dose, the angiogenesis antagonist is administered at a subtherapeutic dose, or any antagonist in a combination thereof is each administered at a subtherapeutic dose.

In certain embodiments, PD-1, PD-L1, TIGIT and/or LAG-3 inhibition is combined with standard cancer treatments (e.g., surgery, radiation, and chemotherapy). PD-1, PD-L1, TIGIT and/or LAG-3 inhibition can be effectively combined with chemotherapeutic regimes. In these instances, it may be possible to reduce the dose of chemotherapeutic reagent administered. An example of such a combination is an anti-TIGIT, anti-PD-1, anti-PD-L1 or anti-LAG-3 antibody in combination with decarbazine for the treatment of melanoma. Another example of such a combination is an anti-PD-1, anti-PD-L1, anti-TIGIT or anti-LAG-3 antibody in combination with interleukin-2 (IL-2) for the treatment of melanoma. It is believed that the combined use of PD-1, PD-L1, TIGIT and/or LAG-3 inhibition and chemotherapy can enhance apoptosis and increase tumor antigen presentation for cytotoxic immunity. Other synergistic combination therapies include PD-1, PD-L1, TIGIT and/or LAG-3 inhibition through cell death when used in combination with radiation, surgery or hormone deprivation. Each of these protocols creates a source of tumor antigen in the host.

In certain embodiments, the checkpoint regulator antagonists described herein can be used in multi-specific antagonists or in combination with bispecific antibodies targeting Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to cancer cells or tumors. This targeting may more effectively activate tumor specific responses. The T cell arm of these responses would be augmented by the inhibition of TIGIT, PD-1, PD-L1 and/or LAG-3. Alternatively, antigen may be delivered directly to DCs by the use of bispecific antibodies that bind to tumor antigen and a dendritic cell specific cell surface marker.

VI. Methods of Making the Antitumor Antagonists

A. Nucleic Acids and Host Cells for Expressing Antagonists

In one aspect, the present application provides nucleic acids encoding the antitumor antagonist of the present application, and expression vectors comprising such nucleic acids. In some embodiments, nucleic acids encodes an HCVR and/or LCVR fragment of an antibody or fragment in accordance with the embodiments described herein, or any of the other antibodies and antibody fragments described herein.

DNA encoding an antigen binding site in a monoclonal antibody can be isolated and sequenced from the hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

Expression vectors encoding a particular monospecific, bispecific or trispecific antitumor antagonist may be used to synthesize the antitumor antagonists of the present disclosure in cultured cells in vitro or they may be directly administered to a patient to express the antitumor antagonist in vivo or ex vivo. As used herein, an "expression vector" refers to a viral or non-viral vector comprising a polynucleotide encoding one or more polypeptide chains corresponding to the monospecific, bispecific or trispecific antitumor antagonists of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the antitumor antagonists typically include an amino terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of antitumor antagonists. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the antitumor antagonist in one or more cell types.

In certain embodiments, one or more expression vectors may be engineered to express both the antitumor antagonist and one or more siRNA targeting the Tie2 pathway, the VEGF pathway or an immune checkpoint regulator.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the antitumor antagonist, a suitable splice donor and splice acceptor sequences may be incorporated for expressing both products. Alternatively, an internal ribosome binding sequence (IRES) or a 2A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within a mRNA, allowing more than one polypeptide to be produced from a single mRNA. A 2A peptide contains short sequences mediating co-translational self-cleavage of the peptides upstream and downstream from the 2A site, allowing production of two different proteins from a single transcript in equimolar amounts. CHYSEL is a non-limiting example of a 2A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the antitumor antagonist-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and chemically linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

B. Methods for Producing Monospecific or Multispecific Antibodies

In one aspect, the present application provides host cells transformed with the anti-PD-1, anti-PD-L1, anti-TIGIT, and/or anti-LAG-3 HCVRs and/or LCVRs, encoding nucleic acids or expression vectors, or nucleic acids/expression vectors encoding the bi-specific and/or trispecific antitumor antagonist of the present application. The host cells can be any bacterial or eukaryotic cell capable of expressing the anti-PD-1, anti-PD-L1, anti-TIGIT and/or anti-LAG-3 HCVRs and/or LCVRs encoding nucleic acids or expression vectors or any of the other co-administered antibodies or antagonists described herein.

In another aspect, a method of producing an antitumor antagonist comprises culturing a host cell transformed with one or more anti-PD-1, anti-PD-L1 anti-TIGIT, and/or anti-LAG-3 HCVRs and/or LCVRs encoding nucleic acids or expression vectors under conditions that allows production of the antibody or fragment, and purifying the antibody from the cell.

In a further aspect, the present application provides a method for producing an antibody comprising culturing a cell transiently or stably expressing one or more constructs encoding one or more polypeptide chains in the antibody; and purifying the antibody from the cultured cells. Any cell capable of producing a functional antibody may be used. In preferred embodiments, the antibody-expressing cell is of eukaryotic or mammalian origin, preferably a human cell. Cells from various tissue cell types may be used to express the antibodies. In other embodiments, the cell is a yeast cell, an insect cell or a bacterial cell. Preferably, the antibody-producing cell is stably transformed with a vector expressing the antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the antibody along with a selectable marker facilitating selection of stably transformed clones expressing the antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell line expresses at least 1 mg, at least 2 mg, at least 5 mg, at least 10 mg, at least 20 mg, at least 50 mg, at least 100 mg, at least 200 mg, at least 300 mg, at least 400 mg, or at least 500 mg of the antibody/liter of culture.

The antibodies in the present application may be isolated from antibody expressing cells following culture and maintenance in any appropriate culture medium, such as RPMI, DMEM, and AIM V®. The antibodies can be purified using conventional protein purification methodologies (e.g., affinity purification, chromatography, etc.), including the use of Protein-A or Protein-G immunoaffinity purification. In some embodiments, antibodies are engineered for secretion into culture supernatants for isolation therefrom.

The present application is further illustrated by the following examples which should not be construed as limiting. The contents of all references, patents and published patent applications cited throughout this application, as well as the Figures and Tables are incorporated herein by reference.

C. Homodimers and Heterodimers

One of the challenges for efficiently producing bispecific and trispecific antibody preparations concerns mispairing of heavy and light chains, when co-expressing chains of different binding specificities. Table 1 lists several amino acid substitution options for overcoming mispairing between heavy chains of different binding specificities, which "enforce" or preferentially promote correct association between desired heavy chains. Any approach to prevent or reduce mispairing between heavy chains may be used to make the bispecific trispecific antitumor antagonists according to the present disclosure.

The "knobs-into-hole" (KiH) approach relies on modifications of the interface between the two CH3 domains where most interactions occur. Typically, a bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges.

An alternative approach is based on charged residues with ionic interactions or steric complementarity. This includes altering the charge polarity in the CH3 interface so that co-expression of electrostatically matched Fc domains support favorable attractive interactions and heterodimer formation while retaining the hydrophobic core, whereas unfavorable repulsive charge interactions suppress homodimerization. See Table 1. The amino acid numbering in Table 1 follows the Kabat numbering scheme and can be applied to heavy chain amino acid sequences of the antibodies described herein.

In a further approach, leucine zipper (LZ) domains may be incorporated into a protein scaffold. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers.

A leucine zipper domain may be incorporated in place of CH2-CH3 sequences in the protein scaffold or it may be placed at the carboxy terminal end of the two heavy chains in the bispecific or trispecific antitumor antagonist. In the case of the latter, a furin cleavage site may be introduced between the carboxy terminal end of CH3 and the amino terminal end of the leucine zipper. This can facilitate furin-mediated cleavage of the leucine zipper following the heterodimerization step when co-expressing the heavy and light chains of the bispecific or trispecific antitumor antagonist in an appropriate mammalian cell expression system (see Wranik et al., J. Biol. Chem., 287(5):43331-43339, 2012).

TABLE 1

| Type | HC1 | HC2 |
| --- | --- | --- |
| Knobs-into-holes | Y349C, T366S, L368A, Y407V | S354C, T366W |
| Ionic, electrostatic | S183E, E356K, E357K, D399K | S183K, K370E, K409D, K439E |
| Ionic, electrostatic | K392D, K409D | E356K, D399K |
| HA-TF substitutions | S364H, F405A | Y349T, T394F |
| HF-TA substitutions | S364H, T394F | Y349T, F405A |
| Leucine zipper heterodimer | human c-Jun leucine zipper | human c-fos leucine zipper |

The amino acid numbering in Table 1 follows the Kabat numbering scheme and can be applied to heavy chain amino acid sequences of the antibodies described herein. The mutations described in Table 1 may be applied to the sequence (published or otherwise) of any immunoglobulin IgG1 heavy chain, as well as other immunoglobulin classes, and subclasses (or isotypes) therein.

When co-expressing heavy and light chains of bispecific or trispecific antibodies, the light chains of one binding specificity can also mispair with heavy chains of a different binding specificity. Therefore, in certain embodiments, portions of the heavy chain, light chain or both may be modified relative to the "wild-type" antibody chains from which they are derived to prevent or reduce mispairing of both heavy chain constant regions to one another, as well mispairing of light chain constant regions to their heavy chain counterparts.

The light chain mispairing problem can be addressed in several ways. In some embodiments, sterically complementary mutations and/or disulfide bridges may be incorporated into the two VL/VH interfaces. In other embodiments, mutations can be incorporated based on ionic or electrostatic interactions. In some embodiments, light chain mispairing may be prevented or reduced by employing a first arm with an S183E mutation in the CH1 domain of the heavy chain and an S176K mutation in the CL domain of the light chain. A second arm may include an S183K mutation in the in the CH1 domain of the heavy chain and an S176E mutation in the CL domain of the light chain. In other embodiments, a "CrossMab" approach is employed, where one arm in the bispecific or trispecific antitumor antagonist (e.g., Fab) is left untouched, but in the other arm containing the other binding specificity, one or more domains in the light chain are swapped with one or more domains in the heavy chain at the heavy chain:light chain interface.

Methods, immunoglobulin domain sequences, including specific mutations for preventing mispairing of heavy and light chains as disclosed above are further described in U.S. Patent Application Publication Nos. 2014/0243505, 2013/0022601.

D. Conjugates

In certain embodiments, the antitumor antagonists of the present application are chemically conjugated to one or more peptides and/or small molecule drugs. The peptides or small molecule drug can be the same or different. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using a heterobifunctional cross-linkers, such as N-succinyl 3-(2-pyridyldithio)propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties are well-known to those of skill in the art. For example, in one embodiment, the method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Application Publication No. 2014/0356385.

Preferably, the antitumor antagonists in the present disclosure retain certain desirable characteristics and pharmacokinetic properties of antibodies, including a desirable in vitro and in vivo stability (e.g., lone half-life and shelf-life stability), efficient delivery into desired target cells, increased affinity for binding partners, desirable antibody-dependent cell-mediated cytotoxicity and complement-dependent cytotoxicity, and reduced renal clearance or excretion. Accordingly, careful attention to size and need for particular constant region effector functions may be considered in the design of the antitumor antagonists.

The anti-PD-1, anti-PD-L1 and anti-TIGIT, inhibitors, including monospecific, bispecific and trispecific antitumor antagonists therefrom, may range in size from 50 kD to 300 kD, from 50 kD to 250 kD, from 60 kD to 250 kD, from 80 kD to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or any range encompassed by any combination of whole numbers listed in the above cited ranges or any ranges specified by any combination of whole numbers between any of the above cited ranges.

EXAMPLES

Example 1: Generation of Monoclonal Antibodies

Monoclonal antibodies (mAbs) of the present application are generated and screened using techniques well known in the art, see, e.g., Harlow and Lane (1988) *Antibodies, A Laboratory Manual*, Cold Spring Harbor Publications New York. The antigen specific hybridoma Mabs are cloned, sequenced and engineered using techniques well known in the art, see, e.g., Lo. B. K. C Methods in Molecular Biology™. Volume 248 2004. Antibody Engineering.

Example 2: Trispecific Antagonists Having a PD-1 Targeting Domain and Multiple Angiogenesis Targeting Moieties FIG. 1 shows VH and VL sequences of anti-PD-1, anti-PD-L1, anti-LAG-3 and anti-TIGIT mAbs. FIG. 2 shows other functional domains including VH and VL of ranibizumab, bevacizumab and a mutant variant of the VH, the VEGF binding domain of aflibercept, trebananib-short peptide and the trebananib-long peptide, and extracellular domain of TGFβR-II (TGFβR-II ECD).

The aflibercept fusion protein domain comprises vascular endothelial growth factor (VEGF)-binding portions from the extracellular domains of human VEGF receptors 1 and 2 and prevents the binding of VEGF-A, VEGF-B and PLGF to their receptors, VEGFR-1 and VEGFR-2. The trebananib peptide targets and binds to Ang1 and Ang2, thereby preventing the interaction of Ang1 and/or Ang2 with their cognate Tie2 receptors. The antitumor antagonists may be constructed with an IgG1, IgG1agly, or IgG4 backbone.

Figure 3H:
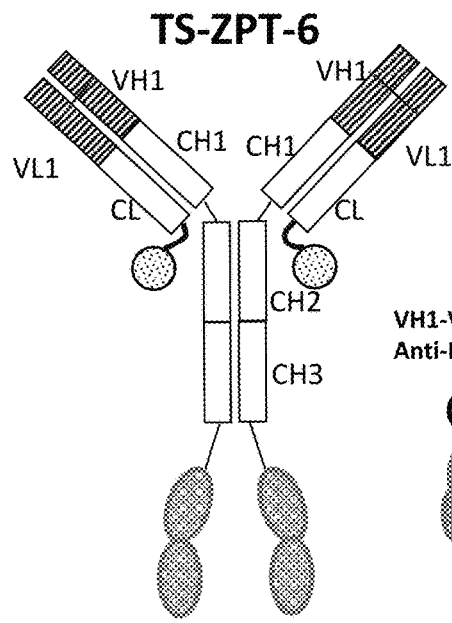

A variety of trispecific antitumor antagonists were constructed, each comprising (1) one or more anti-PD-1, or other checkpoint antibody variable region domains; an aflibercept peptide; and a trebananib peptide or peptide sequences thereof. FIGS. 3A-3H show eight different trispecific antitumor antagonists, TS-ZPT-1.1, -1.2, -1.3 and -2 to -6, respectively (1) anti-PD-1 variable region (VH1, VL1) (FIGS. 3A-3H); (2) an aflibercept fusion protein domain: (i) at the amino terminal end of one or both IgG arms (FIGS. 3A-3C, 3F); (ii) at the carboxy-terminal end of each antagonist (FIGS. 3D, 3E, 3H); or (iii) between the carboxy-terminal end of the CH3 domain and a trebananib peptide (or other biological peptide) (FIG. 3G) (3) a trebananib peptide (or other biological peptide): (i) fused to the carboxy-terminal end of each IgG4 CH3 region (FIGS. 3A-3D); (ii) inserted within each of the two CH3 regions (FIG. 3E); (iii) fused to the carboxy-terminal end of each CH1 region (FIG. 3F); (iv) fused to the carboxy-terminal end of each aflibercept fusion protein domain (FIG. 3G); or (v) fused to the carboxy-terminal end of each CL region (FIG. 3H).

FIGS. 4A-4C show five different trispecific antitumor antagonists, TS-ZPT-7, TS-ZPT-8, TS-ZPT-9, respectively: (1) anti-PD-1 or other checkpoint antibody Fab domains (VH1-CH1, VL1-CL1) fused to the carboxy-terminus of the CH3 domain; (2) an aflibercept fusion protein domain at the amino-terminal end of the CH2 domain fused to the amino-terminus of the CH2 domain; (3) a trebananib peptide (or other biological peptide): (i) inserted within each of the two CH3 domains (FIG. 4A); (ii) fused to the amino-terminus of the CH2 domain (FIG. 4B); (iii) fused to the carboxy-terminal end of the CH1 domain (FIG. 4C)

Figure 5D:
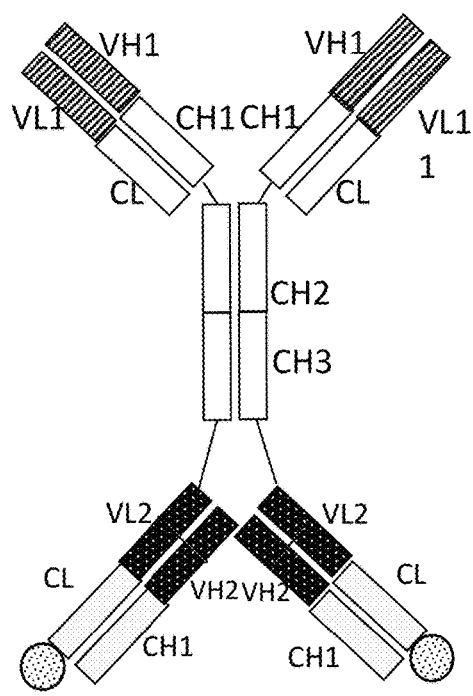
Figure 5E:
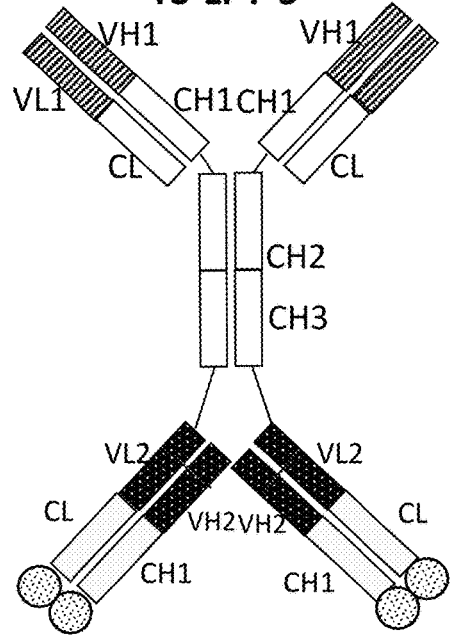

FIGS. 5A-5G show seven different trispecific antitumor antagonist, TS-LPT-1, TS-LPT-2, TS-LPT-3, TS-LPT-4, TS-LPT-5, TS-M3, TS-M4, respectively; (1) anti-PD-1 or other checkpoint antibody variable domains (VH1, VL1) (i) fused to the amino-terminus of the CH1 and CL1, respectively (FIG. 5F); (ii) fused to the amino-terminus of the VH1 and VL1, respectively (FIG. 5G); (2) Lucentis, bevacizumab or other anti-VEGF antibody variable domains (VH1, VL1); (i) fused to the amino-terminus of the VH1 and VL1, respectively fused to the amino-terminus of the CH1 and CL1, respectively (FIG. 5F); (ii) fused to the amino-terminus of the CH1 and CL1, respectively (FIG. 5G); (iii) fused to the carboxy terminus of the CH3 domain and the amino-terminus of CH1 and CL1 domains, respectively (3) a trebananib peptide (or other biological peptide): (i) inserted within each of the two CH3 domains (FIG. 5A); (ii) fused to the carboxy-terminus of the CL1 domain (FIG. 5B); (iii) fused to one or two of the carboxy-terminal ends of the CHI domain (FIG. 5C-5E); (iv) fused to the carboxy-terminus of the CH3 domain (FIG. 5F-5G).

The amino acid sequences demonstrated in SEQ ID NOS:200 and 201 (LC) shows exemplary sequences of TS-ZPT-3 S. The amino acid sequences demonstrated in SEQ ID NOS:201 and 202 show exemplary sequences of TS-ZPT-3L. The amino acid sequences demonstrated in SEQ ID NOS:187 and 188 show exemplary sequences of TS-LPT-1. The amino acid sequences demonstrated in SEQ ID NOS:201 and 203 show exemplary sequences of TS-ZPT-2. The amino acid sequences demonstrated in SEQ ID NOS:201 and 204 show exemplary sequences of TS-ZPT-5. The amino acid sequences demonstrated in SEQ ID NOS: 234 and 235 show exemplary sequences for TS-ZPT-6.

Example 3: Characterization of Trispecific Antitumor Antagonists Made with the Anti-PD-1 Antibody 2P16

Versions of the trispecific antitumor antagonists depicted in FIGS. 3A-3H were made utilizing the 2P16 anti-PD-1 antibody, trebananib-long peptide, and the VEGF binding domain of aflibercept. TS-ZPT-1.1 (SEQ ID NOS:236-237), TS-ZPT-1.2 (SEQ ID NOS:238-239), TS-ZPT-1.3 (SEQ ID NOS:240-241), TS-ZPT-2 (SEQ ID NOS:242-243), TS-ZPT-3 (SEQ ID NOS:201-202), TS-ZPT-5 (SEQ ID NOS: 244 and 298), TS-ZPT-6 were constructed and compared to TS-LPT-1 (SEQ ID NOS:234-235), a trispecific antitumor antagonist that utilized the 2P16 antibody, trebananib and the Fab portion of Lucentis.

Figure 6A:
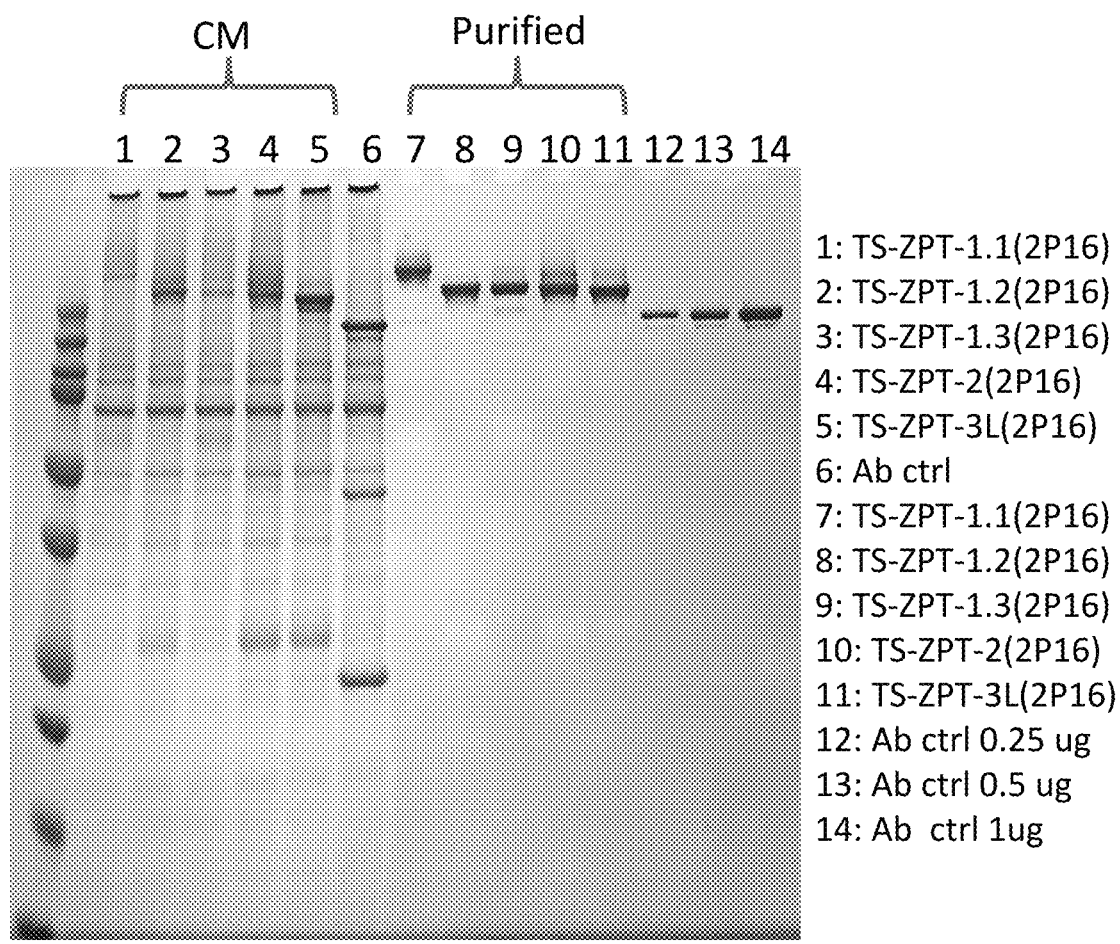
FIGS. 6A and 6B show non-reducing SDS-polyacrylamide gel electrophoresis (SDS-PAGE) analysis of trispecific antitumor antagonists depicted in FIGS. 3A-3E, 3G, 3H and 5A and expressed in transiently transfected HEK293 cells.
Figure 6B:
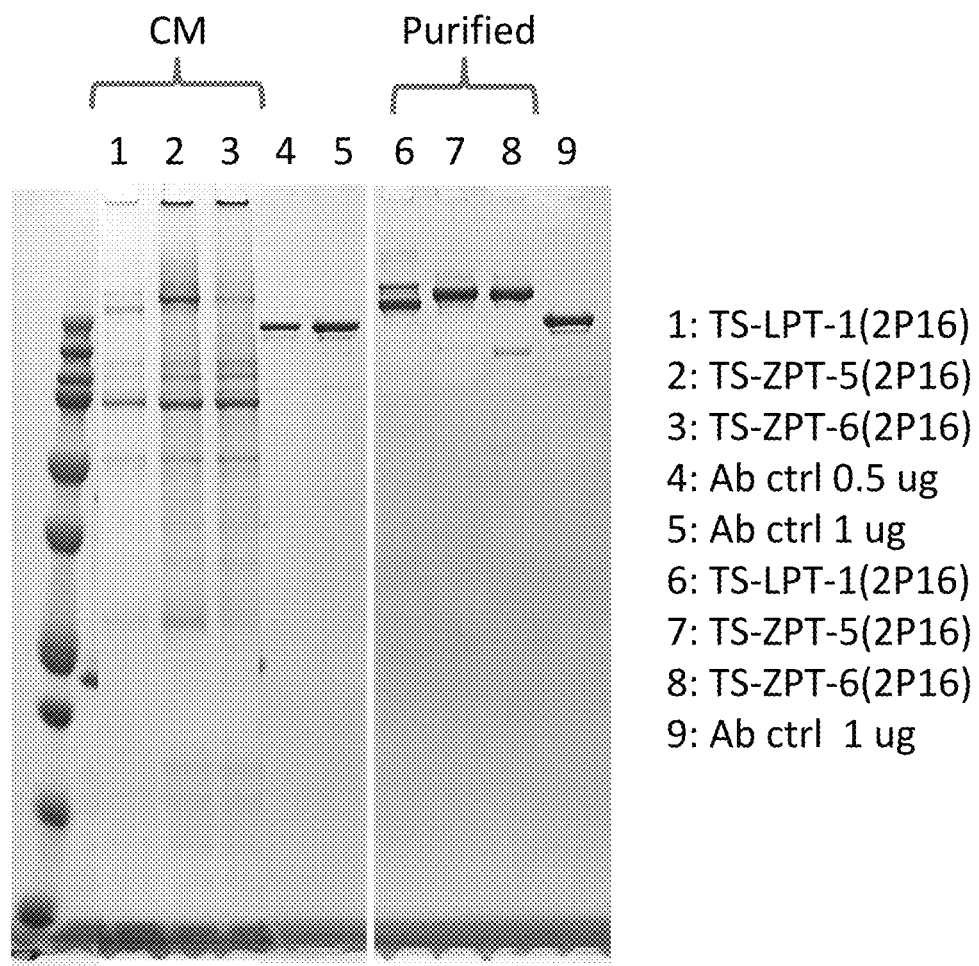

FIGS. 6A and 6B show non-reducing SDS-PAGE analysis of the trispecific antitumor antagonists expressed by transiently transfected HEK293 cells. Samples were assessed before and after purification of the molecules. The results show all the molecules expressed and could be purified, and that TS-ZPT-2(2P16), TS-ZPT-3(2P16), TS-ZPT-5(2P16) expressed better than TS-ZPT-6(2P16), and TS-LPT-1 (2P16).

A blocking assay was carried out to calculate the IC50 for selected trispecific molecules. Briefly, 2 or 3 fold serial dilutions of anti-human PD-1 mAb were prepared. Human PD-1 transfected CHO-K1 cells were washed with FACS buffer (0.5% BSA 2 mM EDTA in PBS) and re-suspended at a concentration of $10^6$ cells/ml. FITC labeled human PD-L1-Fc protein was added to the human PD-1 transfected CHO-K1 cells at a final concentration of 7 µg/ml and mixed well. Without incubation, 2,000 of these CHO-K1 cells (with PD-L1 Protein) in 20 µl FACS buffer was immediately added to a 96-well round bottom plate and 20 µl or 2 or 3 fold serial diluted trispecific molecules were immediately added to the cells and incubated at 4° C. for 30 mins. The cells were then washed and re-suspended in 30 µl 7AAD solution; 35 µl 10% neutral buffered formalin solution was then added and incubated for 15 mins before analysis using the iQue intellicyt system.

FIGS. 7A-B show the IC50s for the exemplary trispecific antitumor antagonists, TS-ZPT-1.1(2P16), TS-ZPT-1.2 (2P16), TS-ZPT-1.3(2P16), TS-ZPT-2(2P16), TS-ZPT-3

(2P16), TS-ZPT-5(2P16), TS-ZPT-6(2P16) along with an anti-PD-1 mAb and a positive control or benchmark ("BM") antibody (nivolumab). The IC50s were comparable to the benchmark antibodies in blocking this interaction.

The ability of the trispecific antitumor antagonists TS-ZPT-2(2P16), TS-ZPT-3(2P16), TS-ZPT-5(2P16), TS-ZPT-6(2P16) to block the interaction between VEGF and its receptor, VEGFR2 was determined. In brief, 96-well assay plates were coated with 0.5 ug/ml of recombinant human VEGF 165 (R&D) in carbonate-bicarbonate buffer (pH 9.6) at 4° C. overnight followed by blocking with 1% BSA/PBS for 1 hour at room temperature. Serially diluted antibodies were then added to the plate and incubated for 30 minutes at room temperature. Recombinant human VEGFR-2 was added and incubated for 1 hour at room temperature. The plate was washed with Wash Buffer (0.1% Tween-20 in PBS) and then incubated with anti-VEGFR-2 antibody for 1 hour at room temperature. Followed by washing with Wash Buffer, goat anti-mouse IgG-HRP were added to the plate and incubated for 1 hour at room temperature. The amount of VEGFR-2 binding was detected by measuring light absorbance at 650 nm after addition of TMB to the plate. IC50 values were determined as the mid-point in the activity curve.

FIGS. 8A and 8B show the IC50 values calculated from the VEGF-VEGFR2 blocking assays using the trispecific antagonists TS-ZPT-1.2(2P16), TS-ZPT-2(2P16), TS-ZPT-5(2P16), TS-ZPT-6(2P16) and TS-LPT-1(2P16), which were compared to positive controls corresponding to the aflibercept peptide and the bevacizumab antibody. The results of these analyses showed that the trispecific antagonists exhibited comparable or lower (i.e., better) IC50 values than the corresponding controls.

The ability of the trispecific antagonists TS-ZPT-1.2 (2P16), TS-ZPT-2(2P16), TS-ZPT-5(2P16), TS-ZPT-6 (2P16) and TS-LPT-1 to block the interaction between Ang-2 and its receptor, Tie2 was determined. Briefly, 96-well assay plates were coated with 1 ug/ml of recombinant human Ang2 (R&D) in PBS at 37° C. for 1 hour and then blocked with 1% BSA/PBS for 1 hour at room temperature. Serially diluted antibodies and recombinant human Tie2 mixture were then added to the plate and incubated for 2 hours at room temperature. The plate was washed with Wash Buffer (0.1% Tween-20 in PBS) and then incubated with anti-Tie2 antibody for 1 hour at room temperature. After washing with Wash Buffer, goat anti-mouse IgG-HRP were added to the plate and incubated for 1 hour at room temperature. Tie2 binding was detected by measuring light absorbance at 650 nm after addition of TMB to the plate. IC50 values were determined as the mid-point in the activity curve.

FIG. 9 shows the IC50 values calculated from the Tie2-Ang2 blocking assay testing the trispecific antagonists TS-ZPT-1.2(2P16), TS-ZPT-2(2P16), TS-ZPT-5(2P16), TS-ZPT-6(2P16) and TS-LPT-1(2P16) which were compared to positive controls corresponding to an antagonist, bevacizumab-trebananib. The results of this analysis showed that the trispecific antagonists exhibited comparable or lower (i.e., better) IC50 values than the corresponding controls.

Example 4: Characterization of TS-ZPT-2, TS-ZPT-3L and TS-ZPT-5 Molecules Constructed with the Anti-PD-1 Antibody 2P17

TS-ZPT-2, TS-ZPT-3L and TS-ZPT-5 trispecific antitumor antagonists were made with the anti-PD-1 antibody 2P17 (SEQ ID NOS:203 and 201, 233 and 201, 204 and 201, respectively) and characterized for homogeneity and stability by size exclusion chromatography after purification by protein A chromatography. SEC chromatography was performed using a Tosoh TSKgel UP-G3000SWXL column. The mobile phase system was 100 mM sodium phosphate, 400 mM sodium chloride with 6% isopropyl alcohol, pH 6.8 at 0.2 mL/minute. Detection was done at 214 nm for relative area integration FIG. 10 shows the results of size exclusion chromatography analysis of TS-ZPT-2(2P17), TS-ZPT-3L(2P17) and TS-ZPT-5(2P17), and parental 2P17 antibody produced by HEK293 transiently transfected cells. The percentages of high molecular weight (HWM) species and low molecular weight (LMW) species in comparison to dimerized molecule (Dimer) indicate that of the three trispecific antagonists, TS-ZPT-3L(2P17) has the lowest percentage of LMW species and the highest percentage of Dimers.

FIG. 11 shows the relative amounts of HWM and LMW species in comparison to Dimers of three trispecific antagonists: TS-ZPT-2(2P17), TS-ZPT-3L (2P17)(purified from two pools) and TS-ZPT-5(2P17) produced from stable CHO cell pools. The results show that of the three trispecific antagonists, TS-ZPT-3L(2P17) has the lowest percentage of LMW species and the highest percentage of Dimers.

Therefore, in both transient and stable cell lines, TS-ZPT-3L(2P17) exhibited lowest amount of clipping, indicating that inserting the trebananib peptide into the CH3 region protects the aflibercept fusion protein, and reduces clipping.

Figures 12A, 12B:
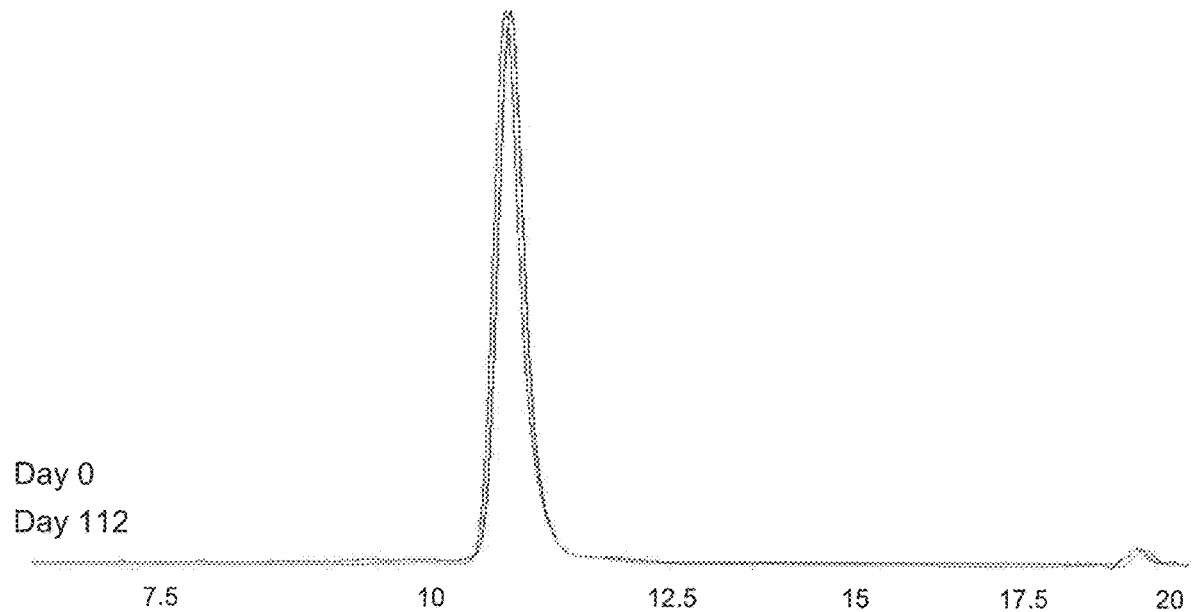
FIGS. 12A and 12B show the chromatography traces and results of a size exclusion chromatography analysis (SEC) of purified trispecific antitumor antagonist TS-ZPT-3L(2P17) purified from the CHO stable pool and stored at 4 degrees C. for 112 days. The percentage of high molecular weight (HWM %) species, low molecular weight (LMW %) species and dimerized molecule (Dimer %) are shown.

FIGS. 12A and 12B shows that the Dimer, HMW and LMW species of TS-ZPT-3L(2P17) exhibit good stability for at least 112 days at 4° C.

Example 5: Expression and Purification of TS-ZPT-3S and TS-ZPT-3L Trispecific Antitumor Antagonists TS-ZPT-3 versions were made using the anti-PD-1 antibodies 2P16 and 2P17 with both the full length trebananib peptide, TS-ZPT-3L, and a single copy, or trebananib-short, peptide for TS-ZPT-3S. These four molecules were compared to trispecific molecules utilizing the VH and VL of bevacizumab, TS-M3 and TS-M4 (depicted in FIG. 5F), utilizing anti-PD-1 antibodies nivolumab, 2P16 and 2P17 whose variable domain sequences are shown in FIG. 1 with sequences SEQ ID NOS:247-254.

FIG. 13A shows the heavy- and light chain amino acid sequences for an exemplary trispecific antitumor antagonist with the trebananib peptide, i.e., TS-ZPT-3L(2P17). FIG. 13B depicts an exemplary molecule derived from these sequences.

FIG. 14A shows the heavy and light chains amino acid sequences for an exemplary trispecific antitumor antagonist with the trebananib Short peptide, i.e., TS-ZPT-3S(2P17). FIG. 14B depicts an exemplary molecule derived from these sequences.

Figure 15:
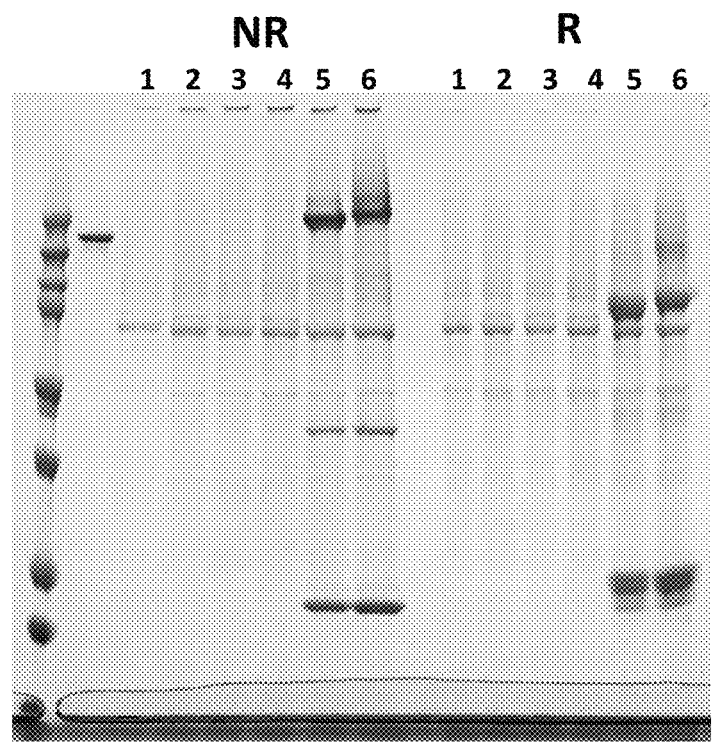
FIG. 15 show SDS-PAGE of various trispecific antitumor antagonists depicted in FIGS. 5F and 5G and FIGS. 13A-14B that were produced by transiently transfected HEK293 cells.

FIG. 15 shows Coomassie stained non-reducing SDS-PAGE analysis of trispecific the TS-ZPT-3 S(2P17), TS-ZPT-3L(2P17), TS-M3(2P17), TS-M4(2P17), TS-M3 (2P16) and TS-M3 (nivolumab) trispecific antitumor antagonist after production by transiently transfected HEK293 cells. The results show that trispecific antitumor antagonists TS-ZPT-3S(2P17), TS-ZPT-3L(2P17), which contains aflibercept fusion protein domains, exhibited higher levels of expression than trispecific antitumor antagonists TS-M3 (nivolumab), TS-M4 (nivolumab), TS-M3(2P17) and TS-M3(2P16), which contains anti-VEGF variable domains.

Figure 16:
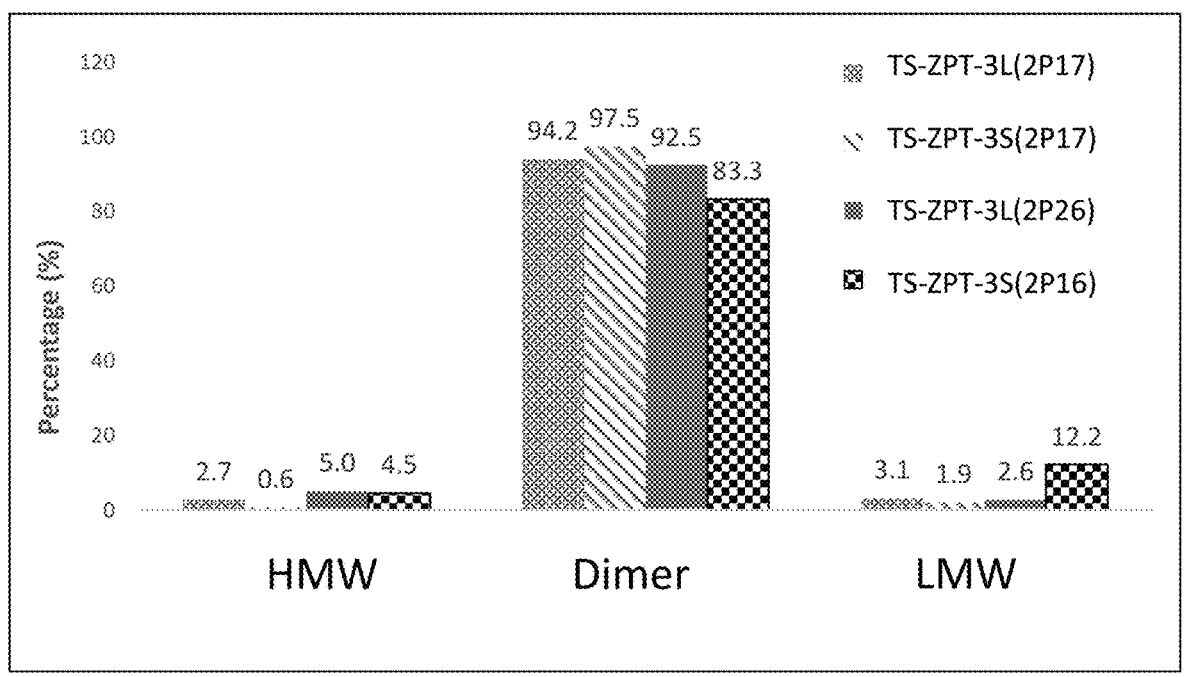
FIG. 16 shows the results from a size exclusion chromatography analysis of TS-ZPT-3L(2P17), TS-ZPT-3 S(2P17), TS-ZPT-3L(2P16), and TS-ZPT-3 S(2P16) produced from HEK293 cells.

FIG. 16 Shows the results from a size exclusion chromatography analysis of TS-ZPT-3L(2P17), TS-ZPL-3 S(2P17), TS-ZPT-3L(2P16), TS-ZPT-3 S(2P16) after purification by protein A chromatography. The percentages of high molecular weight (HWM) species and low molecular weight (LMW) species in comparison to dimerized molecule (Dimer) indicate the molecules comprising the 2P17 antibody have higher levels of the preferred dimer species.

FIG. 17 shows the size exclusion chromatography analysis of TS-ZPT-3S(2P17) and TS-ZPT-3L(2P17) stored at 4 degrees C. for 48 days, indicating both molecules are stable when stored.

Example 6: Functional Characterization of Trispecific Antagonist TS-ZPT-3

Figures 18A, 18B:
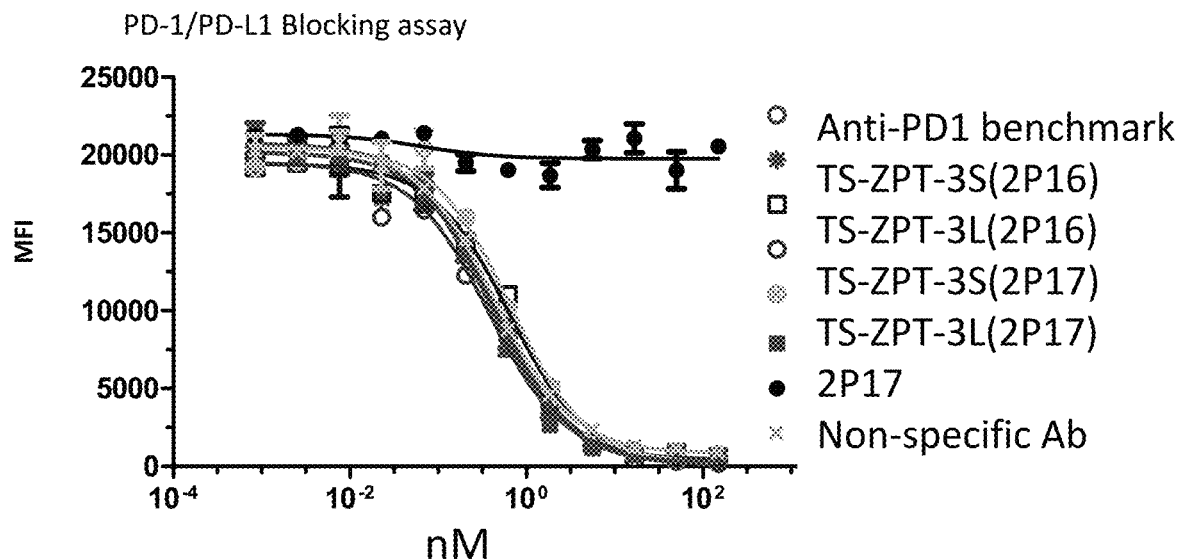
FIG. 18A shows the results of a cell-based binding assay measuring the ability of TS-ZPT-3S(2P16 and 2P17) and TS-ZPT-3L(2P16 and 2P17) trispecific antitumor antagonists compared to parental antibody 2P17 to block the interaction between PD-1 and PD-L1.
FIG. 18B shows the IC50 values (nM) obtained from this analysis.

The PD-1-PDL1 cell-based blocking assay in Example 5 was used to evaluate the ability of four variations of the trispecific antitumor antagonist, TS-ZPT-3 S(2P16), TS-ZPT-3L(2P16), TS-ZPT-3 S(2P17) and TS-ZPT-3L (2P17), to block the interaction between PD-1 and its ligand, PD-L1. The results were used to calculate the corresponding IC50s along with 2P17 and a benchmark antibody (nivolumab). FIGS. 18A-18B show that the IC50s were comparable to the benchmark antibodies in blocking this interaction.

Figures 19A, 19B:
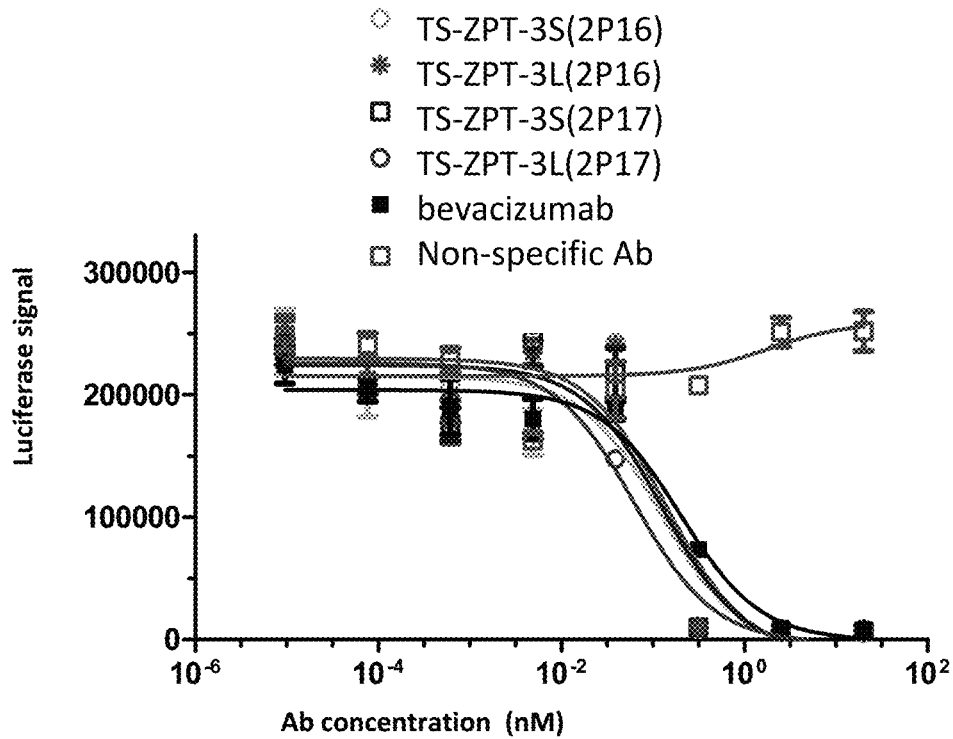
FIG. 19A shows the results of a cell-based bioassay measuring the ability of TS-ZPT-3S(2P16 and 2P17) and TS-ZPT-3L(2P16 and 2P17) trispecific antitumor antagonists compared to the benchmark antibody bevacizumab and a non-specific control antibody to block the interaction between VEGF and VEGFR-2.
FIG. 19B shows the IC50 values (nM) obtained from this analysis.

The VEGF-VEGFR-2 bioassay was used to evaluate the ability of TS-ZPT-3 S(2P16), TS-ZPT-3L(2P16), TS-ZPT-3S(2P17) and TS-ZPT-3L(2P17) to block the interaction between VEGF and its receptor, VEGFR-2 and to calculate the corresponding IC50s along with a benchmark antibody (bevacizumab). Briefly, VEGFR2/NFAT Reporter—HEK293 Recombinant Cell Line (BPS Bioscience Catalog #: 79387) was plated at a density of 30 k cells per well into a white clear-bottom 96-well microplate. After 24 hours serial dilutions of indicated molecules and human VEGF 165 were added to the wells. After 4 hours of incubation, 100 µl of ONE-Step™ Luciferase reagent was added, the plates were rocked at room temperature for ~15 minutes, and the plates read for the luminescence signal. FIGS. 19A-19B show that the IC50s were comparable to the benchmark antibodies in blocking this interaction.

Figures 20A, 20B:
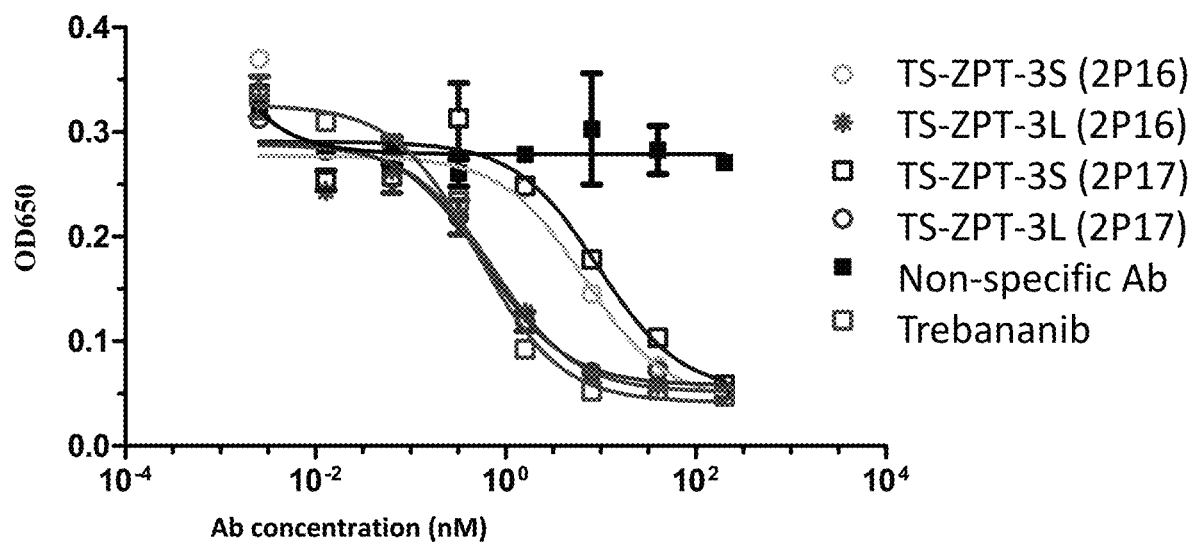
FIG. 20A shows the results of a binding assay measuring the ability of TS-TS-ZPT-3S(2P16 and 2P17) and TS-ZPT-3L(2P16 and 2P17) trispecific antitumor antagonists compared to the benchmark molecule trebananib and a non-specific control antibody to block the interaction between Ang2 and Tie2.
FIG. 20B shows the IC50 values (nM) obtained from this analysis.
Figure 21A:
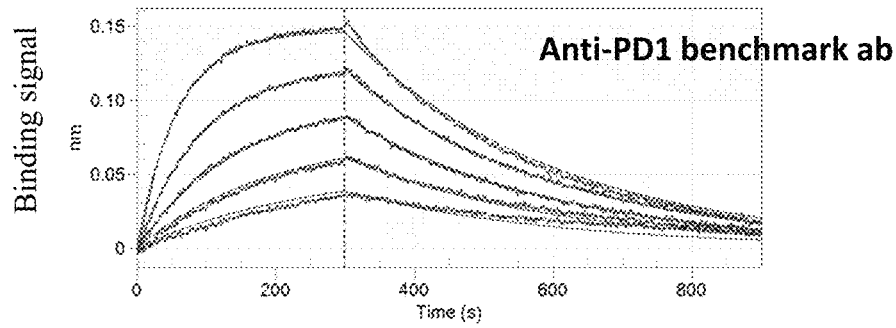
Figure 21B:
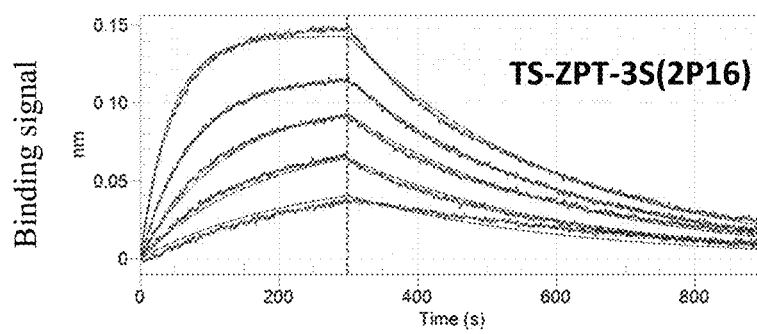
Figure 21C:
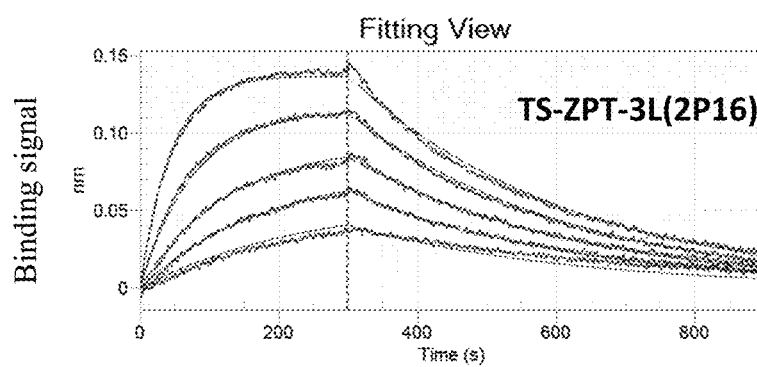
Figure 22A:
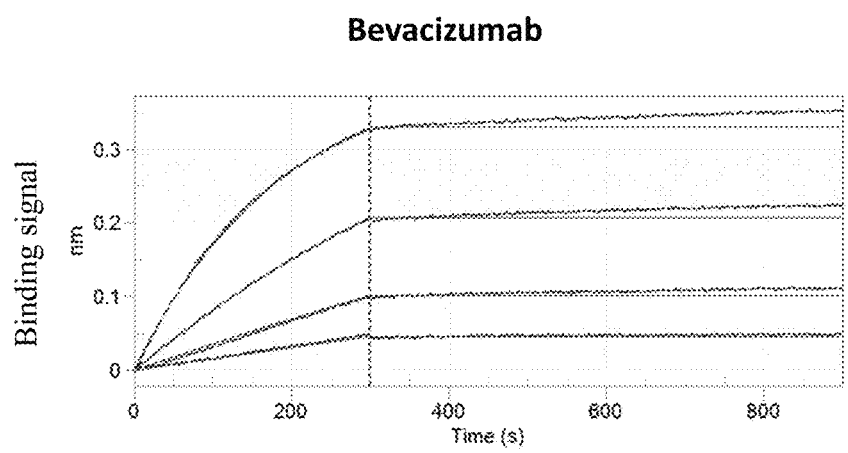
Figure 22B:
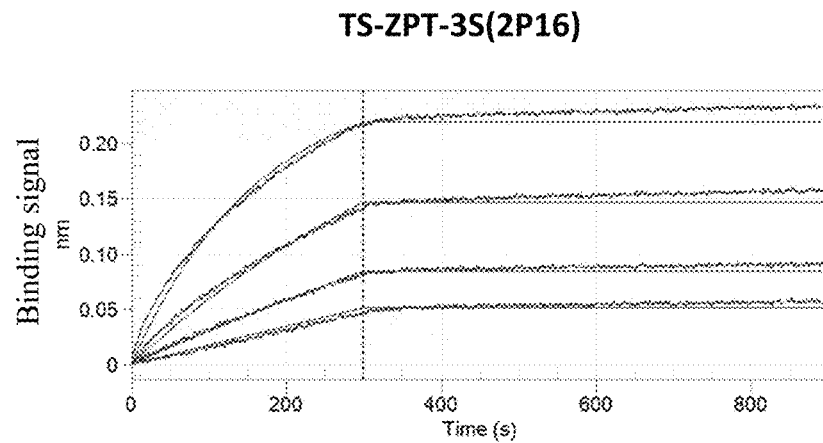
Figure 22C:
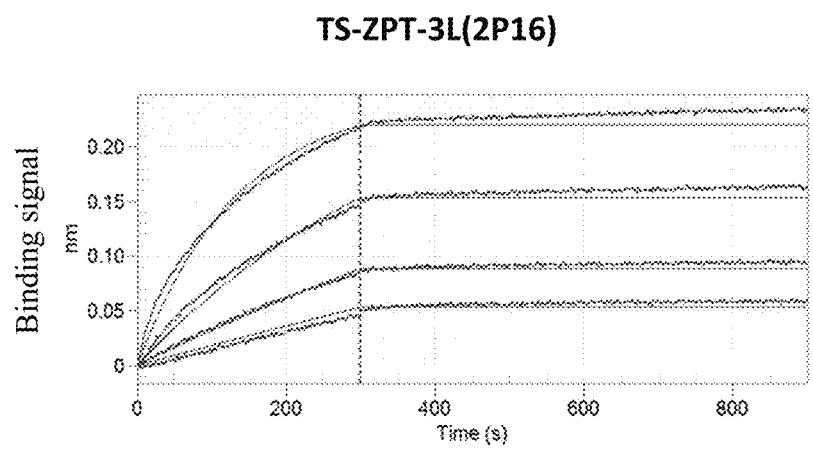
Figure 23A:
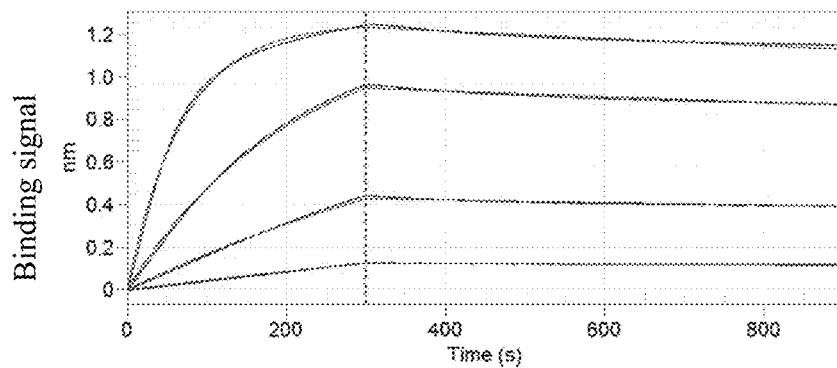
Figure 23B:
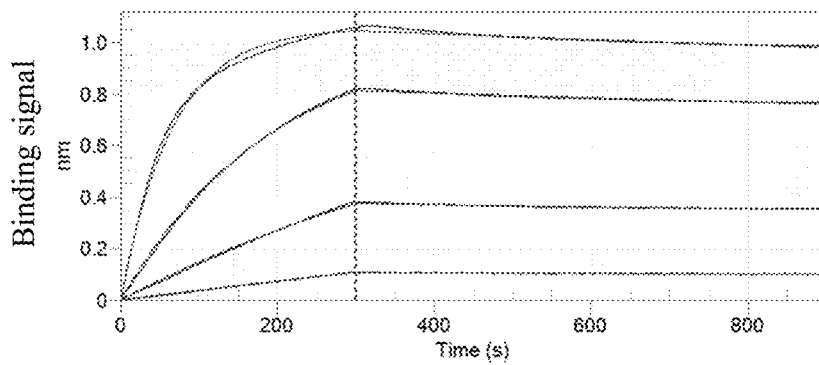
Figure 23C:
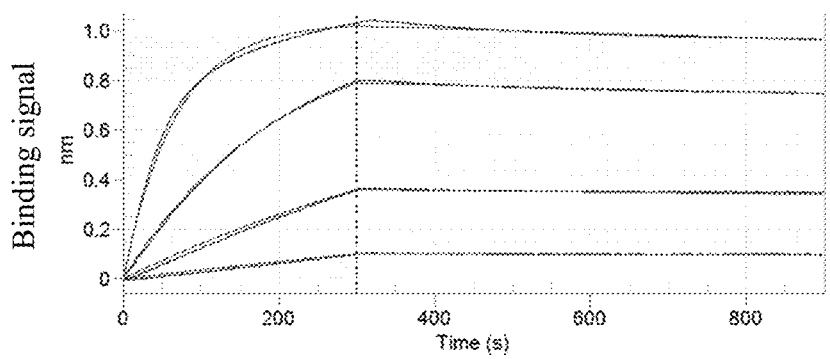

The Ang2-Tie2 blocking assay in Example 5 was used to evaluate the ability of TS-ZPT-3 S(2P16), TS-ZPT-3L (2P16), TS-ZPT-3 S(2P17) and TS-ZPT-3L(2P17) to block the interaction between Tie2 and its ligand, Ang-2 and to calculate the corresponding IC50s along with a benchmark antibody (trebananib). FIGS. 20A-20B shows that the IC50s of TS-ZPT-3L(2P16) and TS-ZPT-3L(2P17) with two Ang-2 blocking peptides were comparable to the benchmark, while TS-ZPT-3S(2P16) and TS-ZPT-3S(2P17) with only one Ang-2 blocking peptide have higher IC50s than the benchmark.

The bio-layer interferometry assay in Example 9 was used to evaluate the binding affinity of TS-ZPT-3 S(2P16), TS-ZPT-3L(2P16), TS-ZPT-3 S(2P17) and TS-ZPT-3L (2P17) against PD-1 protein. FIGS. 21A-21F show the binding and the resultant binding affinity constants. The results show that TS-ZPT-3S(2P16), TS-ZPT-3L(2P16), TS-ZPT-3S(2P17) and TS-ZPT-3L(2P17) exhibited higher affinity than the benchmark (nivolumab).

A similar bio-layer interferometry assay was used to evaluate the binding affinity of TS-ZPT-3 S(2P16), TS-ZPT-3L(2P16), TS-ZPT-3 S(2P17) and TS-ZPT-3L(2P17) against VEGF 165. FIGS. 22A-22F show the binding and the resultant binding affinity constants. The results show that TS-ZPT-3S(2P16), TS-ZPT-3L(2P16), TS-ZPT-3S(2P17) and TS-ZPT-3L(2P17) exhibited higher affinity than the benchmark (bevacizumab).

A similar bio-layer interferometry assay was used to evaluate the binding affinity of TS-ZPT-3 S(2P16), TS-ZPT-3L(2P16), TS-ZPT-3 S(2P17) and TS-ZPT-3L(2P17) against Ang-2. FIGS. 23A-23F show the binding and the resultant binding affinity constants. The results show that TS-ZPT-3S (2P16), TS-ZPT-3L(2P16), TS-ZPT-3S(2P17) and TS-ZPT-3L(2P17) exhibited similar affinity than the benchmark (trebananib).

Figure 24:
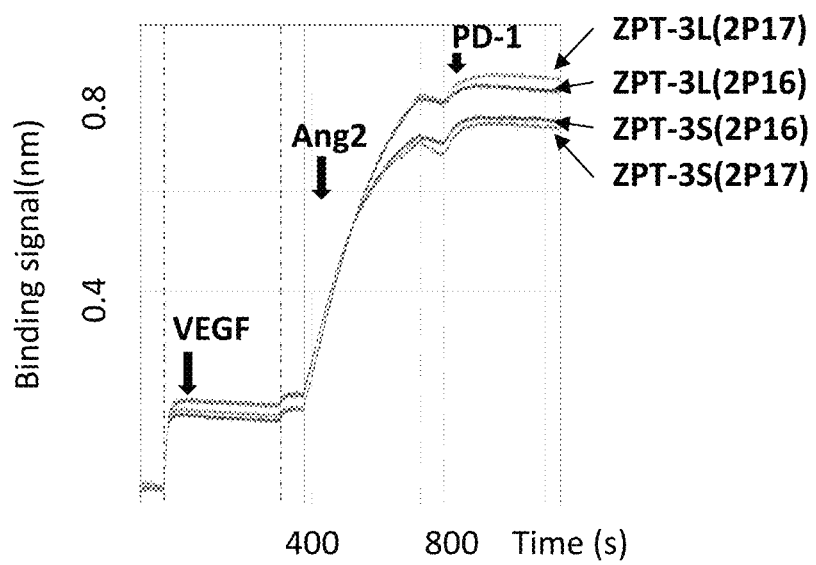
FIG. 24 shows the use of bio-layer interferometry to characterize the sequential binding of TS-ZPT-3S(2P16 and 2P17) and TS-ZPT-3L(2P16 and 2P17) trispecific antitumor antagonists to each of its three binding partners using the Octet RED96 System (ForteBio).

FIG. 24 shows the use of bio-layer interferometry to characterize the sequential binding of TS-ZPT-3 S(2P16), TS-ZPT-3L(2P16), TS-ZPT-3 S(2P17) and TS-ZPT-3L (2P17) to each of its three binding partners using the Octet RED96 System (ForteBio), largely as described in Example 11 above. Briefly, 20 nM of TS-ZPT-3 trispecific antibodies were loaded onto the anti-human IgG capture biosensors. To monitor sequential binding of the three antigens to the four TS-ZPT-3 molecules, biosensors were placed into wells containing saturating concentrations (>10 $K_D$) of each antigen (240 nM His tagged human PD-I, 120 nM human VEGF 165, 40 nM His tagged human Angiopoietin-2) for 5 min followed by 1 min dissociation. Three different sequential binding combinations were observed. These results show that TS-ZPT-3 S(2P16), TS-ZPT-3L(2P16), TS-ZPT-3 S(2P17) and TS-ZPT-3L(2P17) are able to bind to VEGF, Ang-2 and PD-1 simultaneously.

Figure 25:
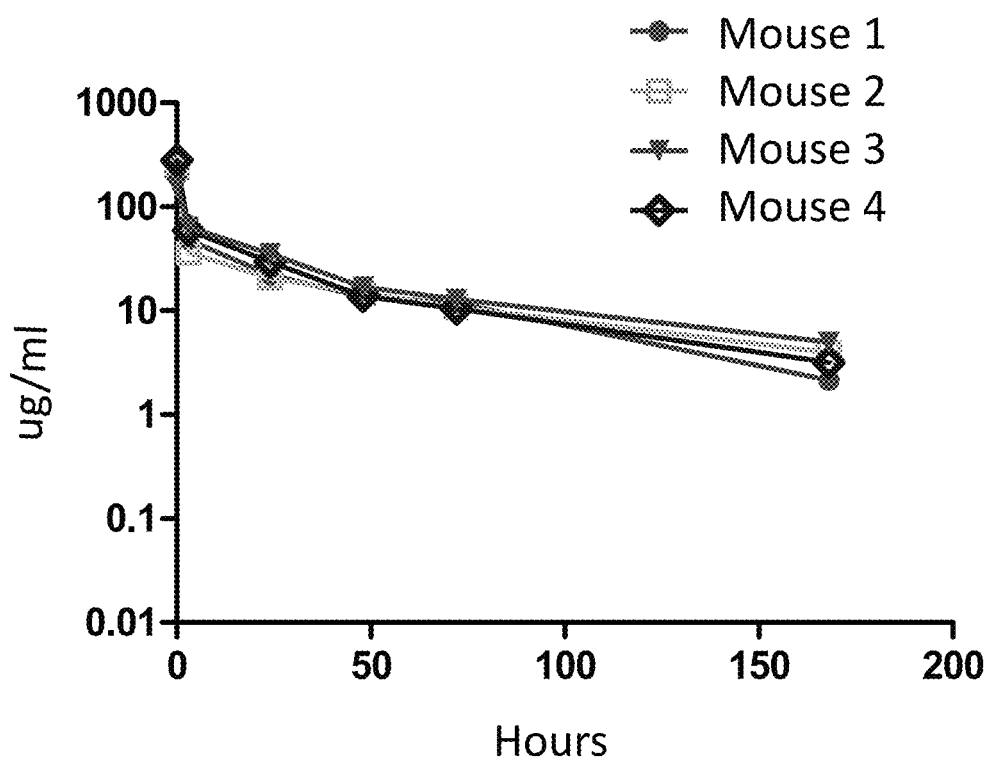
FIG. 25 shows pharmacokinetic profiles of the TS-ZPT-3L(2P17) trispecific antitumor antagonists in 4 separate mice.

To evaluate the pharmacokinetic properties of TS-ZPT-3L(2P17) in vivo, pharmacokinetic profiles were generated. Briefly, 10 mg/kg of the antagonist was intravenously injected into the tail vein of four 6-10 week old female CD 1 mice (n=2 mice per molecule). Serum was harvested at 3 minutes, 3 hours, 1 day, 3 days, 7 days and 10 days post injection. To detect the antibodies in the serum, 96 well ELISA plates were coated with 5 µg/ml goat anti-human IgG F(ab')2 fragment and then blocked with 5% milk in PBS. Serially diluted mouse serum in 5% milk and serially diluted purified protein molecule as standard were added to the plates. Following incubation with peroxidase conjugated mouse anti-human IgG and further washes, TS-ZP17T-3 were detected following incubation with TMB-ELISA substrate. The results of this analysis showed that the half-life (T½) of TS-ZP17T-3 is about 2 days (FIG. 25).

Thus, the insertion of trebananib, or a variant thereof, allows for the creation of a stable and potent trispecific therapeutic molecule.

Figure 26A:
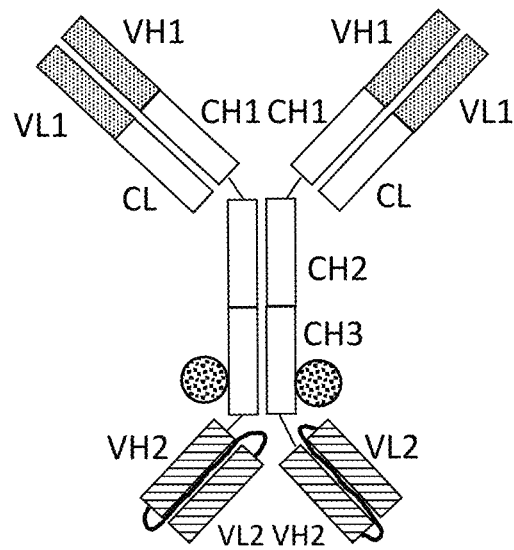
FIGS. 26A-26B show certain trispecific antitumor checkpoint antagonist configurations, where: (1) the VH1 and VL1 regions correspond to checkpoint #1, for example anti-PD-1 or anti-PD-L1 variable domains; (2) the VH2 and VL2 regions correspond to checkpoint #2, for example, anti-TIGIT, anti-LAG-3 variable domains; and (3) the circular region corresponds to trebananib (or any other biological peptide) inserted within the CH3 domain.
Figure 26B:
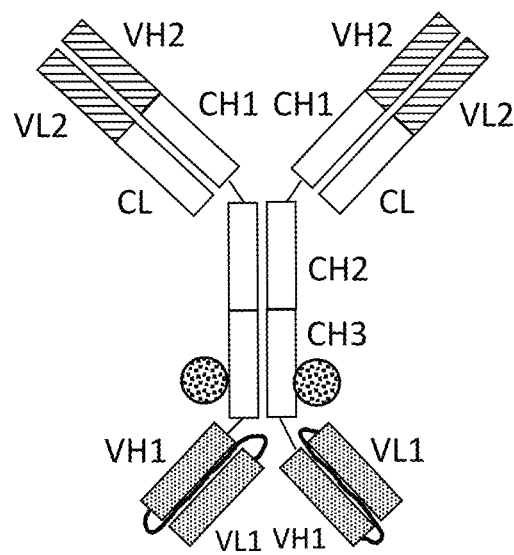

FIGS. 26A-26B show two additional trispecific molecules utilizing two checkpoint antibodies and the trebananib peptide inserted into the CH3 domain. These molecules comprise sequences shown in FIG. 1 with (1) the VH and VL from the first checkpoint antibody, for example anti-PD-1 or anti-PD-L1, (2) trebananib inserted into the CH3, (3) the VH and VL with a 3-6×G4S linker from a second checkpoint inhibitor, for example anti-TIGIT or anti-LAG3.

Figure 28:
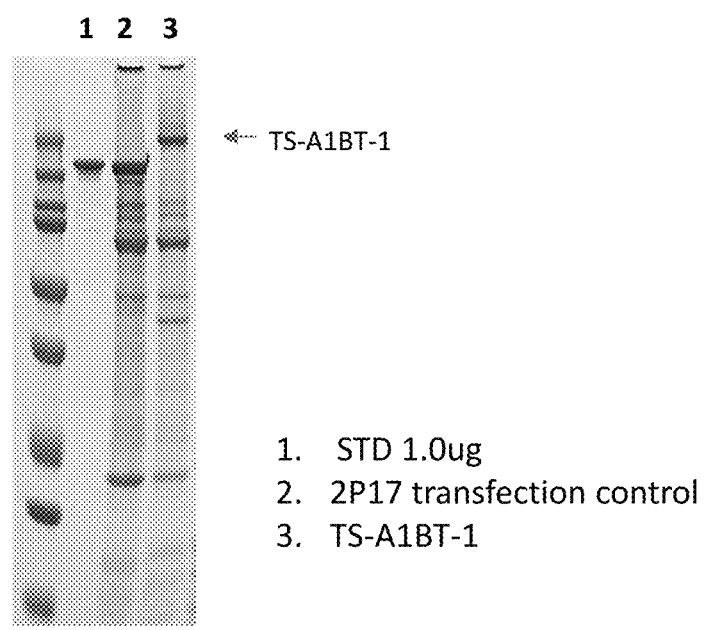
FIG. 28 shows a non-reducing SDS-PAGE analysis of TS-AiBT-1 produced by HEK293 transiently transfected cells compared to the control transfection antibody, 2P17, showing good expression levels of the trispecific antitumor antagonist.
Figure 29:
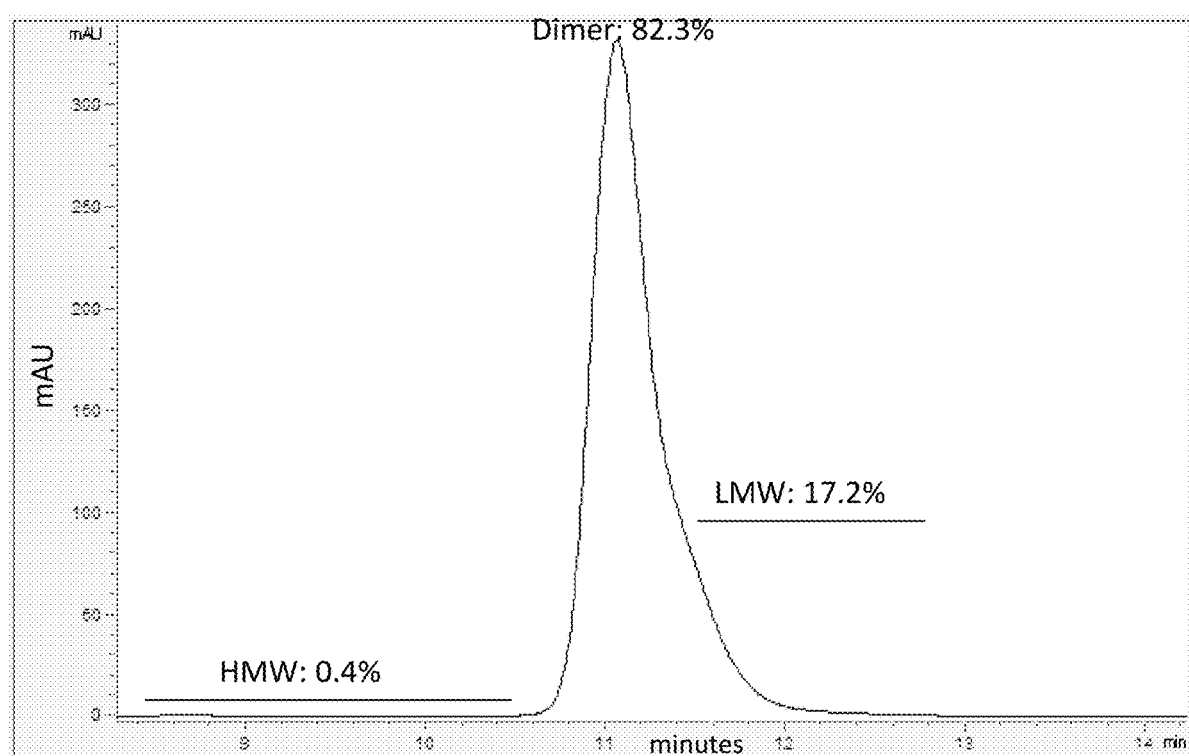
FIG. 29 shows the size exclusion chromatography analysis of TS-AIBT-1.

FIG. 27 shows an additional trispecific molecule, TS-AiBT-1 (SEQ ID NOS:229-230), with (1) the VH and VL domains encoding bevacizumab, or another anti-VEGF antibody, (2) trebananib peptide inserted into the CH3 domain, (3) the TGFBR-II ECD fused to the carboxy-terminus of the CH3 domain. This molecule was produced by transiently transfected HEK 293 cells. In FIG. 28, a non-reducing SDS-PAGE analysis of unpurified supernatants from the HEK293 cells indicate the molecule expresses well. FIG. 29 show a size exclusion chromatography analysis of protein A chromatography purified TS-AiBT-1.

Example 7: Design of Trispecific Antitumor Antagonists Comprising a TGF-β RII Extracellular Domain (TGF-β-RII ECD)

Figure 30A:
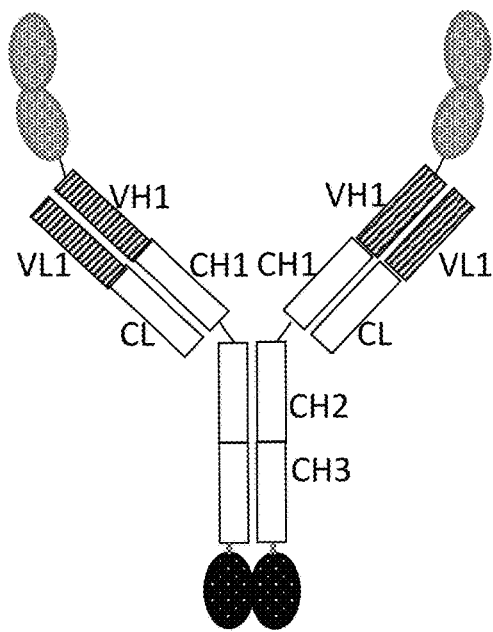
Figure 30B:
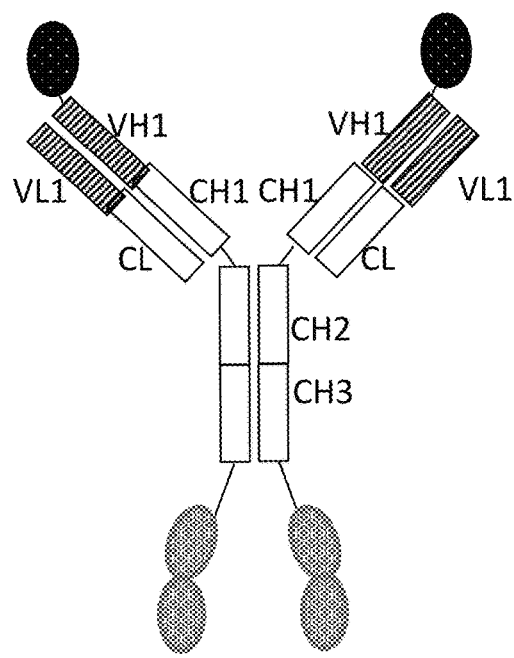
Figure 30C:
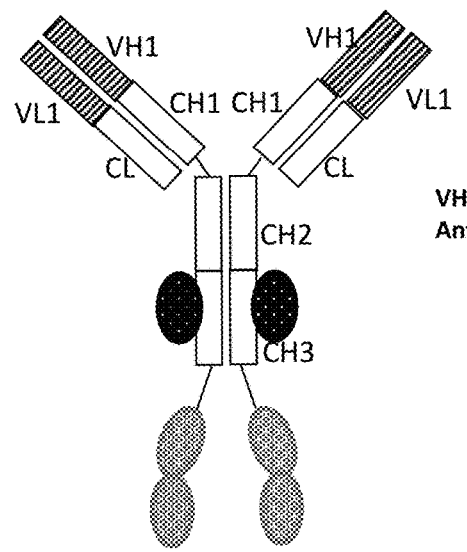

FIGS. 30A-30F show six trispecific antitumor antagonists, TS-ZPB-1, TS-ZPB-2, TS-ZPB-3, TS-ZPB-4, TS-ZPB-5 and TS-ZPB-6, respectively. These antagonists comprise: (1) anti-PD-1 or another checkpoint antibody variable domains (VH1, VL1) (FIGS. 30A-30F); (2) an aflibercept fusion protein domain: (i) fused to the amino-terminal end of each heavy chain VH1 region (FIGS. 30A, 30D, 30F) or (ii) fused to the carboxy-terminal end of each heavy chain CH3 region (FIGS. 30B, 30C, 30E) each carboxy-terminal end; and (3) a TGF-3 RII extracellular domain (ECD): (i) fused to the carboxy-terminal end of each heavy chain CH3 region (FIG. 30A), (ii) fused to the amino-terminal end of each heavy chain VH1 region (FIG. 30B), (iii) inserted within the Fc loop in each heavy chain CH3 region (FIGS. 30C, 30F), (iv) fused to the amino terminal end of each heavy chain, upstream of the aflibercept fusion protein domain (FIG. 30D), or (v) fused to the carboxyl-terminal end of each heavy chain, downstream of the aflibercept fusion protein domain (FIG. 30E).

The amino acid sequences demonstrated in SEQ ID NOS:187 and 188 show exemplary sequences of TS-ZPLB-1. The amino acid sequences demonstrated in SEQ ID NOS:270 and 271 show exemplary sequences of TS-ZPB-1. The amino acid sequences demonstrated in SEQ ID NOS: 272 and 273 show exemplary sequences for TS-ZPB-2. The amino acid sequences demonstrated in SEQ ID NOS:188 and 189 show exemplary sequences of TS-ZPLB-3. The amino acid sequences demonstrated in SEQ ID NOS:190 and 191 show exemplary sequences of TS-ZPB-3. The amino acid sequences demonstrated in SEQ ID NOS:192 and 193 show exemplary sequences of TS-ZPB-5.

Example 8: Transient Expression of TS-ZPB and TS-ZPLB Molecules

TS-ZPB-1(2P17), TS-ZPB-2(2P17), TS-ZPB-3(2P17), TS-ZPB-5(2P17) and TS-ZPLB molecules were transiently expressed in human embryonic kidney HEK293 cells, which were cultured for 7 days. Titers were quantified using a POROS A 20 m column, 2.1×30 mm, 0.1 mL by Applied Biosystems. Standard curves were generated using purified recombinant TIGIT mAb at wavelength 280 nm. Samples were injected neat at 30 μL of supernatant into the HPLC. Mobile phase A was PBS at pH 7.3; mobile phase B was PBS at pH 2.2. Multiple step gradients were done starting at 100% A for 0.2 minute, followed by 100% B from 0.22-1.22 minute, and 1.23-2.30 minute was back to 100% A, then 2.32-3.32 minute with 100% B, and finalized with 3.4-4.00 minute at 100% A. Flow rate used was 1 mL/min with a total of 4 minutes/run.

Figure 31A:
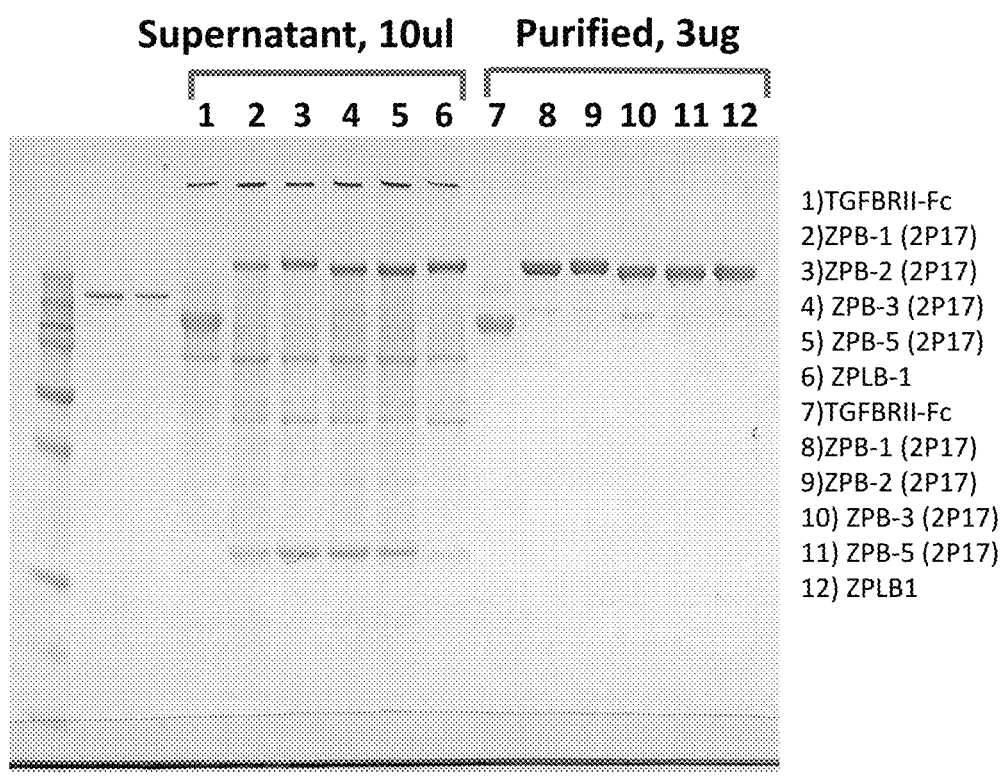
FIG. 31A shows a non-reducing SDS-PAGE analysis of trispecific antitumor antagonists TS-ZPB-1(2P17), TS-ZPB-2(2P17), TS-ZPB-3(2P17), TS-ZPB-5(2P17), and TS-ZPLB-1 transiently expressed by HEK 293 cells, before and after purification.

As shown in FIG. 31A, an SDS-PAGE analysis of TS-ZPB-1(2P17), TS-ZPB-2(2P17), TS-ZPB-3(2P17), TS-ZPB-5(2P17) and TS-ZPLB produced by transiently transfected HEK293 cells. The results of this analysis all of the molecules express well (FIG. 31B).

Figures 32A, 32B:
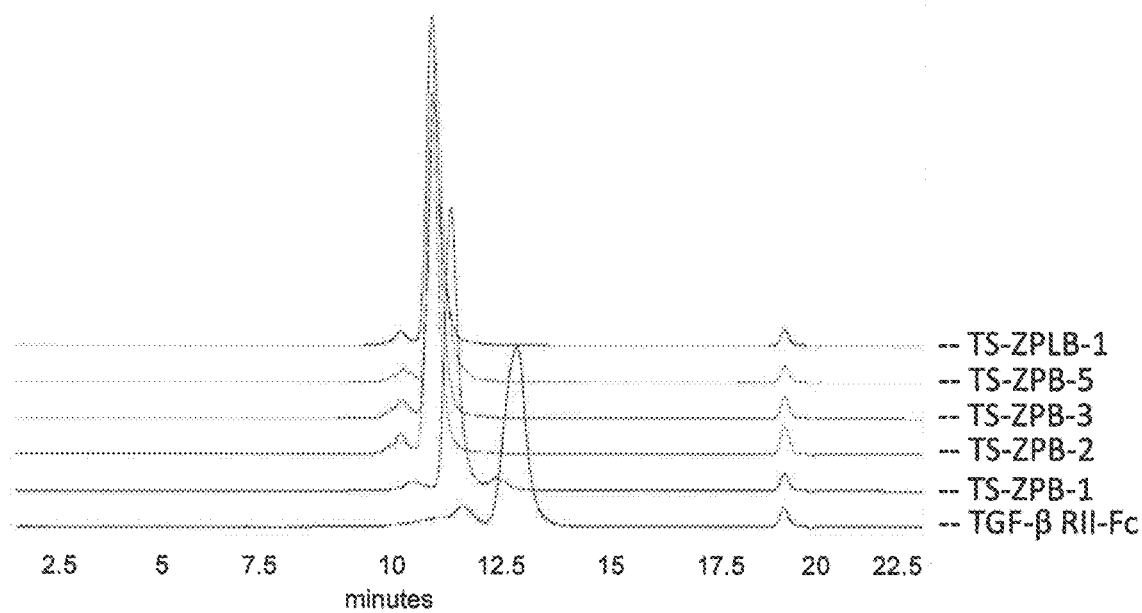
FIG. 32A shows exemplary size exclusion chromatograph (SEC) profiles for TS-ZPB-1(2P17), TS-ZPB-2(2P17), TS-ZPB-3(2P17), TS-ZPB-5(2P17), and TS-ZPLB-1 compared to TGF-3-RII-Fc. The percentage of high molecular weight (HWM %) species, low molecular weight (LMW %) species and dimerized molecule (Dimer %) are shown in FIG. 32B.

FIG. 32A shows exemplary size exclusion chromatograph (SEC) profiles for TS-ZPB-1(2P17), TS-ZPB-2(2P17), TS-ZPB-3(2P17), TS-ZPB-5(2P17) and TS-ZPLB using a Tosoh TSKgel UP-G3000SWXL column with detection at 214 nm. The results show that TS-ZPLB-1 and TS-ZPB-5 (2P17) retain the most Dimers compared to other TS-ZPB molecules.

Figures 33A, 33B:
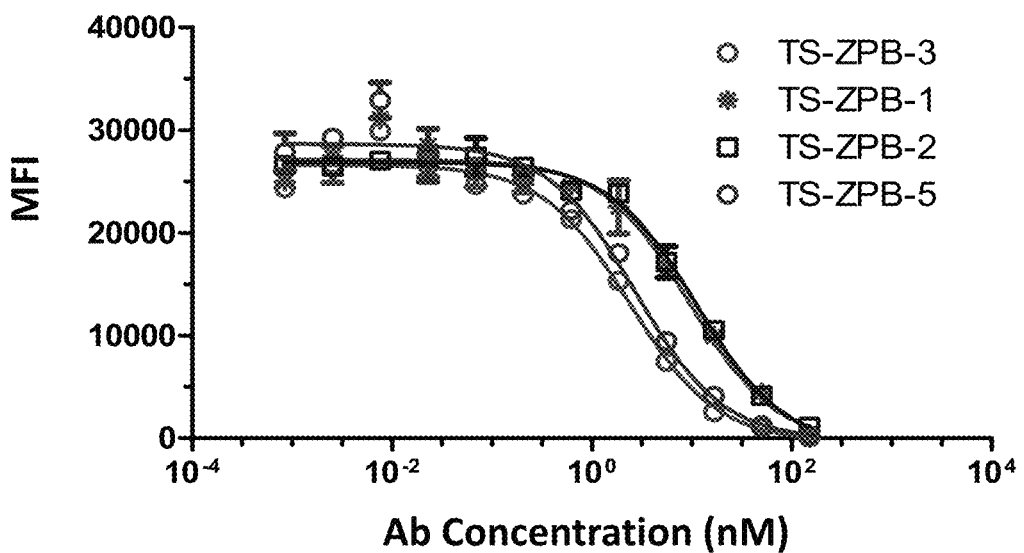
FIG. 33A shows the results of a cell-based binding assay measuring the ability of TS-ZPB-1(2P17), TS-ZPB-2 (2P17), TS-ZPB-3(2P17), and TS-ZPB-5(2P17) to block the interaction between PD-1 and PD-L1.
FIG. 33B shows the IC50 values (nM) obtained from this analysis.

Example 9: Functional Characterization of the TS-ZPB Trispecific Antagonists Relative to Controls FIG. 33A shows the results of a cell-based assay measuring the ability of TS-ZPB-1(2P17), TS-ZPB-2(2P17), TS-ZPB-3(2P17), and TS-ZPB-5(2P17) to block the interaction between PD-1 and PD-L1. In this experiment, 3 fold serial dilutions of the TS-ZPB molecules (as indicated; highest Ab concentration: 300 nM; triplicates for each mAb) were prepared; human PD-1 transfected CHOK1 cells were washed with FACS buffer (0.5% BSA 2 mM EDTA in PBS) and re-suspended at a concentration of $10^6$ cells/ml; FITC-labeled human PD-L1-Fc protein was added to human PD-1 transfected CHOK1 cells at a final concentration of 7 g/ml; mixed well; without incubation, $20 \times 10^3$ of the transfected CHOK1 cells (with PD-L1 Protein) were immediately added to 20 μl FACS buffer in a 96-well round bottom plate; 20 μl 3-fold serial dilutions of the TS-ZPB molecules were then immediately added to the cells, which were then incubated at 4° C. for 30 mins; cells were then washed and re-suspended in 30 μl 7AAD to which 35 μl of 10% neutral buffered formalin solution was added. Incubate for 15 mins before analysis with the iQue intellicyt system. FIG. 33B shows the IC50 values (nM) obtained from this analysis indicating all of the molecules are able to inhibit the interaction of PD-1 with PD-L1.

Figures 34A, 34B:
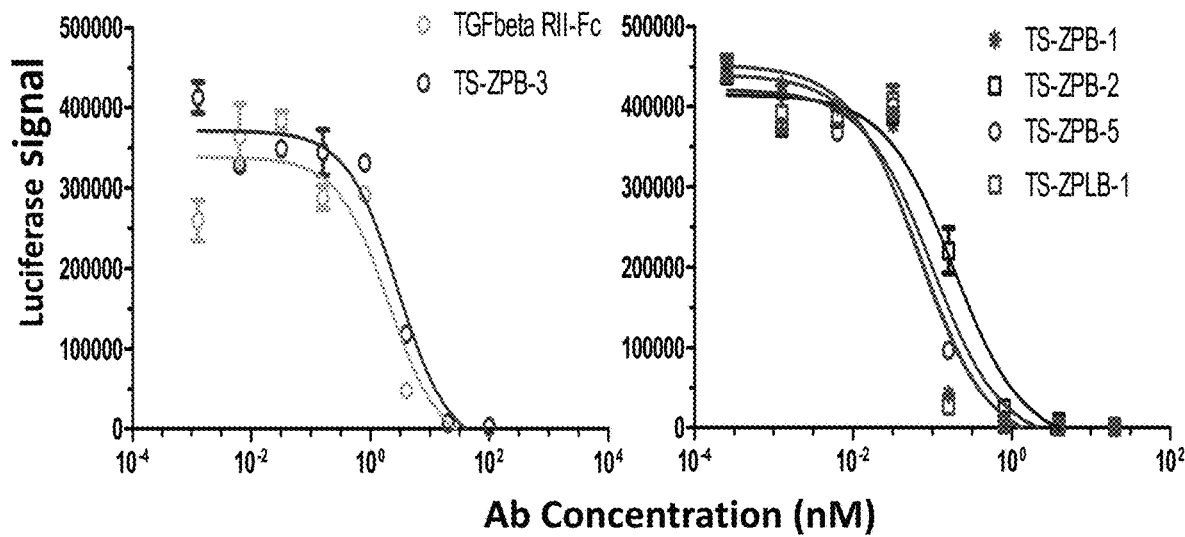
FIG. 34A shows the results of a bioassay to measure the ability of TS-ZPB-1(2P17), TS-ZPB-2(2P17), TS-ZPB-3 (2P17), TS-ZPB-5(2P17), and TS-ZPLB-1 to block TGFβ1 signaling compared to the benchmark TGF-β1 RII-Fc.
FIG. 34B shows the IC50 values (nM) obtained from this analysis.

FIG. 34A shows the results of a cell-based assay using a TGFβ/SMAD Signaling Pathway SBE Reporter-HEK293 Cell Line (BPS Bioscience, Inc., San Diego, Calif., Catalog #: 60653) to measure the ability of TS-ZPB-1(2P17), TS-ZPB-2(2P17), TS-ZPB-3(2P17), TS-ZPB-5(2P17) and TS-ZPLB and a benchmark, TGFβ1 RII-Fc to block TGFβ1 signaling. Briefly, SBE reporter-HEK293 cells were seeded at a density of ~35,000 cells per well in a white clear-bottom 96-well microplate in 100 μl of growth medium. 24 hours after seeding, the cells were treated with fivefold serial dilutions of TS-ZPB molecules in 90 μl assay medium. Then, 10 μl of diluted human TGFβ1 was added to stimulated wells (final TGFβ1 concentration=10 ng/ml); 10 μl of assay medium was added to unstimulated control wells (for determining the basal activity), while 100 μl of assay medium was added to cell-free control wells (for determining background luminescence). The plates were then incubated at 37° C. in a $CO_2$ incubator overnight (~18 hours). Following the overnight incubation, a luciferase assay was conducted using the ONE-Step™ Luciferase Assay System (BPS Bioscience, Inc.) according to the protocol provided (i.e., 100 μl of ONE-Step™ Luciferase reagent was added per well and rocked at room temperature for ~15 to 30 minutes before reading luminescence signal. FIG. 34B shows the IC50 values (nm) obtained from this analysis and indicates all of the molecules are able to block the bioactivity of TGFβ1.

Figures 35A, 35B:
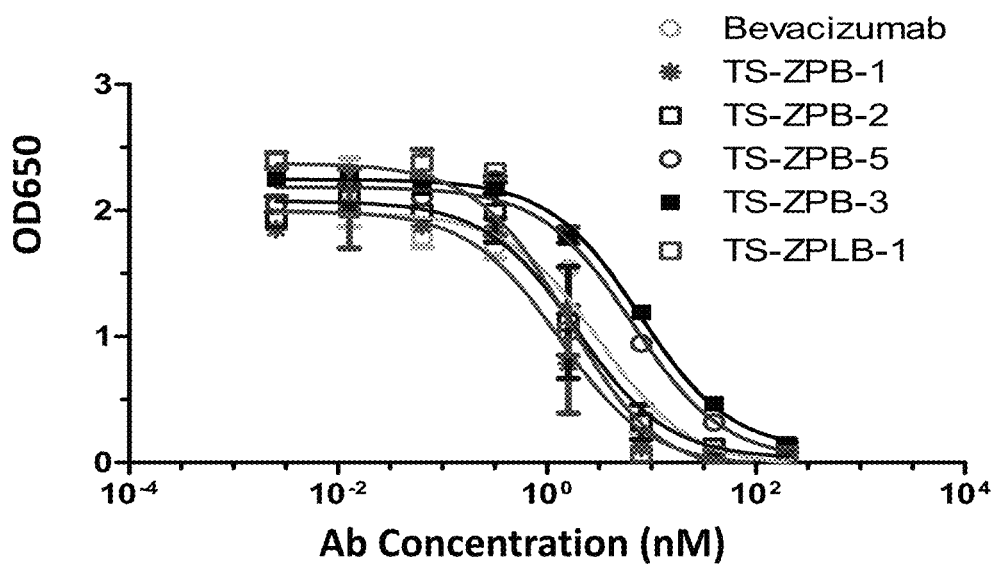
FIG. 35A shows the results of an ELISA assay measuring the ability of TS-ZPB-1(2P17), TS-ZPB-2(2P17), TS-ZPB-3(2P17), TS-ZPB-5(2P17), and TS-ZPLB-1 to block the interaction between VEGF and VEGFR-2, as compared to the benchmark bevacizumab.
FIG. 35B shows the IC50 values (nM) obtained from this analysis.

FIG. 35A shows the results of an ELISA assay measuring the ability of TS-ZPB-1(2P17), TS-ZPB-2(2P17), TS-ZPB-3(2P17), TS-ZPB-5(2P17) and TS-ZPLB to block the interaction between VEGF and VEGFR-2, as compared to the benchmark antibody, bevacizumab. Briefly, 0.5 ug/ml of recombinant human VEGF-165 (R&D #293-VE-050/CF) in carbonate-bicarbonate buffer was coated to the wells in a 96-well assay plate and incubated overnight at 4° C. The wells were then washed 3 times with 0.05% Tween 20 in PBS (wash buffer), blocked with 1% BSA in PBS for 1 hour at room temperature, and washed 3 times with wash buffer. 50 μl 5-fold serially diluted antibodies were then added to wells in the plate and incubated for 30 minutes at room temperature. Then, 50 μl 0.6 g/ml recombinant human VEGFR-2-hu IgG1-His Tag (R&D #357-KD-050) was added to the antibodies in the wells and incubated for 1 hour at room temperature, followed by 3 washes with wash buffer. 100 μl anti-His tag HRP (1:10,000) was then added and the plates were incubated for 40 mins at room temperature and washed 3 times with wash buffer. VEGFR-2 binding (His-Tag) was detected by measuring light absorbance at 650 nm after addition of 3,3',5,5'-Tetramethylbenzidine to each well in the plate. FIG. 35B shows the IC50 values (nM) obtained from this analysis and indicates all of the molecules are able to inhibit the binding of VEGF with VEGFR-2.

Example 10: Functional Characterization of TS-ZPT-5 Variant with a-Glycosylated VEGFR (Aflibercept)

Two variants of TS-ZPB-5 were produced to improve the pharmacokinetics of TS-ZPB-5. The heavy chain of TS-ZPB-5A (SEQ ID NO:205), was mutated at codon for the carboxy-terminal lysine of the CH3 domain to reduce potential proteolytic activity by proteases present in the blood. The heavy chain of TS-ZPB-5B (SEQ ID NO:206) additionally has mutations that eliminate the glycosylation sites in aflibercept, to reduce clearance by ASGRI and ASGRII.

FIGS. 36A-36C depict the three trispecific antitumor antagonists TS-ZPB-5, TS-ZPB-5A and TS-ZPB-5B.

Figure 37:
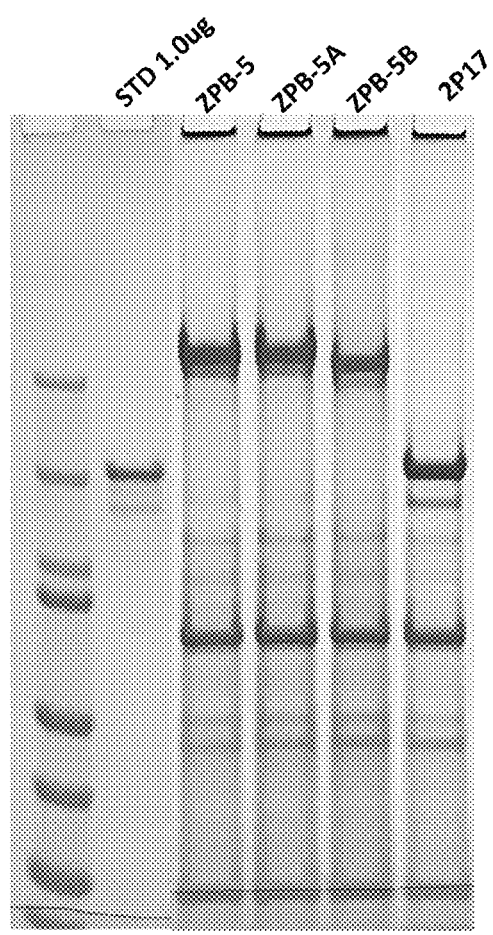
FIG. 37 shows expression levels of the trispecific antitumor antagonists TS-ZPB-5, TS-ZPB-5A and TS-ZPB-5B produced from transiently transfected HEK293 cells.

FIG. 37 shows transient HEK293 cell expression levels of TS-TPB-5, TS-ZPB-5A and TS-ZPB-5B are similar to the parental 2P17 antibody.

Figure 38:
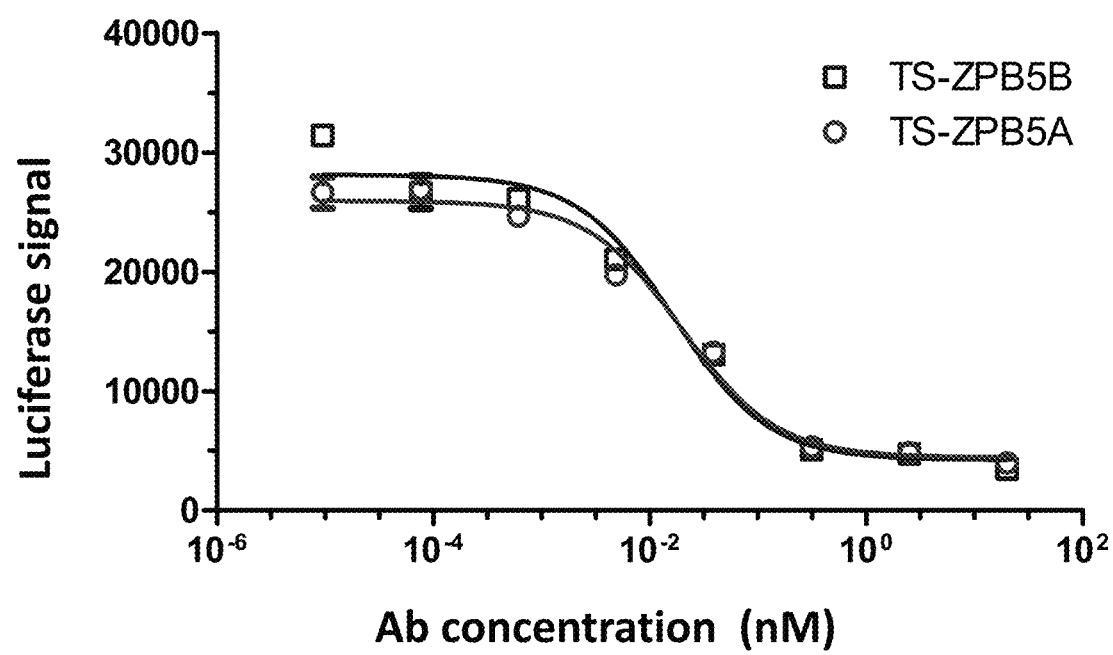
FIG. 38 shows the results of a cell-based assay measuring the ability of trispecific antitumor antagonists TS-ZPB-5, TS-ZPB-5A and TS-ZPB-5B to block the interaction between VEGF and VEGFR-2.
Figure 39:
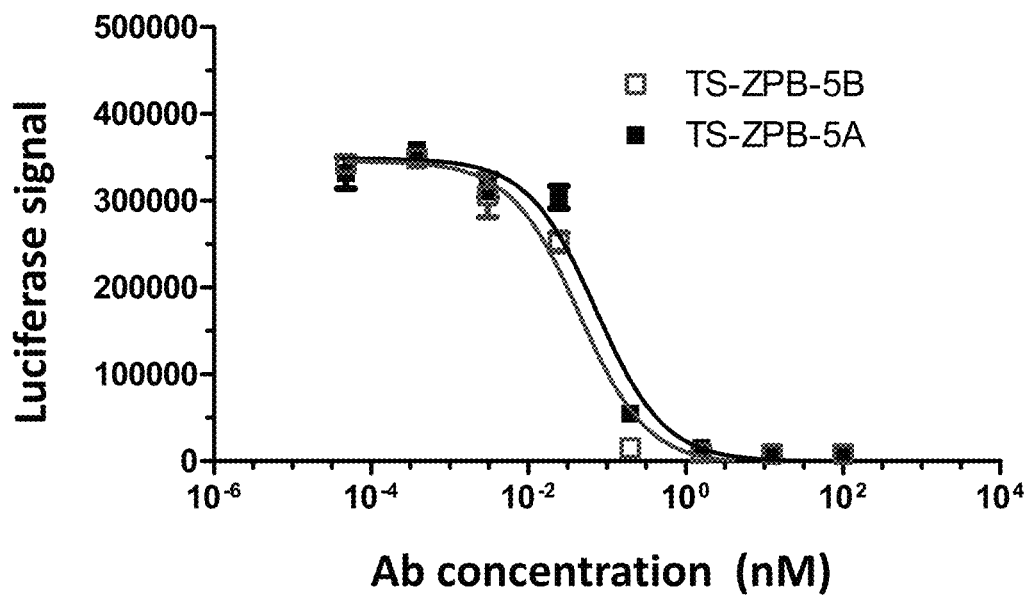
FIG. 39 shows the results of a bioassay measuring the ability of trispecific antitumor antagonists TS-ZPB-5, TS-ZPB-5A and TS-ZPB-5B to block TGFβ1 signaling.

The VEGF-VEGFR-2 blocking assay in Example 10 was used to evaluate the ability of TS-TPB-5, TS-ZPB-5A and TS-ZPB-5B to block the interaction between VEGF and VEGFR-2 (FIG. 38). The results show that binding and bioactivity of the VEGFR component are retained after mutation of aflibercept glycosylation sites from the Asn to Glu. The TGFB signaling assay described in Example 10 was used to evaluate the ability of TS-TPB-5, TS-ZPB-5A and TS-ZPB-5B to block the TGFβ signaling (FIG. 39). The results show that binding and bioactivity of TGFβR-II are retained after mutation of aflibercept glycosylation sites from the Asn to Glu.

The in vivo pharmacokinetic properties of TS-ZPT-5B variant with a-glycosylated VEGFR compared to the glycosylated version, TS-ZPT-5A was performed as described in Example 7.

FIG. 39 shows the TS-ZPB-5B variant with the mutation of aflibercept glycosylation sites from the Asn to Glu improved the pharmacokinetics by approximately five fold.

Example 11: Production and Characterization of Bispecific Inhibitors of PD-1/PD-L1 and VEGF FIGS. 41A-41C show bispecific molecules TS-ZPL-1 (or TS-ZP-1), TS-ZPL-2 (or TS-ZP-2) and TS-ZPL-3 (or TS-ZP-3) comprising (1) a PD-1, PD-L1 or other checkpoint antibody variable domains (VH and VL) (2) aflibercept fuse (i) to the amino-terminus of the VH domain (FIGS. 40A and 40B); (ii) to the carboxy-terminus of the CH3 domain (FIG. 40C). Exemplary sequences for these molecules are SEQ ID NOS:218-225.

Figures 42A, 42B:
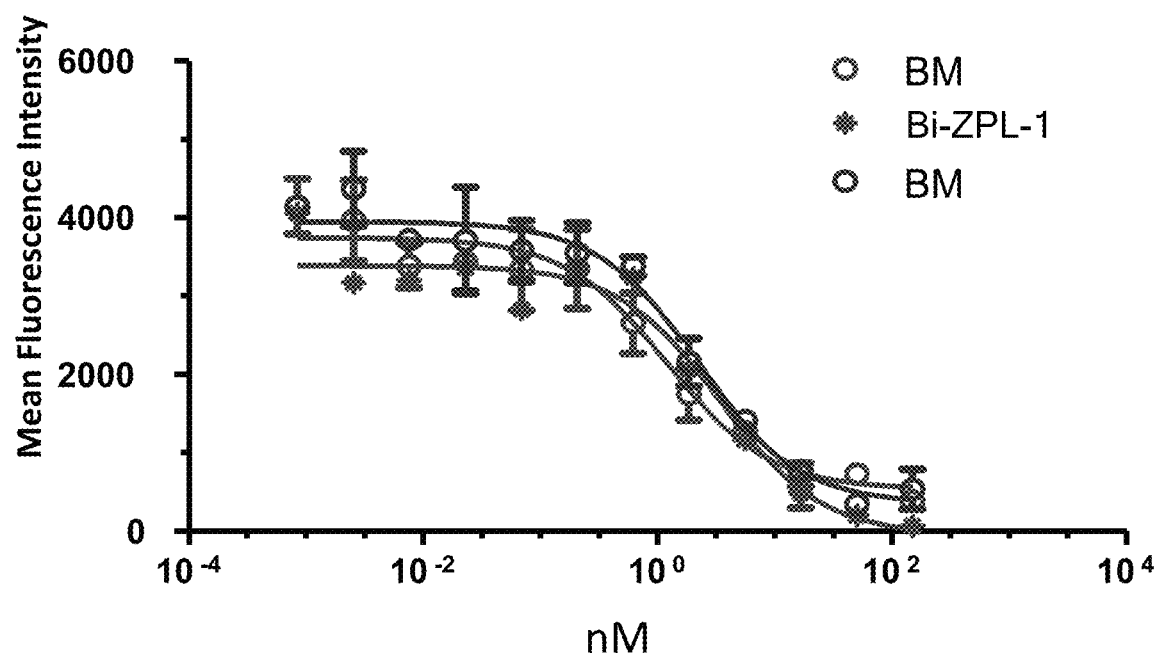
FIG. 42A shows the results of a cell-based assay measuring the ability of Bi-ZPL-1 molecules compared to the benchmark anti-PD-1 antibody for the inhibition of the interaction between PD-L1 and PD-1.
FIG. 42B shows the resulting IC50 values (nM) obtained from this analysis.

FIG. 42A shows the results of a cell-based binding assay measuring the ability of Bi-ZPL-1 molecules to block the interaction between PD-L1 and PD-1. Briefly, 2 or 3 fold serial dilutions of Anti-human PD-L1 mAb or bispecific Ab (Highest Ab concentration: 128 nM; Triplicates for each mAb) were prepared. Human PD-L1 transfected CHOK1 cells were washed with FACS buffer (0.5% BSA 2 mM EDTA in PBS) and re-suspend to a concentration of 10^6 cells/ml. FITC labeled human PD-1-Fc protein at 7 ug/ml was added to the cells and 20 ul of the mixture was added to the 2 or 3 fold serial dilutions of Anti-human PD-L1 mAb or bispecific Ab. After incubation at 4 degree for 30 mins, cells were washed and re-suspend cells in 30 ul 7AAD and 35 ul 10% neutral buffered formalin solution was added. 15 minutes later the wells were analyzed with an iQue Intellicyt system. The resulting IC50 values (nM) obtained from this analysis are shown in FIG. 42B, and indicate Bi-ZPL-1 retains the ability to inhibit PD-1-PD-L1 binding.

Figures 43A, 43B:
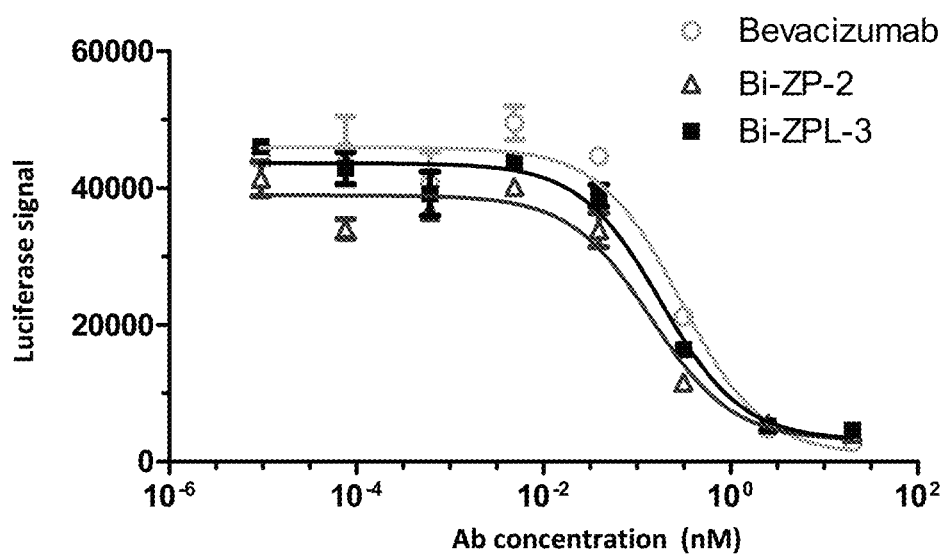
FIG. 43A shows the results of a bioassay measuring the ability of Bi-ZPL-1 molecules compared to the benchmark anti-PD-1 antibody for the inhibition of the interaction between VEGF and VEGFR-2.
FIG. 43B shows the resulting IC50 values (nM).

FIG. 43A the bioassay of example 10 testing the ability of Bi-ZP-2 and Bi-ZPL-3 to block the bioactivity of VEGF165 on VEGFR-2 expressing cells. The tabular results are shown in FIG. 43B, and indicate the molecules retain bioactivity relative the benchmark antibody, bevacizumab.

Figure 44:
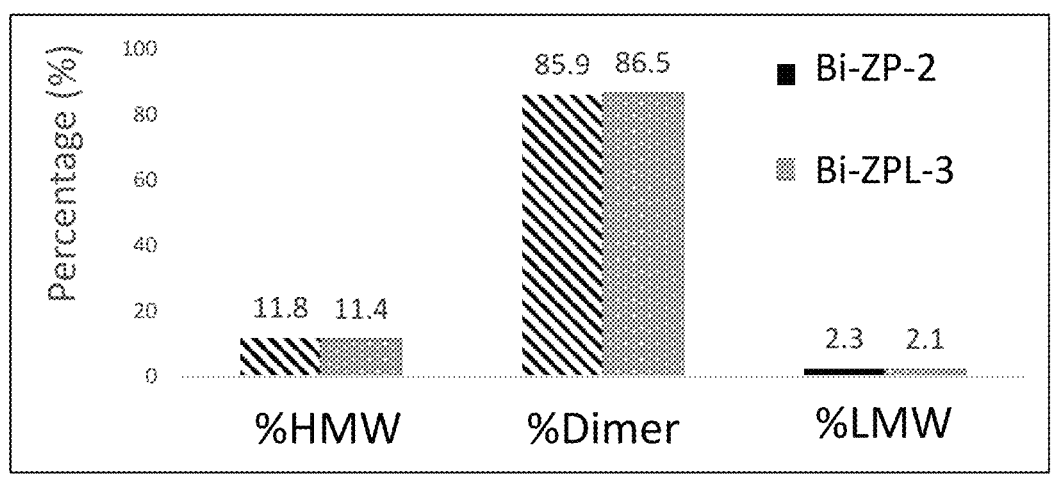
FIG. 44 shows the results of a size exclusion chromatography analysis of protein A purified Bi-ZP-2 and Bi-ZPL-3.

Both Bi-ZP-2 and Bi-ZPL-3 were assessed by size exclusion chromatography and had similar percentages of HMW, Dimer, and LMW species, as shown in FIG. 44.

FIG. 45 shows the pharmacokinetics of Bi-ZP-2 and Bi-ZPL-3 in two mice each. Bi-ZP-2 exhibits a longer half-life in vivo than Bi-ZPL-3.

The above description is for the purpose of teaching a person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A trispecific antagonist, comprising:

an immunoglobulin scaffold comprising a CH1 domain, a CH2 domain and a CH3 domain;

a first targeting domain comprising one or more immunoglobulin variable domains selected from the group consisting of (1) an anti-PD-1 variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:48, 51, 54, 56 and 59, the HCDR2 is selected from the group consisting of SEQ ID NOS:49, 52, 57 and 60, HCDR3 is selected from the group consisting of SEQ ID NOS:50, 53, 55, 58 and 61, the LCDR1 is selected from the group consisting of SEQ ID NOS:62, 65, 68, 69, 70 and 73, the LCDR2 is selected from the group consisting of SEQ ID NOS:63, 66, 71 and 74, and the LCDR3 is selected from the group consisting of SEQ ID NOS:64, 67, 72 and 75, (2) an anti-PD-L1 variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:76, 79, 85 and 88, the HCDR2 is selected from the group consisting of SEQ ID NOS:77, 80, 82, 84, 86 and 89, the HCDR3 is selected from the group consisting of SEQ ID NOS:78, 81, 83, 87 and 90, the LCDR1 is selected from the group consisting of SEQ ID NOS:91, 94, 98, 101 and 104, the LCDR2 is selected from the group consisting of SEQ ID NOS:92, 95, 99, 102, 105, and the LCDR3 is selected from the group consisting of SEQ ID NOS:93, 96, 97, 100 and 106, (3) an anti-TIGIT variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:1, 6, 11, 15, 17, 20, 23, the HCDR2 is selected from the group consisting of SEQ ID NOS:2, 4, 7, 9, 12, 13, 16, 18, 21 and 24, the HCDR3 is selected from the group consisting of SEQ ID NOS:3, 5, 8, 10, 14, 19, 22, 25, the LCDR1 is selected from the group consisting of SEQ ID NOS:26, 29, 31, 33, 35, 39, 42 and 45, the LCDR2 is selected from the group consisting of SEQ ID NOS:27, 30, 36, 37, 40, 43, 46, and the LCDR3 is selected from the group consisting of SEQ ID NOS:28, 32, 34, 38, 41, 44 and 47, and (4) an anti-LAG-3 variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:155-157, the HCDR2 is selected from the group consisting of SEQ ID NOS:158-160, the HCDR3 is selected from the group consisting of SEQ ID NOS:161-163, the LCDR1 is selected from the group consisting of SEQ ID NOS:164-166, the LCDR2 is selected from the group consisting of SEQ ID NOS:167 and 168, and the LCDR3 is selected from the group consisting of SEQ ID NOS:169 and 170, a second targeting domain that binds specifically to VEGF and comprises SEQ ID NO:185 or 207; and a third targeting domain comprising a peptide inhibitor of the angiopoietin/Tie-2 signaling pathway, wherein the peptide inhibitor comprises SEQ ID NO:194.

2. The trispecitic antagonist of claim 1, wherein the first targeting domain comprises an anti-PD-1 variable domain and wherein the second targeting domain is structurally linked to a carboxy-terminal of the CH3 domain via a peptide linker comprising an amino acid sequence selected from the group consisting of SEQ ID NOS: 284-289, and wherein the third targeting domain is inserted within the CH3 domain.

3. The trispecific antagonist of claim 1, wherein the first targeting domain comprises:

(1) an immunoglobulin HCVR comprising the amino acid sequence of SEQ ID NO:137; and (2) an immunoglobulin LCVR comprising the amino acid sequence of SEQ ID NO: 138, or wherein the first targeting domain comprises:

(1) an immunoglobulin HCVR comprising the amino acid sequence of SEQ ID NO:135; and (2) an immunoglobulin LCVR comprising the amino acid sequence of SEQ ID NO:136.

4. The trispecific antagonist of claim 1, wherein
(A) the first targeting domain comprises an anti-PD-1 variable domain comprising
(1) an HCVR comprising three complementarity determining regions (HCDRs): HCDR1, HCDR2 and HCDR3,
wherein the HCDR1 comprises the amino acid sequence of SEQ ID NO:56,
wherein the HCDR2 comprises the amino acid sequence SEQ ID NO:57, and
wherein the HCDR3 comprises the amino acid sequence of SEQ ID NO:58; and
(2) an LCVR comprising three complementarity determining regions (LCDRs): LCDR1, LCDR2 and LCDR3,
wherein the LCDR1 comprises the amino acid sequence of SEQ ID NO:70,
wherein the LCDR2 comprises the amino acid sequence of SEQ ID NO:71, and
wherein the LCDR3 comprises the amino acid sequence of SEQ ID NO:72, or
(B) the first targeting domain comprises an anti-PD-1 variable domain comprising:
(1) an HCVR comprising three complementarity determining regions (HCDRs): HCDR1, HCDR2 and HCDR3,
wherein the HCDR1 comprises the amino acid sequence of SEQ ID NO:59,
wherein the HCDR2 comprises the amino acid sequence SEQ ID NO:60, and
wherein the HCDR3 comprises the amino acid sequence of SEQ ID NO:61; and
(2) an LCVR comprising three complementarity determining regions (LCDRs): LCDR1, LCDR2 and LCDR3,
wherein the LCDR1 comprises the amino acid sequence of SEQ ID NO:73,
wherein the LCDR2 comprises the amino acid sequence of SEQ ID NO:74, and
wherein the LCDR3 comprises the amino acid sequence of SEQ ID NO:75.

5. The trispecific antagonist of claim 4, wherein the second targeting domain comprises the amino acid sequence of SEQ ID NO:185.

6. The trispecific antagonist of claim 1, wherein the third targeting domain comprises the amino acid sequence of SEQ ID NO:182.

7. The trispecific antagonist of claim 1, comprising:
an immunoglobulin light chain comprising the amino acid sequence of SEQ ID NO:201 and an immunoglobulin heavy chain comprising the amino acid sequence of SEQ ID NO:200 or SEQ ID NO:202, or
an immunoglobulin light chain comprising the amino acid sequence of SEQ ID NO: 232 and and an immunoglobulin heavy chain comprising the amino acid sequence of SEQ ID NO:231 or SEQ ID NO:233.

8. A trispecific antagonist, comprising:
an immunoglobulin scaffold comprising a CH1 domain, a CH2 domain and a CH3 domain;
a first targeting domain comprising
(1) an anti-PD-1 variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:48, 51, 54, 56 and 59, the HCDR2 is selected from the group consisting of SEQ ID NOS:49, 52, 57 and 60, HCDR3 is selected from the group consisting of SEQ ID NOS:50, 53, 55, 58 and 61, the LCDR1 is selected from the group consisting of SEQ ID NOS:62, 65, 68, 69, 70 and 73, the LCDR2 is selected from the group consisting of SEQ ID NOS:63, 66, 71 and 74, and the LCDR3 is selected from the group consisting of SEQ ID NOS: 64, 67, 72 and 75, or
(2) an anti-PD-L1 variable domain comprising three heavy chain complementary regions HCDR1, HCDR2 and HCDR3, and three light chain complementary regions LCDR1, LCDR2 and LCDR3, wherein the HCDR1 is selected from the group consisting of SEQ ID NOS:76, 79, 85 and 88, the HCDR2 is selected from the group consisting of SEQ ID NOS:77, 80, 82, 84, 86 and 89, the HCDR3 is selected from the group consisting of SEQ ID NOS:78, 81, 83, 87 and 90, the LCDR1 is selected from the group consisting of SEQ ID NOS:91, 94, 98, 101 and 104, the LCDR2 is selected from the group consisting of SEQ ID NOS:92, 95, 99, 102, 105, and the LCDR3 is selected from the group consisting of SEQ ID NOS:93, 96, 97, 100 and 106;
a second targeting domain comprising a component of VEGFR comprising SEQ ID NO:185 or 207; and
a third targeting domain comprising a TGF-β pathway inhibitor comprising SEQ ID NO:186 or 197.

9. The trispecific antagonist of claim 8, wherein the first targeting domain comprises an anti-PD-1 variable domain.

10. The trispecific antagonist of claim 8, wherein
(A) the first targeting domain comprises an anti-PD-1 variable domain comprising:
(1) an immunoglobulin HCVR comprising three complementarity determining regions (HCDRs): HCDR1, HCDR2 and HCDR3,
wherein the HCDR1 comprises the amino acid sequence of SEQ ID NO:59,
wherein the HCDR2 comprises the amino acid sequence of SEQ ID NO:60, and
wherein the HCDR3 comprises the amino acid sequence of SEQ ID NO:61; and/or
(2) an immunoglobulin LCVR, wherein the light chain variable region comprises three complementarity determining regions (LCDRs): LCDR1, LCDR2 and LCDR3,
wherein the LCDR1 comprises the amino acid sequence of SEQ ID NO:73,
wherein the LCDR2 comprises the amino acid sequence of SEQ ID NO:74, and
wherein the LCDR3 comprises the amino acid sequence of SEQ ID NO:75, or
(B) the first targeting domain comprises an anti-PD-1 variable domain comprising:
(1) an immunoglobulin HCVR comprising three complementarity determining regions (HCDRs): HCDR1, HCDR2 and HCDR3,
wherein the HCDR1 comprises the amino acid sequence of SEQ ID NO:56,
wherein the HCDR2 comprises the amino acid sequence of SEQ ID NO:57, and
wherein the HCDR3 comprises the amino acid sequence of SEQ ID NO:58; and/or
(2) an immunoglobulin LCVR comprising three complementarity determining regions (LCDRs): LCDR1, LCDR2 and LCDR3,
wherein the LCDR1 comprises the amino acid sequence of SEQ ID NO:70, wherein the LCDR2 comprises the amino acid sequence of SEQ ID NO:71, and wherein the LCDR3 comprises the amino acid sequence of SEQ ID NO:72.

11. The trispecific antagonist of claim 8, wherein the third targeting domain comprises SEQ ID NO:186.

12. The trispecific antagonist of claim 8, comprising:

an immunoglobulin light chain comprising the amino acid sequence of SEQ ID NO: 193, and/or an immunoglobulin heavy chain comprising an amino acid sequence selected from the group consisting of SEQ ID NOS:192, 205 and 206.

13. The trispecific antagonist of claim 8, wherein (1) the first targeting domain is structurally linked to the amino-terminal of the immunoglobulin scaffold via a peptide linker, and wherein the peptide linker comprises an amino acid sequence selected from the group consisting of SEQ ID NOS: 284-289, or (2) the second targeting, domain is structurally linked to the carboxyl-terminal of the immunoglobulin scaffold via a peptide linker, and wherein the peptide linker comprises an amino acid sequence selected from the group consisting of SEQ ID NOS: 284-289, or (3) the third targeting domain is structurally linked to the carboxyl-terminal of the second targeting domain via a peptide linker, and wherein the peptide linker comprises an amino acid sequence selected from the group consisting of SEQ ID NOS: 284-289.

14. A method for treating a cell proliferative disorder, comprising:

administering to a subject in need thereof an effective amount of the trispecific antagonist of claim 1.

15. A method for treating a cell proliferative disorder, comprising:

administering to a subject in need thereof an effective amount of the trispecific antagonist of claim 8.

* * * * *

SEQUENCE LISTING

```
<160> NUMBER OF SEQ ID NOS: 420

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1
```

```
Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Tyr Ile Ser Tyr Ser Gly Ser Thr Gly Tyr Asn Pro Ser Leu Lys Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Arg Met Ile Gly Tyr Ala Met Asp Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Tyr Ile Thr Tyr Ser Gly Gly Ser Thr Ser Tyr Asn Pro Ser Leu Lys
1               5                   10                  15

Ser

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Arg Gln Ile Gly Leu Gly Phe Thr Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Asp His Thr Ile His
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 7

Tyr Phe Tyr Pro Arg Asp Gly Ser Thr Lys Tyr Asn Glu Lys Phe Lys
1               5                   10                  15
Gly

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Gly Met Leu Arg Trp Phe Ala Asp
1               5

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Tyr Ile Tyr Pro Arg Asp Gly Ser Ser Lys Tyr Asn Val Lys Phe Lys
1               5                   10                  15
Gly

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Met Leu Arg Trp Phe Ala Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Asp Gln Ala Ile His
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Tyr Ile Tyr Pro Arg Asp Gly Ser Thr Lys Tyr Asn Glu Thr Phe Lys
1               5                   10                  15
Gly

<210> SEQ ID NO 13
<211> LENGTH: 16
```

```
<212> TYPE: PRT
<213> ORGANISM: Artificial Sequence
<220> FEATURE:
<223> OTHER INFORMATION: Synthetic

<400> SEQUENCE: 13

Tyr Ile Thr Tyr Ser Gly Ser Thr Ser Tyr Asn Pro Ser Leu Lys Ser
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Arg Gln Val Gly Leu Gly Phe Ala Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Ser Asp Ser Ala Trp Asn
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic

<400> SEQUENCE: 16

Tyr Ile Thr Tyr Ser Gly Ser Thr Asn Tyr Asn Pro Ser Leu Arg Ser
1               5                   10                  15

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Asn Tyr Gly Met Asn
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Trp Ile Asn Thr Tyr Thr Gly Glu Pro Thr Tyr Ala Asp Asp Phe Lys
1               5                   10                  15
Gly

<210> SEQ ID NO 19
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 19

Ala Pro Pro Tyr Gly Tyr Asp Val Arg Phe Ala Tyr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Thr Phe Ala Met Gly Val Gly
1               5

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

His Ile Trp Trp Asp Asp Lys Tyr Tyr Asn Pro Ala Leu Lys Ser
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Met Asp Tyr Ser Tyr Phe Ala Trp Phe Ala Tyr
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Ser Tyr Tyr Met His
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Ile Asn Pro Ser Gly Gly Arg Thr Ser Tyr Ala Gln Met Phe Gln Gly
1               5                   10                  15

<210> SEQ ID NO 25
<211> LENGTH: 13
```

<212> TYPE: PRT
<213> ORGANISM: Artificial Sequence
<220> FEATURE:
<223> OTHER INFORMATION: Synthetic

<400> SEQUENCE: 25

Asp Arg Glu Glu Gln Trp Pro Val Gly Gly Phe Asp Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Lys Ala Ser Gln Asp Val Ser Thr Val Val Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Ser Ala Ser Tyr Arg Tyr Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Gln His Tyr Ser Thr Pro Trp Thr
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic

<400> SEQUENCE: 29

Lys Ala Ser Gln Asp Leu Ser Thr Ala Val Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Ser Ser Ser Tyr Arg Tyr Thr
1               5

<210> SEQ ID NO 31
<211> LENGTH: 11
<212> TYPE: PRT

```
<213> ORGANISM: Artificial Sequence
<220> FEATURE:
<223> OTHER INFORMATION: Synthetic

<400> SEQUENCE: 31

Lys Ala Ser Gln Asp Val Ser Thr Val Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln His Tyr Ser Thr Pro Leu Thr
1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Lys Ala Ser Gln Asp Val Phe Thr Ala Val Ala
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln Gln His Tyr Ser Ile Pro Leu Thr
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Lys Ala Ser Gln Asp Val Ser Thr Ala Val Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Ser Ala Ser Tyr His Tyr Thr
1               5

<210> SEQ ID NO 37
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 37

Ser Ala Ser Tyr Arg Phe Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Gln His His Tyr Ser Thr Pro Trp Thr
1               5

<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

Arg Ser Ser Gln Ser Ile Val His Ser Asn Gly Asn Thr Tyr Leu Glu
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Lys Val Ser Asp Arg Phe Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Phe Gln Gly Ser His Val Pro Trp Thr
1               5

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Arg Ser Ser Thr Gly Ala Val Thr Thr Ser Asn Tyr Ala Asn
1               5                   10

<210> SEQ ID NO 43
<211> LENGTH: 7
<212> TYPE: PRT
<213> ORGANISM: Artificial Sequence
<220> FEATURE:
```

```
<223> OTHER INFORMATION: Synthetic

<400> SEQUENCE: 43

Gly Thr Asn Asn Arg Ala Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Ala Leu Trp Tyr Ser Asn His Trp Val
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Arg Ala Ser Gln Ser Ile Arg Arg Tyr Leu Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Ser Ala Ser Asn Leu Gln Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Gln Gln Ser Tyr Ile Ile Pro Pro Thr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Asn Phe Leu Met Ser
1               5

<210> SEQ ID NO 49
<211> LENGTH: 17
<212> TYPE: PRT
<213> ORGANISM: Artificial Sequence
<220> FEATURE:
<223> OTHER INFORMATION: Synthetic
```

<400> SEQUENCE: 49

Thr Ile Ser Gly Gly Gly Arg Asp Thr Tyr Tyr Val Asp Ser Val Lys
1               5                   10                  15

Gly

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

Arg Thr Thr Tyr Ser Met Asp Tyr
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic

<400> SEQUENCE: 51

Asn Ser Tyr Leu Tyr
1               5

<210> SEQ ID NO 52
<211> LENGTH: 17
<212> TYPE: PRT
<213> ORGANISM: Artificial Sequence
<220> FEATURE:
<223> OTHER INFORMATION: Synthetic

<400> SEQUENCE: 52

Gly Ile Asn Pro Ser Asn Gly Gly Thr Asn Phe Asn Glu Lys Phe Lys
1               5                   10                  15

Thr

<210> SEQ ID NO 53
<211> LENGTH: 11
<212> TYPE: PRT
<213> ORGANISM: Artificial Sequence
<220> FEATURE:
<223> OTHER INFORMATION: Synthetic

<400> SEQUENCE: 53

Arg Asp Tyr Asn Tyr Asp Gly Gly Phe Asp Ser
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Synthetic

<400> SEQUENCE: 54

Asn Ser Tyr Ile Tyr
1               5

<210> SEQ ID NO 55
<211> LENGTH: 12
<212> TYPE: PRT

```
<213> ORGANISM: Artificial Sequence
<220> FEATURE:
<223> OTHER INFORMATION: Synthetic

<400> SEQUENCE: 55

Arg Arg Asp Tyr Arg Tyr Asp Gly Gly Phe Asp Ser
1               5                   10

<210> SEQ ID NO 56
<211> LENGTH: 5
<212> TYPE: PRT
<213> ORGANISM: Artificial Sequence
<220> FEATURE:
<223> OTHER INFORMATION: Synthetic

<400> SEQUENCE: 56

Thr Tyr Tyr Ile Tyr
1               5

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Gly Ile Asn Pro Gly Asn Gly Gly Thr Asn Phe Asn Glu Lys Phe Lys
1               5                   10                  15

Ile

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Arg Tyr His Gly Tyr Asp Gly Gly Leu Asp Tyr
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Synthetic

<400> SEQUENCE: 59

Ser Tyr Tyr Ile His
1               5

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

Trp Ile Phe Pro Gly Ser Gly Asn Ser Lys Tyr Asn Glu Asn Phe Lys
1               5                   10                  15

Gly
```

```
<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Ser Glu Thr Tyr Asp Tyr Gly Asp Tyr
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Leu Ala Ser Gln Thr Ile Gly Thr Trp Leu Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Ala Ala Thr Ser Leu Ala Asp
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Phe Tyr Ser Ile Pro Trp Thr
1               5

<210> SEQ ID NO 65
<211> LENGTH: 12
<212> TYPE: PRT
<213> ORGANISM: Artificial Sequence
<220> FEATURE:
<223> OTHER INFORMATION: Synthetic

<400> SEQUENCE: 65

Arg Ala Ser Ser Thr Leu Tyr Ser Asn Tyr Leu His
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Arg Ala Ser Phe Leu Ala Ser
1               5

<210> SEQ ID NO 67
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 67

Gln Gln Gly Ser Ser Ile Pro Leu Thr
1               5

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Ser Ala Ser Ser Ser Leu Tyr Ser Ser Tyr Leu His
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Arg Ala Ser Ser Ser Leu Tyr Ser Asn Tyr Leu His
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Synthetic

<400> SEQUENCE: 70

Arg Ala Ser Lys Ser Val Ser Thr Ser Gly Phe Ser Tyr Ile His
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: Synthetic

<400> SEQUENCE: 71

Leu Ala Ser Asn Leu Glu Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Gln His Thr Trp Glu Leu Pro Asn Thr
1               5

<210> SEQ ID NO 73
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 73

Lys Ala Ser Gln Asn Val Gly Thr Asn Val Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic

<400> SEQUENCE: 74

Ser Ala Ser Tyr Arg Tyr Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Gln Gln Tyr Tyr Ser Tyr Pro Tyr Thr
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic

<400> SEQUENCE: 76

Asn Tyr Trp Met His
1               5

<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Met Ile His Pro Asn Thr Asn Tyr Asn Tyr Asn Glu Lys Phe Lys
1               5                   10                  15

Ser

<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

Ser Asp Tyr Gly Ser Ser Pro Tyr Tyr Phe Asp Tyr
1               5                   10

<210> SEQ ID NO 79
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 79

Ser Tyr Trp Met His
1               5

<210> SEQ ID NO 80
<211> LENGTH: 17
<212> TYPE: PRT
<213> ORGANISM: Artificial Sequence
<220> FEATURE:
<223> OTHER INFORMATION: Synthetic

<400> SEQUENCE: 80

Met Ile His Pro Asn Val Gly Ser Thr Asn Tyr Asn Glu Lys Phe Lys
1               5                   10                  15

Ser

<210> SEQ ID NO 81
<211> LENGTH: 12
<212> TYPE: PRT
<213> ORGANISM: Artificial Sequence
<220> FEATURE:
<223> OTHER INFORMATION: Synthetic

<400> SEQUENCE: 81

Ser Arg Tyr Gly Ser Ser Pro Tyr Tyr Phe Asp Tyr
1               5                   10

<210> SEQ ID NO 82
<211> LENGTH: 17
<212> TYPE: PRT
<213> ORGANISM: Artificial Sequence
<220> FEATURE:
<223> OTHER INFORMATION: Synthetic

<400> SEQUENCE: 82

Met Ile His Pro Asn Ser Gly Gly Asn Asn Tyr Asn Glu Lys Phe Lys
1               5                   10                  15

Ser

<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Ser Trp Tyr Gly Ser Ser Pro Tyr Tyr Phe Asp Tyr
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Synthetic

<400> SEQUENCE: 84

Met Ile His Pro Thr Gly Val Ser Thr Asp Tyr Asn Glu Lys Phe Lys
1               5                   10                  15
```

Ser

<210> SEQ ID NO 85
<211> LENGTH: 6
<212> TYPE: PRT
<213> ORGANISM: Artificial Sequence
<220> FEATURE:
<223> OTHER INFORMATION: Synthetic

<400> SEQUENCE: 85

Ser Asp Tyr Ala Trp Asn
1               5

<210> SEQ ID NO 86
<211> LENGTH: 16
<212> TYPE: PRT
<213> ORGANISM: Artificial Sequence
<220> FEATURE:
<223> OTHER INFORMATION: Synthetic

<400> SEQUENCE: 86

Tyr Ile Ser Asp Ser Gly Ser Thr Ser Tyr Asn Pro Ser Leu Lys Ser
1               5                   10                  15

<210> SEQ ID NO 87
<211> LENGTH: 11
<212> TYPE: PRT
<213> ORGANISM: Artificial Sequence
<220> FEATURE:
<223> OTHER INFORMATION: Synthetic

<400> SEQUENCE: 87

Ser Phe Leu Arg Leu Arg Ser Tyr Phe Asp His
1               5                   10

<210> SEQ ID NO 88
<211> LENGTH: 5
<212> TYPE: PRT
<213> ORGANISM: Artificial Sequence
<220> FEATURE:
<223> OTHER INFORMATION: Synthetic

<400> SEQUENCE: 88

Ser Tyr Gly Ile Asn
1               5

<210> SEQ ID NO 89
<211> LENGTH: 17
<212> TYPE: PRT
<213> ORGANISM: Artificial Sequence
<220> FEATURE:
<223> OTHER INFORMATION: Synthetic

<400> SEQUENCE: 89

Cys Ile Tyr Ile Gly Asn Asp Tyr Thr Asn Tyr Asn Glu Lys Phe Lys
1               5                   10                  15

Gly

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

```
Ala Tyr Tyr Gly Ser Arg Val Asp Tyr
1               5

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

Arg Ala Ser Gln Asp Ile Asp Asn Tyr Leu Asn
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Tyr Thr Ser Arg Leu His Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gln Gln Gly Tyr Thr Leu Pro Trp Thr
1               5

<210> SEQ ID NO 94
<211> LENGTH: 11
<212> TYPE: PRT
<213> ORGANISM: Artificial Sequence
<220> FEATURE:
<223> OTHER INFORMATION: Synthetic

<400> SEQUENCE: 94

Arg Ala Ser Gln Asp Ile Ser Asn Tyr Leu Asn
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Tyr Thr Ser Arg Leu Gln Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96
```

Gln Gln Gly Asn Thr Leu Pro Trp Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Gln Gln Gly Asp Thr Leu Pro Trp Thr
1               5

<210> SEQ ID NO 98
<211> LENGTH: 11
<212> TYPE: PRT
<213> ORGANISM: Artificial Sequence
<220> FEATURE:
<223> OTHER INFORMATION: Synthetic

<400> SEQUENCE: 98

Lys Ala Ser Gln Asp Val Asn Val Ala Val Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Trp Ala Ser Thr Arg His Ile
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

Gln Gln His Tyr Ser Thr Pro Tyr Thr
1               5

<210> SEQ ID NO 101
<211> LENGTH: 11
<212> TYPE: PRT
<213> ORGANISM: Artificial Sequence
<220> FEATURE:
<223> OTHER INFORMATION: Synthetic

<400> SEQUENCE: 101

Lys Ala Ser Gln Asp Ile Asn Lys Tyr Ile Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Tyr Thr Ser Thr Leu Gln Pro

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Leu Gln Tyr Asp Asn Leu Tyr Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

Gln Ser Ile Ser Asp Tyr Leu His
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Cys Ala Ser Gln Ser Ile Ser Gly
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic

<400> SEQUENCE: 106

Gln Asn Gly His Ser Phe Pro Tyr Thr
1               5

<210> SEQ ID NO 107
<211> LENGTH: 118
<212> TYPE: PRT
<213> ORGANISM: Artificial Sequence
<220> FEATURE:
<223> OTHER INFORMATION: Synthetic

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Gly Tyr Asn Pro Ser Leu
    50                  55                  60

Lys Ser Arg Val Thr Ile Ser Val Asp Thr Ser Lys Asn Gln Phe Ser
65                  70                  75                  80

```
Leu Lys Leu Ser Ser Val Thr Ala Ala Asp Thr Ala Val Tyr Tyr Cys
                 85                  90                  95

Ala Arg Arg Met Ile Gly Tyr Ala Met Asp Tyr Trp Gly Gln Gly Thr
            100                 105                 110

Ser Val Thr Val Ser Ser
            115

<210> SEQ ID NO 108
<211> LENGTH: 115
<212> TYPE: PRT
<213> ORGANISM: Artificial Sequence
<220> FEATURE:
<223> OTHER INFORMATION: Synthetic

<400> SEQUENCE: 108

Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asp Val Ser Thr Val
            20                  25                  30

Val Ala Trp His Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Gln His Tyr Ser Thr Pro Trp Thr Phe Gly Gly Gly Thr Lys Leu Glu
            100                 105                 110

Ile Lys Arg
        115

<210> SEQ ID NO 109
<211> LENGTH: 118
<212> TYPE: PRT
<213> ORGANISM: Artificial Sequence
<220> FEATURE:
<223> OTHER INFORMATION: Synthetic

<400> SEQUENCE: 109

Gln Val Lys Leu Gln Glu Ser Gly Pro Gly Leu Val Lys Pro Ser Gln
1               5                  10                  15

Thr Leu Ser Leu Thr Cys Thr Val Thr Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Gly Thr Ser Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Ser Cys
                85                  90                  95

Ala Arg Arg Gln Ile Gly Leu Phe Thr Tyr Trp Gly Gln Gly Thr
            100                 105                 110

Leu Val Thr Val Ser Ala
        115

<210> SEQ ID NO 110
```

<211> LENGTH: 114
<212> TYPE: PRT
<213> ORGANISM: Artificial Sequence
<220> FEATURE:
<223> OTHER INFORMATION: Synthetic

<400> SEQUENCE: 110

Asp Ile Gln Met Thr Gln Ser Pro Ser Ser Leu Ser Ala Ser Val Gly
1               5                   10                  15

Asp Arg Val Thr Ile Pro Cys Lys Ala Ser Gln Asp Leu Ser Thr Ala
            20                  25                  30

Val Ala Trp Tyr Gln Gln Lys Pro Gly Lys Ala Pro Lys Leu Leu Ile
        35                  40                  45

Tyr Ser Ser Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Gln His Tyr Ser Thr Pro Trp Thr Phe Gly Glu Gly Thr Lys Leu Glu
            100                 105                 110

Ile Lys

<210> SEQ ID NO 111
<211> LENGTH: 118
<212> TYPE: PRT
<213> ORGANISM: Artificial Sequence
<220> FEATURE:
<223> OTHER INFORMATION: Synthetic

<400> SEQUENCE: 111

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Ile His Trp Val Gln Gln Ala Pro Gly Lys Gly Leu Glu Trp Met
        35                  40                  45

Gly Tyr Phe Tyr Pro Arg Asp Gly Ser Thr Lys Tyr Asn Glu Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Met Leu Arg Trp Phe Ala Asp Trp Gly Gln Gly Thr Leu
            100                 105                 110

Ile Thr Val Ser Val Ala
        115

<210> SEQ ID NO 112
<211> LENGTH: 107
<212> TYPE: PRT
<213> ORGANISM: Artificial Sequence
<220> FEATURE:
<223> OTHER INFORMATION: Synthetic

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Thr

```
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Thr Pro Leu
                85                  90                  95

Thr Phe Gly Ala Gly Thr Lys Leu Glu Leu Lys
                100                 105

<210> SEQ ID NO 113
<211> LENGTH: 117
<212> TYPE: PRT
<213> ORGANISM: Artificial Sequence
<220> FEATURE:
<223> OTHER INFORMATION: Synthetic

<400> SEQUENCE: 113

Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Asp His
                20                  25                  30

Thr Ile His Trp Val Gln Gln Ala Pro Gly Lys Gly Leu Glu Trp Met
            35                  40                  45

Gly Tyr Ile Tyr Pro Arg Asp Gly Ser Ser Lys Tyr Asn Val Lys Phe
 50                  55                  60

Lys Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Thr Gly Met Leu Arg Trp Phe Ala Tyr Trp Gly Gln Gly Thr Leu
                100                 105                 110

Val Thr Val Ser Ser
        115

<210> SEQ ID NO 114
<211> LENGTH: 107
<212> TYPE: PRT
<213> ORGANISM: Artificial Sequence
<220> FEATURE:
<223> OTHER INFORMATION: Synthetic

<400> SEQUENCE: 114

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Phe Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Ile Pro Leu
                85                  90                  95
```

```
Thr Phe Gly Ala Gly Thr Lys Leu Glu Ile Lys
            100                 105
```

<210> SEQ ID NO 115
<211> LENGTH: 117
<212> TYPE: PRT
<213> ORGANISM: Artificial Sequence
<220> FEATURE:
<223> OTHER INFORMATION: Synthetic

<400> SEQUENCE: 115

```
Glu Val Gln Leu Lys Gln Ser Gly Ala Glu Val Lys Pro Gly Ala
1               5                   10                  15

Thr Val Lys Ile Ser Cys Lys Val Ser Gly Tyr Thr Phe Thr Asp Gln
            20                  25                  30

Ala Ile His Trp Val Gln Gln Ala Pro Gly Lys Gly Leu Glu Trp Met
        35                  40                  45

Gly Tyr Ile Tyr Pro Arg Asp Gly Ser Thr Lys Tyr Asn Glu Thr Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Gly Met Leu Arg Trp Phe Ala Tyr Trp Gly Gln Gly Thr Leu
            100                 105                 110

Val Thr Val Ser Ser
            115
```

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Ala Gly Thr Lys Leu Glu Leu Lys
            100                 105
```

<210> SEQ ID NO 117
<211> LENGTH: 118
<212> TYPE: PRT
<213> ORGANISM: Artificial Sequence
<220> FEATURE:
<223> OTHER INFORMATION: Synthetic

<400> SEQUENCE: 117

```
Gln Val Gln Leu Gln Glu Ser Gly Pro Gly Leu Val Lys Pro Ser Gln
1               5                   10                  15
```

-continued

```
              1               5                  10                 15
            Thr Leu Ser Leu Thr Cys Thr Val Ser Gly Gly Ser Val Ser Asp
                            20                 25                 30

Tyr Ala Trp Asn Trp Ile Arg Gln Pro Pro Gly Lys Gly Leu Glu Trp
                            35                 40                 45

Ile Gly Tyr Ile Thr Tyr Ser Gly Ser Thr Ser Tyr Asn Pro Ser Leu
             50                 55                 60

Lys Ser Arg Val Thr Ile Ser Val Asp Thr Ser Lys Asn Gln Phe Ser
             65                 70                 75                 80

Leu Lys Leu Ser Ser Val Thr Ala Ala Asp Thr Ala Val Tyr Tyr Cys
                            85                 90                 95

Ala Arg Arg Gln Val Gly Leu Gly Phe Ala Tyr Trp Gly Gln Gly Thr
                            100                105                110

Leu Val Thr Val Ser Ala
                            115
```

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

```
            Asp Ile Gln Met Thr Gln Ser Pro Ser Ser Leu Ser Ala Ser Val Gly
             1               5                  10                 15

Asp Arg Val Thr Ile Thr Cys Lys Ala Ser Gln Asp Val Ser Thr Ala
                            20                 25                 30

Val Ala Trp Tyr Gln Gln Lys Pro Gly Lys Ala Pro Lys Leu Leu Ile
                            35                 40                 45

Tyr Ser Ala Ser Tyr His Tyr Thr Gly Val Pro Ser Arg Phe Ser Gly
             50                 55                 60

Ser Gly Ser Gly Thr Asp Phe Thr Leu Thr Ile Ser Ser Leu Gln Pro
             65                 70                 75                 80

Glu Asp Phe Ala Thr Tyr Tyr Cys Gln Gln His Tyr Ser Thr Pro Trp
                            85                 90                 95

Thr Phe Gly Gly Gly Thr Lys Leu Glu Ile Lys
                            100                105
```

<210> SEQ ID NO 119
<211> LENGTH: 118
<212> TYPE: PRT
<213> ORGANISM: Artificial Sequence
<220> FEATURE:
<223> OTHER INFORMATION: Synthetic

<400> SEQUENCE: 119

```
            Glu Val Gln Leu Gln Glu Ser Gly Pro Gly Leu Val Lys Pro Ser Asp
             1               5                  10                 15

Thr Leu Ser Leu Thr Cys Ala Val Ser Gly Tyr Ser Ile Thr Ser Asp
                            20                 25                 30

Ser Ala Trp Asn Trp Ile Arg Gln Pro Pro Gly Lys Gly Leu Glu Trp
                            35                 40                 45

Ile Gly Tyr Ile Thr Tyr Ser Gly Ser Thr Asn Tyr Asn Pro Ser Leu
             50                 55                 60

Arg Ser Arg Val Thr Met Ser Val Asp Thr Ser Lys Asn Gln Phe Ser
             65                 70                 75                 80
```

-continued

```
Leu Lys Leu Ser Ser Val Thr Ala Val Asp Thr Ala Val Tyr Tyr Cys
                85                  90                  95

Thr Arg Arg Gln Val Gly Leu Gly Phe Ala Tyr Trp Gly Gln Gly Thr
            100                 105                 110

Leu Val Thr Val Ser Ala
        115

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Phe Thr Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Ile Tyr Tyr Cys Gln His Tyr Ser Thr Pro Trp
                85                  90                  95

Thr Phe Gly Gly Gly Thr Lys Leu Glu Phe Lys
            100                 105

<210> SEQ ID NO 121
<211> LENGTH: 121
<212> TYPE: PRT
<213> ORGANISM: Artificial Sequence
<220> FEATURE:
<223> OTHER INFORMATION: Synthetic

<400> SEQUENCE: 121

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ala Pro Pro Tyr Gly Tyr Asp Val Arg Phe Ala Tyr Trp Gly
            100                 105                 110

Gln Gly Thr Leu Val Thr Val Ser Ser
        115                 120

<210> SEQ ID NO 122
<211> LENGTH: 112
<212> TYPE: PRT
<213> ORGANISM: Artificial Sequence
```

<220> FEATURE:
<223> OTHER INFORMATION: Synthetic

<400> SEQUENCE: 122

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Val Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Arg Gly Thr Lys Leu Glu Ile Lys
            100                 105                 110

<210> SEQ ID NO 123
<211> LENGTH: 121
<212> TYPE: PRT
<213> ORGANISM: Artificial Sequence
<220> FEATURE:
<223> OTHER INFORMATION: Synthetic

<400> SEQUENCE: 123

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Ala Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Asp Tyr Ser Tyr Phe Ala Trp Phe Ala Tyr Trp Gly
            100                 105                 110

Gln Gly Thr Leu Val Thr Val Ser Ser
        115                 120

<210> SEQ ID NO 124
<211> LENGTH: 109
<212> TYPE: PRT
<213> ORGANISM: Artificial Sequence
<220> FEATURE:
<223> OTHER INFORMATION: Synthetic

<400> SEQUENCE: 124

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Leu Phe Arg Gly
        35                  40                  45

Leu Ile Gly Gly Thr Asn Asn Arg Ala Pro Trp Val Pro Ala Arg Phe
        50                  55                  60

Ser Gly Ser Leu Ile Gly Asp Lys Ala Ala Leu Thr Leu Ser Gly Val
 65                  70                  75                  80

Gln Pro Glu Asp Glu Ala Glu Tyr Phe Cys Ala Leu Trp Tyr Ser Asn
                85                  90                  95

His Trp Val Phe Gly Gly Gly Thr Lys Leu Thr Val Leu
                100                 105

<210> SEQ ID NO 125
<211> LENGTH: 122
<212> TYPE: PRT
<213> ORGANISM: Artificial Sequence
<220> FEATURE:
<223> OTHER INFORMATION: Synthetic

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Arg Thr Ser Tyr Ala Gln Met Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Glu Gln Trp Pro Val Gly Gly Phe Asp Tyr Trp
                100                 105                 110

Gly Gln Gly Thr Leu Val Thr Val Ser Ser
            115                 120

<210> SEQ ID NO 126
<211> LENGTH: 107
<212> TYPE: PRT
<213> ORGANISM: Artificial Sequence
<220> FEATURE:
<223> OTHER INFORMATION: Synthetic

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
                20                  25                  30

Leu Asn Trp Tyr Gln Gln Lys Pro Gly Lys Ala Pro Lys Leu Leu Ile
            35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ile Pro Pro
                85                  90                  95

Thr Phe Gly Gln Gly Thr Lys Val Glu Ile Arg
                100                 105

<210> SEQ ID NO 127

<211> LENGTH: 117
<212> TYPE: PRT
<213> ORGANISM: Artificial Sequence
<220> FEATURE:
<223> OTHER INFORMATION: Synthetic

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Leu Met Ser Trp Val Arg Gln Ala Pro Gly Lys Gly Leu Glu Trp Val
        35                  40                  45

Ser Thr Ile Ser Gly Gly Gly Arg Asp Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Thr Thr Tyr Ser Met Asp Tyr Trp Gly Gln Gly Thr Ser
            100                 105                 110

Val Thr Val Ser Ser
        115

<210> SEQ ID NO 128
<211> LENGTH: 107
<212> TYPE: PRT
<213> ORGANISM: Artificial Sequence
<220> FEATURE:
<223> OTHER INFORMATION: Synthetic

<400> SEQUENCE: 128

Asp Ile Gln Met Thr Gln Ser Pro Ser Ser Val Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Ile Pro Trp
                85                  90                  95

Thr Phe Gly Gly Gly Thr Lys Leu Glu Ile Lys
            100                 105

<210> SEQ ID NO 129
<211> LENGTH: 120
<212> TYPE: PRT
<213> ORGANISM: Artificial Sequence
<220> FEATURE:
<223> OTHER INFORMATION: Synthetic

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asn Ser
            20                  25                  30

```
Tyr Leu Tyr Trp Leu Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
 50                  55                  60

Lys Thr Arg Thr Thr Ser Thr Arg Asp Thr Ser Ile Ser Thr Ala Tyr
 65                  70                  75                  80

Met Glu Leu Ser Arg Leu Arg Ser Asp Thr Val Val Tyr Tyr Cys
                 85                  90                  95

Thr Arg Arg Asp Tyr Asn Tyr Asp Gly Gly Phe Asp Ser Trp Gly Gln
                100                 105                 110

Gly Thr Leu Val Thr Val Ser Ser
        115                 120
```

<210> SEQ ID NO 130
<211> LENGTH: 108
<212> TYPE: PRT
<213> ORGANISM: Artificial Sequence
<220> FEATURE:
<223> OTHER INFORMATION: Synthetic

<400> SEQUENCE: 130

```
Asp Ile Gln Met Thr Gln Ser Pro Ser Ser Leu Ser Ala Ser Val Gly
 1               5                  10                  15

Asp Arg Val Thr Phe Thr Cys Arg Ala Ser Ser Thr Leu Tyr Ser Asn
                20                  25                  30

Tyr Leu His Trp Tyr Gln Gln Lys Pro Gly Lys Ala Pro Lys Leu Leu
        35                  40                  45

Ile Tyr Arg Ala Ser Phe Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Gly Ser Ser Ile Pro
                 85                  90                  95

Leu Thr Phe Gly Gly Gly Thr Lys Val Glu Ile Lys
                100                 105
```

<210> SEQ ID NO 131
<211> LENGTH: 120
<212> TYPE: PRT
<213> ORGANISM: Artificial Sequence
<220> FEATURE:
<223> OTHER INFORMATION: Synthetic

<400> SEQUENCE: 131

```
Gln Val Gln Leu Val Gln Ser Gly Ala Glu Val Lys Lys Pro Gly Ala
 1               5                  10                  15

Ser Val Lys Val Ser Cys Lys Ala Ser Asp Tyr Thr Phe Thr Asn Ser
                20                  25                  30

Tyr Ile Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
 50                  55                  60

Lys Thr Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
                 85                  90                  95

Ala Arg Arg Asp Tyr Arg Tyr Asp Gly Gly Phe Asp Ser Trp Gly Gln
                100                 105                 110
```

Gly Thr Thr Leu Thr Val Ser Ser
        115                 120

<210> SEQ ID NO 132
<211> LENGTH: 108
<212> TYPE: PRT
<213> ORGANISM: Artificial Sequence
<220> FEATURE:
<223> OTHER INFORMATION: Synthetic

<400> SEQUENCE: 132

Asp Ile Gln Met Thr Gln Ser Pro Ser Leu Ser Ala Ser Val Gly
1               5                   10                  15

Asp Arg Val Thr Ile Thr Cys Ser Ala Ser Ser Ser Leu Tyr Ser Ser
                20                  25                  30

Tyr Leu His Trp Tyr Gln Lys Pro Gly Lys Ala Pro Lys Leu Leu
            35                  40                  45

Ile Tyr Arg Ala Ser Phe Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Ile Pro
                85                  90                  95

Leu Thr Phe Gly Ala Gly Thr Lys Leu Asp Leu Lys
            100                 105

<210> SEQ ID NO 133
<211> LENGTH: 120
<212> TYPE: PRT
<213> ORGANISM: Artificial Sequence
<220> FEATURE:
<223> OTHER INFORMATION: Synthetic

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Asn Ser
                20                  25                  30

Tyr Ile Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Thr Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Arg Asp Tyr Asn Tyr Asp Gly Gly Phe Asp Ser Trp Gly Gln
            100                 105                 110

Gly Thr Leu Val Thr Val Ser Ser
        115                 120

<210> SEQ ID NO 134
<211> LENGTH: 108
<212> TYPE: PRT
<213> ORGANISM: Artificial Sequence
<220> FEATURE:
<223> OTHER INFORMATION: Synthetic

<400> SEQUENCE: 134

Asp Ile Gln Met Thr Gln Ser Pro Ser Ser Leu Ser Ala Ser Val Gly
1               5                   10                  15

Asp Arg Val Thr Phe Thr Cys Arg Ala Ser Ser Ser Leu Tyr Ser Asn
            20                  25                  30

Tyr Leu His Trp Tyr Gln Gln Lys Pro Gly Lys Ala Pro Lys Leu Leu
        35                  40                  45

Ile Tyr Arg Ala Ser Phe Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Ser Ile Pro
                85                  90                  95

Leu Thr Phe Gly Gly Gly Thr Lys Val Glu Ile Lys
            100                 105

<210> SEQ ID NO 135
<211> LENGTH: 120
<212> TYPE: PRT
<213> ORGANISM: Artificial Sequence
<220> FEATURE:
<223> OTHER INFORMATION: Synthetic

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45

Gly Gly Ile Asn Pro Gly Asn Gly Gly Thr Asn Phe Asn Glu Lys Phe
50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Gly Leu Asp Tyr Trp Gly Gln
            100                 105                 110

Gly Thr Leu Val Thr Val Ser Ser
        115                 120

<210> SEQ ID NO 136
<211> LENGTH: 111
<212> TYPE: PRT
<213> ORGANISM: Artificial Sequence
<220> FEATURE:
<223> OTHER INFORMATION: Synthetic

<400> SEQUENCE: 136

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys
            100                 105                 110

<210> SEQ ID NO 137
<211> LENGTH: 117
<212> TYPE: PRT
<213> ORGANISM: Artificial Sequence
<220> FEATURE:
<223> OTHER INFORMATION: Synthetic

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser
        115

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys
            100                 105

<210> SEQ ID NO 139
<211> LENGTH: 121
<212> TYPE: PRT
<213> ORGANISM: Artificial Sequence
<220> FEATURE:
<223> OTHER INFORMATION: Synthetic

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Met Lys Gln Ala Pro Gly Gln Gly Leu Glu Trp Met
        35                  40                  45

Gly Met Ile His Pro Asn Thr Asn Asn Tyr Asn Tyr Asn Glu Lys Phe
    50                  55                  60

Lys Ser Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Ser Asp Tyr Gly Ser Ser Pro Tyr Tyr Phe Asp Tyr Trp Gly
            100                 105                 110

Gln Gly Thr Leu Val Thr Val Ser Ser
            115                 120

<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys
            100                 105

<210> SEQ ID NO 141
<211> LENGTH: 121
<212> TYPE: PRT
<213> ORGANISM: Artificial Sequence
<220> FEATURE:
<223> OTHER INFORMATION: Synthetic

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Val Gly Ser Thr Asn Tyr Asn Glu Lys Phe
    50                  55                  60

Lys Ser Lys Ala Thr Met Thr Arg Asp Lys Ser Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Arg Tyr Gly Ser Ser Pro Tyr Tyr Phe Asp Tyr Trp Gly
            100                 105                 110

Gln Gly Thr Leu Val Thr Val Ser Ser
        115                 120

<210> SEQ ID NO 142
<211> LENGTH: 107
<212> TYPE: PRT
<213> ORGANISM: Artificial Sequence
<220> FEATURE:
<223> OTHER INFORMATION: Synthetic

<400> SEQUENCE: 142

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Trp
            85                  90                  95

Thr Phe Gly Gln Gly Thr Lys Val Glu Ile Lys
            100                 105

<210> SEQ ID NO 143
<211> LENGTH: 121
<212> TYPE: PRT
<213> ORGANISM: Artificial Sequence
<220> FEATURE:
<223> OTHER INFORMATION: Synthetic

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Gly Asn Asn Tyr Asn Glu Lys Phe
50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser
        115                 120

```
<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144
```

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Trp
                85                  90                  95

Thr Phe Gly Gln Gly Thr Lys Val Glu Ile Lys
            100                 105

```
<210> SEQ ID NO 145
<211> LENGTH: 121
<212> TYPE: PRT
<213> ORGANISM: Artificial Sequence
<220> FEATURE:
<223> OTHER INFORMATION: Synthetic

<400> SEQUENCE: 145
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Thr Gly Val Ser Thr Asp Tyr Asn Glu Lys Phe
50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Gly Ser Ser Pro Tyr Tyr Phe Asp Tyr Trp Gly
            100                 105                 110

Gln Gly Thr Leu Val Thr Val Ser Ser
        115                 120

```
<210> SEQ ID NO 146
<211> LENGTH: 107
<212> TYPE: PRT
<213> ORGANISM: Artificial Sequence
<220> FEATURE:
<223> OTHER INFORMATION: Synthetic

<400> SEQUENCE: 146
```

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Lys Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asp Thr Leu Pro Trp
                85                  90                  95

Thr Phe Gly Gly Gly Thr Lys Val Glu Ile Lys
                100                 105

<210> SEQ ID NO 147
<211> LENGTH: 120
<212> TYPE: PRT
<213> ORGANISM: Artificial Sequence
<220> FEATURE:
<223> OTHER INFORMATION: Synthetic

<400> SEQUENCE: 147

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Asp Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Asn Ser Phe Leu Arg Leu Arg Ser Tyr Phe Asp His Trp Gly Gln
                100                 105                 110

Gly Thr Thr Leu Thr Val Ser Ser
            115                 120

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Val Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ile Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys 100                 105

<210> SEQ ID NO 149
<211> LENGTH: 119
<212> TYPE: PRT
<213> ORGANISM: Artificial Sequence
<220> FEATURE:
<223> OTHER INFORMATION: Synthetic

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Arg Leu Glu Trp Met
        35                  40                  45

Gly Trp Cys Ile Tyr Ile Gly Asn Asp Tyr Thr Asn Tyr Asn Glu Lys
    50                  55                  60

Phe Lys Gly Arg Val Thr Ile Thr Arg Asp Thr Ser Ala Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Tyr Tyr Gly Ser Arg Val Asp Tyr Trp Gly Gln Gly
            100                 105                 110

Thr Leu Val Thr Val Ser Ser
        115

<210> SEQ ID NO 150
<211> LENGTH: 106
<212> TYPE: PRT
<213> ORGANISM: Artificial Sequence
<220> FEATURE:
<223> OTHER INFORMATION: Synthetic

<400> SEQUENCE: 150

Asp Ile Gln Met Thr Gln Ser Pro Ser Ser Leu Ser Ala Phe Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Val Glu Ile Lys
            100                 105

<210> SEQ ID NO 151
<211> LENGTH: 119
<212> TYPE: PRT
<213> ORGANISM: Artificial Sequence
<220> FEATURE:
<223> OTHER INFORMATION: Synthetic

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Arg Leu Glu Trp Met
            35                  40                  45

Gly Trp Cys Ile Tyr Ile Gly Asn Asp Tyr Thr Asn Tyr Asn Glu Lys
50                  55                  60

Phe Lys Gly Arg Val Thr Ile Thr Arg Asp Thr Ser Ala Ser Thr Ala
65                  70                  75                  80

Tyr Met Glu Leu Ser Ser Leu Arg Ser Glu Asp Thr Ala Val Tyr Tyr
            85                  90                  95

Cys Ala Arg Ala Tyr Tyr Gly Ser Arg Val Asp Tyr Trp Gly Gln Gly
            100                 105                 110

Thr Leu Val Thr Val Ser Ser
            115

<210> SEQ ID NO 152
<211> LENGTH: 104
<212> TYPE: PRT
<213> ORGANISM: Artificial Sequence
<220> FEATURE:
<223> OTHER INFORMATION: Synthetic

<400> SEQUENCE: 152

Glu Ile Val Leu Thr Gln Ser Pro Val Thr Leu Ser Leu Ser Pro Gly
1               5                   10                  15

Glu Arg Ala Thr Leu Ser Cys Gln Ser Ile Ser Asp Tyr Leu His Trp
            20                  25                  30

Tyr Leu Gln Lys Pro Gly Gln Ala Pro Arg Leu Leu Ile Lys Cys Ala
            35                  40                  45

Ser Gln Ser Ile Ser Gly Ile Pro Ala Arg Phe Ser Gly Ser Gly Ser
50                  55                  60

Gly Ser Asp Phe Thr Leu Thr Ile Ser Ser Leu Glu Pro Glu Asp Phe
65                  70                  75                  80

Ala Val Tyr Tyr Cys Gln Asn Gly His Ser Phe Pro Tyr Thr Phe Gly
            85                  90                  95

Gly Gly Thr Lys Val Glu Ile Lys
            100

<210> SEQ ID NO 153
<211> LENGTH: 121
<212> TYPE: PRT
<213> ORGANISM: Artificial Sequence
<220> FEATURE:
<223> OTHER INFORMATION: Synthetic

<400> SEQUENCE: 153

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Met Ile His Pro Asn Ser Gly Gly Asn Asn Tyr Asn Glu Lys Phe
            50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys

```
                    85                  90                  95
Ala Arg Ser Trp Tyr Gly Ser Ser Pro Tyr Tyr Phe Asp Tyr Trp Gly
            100                 105                 110

Gln Gly Thr Leu Val Thr Val Ser Ser
        115                 120

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys
            100                 105

<210> SEQ ID NO 155
<211> LENGTH: 5
<212> TYPE: PRT
<213> ORGANISM: Artificial Sequence
<220> FEATURE:
<223> OTHER INFORMATION: Synthetic

<400> SEQUENCE: 155

Asp Tyr Tyr Met Asn
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic

<400> SEQUENCE: 156

His Tyr Tyr Met Asn
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic

<400> SEQUENCE: 157

Thr Ala Tyr Thr Ile His
1               5
```

```
<210> SEQ ID NO 158
<211> LENGTH: 17
<212> TYPE: PRT
<213> ORGANISM: Artificial Sequence
<220> FEATURE:
<223> OTHER INFORMATION: Synthetic

<400> SEQUENCE: 158

Val Ile Asn Pro Tyr Asn Gly Asp Thr Ser Tyr Asn Gln Lys Phe Lys
1               5                   10                  15
Gly

<210> SEQ ID NO 159
<211> LENGTH: 17
<212> TYPE: PRT
<213> ORGANISM: Artificial Sequence
<220> FEATURE:
<223> OTHER INFORMATION: Synthetic

<400> SEQUENCE: 159

Leu Ile Asn Pro Tyr Asn Gly Asp Thr Ala Tyr Asn Gln Lys Phe Lys
1               5                   10                  15
Asp

<210> SEQ ID NO 160
<211> LENGTH: 17
<212> TYPE: PRT
<213> ORGANISM: Artificial Sequence
<220> FEATURE:
<223> OTHER INFORMATION: Synthetic

<400> SEQUENCE: 160

Trp Leu Tyr Pro Gly Asn Asp Asn Ile Met Tyr Asn Glu Asn Phe Lys
1               5                   10                  15
Asp

<210> SEQ ID NO 161
<211> LENGTH: 11
<212> TYPE: PRT
<213> ORGANISM: Artificial Sequence
<220> FEATURE:
<223> OTHER INFORMATION: Synthetic

<400> SEQUENCE: 161

Asp Asp Gly Tyr Tyr Val His Tyr Phe Asp Tyr
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic

<400> SEQUENCE: 162

Thr Arg Asp Asp Gly Tyr Tyr Val Glu His
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Synthetic

<400> SEQUENCE: 163
```

```
His Glu Asp Trp Gly Pro Leu Asp Tyr
1               5

<210> SEQ ID NO 164
<211> LENGTH: 11
<212> TYPE: PRT
<213> ORGANISM: Artificial Sequence
<220> FEATURE:
<223> OTHER INFORMATION: Synthetic

<400> SEQUENCE: 164

Arg Ala Ser Gln Asp Ile Ser Ser Arg Leu Thr
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic

<400> SEQUENCE: 165

Arg Ala Ser Gln Asp Ile Gly Ser Arg Leu Asn
1               5                   10

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Arg Ala Ser Gln Ser Ile Ser Ser
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic

<400> SEQUENCE: 167

Ala Thr Ser Ser Leu Asp Ser
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic

<400> SEQUENCE: 168

Arg Ala Ser Asn Leu Glu Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic

<400> SEQUENCE: 169
```

Leu Gln Tyr Ala Ser Ser Pro Leu Thr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic

<400> SEQUENCE: 170

Leu Gln Tyr Ala Ser Ser Pro Pro Thr
1               5

<210> SEQ ID NO 171
<211> LENGTH: 120
<212> TYPE: PRT
<213> ORGANISM: Artificial Sequence
<220> FEATURE:
<223> OTHER INFORMATION: Synthetic

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
                20                  25                  30

Tyr Met Asn Trp Met Arg Gln Ala Pro Gly Gln Gly Leu Glu Trp Met
            35                  40                  45

Gly Val Ile Asn Pro Tyr Asn Gly Asp Thr Ser Cys Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Val Arg Asp Asp Gly Tyr Tyr Val His Tyr Phe Asp Tyr Trp Gly Gln
            100                 105                 110

Gly Thr Leu Val Thr Val Ser Ser
        115                 120

<210> SEQ ID NO 172
<211> LENGTH: 120
<212> TYPE: PRT
<213> ORGANISM: Artificial Sequence
<220> FEATURE:
<223> OTHER INFORMATION: Synthetic

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Val Ile Asn Pro Tyr Asn Gly Asp Thr Ser Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Tyr Val His Tyr Phe Asp Tyr Trp Gly Gln

```
                  100                 105                 110

Gly Thr Leu Val Thr Val Ser Ser
            115                 120

<210> SEQ ID NO 173
<211> LENGTH: 132
<212> TYPE: PRT
<213> ORGANISM: Artificial Sequence
<220> FEATURE:
<223> OTHER INFORMATION: Synthetic

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser His Tyr
            20                  25                  30

Tyr Met Asn Trp Val Arg Gln Ala Pro Gly Gln Gly Leu Glu Trp Met
        35                  40                  45

Gly Leu Ile Asn Pro Tyr Asn Gly Asp Thr Ala Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Thr Arg Asp Asp Gly Tyr Tyr Val Glu His Phe Asp Tyr Trp Asp Asp
            100                 105                 110

Gly Tyr Tyr Val Glu His Phe Asp Tyr Trp Gly Gln Gly Thr Leu Val
            115                 120                 125

Thr Val Ser Ser
            130

<210> SEQ ID NO 174
<211> LENGTH: 118
<212> TYPE: PRT
<213> ORGANISM: Artificial Sequence
<220> FEATURE:
<223> OTHER INFORMATION: Synthetic

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Thr Ile His Trp Val Arg Gln Ala Pro Gly Gln Gly Leu Glu Trp Met
        35                  40                  45

Gly Trp Leu Tyr Pro Gly Asn Asp Asn Ile Met Tyr Asn Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Asp Trp Gly Pro Leu Asp Tyr Trp Gly Gln Gly Thr
            100                 105                 110

Leu Val Thr Val Ser Ser
            115

<210> SEQ ID NO 175
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Arg
            20                  25                  30

Leu Thr Trp Leu Gln Gln Glu Pro Glu Lys Ala Pro Lys Arg Leu Ile
        35                  40                  45

Tyr Ala Thr Ser Ser Leu Asp Ser Gly Val Pro Lys Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Leu
                85                  90                  95

Thr Phe Gly Gly Gly Thr Lys Val Glu Ile Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Arg
            20                  25                  30

Leu Thr Trp Leu Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Leu
                85                  90                  95

Thr Phe Gly Gly Gly Thr Lys Val Glu Ile Lys
            100                 105

<210> SEQ ID NO 177
<211> LENGTH: 107
<212> TYPE: PRT
<213> ORGANISM: Artificial Sequence
<220> FEATURE:
<223> OTHER INFORMATION: Synthetic

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Ala Ser Ser Pro Pro
                 85                  90                  95

Thr Phe Gly Gly Gly Thr Lys Val Glu Ile Lys
            100                 105
```

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
             35                  40                  45

Tyr Arg Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ser Asn Gly Leu Pro Tyr
                 85                  90                  95

Thr Phe Gly Gln Gly Thr Lys Leu Glu Ile Lys
            100                 105
```

<210> SEQ ID NO 179
<211> LENGTH: 222
<212> TYPE: PRT
<213> ORGANISM: Artificial Sequence
<220> FEATURE:
<223> OTHER INFORMATION: Synthetic

<400> SEQUENCE: 179

```
Met Thr Gly Thr Ile Glu Thr Thr Gly Asn Ile Ser Ala Glu Lys Gly
 1               5                  10                  15

Gly Ser Ile Ile Leu Gln Cys His Leu Ser Ser Thr Thr Ala Gln Val
                20                  25                  30

Thr Gln Val Asn Trp Glu Gln Gln Asp Gln Leu Leu Ala Ile Cys Asn
             35                  40                  45

Ala Asp Leu Gly Trp His Ile Ser Pro Ser Phe Lys Asp Arg Val Ala
 50                  55                  60

Pro Gly Pro Gly Leu Gly Leu Thr Leu Gln Ser Leu Thr Val Asn Asp
 65                  70                  75                  80

Thr Gly Glu Tyr Phe Cys Ile Tyr His Thr Tyr Pro Asp Gly Thr Tyr
                 85                  90                  95

Thr Gly Arg Ile Phe Leu Glu Val Leu Glu Ser Ser Val Ala Glu His
            100                 105                 110

Gly Ala Arg Phe Gln Ile Pro Leu Leu Gly Ala Met Ala Ala Thr Leu
            115                 120                 125

Val Val Ile Cys Thr Ala Val Ile Val Val Val Ala Leu Thr Arg Lys
        130                 135                 140
```

```
Lys Lys Ala Leu Arg Ile His Ser Val Glu Gly Asp Leu Arg Arg Lys
145                 150                 155                 160

Ser Ala Gly Gln Glu Glu Trp Ser Pro Ser Ala Pro Ser Pro Pro Gly
                165                 170                 175

Ser Cys Val Gln Ala Glu Ala Pro Ala Gly Leu Cys Gly Glu Gln
            180                 185                 190

Arg Gly Glu Asp Cys Ala Glu Leu His Asp Tyr Phe Asn Val Leu Ser
                195                 200                 205

Tyr Arg Ser Leu Gly Asn Cys Ser Phe Phe Thr Glu Thr Gly
    210                 215                 220

<210> SEQ ID NO 180
<211> LENGTH: 288
<212> TYPE: PRT
<213> ORGANISM: Artificial Sequence
<220> FEATURE:
<223> OTHER INFORMATION: Synthetic

<400> SEQUENCE: 180

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

```
<210> SEQ ID NO 181
<211> LENGTH: 290
<212> TYPE: PRT
<213> ORGANISM: Artificial Sequence
<220> FEATURE:
<223> OTHER INFORMATION: Synthetic

<400> SEQUENCE: 181

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 182
<211> LENGTH: 54
<212> TYPE: PRT
<213> ORGANISM: Artificial Sequence
<220> FEATURE:
<223> OTHER INFORMATION: Synthetic

<400> SEQUENCE: 182

Ala Gln Gln Glu Glu Cys Glu Trp Asp Pro Trp Thr Cys Glu His Met
1               5                   10                  15
```

```
Gly Ser Gly Ser Ala Thr Gly Ser Gly Ser Thr Ala Ser Ser Gly
            20                  25                  30

Ser Gly Ser Ala Thr His Gln Glu Glu Cys Glu Trp Asp Pro Trp Thr
            35                  40                  45

Cys Glu His Met Leu Glu
         50
```

<210> SEQ ID NO 183
<211> LENGTH: 286
<212> TYPE: PRT
<213> ORGANISM: Artificial Sequence
<220> FEATURE:
<223> OTHER INFORMATION: Synthetic

<400> SEQUENCE: 183

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys Gly Gly Gly Gly Ala Gln Gln Glu Glu Cys Glu Trp
225                 230                 235                 240

Asp Pro Trp Thr Cys Glu His Met Gly Ser Gly Ser Ala Thr Gly Gly
                245                 250                 255

Ser Gly Ser Thr Ala Ser Ser Gly Ser Gly Ser Ala Thr His Gln Glu
            260                 265                 270

Glu Cys Glu Trp Asp Pro Trp Thr Cys Glu His Met Leu Glu
            275                 280                 285
```

<210> SEQ ID NO 184
<211> LENGTH: 12
<212> TYPE: PRT
<213> ORGANISM: Artificial Sequence -continued

```
<220> FEATURE:
<223> OTHER INFORMATION: Synthetic

<400> SEQUENCE: 184

Glu Thr Phe Leu Ser Thr Asn Lys Leu Glu Asn Gln
1               5                   10

<210> SEQ ID NO 185
<211> LENGTH: 205
<212> TYPE: PRT
<213> ORGANISM: Artificial Sequence
<220> FEATURE:
<223> OTHER INFORMATION: Synthetic

<400> SEQUENCE: 185

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 186
<211> LENGTH: 136
<212> TYPE: PRT
<213> ORGANISM: Artificial Sequence
<220> FEATURE:
<223> OTHER INFORMATION: Synthetic

<400> SEQUENCE: 186

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60
```

```
Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
130                 135
```

<210> SEQ ID NO 187
<211> LENGTH: 819
<212> TYPE: PRT
<213> ORGANISM: Artificial Sequence
<220> FEATURE:
<223> OTHER INFORMATION: Synthetic

<400> SEQUENCE: 187

```
Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
                 20                  25                  30

Thr Ser Pro Asn Ile Thr Val Thr Leu Lys Lys Phe Pro Leu Asp Thr
             35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
             100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
            130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
            195                 200                 205

Gly Ser Gly Gly Gly Gly Ser Gly Gly Gly Gly Ser Gln Val Gln Leu
210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Ser Tyr Trp Met His Trp
                245                 250                 255

Val Arg Gln Ala Pro Gly Gln Gly Leu Glu Trp Met Gly Met Ile His
            260                 265                 270

Pro Asn Ser Gly Gly Asn Asn Tyr Asn Glu Lys Phe Lys Ser Arg Val
            275                 280                 285
```

```
Thr Met Thr Arg Asp Thr Ser Ile Ser Thr Ala Tyr Met Glu Leu Ser
    290                 295                 300

Arg Leu Arg Ser Asp Asp Thr Ala Val Tyr Tyr Cys Ala Arg Ser Trp
305                 310                 315                 320

Tyr Gly Ser Ser Pro Tyr Tyr Phe Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Cys Ser Arg Ser Thr Ser Glu Ser Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Lys Thr Tyr Thr Cys Asn Val Asp His Lys Pro Ser Asn
            420                 425                 430

Thr Lys Val Asp Lys Arg Val Glu Ser Lys Tyr Gly Pro Pro Cys Pro
        435                 440                 445

Pro Cys Pro Ala Pro Glu Phe Leu Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser Gln Glu Asp Pro Glu Val Gln Phe
                485                 490                 495

Asn Trp Tyr Val Asp Gly Val Glu Val His Asn Ala Lys Thr Lys Pro
            500                 505                 510

Arg Glu Glu Gln Phe Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Gly Leu Pro Ser Ser Ile Glu Lys Thr Ile Ser Lys Ala
545                 550                 555                 560

Lys Gly Gln Pro Arg Glu Pro Gln Val Tyr Thr Leu Pro Pro Ser Gln
                565                 570                 575

Glu Glu Met Thr Lys Asn Gln Val Ser Leu Thr Cys Leu Val Lys Gly
            580                 585                 590

Phe Tyr Pro Ser Asp Ile Ala Val Glu Trp Glu Ser Asn Gly Gln Pro
        595                 600                 605

Glu Asn Asn Tyr Lys Thr Thr Pro Pro Val Leu Asp Ser Asp Gly Ser
    610                 615                 620

Phe Phe Leu Tyr Ser Arg Leu Thr Val Asp Lys Ser Arg Trp Gln Glu
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Leu Gly Lys Gly Gly Gly Gly
            660                 665                 670

Ser Gly Gly Gly Gly Ser Gly Gly Gly Gly Ser Ile Pro Pro His Val
        675                 680                 685

Gln Lys Ser Val Asn Asn Asp Met Ile Val Thr Asp Asn Asn Gly Ala
    690                 695                 700

Val Lys Phe Pro Gln Leu Cys Lys Phe Cys Asp Val Arg Phe Ser Thr
```

```
                705                 710                 715                 720
Cys Asp Asn Gln Lys Ser Cys Met Ser Asn Cys Ser Ile Thr Ser Ile
                725                 730                 735

Cys Glu Lys Pro Gln Glu Val Cys Val Ala Val Trp Arg Lys Asn Asp
                740                 745                 750

Glu Asn Ile Thr Leu Glu Thr Val Cys His Asp Pro Lys Leu Pro Tyr
                755                 760                 765

His Asp Phe Ile Leu Glu Asp Ala Ala Ser Pro Lys Cys Ile Met Lys
                770                 775                 780

Glu Lys Lys Lys Pro Gly Glu Thr Phe Phe Met Cys Ser Cys Ser Ser
785                 790                 795                 800

Asp Glu Cys Asn Asp Asn Ile Ile Phe Ser Glu Glu Tyr Asn Thr Ser
                805                 810                 815

Asn Pro Asp

<210> SEQ ID NO 188
<211> LENGTH: 214
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
                20                  25                  30

Leu Asn Trp Tyr Gln Gln Lys Pro Gly Lys Ala Pro Lys Leu Leu Ile
            35                  40                  45

Lys Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 189
<211> LENGTH: 804
<212> TYPE: PRT
<213> ORGANISM: Artificial Sequence
```

<220> FEATURE:
<223> OTHER INFORMATION: Synthetic

<400> SEQUENCE: 189

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Gly Gly Gly Gly Ser Gln Val Gln Leu
    210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Ser Tyr Trp Met His Trp
                245                 250                 255

Val Arg Gln Ala Pro Gly Gln Gly Leu Glu Trp Met Gly Met Ile His
            260                 265                 270

Pro Asn Ser Gly Gly Asn Asn Tyr Asn Glu Lys Phe Lys Ser Arg Val
        275                 280                 285

Thr Met Thr Arg Asp Thr Ser Ile Ser Thr Ala Tyr Met Glu Leu Ser
    290                 295                 300

Arg Leu Arg Ser Asp Asp Thr Ala Val Tyr Tyr Cys Ala Arg Ser Trp
305                 310                 315                 320

Tyr Gly Ser Ser Pro Tyr Tyr Phe Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Cys Ser Arg Ser Thr Ser Glu Ser Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

-continued

Ser Gly Leu Tyr Ser Leu Ser Val Val Thr Val Pro Ser Ser Ser
                405                 410                 415

Leu Gly Thr Lys Thr Tyr Thr Cys Asn Val Asp His Lys Pro Ser Asn
            420                 425                 430

Thr Lys Val Asp Lys Arg Val Glu Ser Lys Tyr Gly Pro Pro Cys Pro
        435                 440                 445

Pro Cys Pro Ala Pro Glu Phe Leu Gly Gly Pro Ser Val Phe Leu Phe
450                 455                 460

Pro Pro Lys Pro Lys Asp Thr Leu Met Ile Ser Arg Thr Pro Glu Val
465                 470                 475                 480

Thr Cys Val Val Val Asp Val Ser Gln Glu Asp Pro Glu Val Gln Phe
                485                 490                 495

Asn Trp Tyr Val Asp Gly Val Glu Val His Asn Ala Lys Thr Lys Pro
            500                 505                 510

Arg Glu Glu Gln Phe Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Gly Leu Pro Ser Ser Ile Glu Lys Thr Ile Ser Lys Ala
545                 550                 555                 560

Lys Gly Gln Pro Arg Glu Pro Gln Val Tyr Thr Leu Pro Pro Ser Gln
                565                 570                 575

Glu Glu Met Ile Pro Pro His Val Gln Lys Ser Val Asn Asn Asp Met
            580                 585                 590

Ile Val Thr Asp Asn Asn Gly Ala Val Lys Phe Pro Gln Leu Cys Lys
        595                 600                 605

Phe Cys Asp Val Arg Phe Ser Thr Cys Asp Asn Gln Lys Ser Cys Met
    610                 615                 620

Ser Asn Cys Ser Ile Thr Ser Ile Cys Glu Lys Pro Gln Glu Val Cys
625                 630                 635                 640

Val Ala Val Trp Arg Lys Asn Asp Glu Asn Ile Thr Leu Glu Thr Val
                645                 650                 655

Cys His Asp Pro Lys Leu Pro Tyr His Asp Phe Ile Leu Glu Asp Ala
            660                 665                 670

Ala Ser Pro Lys Cys Ile Met Lys Glu Lys Lys Lys Pro Gly Glu Thr
        675                 680                 685

Phe Phe Met Cys Ser Cys Ser Ser Asp Glu Cys Asn Asp Asn Ile Ile
    690                 695                 700

Phe Ser Glu Glu Tyr Asn Thr Ser Asn Pro Asp Thr Lys Asn Gln Val
705                 710                 715                 720

Ser Leu Thr Cys Leu Val Lys Gly Phe Tyr Pro Ser Asp Ile Ala Val
                725                 730                 735

Glu Trp Glu Ser Asn Gly Gln Pro Glu Asn Asn Tyr Lys Thr Thr Pro
            740                 745                 750

Pro Val Leu Asp Ser Asp Gly Ser Phe Phe Leu Tyr Ser Arg Leu Thr
        755                 760                 765

Val Asp Lys Ser Arg Trp Gln Glu Gly Asn Val Phe Ser Cys Ser Val
    770                 775                 780

Met His Glu Ala Leu His Asn His Tyr Thr Gln Lys Ser Leu Ser Leu
785                 790                 795                 800

Ser Leu Gly Lys

<210> SEQ ID NO 190
<211> LENGTH: 800
<212> TYPE: PRT
<213> ORGANISM: Artificial Sequence
<220> FEATURE:
<223> OTHER INFORMATION: Synthetic

<400> SEQUENCE: 190

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Ile Pro Pro His Val Gln Lys Ser Val Asn Asn Asp Met
        355                 360                 365

Ile Val Thr Asp Asn Asn Gly Ala Val Lys Phe Pro Gln Leu Cys Lys
```

```
            370                 375                 380
Phe Cys Asp Val Arg Phe Ser Thr Cys Asp Asn Gln Lys Ser Cys Met
385                 390                 395                 400

Ser Asn Cys Ser Ile Thr Ser Ile Cys Glu Lys Pro Gln Glu Val Cys
                405                 410                 415

Val Ala Val Trp Arg Lys Asn Asp Glu Asn Ile Thr Leu Glu Thr Val
                420                 425                 430

Cys His Asp Pro Lys Leu Pro Tyr His Asp Phe Ile Leu Glu Asp Ala
                435                 440                 445

Ala Ser Pro Lys Cys Ile Met Lys Glu Lys Lys Pro Gly Glu Thr
450                 455                 460

Phe Phe Met Cys Ser Cys Ser Ser Asp Glu Cys Asn Asp Asn Ile Ile
465                 470                 475                 480

Phe Ser Glu Glu Tyr Asn Thr Ser Asn Pro Asp Thr Lys Asn Gln Val
                485                 490                 495

Ser Leu Thr Cys Leu Val Lys Gly Phe Tyr Pro Ser Asp Ile Ala Val
                500                 505                 510

Glu Trp Glu Ser Asn Gly Gln Pro Glu Asn Asn Tyr Lys Thr Thr Pro
                515                 520                 525

Pro Val Leu Asp Ser Asp Gly Ser Phe Phe Leu Tyr Ser Arg Leu Thr
                530                 535                 540

Val Asp Lys Ser Arg Trp Gln Glu Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Leu Gly Lys Gly Gly Gly Gly Ser Gly Gly Gly Ser Gly Gly
                580                 585                 590

Gly Gly Ser Ser Asp Thr Gly Arg Pro Phe Val Glu Met Tyr Ser Glu
                595                 600                 605

Ile Pro Glu Ile Ile His Met Thr Glu Gly Arg Glu Leu Val Ile Pro
                610                 615                 620

Cys Arg Val Thr Ser Pro Asn Ile Thr Val Thr Leu Lys Lys Phe Pro
625                 630                 635                 640

Leu Asp Thr Leu Ile Pro Asp Gly Lys Arg Ile Ile Trp Asp Ser Arg
                645                 650                 655

Lys Gly Phe Ile Ile Ser Asn Ala Thr Tyr Lys Glu Ile Gly Leu Leu
                660                 665                 670

Thr Cys Glu Ala Thr Val Asn Gly His Leu Tyr Lys Thr Asn Tyr Leu
                675                 680                 685

Thr His Arg Gln Thr Asn Thr Ile Ile Asp Val Val Leu Ser Pro Ser
                690                 695                 700

His Gly Ile Glu Leu Ser Val Gly Glu Lys Leu Val Leu Asn Cys Thr
705                 710                 715                 720

Ala Arg Thr Glu Leu Asn Val Gly Ile Asp Phe Asn Trp Glu Tyr Pro
                725                 730                 735

Ser Ser Lys His Gln His Lys Lys Leu Val Asn Arg Asp Leu Lys Thr
                740                 745                 750

Gln Ser Gly Ser Glu Met Lys Lys Phe Leu Ser Thr Leu Thr Ile Asp
                755                 760                 765

Gly Val Thr Arg Ser Asp Gln Gly Leu Tyr Thr Cys Ala Ala Ser Ser
                770                 775                 780

Gly Leu Met Thr Lys Lys Asn Ser Thr Phe Val Arg Val His Glu Lys
785                 790                 795                 800
```

<210> SEQ ID NO 191
<211> LENGTH: 214
<212> TYPE: PRT
<213> ORGANISM: Artificial Sequence
<220> FEATURE:
<223> OTHER INFORMATION: Synthetic

<400> SEQUENCE: 191

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 192
<211> LENGTH: 815
<212> TYPE: PRT
<213> ORGANISM: Artificial Sequence
<220> FEATURE:
<223> OTHER INFORMATION: Synthetic

<400> SEQUENCE: 192

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                     85                  90                  95
Ala Ser Glu Thr Tyr Asp Tyr Gly Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Gly Ser Gly Gly Gly Ser Ser Asp Thr Gly Arg
    450                 455                 460

Pro Phe Val Glu Met Tyr Ser Glu Ile Pro Glu Ile Ile His Met Thr
465                 470                 475                 480

Glu Gly Arg Glu Leu Val Ile Pro Cys Arg Val Thr Ser Pro Asn Ile
                485                 490                 495

Thr Val Thr Leu Lys Lys Phe Pro Leu Asp Thr Leu Ile Pro Asp Gly
            500                 505                 510
```

```
Lys Arg Ile Ile Trp Asp Ser Arg Lys Gly Phe Ile Ile Ser Asn Ala
            515                 520                 525

Thr Tyr Lys Glu Ile Gly Leu Leu Thr Cys Glu Ala Thr Val Asn Gly
        530                 535                 540

His Leu Tyr Lys Thr Asn Tyr Leu Thr His Arg Gln Thr Asn Thr Ile
545                 550                 555                 560

Ile Asp Val Val Leu Ser Pro Ser His Gly Ile Glu Leu Ser Val Gly
                565                 570                 575

Glu Lys Leu Val Leu Asn Cys Thr Ala Arg Thr Glu Leu Asn Val Gly
            580                 585                 590

Ile Asp Phe Asn Trp Glu Tyr Pro Ser Ser Lys His Gln His Lys Lys
        595                 600                 605

Leu Val Asn Arg Asp Leu Lys Thr Gln Ser Gly Ser Glu Met Lys Lys
    610                 615                 620

Phe Leu Ser Thr Leu Thr Ile Asp Gly Val Thr Arg Ser Asp Gln Gly
625                 630                 635                 640

Leu Tyr Thr Cys Ala Ala Ser Ser Gly Leu Met Thr Lys Lys Asn Ser
                645                 650                 655

Thr Phe Val Arg Val His Glu Lys Gly Gly Gly Ser Gly Gly Gly
            660                 665                 670

Gly Ser Gly Gly Gly Gly Ser Ile Pro Pro His Val Gln Lys Ser Val
        675                 680                 685

Asn Asn Asp Met Ile Val Thr Asp Asn Asn Gly Ala Val Lys Phe Pro
    690                 695                 700

Gln Leu Cys Lys Phe Cys Asp Val Arg Phe Ser Thr Cys Asp Asn Gln
705                 710                 715                 720

Lys Ser Cys Met Ser Asn Cys Ser Ile Thr Ser Ile Cys Glu Lys Pro
                725                 730                 735

Gln Glu Val Cys Val Ala Val Trp Arg Lys Asn Asp Glu Asn Ile Thr
            740                 745                 750

Leu Glu Thr Val Cys His Asp Pro Lys Leu Pro Tyr His Asp Phe Ile
        755                 760                 765

Leu Glu Asp Ala Ala Ser Pro Lys Cys Ile Met Lys Glu Lys Lys Lys
    770                 775                 780

Pro Gly Glu Thr Phe Phe Met Cys Ser Cys Ser Ser Asp Glu Cys Asn
785                 790                 795                 800

Asp Asn Ile Ile Phe Ser Glu Glu Tyr Asn Thr Ser Asn Pro Asp
                805                 810                 815

<210> SEQ ID NO 193
<211> LENGTH: 214
<212> TYPE: PRT
<213> ORGANISM: Artificial Sequence
<220> FEATURE:
<223> OTHER INFORMATION: Synthetic

<400> SEQUENCE: 193

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 194
<211> LENGTH: 14
<212> TYPE: PRT
<213> ORGANISM: Artificial Sequence
<220> FEATURE:
<223> OTHER INFORMATION: Synthetic

<400> SEQUENCE: 194

Gln Glu Glu Cys Glu Trp Asp Pro Trp Thr Cys Glu His Met
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Synthetic

<400> SEQUENCE: 195

Asn Ser Leu Ser Asn Ala Ser Glu Phe Arg Ala Pro Tyr
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Synthetic

<400> SEQUENCE: 196

Asn Leu Leu Met Ala Ala Ser
1               5

<210> SEQ ID NO 197
<211> LENGTH: 15
<212> TYPE: PRT
<213> ORGANISM: Artificial Sequence
<220> FEATURE:
<223> OTHER INFORMATION: Synthetic

<400> SEQUENCE: 197
```

```
Lys Arg Ile Trp Phe Ile Pro Arg Ser Ser Trp Tyr Glu Arg Ala
1               5                   10                  15

<210> SEQ ID NO 198
<211> LENGTH: 724
<212> TYPE: PRT
<213> ORGANISM: Artificial Sequence
<220> FEATURE:
<223> OTHER INFORMATION: Synthetic

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
        35                  40                  45

Gly Met Ile His Pro Asn Ser Gly Gly Asn Asn Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350
```

Pro Pro Ser Gln Glu Glu Met Gly Gly Ala Gln Gln Glu Glu Cys Glu
            355                 360                 365

Trp Asp Pro Trp Thr Cys Glu His Met Gly Ser Gly Ser Ala Thr Gly
        370                 375                 380

Gly Ser Gly Ser Thr Ala Ser Ser Gly Ser Gly Ser Ala Thr His Gln
385                 390                 395                 400

Glu Glu Cys Glu Trp Asp Pro Trp Thr Cys Glu His Met Gly Gly Thr
                405                 410                 415

Lys Asn Gln Val Ser Leu Thr Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
            450                 455                 460

Ser Arg Leu Thr Val Asp Lys Ser Arg Trp Gln Glu Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Leu Gly Lys Gly Gly Gly Gly Ser Gly Gly Gly
            500                 505                 510

Gly Ser Gly Gly Gly Gly Ser Ser Asp Thr Gly Arg Pro Phe Val Glu
        515                 520                 525

Met Tyr Ser Glu Ile Pro Glu Ile Ile His Met Thr Glu Gly Arg Glu
        530                 535                 540

Leu Val Ile Pro Cys Arg Val Thr Ser Pro Asn Ile Thr Val Thr Leu
545                 550                 555                 560

Lys Lys Phe Pro Leu Asp Thr Leu Ile Pro Asp Gly Lys Arg Ile Ile
                565                 570                 575

Trp Asp Ser Arg Lys Gly Phe Ile Ile Ser Asn Ala Thr Tyr Lys Glu
            580                 585                 590

Ile Gly Leu Leu Thr Cys Glu Ala Thr Val Asn Gly His Leu Tyr Lys
            595                 600                 605

Thr Asn Tyr Leu Thr His Arg Gln Thr Asn Thr Ile Ile Asp Val Val
        610                 615                 620

Leu Ser Pro Ser His Gly Ile Glu Leu Ser Val Gly Glu Lys Leu Val
625                 630                 635                 640

Leu Asn Cys Thr Ala Arg Thr Glu Leu Asn Val Gly Ile Asp Phe Asn
                645                 650                 655

Trp Glu Tyr Pro Ser Ser Lys His Gln His Lys Lys Leu Val Asn Arg
            660                 665                 670

Asp Leu Lys Thr Gln Ser Gly Ser Glu Met Lys Lys Phe Leu Ser Thr
        675                 680                 685

Leu Thr Ile Asp Gly Val Thr Arg Ser Asp Gln Gly Leu Tyr Thr Cys
        690                 695                 700

Ala Ala Ser Ser Gly Leu Met Thr Lys Lys Asn Ser Thr Phe Val Arg
705                 710                 715                 720

Val His Glu Lys

<210> SEQ ID NO 199
<211> LENGTH: 214
<212> TYPE: PRT
<213> ORGANISM: Artificial Sequence
<220> FEATURE:
<223> OTHER INFORMATION: Synthetic

<400> SEQUENCE: 199

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 200
<211> LENGTH: 682
<212> TYPE: PRT
<213> ORGANISM: Artificial Sequence
<220> FEATURE:
<223> OTHER INFORMATION: Synthetic

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

```
Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Gly Gly Gln Glu Cys Glu Trp Asp Pro Trp Thr Cys
                355                 360                 365

Glu His Met Gly Gly Thr Lys Asn Gln Val Ser Leu Thr Cys Leu Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
                420                 425                 430

Gln Glu Gly Asn Val Phe Ser Cys Ser Val Met His Glu Ala Leu His
                435                 440                 445

Asn His Tyr Thr Gln Lys Ser Leu Ser Leu Ser Leu Gly Lys Gly Gly
                450                 455                 460

Gly Gly Ser Gly Gly Gly Ser Gly Gly Gly Ser Ser Asp Thr
465                 470                 475                 480

Gly Arg Pro Phe Val Glu Met Tyr Ser Glu Ile Pro Glu Ile Ile His
                485                 490                 495

Met Thr Glu Gly Arg Glu Leu Val Ile Pro Cys Arg Val Thr Ser Pro
                500                 505                 510

Asn Ile Thr Val Thr Leu Lys Lys Phe Pro Leu Asp Thr Leu Ile Pro
                515                 520                 525

Asp Gly Lys Arg Ile Ile Trp Asp Ser Arg Lys Gly Phe Ile Ile Ser
530                 535                 540

Asn Ala Thr Tyr Lys Glu Ile Gly Leu Leu Thr Cys Glu Ala Thr Val
```

```
            545                 550                 555                 560
Asn Gly His Leu Tyr Lys Thr Asn Tyr Leu Thr His Arg Gln Thr Asn
                565                 570                 575

Thr Ile Ile Asp Val Val Leu Ser Pro Ser His Gly Ile Glu Leu Ser
                580                 585                 590

Val Gly Glu Lys Leu Val Leu Asn Cys Thr Ala Arg Thr Glu Leu Asn
                595                 600                 605

Val Gly Ile Asp Phe Asn Trp Glu Tyr Pro Ser Ser Lys His Gln His
                610                 615                 620

Lys Lys Leu Val Asn Arg Asp Leu Lys Thr Gln Ser Gly Ser Glu Met
625                 630                 635                 640

Lys Lys Phe Leu Ser Thr Leu Thr Ile Asp Gly Val Thr Arg Ser Asp
                645                 650                 655

Gln Gly Leu Tyr Thr Cys Ala Ala Ser Ser Gly Leu Met Thr Lys Lys
                660                 665                 670

Asn Ser Thr Phe Val Arg Val His Glu Lys
                675                 680

<210> SEQ ID NO 201
<211> LENGTH: 214
<212> TYPE: PRT
<213> ORGANISM: Artificial Sequence
<220> FEATURE:
<223> OTHER INFORMATION: Synthetic

<400> SEQUENCE: 201

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 202
<211> LENGTH: 720
<212> TYPE: PRT
<213> ORGANISM: Artificial Sequence
<220> FEATURE:
<223> OTHER INFORMATION: Synthetic

<400> SEQUENCE: 202
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Tyr | Ile | His | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Phe | Pro | Gly | Ser | Gly | Asn | Ser | Lys | Tyr | Asn | Glu | Asn | Phe |
| 50 | | | | | 55 | | | | | 60 | | | | | |
| Lys | Gly | Arg | Val | Thr | Leu | Thr | Ala | Asp | Thr | Ser | Thr | Ser | Thr | Val | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Ser | Glu | Thr | Tyr | Asp | Tyr | Gly | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Cys | Ser | Arg | Ser | Thr | Ser | Glu | Ser | Thr | Ala | Ala | Leu | Gly | Cys |
| 130 | | | | | 135 | | | | | 140 | | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Lys | Thr | Tyr | Thr | Cys | Asn | Val | Asp | His | Lys | Pro | Ser | Asn |
| | | 195 | | | | | 200 | | | | | 205 | | | |
| Thr | Lys | Val | Asp | Lys | Arg | Val | Glu | Ser | Lys | Tyr | Gly | Pro | Pro | Cys | Pro |
| 210 | | | | | 215 | | | | | 220 | | | | | |
| Pro | Cys | Pro | Ala | Pro | Glu | Phe | Leu | Gly | Gly | Pro | Ser | Val | Phe | Leu | Phe |
| 225 | | | | | 230 | | | | | 235 | | | | | 240 |
| Pro | Pro | Lys | Pro | Lys | Asp | Thr | Leu | Met | Ile | Ser | Arg | Thr | Pro | Glu | Val |
| | | | | 245 | | | | | 250 | | | | | 255 | |
| Thr | Cys | Val | Val | Val | Asp | Val | Ser | Gln | Glu | Asp | Pro | Glu | Val | Gln | Phe |
| | | | 260 | | | | | 265 | | | | | 270 | | |
| Asn | Trp | Tyr | Val | Asp | Gly | Val | Glu | Val | His | Asn | Ala | Lys | Thr | Lys | Pro |
| | | 275 | | | | | 280 | | | | | 285 | | | |
| Arg | Glu | Glu | Gln | Phe | Asn | Ser | Thr | Tyr | Arg | Val | Val | Ser | Val | Leu | Thr |
| 290 | | | | | 295 | | | | | 300 | | | | | |
| Val | Leu | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | Asn | Lys | Gly | Leu | Pro | Ser | Ser | Ile | Glu | Lys | Thr | Ile | Ser | Lys | Ala |
| | | | | 325 | | | | | 330 | | | | | 335 | |
| Lys | Gly | Gln | Pro | Arg | Glu | Pro | Gln | Val | Tyr | Thr | Leu | Pro | Pro | Ser | Gln |
| | | | 340 | | | | | 345 | | | | | 350 | | |
| Glu | Glu | Met | Gly | Gly | Ala | Gln | Gln | Glu | Cys | Glu | Trp | Asp | Pro | Trp | |
| | | | 355 | | | | | 360 | | | | | 365 | | |
| Thr | Cys | Glu | His | Met | Gly | Ser | Gly | Ser | Ala | Thr | Gly | Gly | Ser | Gly | Ser |

```
                370                 375                 380
Thr Ala Ser Ser Gly Ser Gly Ser Ala Thr His Gln Glu Glu Cys Glu
385                 390                 395                 400

Trp Asp Pro Trp Thr Cys Glu His Met Gly Gly Thr Lys Asn Gln Val
                405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Arg Leu Thr
450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Leu Gly Lys Gly Gly Gly Gly Ser Gly Gly Gly Ser Gly Gly
                500                 505                 510

Gly Gly Ser Ser Asp Thr Gly Arg Pro Phe Val Glu Met Tyr Ser Glu
                515                 520                 525

Ile Pro Glu Ile Ile His Met Thr Glu Gly Arg Glu Leu Val Ile Pro
                530                 535                 540

Cys Arg Val Thr Ser Pro Asn Ile Thr Val Thr Leu Lys Lys Phe Pro
545                 550                 555                 560

Leu Asp Thr Leu Ile Pro Asp Gly Lys Arg Ile Ile Trp Asp Ser Arg
                565                 570                 575

Lys Gly Phe Ile Ile Ser Asn Ala Thr Tyr Lys Glu Ile Gly Leu Leu
                580                 585                 590

Thr Cys Glu Ala Thr Val Asn Gly His Leu Tyr Lys Thr Asn Tyr Leu
                595                 600                 605

Thr His Arg Gln Thr Asn Thr Ile Ile Asp Val Val Leu Ser Pro Ser
610                 615                 620

His Gly Ile Glu Leu Ser Val Gly Glu Lys Leu Val Leu Asn Cys Thr
625                 630                 635                 640

Ala Arg Thr Glu Leu Asn Val Gly Ile Asp Phe Asn Trp Glu Tyr Pro
                645                 650                 655

Ser Ser Lys His Gln His Lys Lys Leu Val Asn Arg Asp Leu Lys Thr
                660                 665                 670

Gln Ser Gly Ser Glu Met Lys Lys Phe Leu Ser Thr Leu Thr Ile Asp
                675                 680                 685

Gly Val Thr Arg Ser Asp Gln Gly Leu Tyr Thr Cys Ala Ala Ser Ser
690                 695                 700

Gly Leu Met Thr Lys Lys Asn Ser Thr Phe Val Arg Val His Glu Lys
705                 710                 715                 720

<210> SEQ ID NO 203
<211> LENGTH: 723
<212> TYPE: PRT
<213> ORGANISM: Artificial Sequence
<220> FEATURE:
<223> OTHER INFORMATION: Synthetic

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30
Tyr Ile His Trp Val Arg Gln Ala Pro Gly Gln Gly Leu Glu Trp Met
            35                  40                  45
Gly Trp Ile Phe Pro Gly Ser Gly Asn Ser Lys Tyr Asn Glu Asn Phe
50                  55                  60
Lys Gly Arg Val Thr Leu Thr Ala Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Ser Glu Thr Tyr Asp Tyr Gly Asp Tyr Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
                195                 200                 205
Thr Lys Val Asp Lys Arg Val Glu Ser Lys Tyr Gly Pro Pro Cys Pro
                210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
                275                 280                 285
Arg Glu Glu Gln Phe Asn Ser Thr Tyr Arg Val Val Ser Val Leu Thr
                290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
                370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly Lys Gly Gly Gly Gly
                435                 440                 445
```

Gly Ala Gln Gln Glu Glu Cys Glu Trp Asp Pro Trp Thr Cys Glu His
            450                 455                 460

Met Gly Ser Gly Ser Ala Thr Gly Gly Ser Gly Ser Thr Ala Ser Ser
465                 470                 475                 480

Gly Ser Gly Ser Ala Thr His Gln Glu Glu Cys Glu Trp Asp Pro Trp
                485                 490                 495

Thr Cys Glu His Met Leu Glu Gly Gly Gly Ser Gly Gly Gly Gly
            500                 505                 510

Ser Gly Gly Gly Ser Ser Asp Thr Gly Arg Pro Phe Val Glu Met
            515                 520                 525

Tyr Ser Glu Ile Pro Glu Ile Ile His Met Thr Glu Gly Arg Glu Leu
            530                 535                 540

Val Ile Pro Cys Arg Val Thr Ser Pro Asn Ile Thr Val Thr Leu Lys
545                 550                 555                 560

Lys Phe Pro Leu Asp Thr Leu Ile Pro Asp Gly Lys Arg Ile Ile Trp
                565                 570                 575

Asp Ser Arg Lys Gly Phe Ile Ile Ser Asn Ala Thr Tyr Lys Glu Ile
                580                 585                 590

Gly Leu Leu Thr Cys Glu Ala Thr Val Asn Gly His Leu Tyr Lys Thr
            595                 600                 605

Asn Tyr Leu Thr His Arg Gln Thr Asn Thr Ile Ile Asp Val Val Leu
            610                 615                 620

Ser Pro Ser His Gly Ile Glu Leu Ser Val Gly Glu Lys Leu Val Leu
625                 630                 635                 640

Asn Cys Thr Ala Arg Thr Glu Leu Asn Val Gly Ile Asp Phe Asn Trp
                645                 650                 655

Glu Tyr Pro Ser Ser Lys His Gln His Lys Lys Leu Val Asn Arg Asp
                660                 665                 670

Leu Lys Thr Gln Ser Gly Ser Glu Met Lys Lys Phe Leu Ser Thr Leu
            675                 680                 685

Thr Ile Asp Gly Val Thr Arg Ser Asp Gln Gly Leu Tyr Thr Cys Ala
690                 695                 700

Ala Ser Ser Gly Leu Met Thr Lys Lys Asn Ser Thr Phe Val Arg Val
705                 710                 715                 720

His Glu Lys

<210> SEQ ID NO 204
<211> LENGTH: 723
<212> TYPE: PRT
<213> ORGANISM: Artificial Sequence
<220> FEATURE:
<223> OTHER INFORMATION: Synthetic

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Phe Pro Gly Ser Gly Asn Ser Lys Tyr Asn Glu Asn Phe
        50                  55                  60

Lys Gly Arg Val Thr Leu Thr Ala Asp Thr Ser Thr Ser Thr Val Tyr
65                  70                  75                  80

```
Met Glu Leu Ser Ser Leu Arg Ser Glu Asp Thr Ala Val Tyr Tyr Cys
                    85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Gly Ser Gly Gly Gly Gly Ser Ser Asp Thr Gly Arg
450                 455                 460

Pro Phe Val Glu Met Tyr Ser Glu Ile Pro Glu Ile Ile His Met Thr
465                 470                 475                 480

Glu Gly Arg Glu Leu Val Ile Pro Cys Arg Val Thr Ser Pro Asn Ile
                485                 490                 495

Thr Val Thr Leu Lys Lys Phe Pro Leu Asp Thr Leu Ile Pro Asp Gly
```

```
                     500                 505                 510
Lys Arg Ile Ile Trp Asp Ser Arg Lys Gly Phe Ile Ile Ser Asn Ala
            515                 520                 525

Thr Tyr Lys Glu Ile Gly Leu Leu Thr Cys Glu Ala Thr Val Asn Gly
        530                 535                 540

His Leu Tyr Lys Thr Asn Tyr Leu Thr His Arg Gln Thr Asn Thr Ile
545                 550                 555                 560

Ile Asp Val Val Leu Ser Pro Ser His Gly Ile Glu Leu Ser Val Gly
                565                 570                 575

Glu Lys Leu Val Leu Asn Cys Thr Ala Arg Thr Glu Leu Asn Val Gly
            580                 585                 590

Ile Asp Phe Asn Trp Glu Tyr Pro Ser Ser Lys His Gln His Lys Lys
        595                 600                 605

Leu Val Asn Arg Asp Leu Lys Thr Gln Ser Gly Ser Glu Met Lys Lys
        610                 615                 620

Phe Leu Ser Thr Leu Thr Ile Asp Gly Val Thr Arg Ser Asp Gln Gly
625                 630                 635                 640

Leu Tyr Thr Cys Ala Ala Ser Ser Gly Leu Met Thr Lys Lys Asn Ser
                645                 650                 655

Thr Phe Val Arg Val His Glu Lys Gly Gly Gly Gly Ala Gln Gln
                660                 665                 670

Glu Glu Cys Glu Trp Asp Pro Trp Thr Cys Glu His Met Gly Ser Gly
            675                 680                 685

Ser Ala Thr Gly Gly Ser Gly Ser Thr Ala Ser Ser Gly Ser Gly Ser
        690                 695                 700

Ala Thr His Gln Glu Glu Cys Glu Trp Asp Pro Trp Thr Cys Glu His
705                 710                 715                 720

Met Leu Glu

<210> SEQ ID NO 205
<211> LENGTH: 815
<212> TYPE: PRT
<213> ORGANISM: Artificial Sequence
<220> FEATURE:
<223> OTHER INFORMATION: Synthetic

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Ala Gly Gly Gly Gly
            435                 440                 445

Ser Gly Gly Gly Gly Ser Gly Gly Gly Gly Ser Ser Asp Thr Gly Arg
    450                 455                 460

Pro Phe Val Glu Met Tyr Ser Glu Ile Pro Glu Ile Ile His Met Thr
465                 470                 475                 480

Glu Gly Arg Glu Leu Val Ile Pro Cys Arg Val Thr Ser Pro Asn Ile
                485                 490                 495

Thr Val Thr Leu Lys Lys Phe Pro Leu Asp Thr Leu Ile Pro Asp Gly
            500                 505                 510

Lys Arg Ile Ile Trp Asp Ser Arg Lys Gly Phe Ile Ile Ser Asn Ala
        515                 520                 525

Thr Tyr Lys Glu Ile Gly Leu Leu Thr Cys Glu Ala Thr Val Asn Gly
    530                 535                 540

His Leu Tyr Lys Thr Asn Tyr Leu Thr His Arg Gln Thr Asn Thr Ile
545                 550                 555                 560
```

```
Ile Asp Val Val Leu Ser Pro Ser His Gly Ile Glu Leu Ser Val Gly
            565                 570                 575

Glu Lys Leu Val Leu Asn Cys Thr Ala Arg Thr Glu Leu Asn Val Gly
        580                 585                 590

Ile Asp Phe Asn Trp Glu Tyr Pro Ser Ser Lys His Gln His Lys Lys
            595                 600                 605

Leu Val Asn Arg Asp Leu Lys Thr Gln Ser Gly Ser Glu Met Lys Lys
        610                 615                 620

Phe Leu Ser Thr Leu Thr Ile Asp Gly Val Thr Arg Ser Asp Gln Gly
625                 630                 635                 640

Leu Tyr Thr Cys Ala Ala Ser Ser Gly Leu Met Thr Lys Lys Asn Ser
            645                 650                 655

Thr Phe Val Arg Val His Glu Lys Gly Gly Gly Ser Gly Gly Gly
        660                 665                 670

Gly Ser Gly Gly Gly Ser Ile Pro Pro His Val Gln Lys Ser Val
    675                 680                 685

Asn Asn Asp Met Ile Val Thr Asp Asn Gly Ala Val Lys Phe Pro
        690                 695                 700

Gln Leu Cys Lys Phe Cys Asp Val Arg Phe Ser Thr Cys Asp Asn Gln
705                 710                 715                 720

Lys Ser Cys Met Ser Asn Cys Ser Ile Thr Ser Ile Cys Glu Lys Pro
            725                 730                 735

Gln Glu Val Cys Val Ala Val Trp Arg Lys Asn Asp Glu Asn Ile Thr
        740                 745                 750

Leu Glu Thr Val Cys His Asp Pro Lys Leu Pro Tyr His Asp Phe Ile
            755                 760                 765

Leu Glu Asp Ala Ala Ser Pro Lys Cys Ile Met Lys Glu Lys Lys
        770                 775                 780

Pro Gly Glu Thr Phe Phe Met Cys Ser Cys Ser Ser Asp Glu Cys Asn
785                 790                 795                 800

Asp Asn Ile Ile Phe Ser Glu Glu Tyr Asn Thr Ser Asn Pro Asp
            805                 810                 815

<210> SEQ ID NO 206
<211> LENGTH: 815
<212> TYPE: PRT
<213> ORGANISM: Artificial Sequence
<220> FEATURE:
<223> OTHER INFORMATION: Synthetic

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110
```

-continued

```
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ala Gly Gly Gly Gly
        435                 440                 445

Ser Gly Gly Gly Gly Ser Gly Gly Gly Gly Ser Ser Asp Thr Gly Arg
450                 455                 460

Pro Phe Val Glu Met Tyr Ser Glu Ile Pro Glu Ile Ile His Met Thr
465                 470                 475                 480

Glu Gly Arg Glu Leu Val Ile Pro Cys Arg Val Thr Ser Pro Glu Ile
                485                 490                 495

Thr Val Thr Leu Lys Lys Phe Pro Leu Asp Thr Leu Ile Pro Asp Gly
            500                 505                 510

Lys Arg Ile Ile Trp Asp Ser Arg Lys Gly Phe Ile Ile Ser Glu Ala
        515                 520                 525

Thr Tyr Lys Glu Ile Gly Leu Leu Thr Cys Glu Ala Thr Val Asn Gly
```

```
                530             535              540
His Leu Tyr Lys Thr Asn Tyr Leu Thr His Arg Gln Thr Asn Thr Ile
545                 550                 555                 560

Ile Asp Val Val Leu Ser Pro Ser His Gly Ile Glu Leu Ser Val Gly
                565                 570                 575

Glu Lys Leu Val Leu Glu Cys Thr Ala Arg Thr Glu Leu Asn Val Gly
                580                 585                 590

Ile Asp Phe Asn Trp Glu Tyr Pro Ser Ser Lys His Gln His Lys Lys
                595                 600                 605

Leu Val Asn Arg Asp Leu Lys Thr Gln Ser Gly Ser Glu Met Lys Lys
                610                 615                 620

Phe Leu Ser Thr Leu Thr Ile Asp Gly Val Thr Arg Ser Asp Gln Gly
625                 630                 635                 640

Leu Tyr Thr Cys Ala Ala Ser Ser Gly Leu Met Thr Lys Lys Glu Ser
                645                 650                 655

Thr Phe Val Arg Val His Glu Lys Gly Gly Gly Ser Gly Gly Gly
                660                 665                 670

Gly Ser Gly Gly Gly Gly Ser Ile Pro Pro His Val Gln Lys Ser Val
                675                 680                 685

Asn Asn Asp Met Ile Val Thr Asp Asn Asn Gly Ala Val Lys Phe Pro
                690                 695                 700

Gln Leu Cys Lys Phe Cys Asp Val Arg Phe Ser Thr Cys Asp Asn Gln
705                 710                 715                 720

Lys Ser Cys Met Ser Asn Cys Ser Ile Thr Ser Ile Cys Glu Lys Pro
                725                 730                 735

Gln Glu Val Cys Val Ala Val Trp Arg Lys Asn Asp Glu Asn Ile Thr
                740                 745                 750

Leu Glu Thr Val Cys His Asp Pro Lys Leu Pro Tyr His Asp Phe Ile
                755                 760                 765

Leu Glu Asp Ala Ala Ser Pro Lys Cys Ile Met Lys Glu Lys Lys
                770                 775                 780

Pro Gly Glu Thr Phe Phe Met Cys Ser Cys Ser Ser Asp Glu Cys Asn
785                 790                 795                 800

Asp Asn Ile Ile Phe Ser Glu Glu Tyr Asn Thr Ser Asn Pro Asp
                805                 810                 815
```

<210> SEQ ID NO 207
<211> LENGTH: 205
<212> TYPE: PRT
<213> ORGANISM: Artificial Sequence
<220> FEATURE:
<223> OTHER INFORMATION: Synthetic

<400> SEQUENCE: 207

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Glu Ile Thr Val Thr Leu Lys Lys Phe Pro Leu Asp Thr
                35                  40                  45

Leu Ile Pro Asp Gly Lys Arg Ile Ile Trp Asp Ser Arg Lys Gly Phe
                50                  55                  60

Ile Ile Ser Glu Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
```

```
                        85                  90                  95
Gln Thr Asn Thr Ile Ile Asp Val Val Leu Ser Pro Ser His Gly Ile
                    100                 105                 110

Glu Leu Ser Val Gly Glu Lys Leu Val Leu Glu Cys Thr Ala Arg Thr
                115                 120                 125

Glu Leu Asn Val Gly Ile Asp Phe Asn Trp Glu Tyr Pro Ser Ser Lys
            130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
                180                 185                 190

Thr Lys Lys Glu Ser Thr Phe Val Arg Val His Glu Lys
            195                 200                 205

<210> SEQ ID NO 208
<211> LENGTH: 227
<212> TYPE: PRT
<213> ORGANISM: Artificial Sequence
<220> FEATURE:
<223> OTHER INFORMATION: Synthetic

<400> SEQUENCE: 208

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

```
<210> SEQ ID NO 209
<211> LENGTH: 285
<212> TYPE: PRT
<213> ORGANISM: Artificial Sequence
<220> FEATURE:
<223> OTHER INFORMATION: Synthetic

<400> SEQUENCE: 209
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 |

| | | | | | | | | | | | | | | |
|---|---|---|---|---|---|---|---|---|---|---|---|---|---|---|
| Gly | Pro | Ser | Val | Phe | Leu | Phe | Pro | Pro | Lys | Pro | Lys | Asp | Thr | Leu | Met |
| | | | 20 | | | | | 25 | | | | | 30 | |

| | | | | | | | | | | | | | | |
|---|---|---|---|---|---|---|---|---|---|---|---|---|---|---|
| Ile | Ser | Arg | Thr | Pro | Glu | Val | Thr | Cys | Val | Val | Val | Asp | Val | Ser | His |
| | | 35 | | | | | 40 | | | | | 45 | | | |

| | | | | | | | | | | | | | | |
|---|---|---|---|---|---|---|---|---|---|---|---|---|---|---|
| Glu | Asp | Pro | Glu | Val | Lys | Phe | Asn | Trp | Tyr | Val | Asp | Gly | Val | Glu | Val |
| 50 | | | | | 55 | | | | | 60 | | | | | |

| | | | | | | | | | | | | | | |
|---|---|---|---|---|---|---|---|---|---|---|---|---|---|---|
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |

| | | | | | | | | | | | | | | |
|---|---|---|---|---|---|---|---|---|---|---|---|---|---|---|
| Arg | Val | Val | Ser | Val | Leu | Thr | Val | Leu | His | Gln | Asp | Trp | Leu | Asn | Gly |
| | | | | 85 | | | | | 90 | | | | | 95 | |

| | | | | | | | | | | | | | | |
|---|---|---|---|---|---|---|---|---|---|---|---|---|---|---|
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |

| | | | | | | | | | | | | | | |
|---|---|---|---|---|---|---|---|---|---|---|---|---|---|---|
| Glu | Lys | Thr | Ile | Ser | Lys | Ala | Lys | Gly | Gln | Pro | Arg | Glu | Pro | Gln | Val |
| | | 115 | | | | | 120 | | | | | 125 | | | |

| | | | | | | | | | | | | | | |
|---|---|---|---|---|---|---|---|---|---|---|---|---|---|---|
| Tyr | Thr | Leu | Pro | Pro | Ser | Arg | Glu | Glu | Met | Gly | Gly | Ala | Gln | Gln | Glu |
| | 130 | | | | | 135 | | | | | 140 | | | | |

| | | | | | | | | | | | | | | |
|---|---|---|---|---|---|---|---|---|---|---|---|---|---|---|
| Glu | Cys | Glu | Trp | Asp | Pro | Trp | Thr | Cys | Glu | His | Met | Gly | Ser | Gly | Ser |
| 145 | | | | | 150 | | | | | 155 | | | | | 160 |

| | | | | | | | | | | | | | | |
|---|---|---|---|---|---|---|---|---|---|---|---|---|---|---|
| Ala | Thr | Gly | Gly | Ser | Gly | Ser | Thr | Ala | Ser | Ser | Gly | Ser | Gly | Ser | Ala |
| | | | | 165 | | | | | 170 | | | | | 175 | |

| | | | | | | | | | | | | | | |
|---|---|---|---|---|---|---|---|---|---|---|---|---|---|---|
| Thr | His | Gln | Glu | Glu | Cys | Glu | Trp | Asp | Pro | Trp | Thr | Cys | Glu | His | Met |
| | | | 180 | | | | | 185 | | | | | 190 | | |

| | | | | | | | | | | | | | | |
|---|---|---|---|---|---|---|---|---|---|---|---|---|---|---|
| Leu | Glu | Gly | Gly | Thr | Lys | Asn | Gln | Val | Ser | Leu | Thr | Cys | Leu | Val | Lys |
| | | 195 | | | | | 200 | | | | | 205 | | | |

| | | | | | | | | | | | | | | |
|---|---|---|---|---|---|---|---|---|---|---|---|---|---|---|
| Gly | Phe | Tyr | Pro | Ser | Asp | Ile | Ala | Val | Glu | Trp | Glu | Ser | Asn | Gly | Gln |
| | 210 | | | | | 215 | | | | | 220 | | | | |

| | | | | | | | | | | | | | | |
|---|---|---|---|---|---|---|---|---|---|---|---|---|---|---|
| Pro | Glu | Asn | Asn | Tyr | Lys | Thr | Thr | Pro | Pro | Val | Leu | Asp | Ser | Asp | Gly |
| 225 | | | | | 230 | | | | | 235 | | | | | 240 |

| | | | | | | | | | | | | | | |
|---|---|---|---|---|---|---|---|---|---|---|---|---|---|---|
| Ser | Phe | Phe | Leu | Tyr | Ser | Lys | Leu | Thr | Val | Asp | Lys | Ser | Arg | Trp | Gln |
| | | | | 245 | | | | | 250 | | | | | 255 | |

| | | | | | | | | | | | | | | |
|---|---|---|---|---|---|---|---|---|---|---|---|---|---|---|
| Gln | Gly | Asn | Val | Phe | Ser | Cys | Ser | Val | Met | His | Glu | Ala | Leu | His | Asn |
| | | | 260 | | | | | 265 | | | | | 270 | | |

| | | | | | | | | | |
|---|---|---|---|---|---|---|---|---|---|
| His | Tyr | Thr | Gln | Lys | Ser | Leu | Ser | Leu | Ser | Pro | Gly | Lys |
| | | 275 | | | | | 280 | | | | | 285 |

```
<210> SEQ ID NO 210
<211> LENGTH: 227
<212> TYPE: PRT
<213> ORGANISM: Artificial Sequence
<220> FEATURE:
<223> OTHER INFORMATION: Synthetic

<400> SEQUENCE: 210
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 |

| | | | | | | | | | | | | | | |
|---|---|---|---|---|---|---|---|---|---|---|---|---|---|---|
| Gly | Pro | Asp | Val | Phe | Leu | Phe | Pro | Pro | Lys | Pro | Lys | Asp | Thr | Leu | Met |
| | | | 20 | | | | | 25 | | | | | 30 | |

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Glu
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 211
<211> LENGTH: 227
<212> TYPE: PRT
<213> ORGANISM: Artificial Sequence
<220> FEATURE:
<223> OTHER INFORMATION: Synthetic

<400> SEQUENCE: 211

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 212
<211> LENGTH: 225
<212> TYPE: PRT
<213> ORGANISM: Artificial Sequence
<220> FEATURE:
<223> OTHER INFORMATION: Synthetic

<400> SEQUENCE: 212

Gly Pro Pro Cys Pro Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Gly Leu Pro Ser Ser Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Gln Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Arg Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Leu Gly
    210                 215                 220

Lys
225

<210> SEQ ID NO 213
<211> LENGTH: 232
<212> TYPE: PRT
<213> ORGANISM: Artificial Sequence
<220> FEATURE:
<223> OTHER INFORMATION: Synthetic

<400> SEQUENCE: 213

Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val His Gln
                85                  90                  95

Asp Trp Leu Asn Gly Lys Glu Tyr Lys Cys Lys Val Ser Asn Lys Gly
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 214
<211> LENGTH: 226
<212> TYPE: PRT
<213> ORGANISM: Artificial Sequence
<220> FEATURE:
<223> OTHER INFORMATION: Synthetic

<400> SEQUENCE: 214

Asp Lys Thr His Thr Cys Pro Pro Cys Pro Ala Pro Glu Leu Leu Gly
1               5                   10                  15

Gly Pro Asp Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Glu
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly
225

<210> SEQ ID NO 215
<211> LENGTH: 226
<212> TYPE: PRT
<213> ORGANISM: Artificial Sequence
<220> FEATURE:
<223> OTHER INFORMATION: Synthetic

<400> SEQUENCE: 215

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly
225

<210> SEQ ID NO 216
```

<211> LENGTH: 224
<212> TYPE: PRT
<213> ORGANISM: Artificial Sequence
<220> FEATURE:
<223> OTHER INFORMATION: Synthetic

<400> SEQUENCE: 216

Gly Pro Pro Cys Pro Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
                35                  40                  45

Pro Glu Val Gln Phe Asn Trp Tyr Val Asp Gly Val Glu Val His Asn
        50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

<210> SEQ ID NO 217
<211> LENGTH: 231
<212> TYPE: PRT
<213> ORGANISM: Artificial Sequence
<220> FEATURE:
<223> OTHER INFORMATION: Synthetic

<400> SEQUENCE: 217

Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly

```
                100             105             110
Leu Pro Ala Pro Ile Glu Lys Thr Ile Ser Lys Thr Lys Gly Gln Pro
            115                 120                 125
Arg Glu Pro Gln Val Tyr Thr Leu Pro Pro Ser Arg Glu Glu Met Thr
        130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Met Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly
225                 230

<210> SEQ ID NO 218
<211> LENGTH: 668
<212> TYPE: PRT
<213> ORGANISM: Artificial Sequence
<220> FEATURE:
<223> OTHER INFORMATION: Synthetic

<400> SEQUENCE: 218

Ser Asp Thr Gly Arg Pro Phe Val Glu Met Tyr Ser Glu Ile Pro Glu
1               5                   10                  15
Ile Ile His Met Thr Glu Gly Arg Glu Leu Val Ile Pro Cys Arg Val
                20                  25                  30
Thr Ser Pro Asn Ile Thr Val Thr Leu Lys Lys Phe Pro Leu Asp Thr
            35                  40                  45
Leu Ile Pro Asp Gly Lys Arg Ile Ile Trp Asp Ser Arg Lys Gly Phe
        50                  55                  60
Ile Ile Ser Asn Ala Thr Tyr Lys Glu Ile Gly Leu Leu Thr Cys Glu
65                  70                  75                  80
Ala Thr Val Asn Gly His Leu Tyr Lys Thr Asn Tyr Leu Thr His Arg
                85                  90                  95
Gln Thr Asn Thr Ile Ile Asp Val Val Leu Ser Pro Ser His Gly Ile
            100                 105                 110
Glu Leu Ser Val Gly Glu Lys Leu Val Leu Asn Cys Thr Ala Arg Thr
        115                 120                 125
Glu Leu Asn Val Gly Ile Asp Phe Asn Trp Glu Tyr Pro Ser Ser Lys
        130                 135                 140
His Gln His Lys Lys Leu Val Asn Arg Asp Leu Lys Thr Gln Ser Gly
145                 150                 155                 160
Ser Glu Met Lys Lys Phe Leu Ser Thr Leu Thr Ile Asp Gly Val Thr
                165                 170                 175
Arg Ser Asp Gln Gly Leu Tyr Thr Cys Ala Ala Ser Ser Gly Leu Met
            180                 185                 190
Thr Lys Lys Asn Ser Thr Phe Val Arg Val His Glu Lys Gly Gly Gly
        195                 200                 205
Gly Ser Gly Gly Gly Gly Ser Gly Gly Gly Gly Ser Gln Val Gln Leu
    210                 215                 220
Val Gln Ser Gly Ala Glu Val Lys Lys Pro Gly Ala Ser Val Lys Val
```

```
            225                 230                 235                 240
Ser Cys Lys Ala Ser Gly Tyr Thr Phe Thr Ser Tyr Trp Met His Trp
                245                 250                 255

Val Arg Gln Ala Pro Gly Gln Gly Leu Glu Trp Met Gly Met Ile His
                260                 265                 270

Pro Asn Ser Gly Gly Asn Asn Tyr Asn Glu Lys Phe Lys Ser Arg Val
                275                 280                 285

Thr Met Thr Arg Asp Thr Ser Ile Ser Thr Ala Tyr Met Glu Leu Ser
    290                 295                 300

Arg Leu Arg Ser Asp Asp Thr Ala Val Tyr Tyr Cys Ala Arg Ser Trp
305                 310                 315                 320

Tyr Gly Ser Ser Pro Tyr Tyr Phe Asp Tyr Trp Gly Gln Gly Thr Leu
                325                 330                 335

Val Thr Val Ser Ser Ala Ser Thr Lys Gly Pro Ser Val Phe Pro Leu
                340                 345                 350

Ala Pro Cys Ser Arg Ser Thr Ser Glu Ser Thr Ala Ala Leu Gly Cys
                355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Lys Thr Tyr Thr Cys Asn Val Asp His Lys Pro Ser Asn
                420                 425                 430

Thr Lys Val Asp Lys Arg Val Glu Ser Lys Tyr Gly Pro Pro Cys Pro
            435                 440                 445

Pro Cys Pro Ala Pro Glu Phe Leu Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser Gln Glu Asp Pro Glu Val Gln Phe
                485                 490                 495

Asn Trp Tyr Val Asp Gly Val Glu Val His Asn Ala Lys Thr Lys Pro
                500                 505                 510

Arg Glu Glu Gln Phe Asn Ser Thr Tyr Arg Val Val Ser Val Leu Thr
            515                 520                 525

Val Leu His Gln Asp Trp Leu Asn Gly Lys Glu Tyr Lys Cys Lys Val
    530                 535                 540

Ser Asn Lys Gly Leu Pro Ser Ser Ile Glu Lys Thr Ile Ser Lys Ala
545                 550                 555                 560

Lys Gly Gln Pro Arg Glu Pro Gln Val Tyr Thr Leu Pro Pro Ser Gln
                565                 570                 575

Glu Glu Met Thr Lys Asn Gln Val Ser Leu Thr Cys Leu Val Lys Gly
                580                 585                 590

Phe Tyr Pro Ser Asp Ile Ala Val Glu Trp Glu Ser Asn Gly Gln Pro
                595                 600                 605

Glu Asn Asn Tyr Lys Thr Thr Pro Pro Val Leu Asp Ser Asp Gly Ser
            610                 615                 620

Phe Phe Leu Tyr Ser Arg Leu Thr Val Asp Lys Ser Arg Trp Gln Glu
625                 630                 635                 640

Gly Asn Val Phe Ser Cys Ser Val Met His Glu Ala Leu His Asn His
                645                 650                 655
```

Tyr Thr Gln Lys Ser Leu Ser Leu Ser Leu Gly Lys
            660                 665

<210> SEQ ID NO 219
<211> LENGTH: 214
<212> TYPE: PRT
<213> ORGANISM: Artificial Sequence
<220> FEATURE:
<223> OTHER INFORMATION: Synthetic

<400> SEQUENCE: 219

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 220
<211> LENGTH: 672
<212> TYPE: PRT
<213> ORGANISM: Artificial Sequence
<220> FEATURE:
<223> OTHER INFORMATION: Synthetic

<400> SEQUENCE: 220

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Thr Ser Thr Val Tyr

```
                65                  70                  75                  80
            Met Glu Leu Ser Ser Leu Arg Ser Glu Asp Thr Ala Val Tyr Tyr Cys
                            85                  90                  95

Ala Ser Glu Thr Tyr Asp Tyr Gly Asp Tyr Trp Gly Gln Gly Thr Leu
                            100                 105                 110

Val Thr Val Ser Ser Ala Ser Thr Lys Gly Pro Ser Val Phe Pro Leu
                            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
            145                 150                 155                 160

Gly Ala Leu Thr Ser Gly Val His Thr Phe Pro Ala Val Leu Gln Ser
                            165                 170                 175

Ser Gly Leu Tyr Ser Leu Ser Ser Val Val Thr Val Pro Ser Ser Ser
                            180                 185                 190

Leu Gly Thr Gln Thr Tyr Ile Cys Asn Val Asn His Lys Pro Ser Asn
                            195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Leu Leu Gly Gly Pro Ser Val
            225                 230                 235                 240

Phe Leu Phe Pro Pro Lys Pro Lys Asp Thr Leu Met Ile Ser Arg Thr
                            245                 250                 255

Pro Glu Val Thr Cys Val Val Val Asp Val Ser His Glu Asp Pro Glu
                            260                 265                 270

Val Lys Phe Asn Trp Tyr Val Asp Gly Val Glu Val His Asn Ala Lys
                            275                 280                 285

Thr Lys Pro Arg Glu Glu Gln Tyr Ala Ser Thr Tyr Arg Val Val Ser
                            290                 295                 300

Val Leu Thr Val Leu His Gln Asp Trp Leu Asn Gly Lys Glu Tyr Lys
            305                 310                 315                 320

Cys Lys Val Ser Asn Lys Ala Leu Pro Ala Pro Ile Glu Lys Thr Ile
                            325                 330                 335

Ser Lys Ala Lys Gly Gln Pro Arg Glu Pro Gln Val Tyr Thr Leu Pro
                            340                 345                 350

Pro Ser Arg Glu Glu Met Thr Lys Asn Gln Val Ser Leu Thr Cys Leu
                            355                 360                 365

Val Lys Gly Phe Tyr Pro Ser Asp Ile Ala Val Glu Trp Glu Ser Asn
                            370                 375                 380

Gly Gln Pro Glu Asn Asn Tyr Lys Thr Thr Pro Pro Val Leu Asp Ser
            385                 390                 395                 400

Asp Gly Ser Phe Phe Leu Tyr Ser Lys Leu Thr Val Asp Lys Ser Arg
                            405                 410                 415

Trp Gln Gln Gly Asn Val Phe Ser Cys Ser Val Met His Glu Ala Leu
                            420                 425                 430

His Asn His Tyr Thr Gln Lys Ser Leu Ser Leu Ser Pro Gly Ala Gly
                            435                 440                 445

Gly Gly Gly Ser Gly Gly Gly Ser Gly Gly Gly Gly Ser Gly Gly Gly
            450                 455                 460

Gly Gly Ser Ser Asp Thr Gly Arg Pro Phe Val Glu Met Pro Ser Glu
            465                 470                 475                 480

Ile Pro Glu Ile Ile His Met Thr Glu Gly Arg Glu Leu Val Ile Pro
                            485                 490                 495
```

```
Cys Arg Val Thr Ser Pro Glu Ile Thr Val Thr Leu Lys Lys Phe Pro
            500                 505                 510

Leu Asp Thr Leu Ile Pro Asp Gly Lys Arg Ile Ile Trp Asp Ser Arg
            515                 520                 525

Lys Gly Phe Ile Ile Ser Glu Ala Thr Tyr Lys Glu Ile Gly Leu Leu
            530                 535                 540

Thr Cys Glu Ala Thr Val Asn Gly His Leu Tyr Lys Thr Asn Tyr Leu
545                 550                 555                 560

Thr His Arg Gln Thr Asn Thr Ile Ile Asp Val Val Leu Ser Pro Ser
                565                 570                 575

His Gly Ile Glu Leu Ser Val Gly Glu Lys Leu Val Leu Glu Cys Thr
            580                 585                 590

Ala Arg Thr Glu Leu Asn Val Gly Ile Asp Phe Asn Trp Glu Tyr Pro
            595                 600                 605

Ser Ser Lys His Gln His Lys Lys Leu Val Asn Arg Asp Leu Lys Thr
            610                 615                 620

Gln Ser Gly Ser Glu Met Lys Lys Phe Leu Ser Thr Leu Thr Ile Asp
625                 630                 635                 640

Gly Val Thr Arg Ser Asp Gln Gly Leu Tyr Thr Cys Ala Ala Ser Ser
                645                 650                 655

Gly Leu Met Thr Lys Lys Glu Ser Thr Phe Val Arg Val His Glu Lys
            660                 665                 670
```

<210> SEQ ID NO 221
<211> LENGTH: 214
<212> TYPE: PRT
<213> ORGANISM: Artificial Sequence
<220> FEATURE:
<223> OTHER INFORMATION: Synthetic

<400> SEQUENCE: 221

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 222
<211> LENGTH: 672
<212> TYPE: PRT
<213> ORGANISM: Artificial Sequence
<220> FEATURE:
<223> OTHER INFORMATION: Synthetic

<400> SEQUENCE: 222

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
50                  55                  60

Lys Gly Arg Val Thr Leu Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Ala Gly
                435                 440                 445

Gly Gly Gly Ser Gly Gly Gly Gly Ser Gly Gly Gly Gly Ser Gly Gly
            450                 455                 460

Gly Gly Ser Ser Asp Thr Gly Arg Pro Phe Val Glu Met Pro Ser Glu
465                 470                 475                 480

Ile Pro Glu Ile Ile His Met Thr Glu Gly Arg Glu Leu Val Ile Pro
                485                 490                 495

Cys Arg Val Thr Ser Pro Glu Ile Thr Val Thr Leu Lys Lys Phe Pro
            500                 505                 510

Leu Asp Thr Leu Ile Pro Asp Gly Lys Arg Ile Ile Trp Asp Ser Arg
            515                 520                 525

Lys Gly Phe Ile Ile Ser Glu Ala Thr Tyr Lys Glu Ile Gly Leu Leu
            530                 535                 540

Thr Cys Glu Ala Thr Val Asn Gly His Leu Tyr Lys Thr Asn Tyr Leu
545                 550                 555                 560

Thr His Arg Gln Thr Asn Thr Ile Ile Asp Val Val Leu Ser Pro Ser
                565                 570                 575

His Gly Ile Glu Leu Ser Val Gly Glu Lys Leu Val Leu Glu Cys Thr
            580                 585                 590

Ala Arg Thr Glu Leu Asn Val Gly Ile Asp Phe Asn Trp Glu Tyr Pro
            595                 600                 605

Ser Ser Lys His Gln His Lys Lys Leu Val Asn Arg Asp Leu Lys Thr
            610                 615                 620

Gln Ser Gly Ser Glu Met Lys Lys Phe Leu Ser Thr Leu Thr Ile Asp
625                 630                 635                 640

Gly Val Thr Arg Ser Asp Gln Gly Leu Tyr Thr Cys Ala Ala Ser Ser
                645                 650                 655

Gly Leu Met Thr Lys Lys Glu Ser Thr Phe Val Arg Val His Glu Lys
            660                 665                 670

<210> SEQ ID NO 223
<211> LENGTH: 214
<212> TYPE: PRT
<213> ORGANISM: Artificial Sequence
<220> FEATURE:
<223> OTHER INFORMATION: Synthetic

<400> SEQUENCE: 223

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

```
Val Ala Trp Tyr Gln Gln Lys Pro Gly Lys Ala Pro Lys Ala Leu Ile
         35                  40                  45

Tyr Ser Ala Ser Tyr Arg Tyr Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 224
<211> LENGTH: 671
<212> TYPE: PRT
<213> ORGANISM: Artificial Sequence
<220> FEATURE:
<223> OTHER INFORMATION: Synthetic

<400> SEQUENCE: 224

Ser Asp Thr Gly Arg Pro Phe Val Glu Met Pro Ser Glu Ile Pro Glu
 1               5                  10                  15

Ile Ile His Met Thr Glu Gly Arg Glu Leu Val Ile Pro Cys Arg Val
                 20                  25                  30

Thr Ser Pro Glu Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Glu Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Glu Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

```
Arg Ser Asp Gln Gly Leu Tyr Thr Cys Ala Ala Ser Ser Gly Leu Met
            180                 185                 190

Thr Lys Lys Glu Ser Thr Phe Val Arg Val His Glu Lys Gly Gly Gly
        195                 200                 205

Gly Ser Gly Gly Gly Gly Ser Gly Gly Gly Ser Gln Val Gln Leu
    210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Ser Tyr Trp Met His Trp
                245                 250                 255

Val Arg Gln Ala Pro Gly Gln Gly Leu Glu Trp Met Gly Met Ile His
            260                 265                 270

Pro Asn Ser Gly Gly Asn Asn Tyr Asn Glu Lys Phe Lys Ser Arg Val
        275                 280                 285

Thr Met Thr Arg Asp Thr Ser Ile Ser Thr Ala Tyr Met Glu Leu Ser
    290                 295                 300

Arg Leu Arg Ser Asp Asp Thr Ala Val Tyr Tyr Cys Ala Arg Ser Trp
305                 310                 315                 320

Tyr Gly Ser Ser Pro Tyr Tyr Phe Asp Tyr Trp Gly Gln Gly Thr Leu
                325                 330                 335

Val Thr Val Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Leu Leu Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Asp Glu Leu Thr Lys Asn Gln Val Ser Leu Thr Cys Leu
            580                 585                 590
```

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
        610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 225
<211> LENGTH: 214
<212> TYPE: PRT
<213> ORGANISM: Artificial Sequence
<220> FEATURE:
<223> OTHER INFORMATION: Synthetic

<400> SEQUENCE: 225

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 226
<211> LENGTH: 123
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120

<210> SEQ ID NO 227
<211> LENGTH: 107
<212> TYPE: PRT
<213> ORGANISM: Artificial Sequence
<220> FEATURE:
<223> OTHER INFORMATION: Synthetic

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 228
<211> LENGTH: 123
<212> TYPE: PRT
<213> ORGANISM: Artificial Sequence
<220> FEATURE:
<223> OTHER INFORMATION: Synthetic

<400> SEQUENCE: 228

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys

```
                      85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120
```

<210> SEQ ID NO 229
<211> LENGTH: 214
<212> TYPE: PRT
<213> ORGANISM: Artificial Sequence
<220> FEATURE:
<223> OTHER INFORMATION: Synthetic

<400> SEQUENCE: 229

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 230
<211> LENGTH: 628
<212> TYPE: PRT
<213> ORGANISM: Artificial Sequence
<220> FEATURE:
<223> OTHER INFORMATION: Synthetic

<400> SEQUENCE: 230

```
Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45
```

-continued

```
Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Gly Gly Gln Glu
        355                 360                 365

Glu Cys Glu Trp Asp Pro Trp Thr Cys Glu His Met Gly Gly Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Ala Gly Gly Gly Gly Ser Gly Gly Gly Gly
```

```
                465                 470                 475                 480
Ser Gly Gly Gly Gly Ser Gly Gly Gly Ser Gly Ile Pro Pro His
                    485                 490                 495

Val Gln Lys Ser Val Asn Asn Asp Met Ile Val Thr Asp Asn Asn Gly
                500                 505                 510

Ala Val Lys Phe Pro Gln Leu Cys Lys Phe Cys Asp Val Arg Phe Ser
                515                 520                 525

Thr Cys Asp Asn Gln Lys Ser Cys Met Ser Asn Cys Ser Ile Thr Ser
            530                 535                 540

Ile Cys Glu Lys Pro Gln Glu Val Cys Val Ala Val Trp Arg Lys Asn
545                 550                 555                 560

Asp Glu Asn Ile Thr Leu Glu Thr Val Cys His Asp Pro Lys Leu Pro
                    565                 570                 575

Tyr His Asp Phe Ile Leu Glu Asp Ala Ala Ser Pro Lys Cys Ile Met
                580                 585                 590

Lys Glu Lys Lys Lys Pro Gly Glu Thr Phe Phe Met Cys Ser Cys Ser
            595                 600                 605

Ser Asp Glu Cys Asn Asp Asn Ile Ile Phe Ser Glu Glu Tyr Asn Thr
    610                 615                 620

Ser Asn Pro Asp
625

<210> SEQ ID NO 231
<211> LENGTH: 685
<212> TYPE: PRT
<213> ORGANISM: Artificial Sequence
<220> FEATURE:
<223> OTHER INFORMATION: Synthetic

<400> SEQUENCE: 231

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Tyr Ile Tyr Trp Val Arg Gln Ala Pro Gly Gln Gly Leu Glu Trp Met
            35                  40                  45

Gly Gly Ile Asn Pro Gly Asn Gly Gly Thr Asn Phe Asn Glu Lys Phe
    50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
```

```
                195                 200                 205
Pro Ser Asn Thr Lys Val Asp Lys Arg Val Glu Ser Lys Tyr Gly Pro
210                 215                 220

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Gly Gly Gln Glu Cys Glu Trp Asp Pro
                355                 360                 365

Trp Thr Cys Glu His Met Gly Gly Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
450                 455                 460

Lys Gly Gly Gly Gly Ser Gly Gly Gly Gly Ser Gly Gly Gly Gly Ser
465                 470                 475                 480

Ser Asp Thr Gly Arg Pro Phe Val Glu Met Tyr Ser Glu Ile Pro Glu
                485                 490                 495

Ile Ile His Met Thr Glu Gly Arg Glu Leu Val Ile Pro Cys Arg Val
                500                 505                 510

Thr Ser Pro Asn Ile Thr Val Thr Leu Lys Lys Phe Pro Leu Asp Thr
                515                 520                 525

Leu Ile Pro Asp Gly Lys Arg Ile Ile Trp Asp Ser Arg Lys Gly Phe
                530                 535                 540

Ile Ile Ser Asn Ala Thr Tyr Lys Glu Ile Gly Leu Leu Thr Cys Glu
545                 550                 555                 560

Ala Thr Val Asn Gly His Leu Tyr Lys Thr Asn Tyr Leu Thr His Arg
                565                 570                 575

Gln Thr Asn Thr Ile Ile Asp Val Val Leu Ser Pro Ser His Gly Ile
                580                 585                 590

Glu Leu Ser Val Gly Glu Lys Leu Val Leu Asn Cys Thr Ala Arg Thr
                595                 600                 605

Glu Leu Asn Val Gly Ile Asp Phe Asn Trp Glu Tyr Pro Ser Ser Lys
610                 615                 620
```

His Gln His Lys Lys Leu Val Asn Arg Asp Leu Lys Thr Gln Ser Gly
625                 630                 635                 640

Ser Glu Met Lys Lys Phe Leu Ser Thr Leu Thr Ile Asp Gly Val Thr
                645                 650                 655

Arg Ser Asp Gln Gly Leu Tyr Thr Cys Ala Ala Ser Ser Gly Leu Met
            660                 665                 670

Thr Lys Lys Asn Ser Thr Phe Val Arg Val His Glu Lys
        675                 680                 685

<210> SEQ ID NO 232
<211> LENGTH: 218
<212> TYPE: PRT
<213> ORGANISM: Artificial Sequence
<220> FEATURE:
<223> OTHER INFORMATION: Synthetic

<400> SEQUENCE: 232

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 233
<211> LENGTH: 723
<212> TYPE: PRT
<213> ORGANISM: Artificial Sequence
<220> FEATURE:
<223> OTHER INFORMATION: Synthetic

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr

```
            20                  25                  30
Tyr Ile Tyr Trp Val Arg Gln Ala Pro Gly Gln Gly Leu Glu Trp Met
             35                  40                  45
Gly Gly Ile Asn Pro Asn Gly Gly Thr Asn Phe Asn Glu Lys Phe
     50                  55                  60
Lys Ile Arg Val Thr Met Thr Arg Asp Thr Ser Ile Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Arg Tyr His Gly Tyr Asp Gly Gly Leu Asp Tyr Trp Gly Gln
                100                 105                 110
Gly Thr Leu Val Thr Val Ser Ser Ala Ser Thr Lys Gly Pro Ser Val
             115                 120                 125
Phe Pro Leu Ala Pro Cys Ser Arg Ser Thr Ser Glu Ser Thr Ala Ala
             130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Lys Thr Tyr Thr Cys Asn Val Asp His Lys
             195                 200                 205
Pro Ser Asn Thr Lys Val Asp Lys Arg Val Glu Ser Lys Tyr Gly Pro
         210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                 245                 250                 255
Pro Glu Val Thr Cys Val Val Val Asp Val Ser Gln Glu Asp Pro Glu
             260                 265                 270
Val Gln Phe Asn Trp Tyr Val Asp Gly Val Glu Val His Asn Ala Lys
         275                 280                 285
Thr Lys Pro Arg Glu Glu Gln Phe Asn Ser Thr Tyr Arg Val Val Ser
     290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                 325                 330                 335
Ser Lys Ala Lys Gly Gln Pro Arg Glu Pro Gln Val Tyr Thr Leu Pro
             340                 345                 350
Pro Ser Gln Glu Glu Met Gly Gly Ala Gln Glu Cys Glu Trp
             355                 360                 365
Asp Pro Trp Thr Cys Glu His Met Gly Ser Gly Ser Ala Thr Gly Gly
         370                 375                 380
Ser Gly Ser Thr Ala Ser Ser Gly Ser Gly Ser Ala Thr His Gln Glu
385                 390                 395                 400
Glu Cys Glu Trp Asp Pro Trp Thr Cys Glu His Met Gly Gly Thr Lys
                 405                 410                 415
Asn Gln Val Ser Leu Thr Cys Leu Val Lys Gly Phe Tyr Pro Ser Asp
             420                 425                 430
Ile Ala Val Glu Trp Glu Ser Asn Gly Gln Pro Glu Asn Asn Tyr Lys
             435                 440                 445
```

```
Thr Thr Pro Pro Val Leu Asp Ser Asp Gly Ser Phe Phe Leu Tyr Ser
            450                 455                 460

Arg Leu Thr Val Asp Lys Ser Arg Trp Gln Glu Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Leu Gly Lys Gly Gly Gly Ser Gly Gly Gly Gly
                500                 505                 510

Ser Gly Gly Gly Ser Ser Asp Thr Gly Arg Pro Phe Val Glu Met
            515                 520                 525

Tyr Ser Glu Ile Pro Glu Ile Ile His Met Thr Glu Gly Arg Glu Leu
            530                 535                 540

Val Ile Pro Cys Arg Val Thr Ser Pro Asn Ile Thr Val Thr Leu Lys
545                 550                 555                 560

Lys Phe Pro Leu Asp Thr Leu Ile Pro Asp Gly Lys Arg Ile Ile Trp
                565                 570                 575

Asp Ser Arg Lys Gly Phe Ile Ile Ser Asn Ala Thr Tyr Lys Glu Ile
                580                 585                 590

Gly Leu Leu Thr Cys Glu Ala Thr Val Asn Gly His Leu Tyr Lys Thr
            595                 600                 605

Asn Tyr Leu Thr His Arg Gln Thr Asn Thr Ile Ile Asp Val Val Leu
            610                 615                 620

Ser Pro Ser His Gly Ile Glu Leu Ser Val Gly Glu Lys Leu Val Leu
625                 630                 635                 640

Asn Cys Thr Ala Arg Thr Glu Leu Asn Val Gly Ile Asp Phe Asn Trp
                645                 650                 655

Glu Tyr Pro Ser Ser Lys His Gln His Lys Lys Leu Val Asn Arg Asp
                660                 665                 670

Leu Lys Thr Gln Ser Gly Ser Glu Met Lys Lys Phe Leu Ser Thr Leu
            675                 680                 685

Thr Ile Asp Gly Val Thr Arg Ser Asp Gln Gly Leu Tyr Thr Cys Ala
            690                 695                 700

Ala Ser Ser Gly Leu Met Thr Lys Lys Asn Ser Thr Phe Val Arg Val
705                 710                 715                 720

His Glu Lys

<210> SEQ ID NO 234
<211> LENGTH: 667
<212> TYPE: PRT
<213> ORGANISM: Artificial Sequence
<220> FEATURE:
<223> OTHER INFORMATION: Synthetic

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Tyr Ile Tyr Trp Val Arg Gln Ala Pro Gly Gln Cys Leu Glu Trp Met
            35                  40                  45

Gly Gly Ile Asn Pro Gly Asn Gly Gly Thr Asn Phe Asn Glu Lys Phe
        50                  55                  60

Lys Ile Arg Val Thr Met Thr Arg Asp Thr Ser Ile Ser Thr Ala Tyr
65                  70                  75                  80
```

```
Met Glu Leu Ser Ser Leu Arg Ser Glu Asp Thr Ala Val Tyr Tyr Cys
                85                  90                  95
Ala Arg Arg Tyr His Gly Tyr Asp Gly Leu Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys Gly
            435                 440                 445
Gly Gly Gly Ser Gly Gly Gly Ser Gly Gly Gly Ser Ser Asp
450                 455                 460
Thr Gly Arg Pro Phe Val Glu Met Tyr Ser Glu Ile Pro Glu Ile Ile
465                 470                 475                 480
His Met Thr Glu Gly Arg Glu Leu Val Ile Pro Cys Arg Val Thr Ser
                485                 490                 495
Pro Asn Ile Thr Val Thr Leu Lys Lys Phe Pro Leu Asp Thr Leu Ile
```

```
                500             505             510
Pro Asp Gly Lys Arg Ile Ile Trp Asp Ser Arg Lys Gly Phe Ile Ile
            515                 520             525

Ser Asn Ala Thr Tyr Lys Glu Ile Gly Leu Leu Thr Cys Glu Ala Thr
            530                 535             540

Val Asn Gly His Leu Tyr Lys Thr Asn Tyr Leu Thr His Arg Gln Thr
545             550                 555                 560

Asn Thr Ile Ile Asp Val Val Leu Ser Pro Ser His Gly Ile Glu Leu
            565                 570             575

Ser Val Gly Glu Lys Leu Val Leu Asn Cys Thr Ala Arg Thr Glu Leu
            580                 585             590

Asn Val Gly Ile Asp Phe Asn Trp Glu Tyr Pro Ser Ser Lys His Gln
            595                 600             605

His Lys Lys Leu Val Asn Arg Asp Leu Lys Thr Gln Ser Gly Ser Glu
            610                 615             620

Met Lys Lys Phe Leu Ser Thr Leu Thr Ile Asp Gly Val Thr Arg Ser
625             630                 635                 640

Asp Gln Gly Leu Tyr Thr Cys Ala Ala Ser Ser Gly Leu Met Thr Lys
            645                 650             655

Lys Asn Ser Thr Phe Val Arg Val His Glu Lys
            660                 665
```

<210> SEQ ID NO 235
<211> LENGTH: 277
<212> TYPE: PRT
<213> ORGANISM: Artificial Sequence
<220> FEATURE:
<223> OTHER INFORMATION: Synthetic

<400> SEQUENCE: 235

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Cys Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
```

```
                195                 200                 205
Val Thr Lys Ser Phe Asn Arg Gly Glu Cys Gly Gly Gly Gly Ala
    210                 215                 220

Gln Gln Glu Glu Cys Glu Trp Asp Pro Trp Thr Cys Glu His Met Gly
225                 230                 235                 240

Ser Gly Ser Ala Thr Gly Gly Ser Gly Ser Thr Ala Ser Ser Gly Ser
                245                 250                 255

Gly Ser Ala Thr His Gln Glu Glu Cys Glu Trp Asp Pro Trp Thr Cys
            260                 265                 270

Glu His Met Leu Glu
            275

<210> SEQ ID NO 236
<211> LENGTH: 726
<212> TYPE: PRT
<213> ORGANISM: Artificial Sequence
<220> FEATURE:
<223> OTHER INFORMATION: Synthetic

<400> SEQUENCE: 236

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Gly Gly Gly Ser Gln Val Gln Leu
    210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Thr Tyr Ile Tyr Trp
                245                 250                 255

Val Arg Gln Ala Pro Gly Gln Gly Leu Glu Trp Met Gly Gly Ile Asn
            260                 265                 270

Pro Gly Asn Gly Gly Thr Asn Phe Asn Glu Lys Phe Lys Ile Arg Val
```

```
              275                 280                 285
Thr Met Thr Arg Asp Thr Ser Ile Ser Thr Ala Tyr Met Glu Leu Ser
    290                 295                 300
Ser Leu Arg Ser Glu Asp Thr Ala Val Tyr Tyr Cys Ala Arg Arg Tyr
305                 310                 315                 320
His Gly Tyr Asp Gly Gly Leu Asp Tyr Trp Gly Gln Gly Thr Leu Val
                    325                 330                 335
Thr Val Ser Ser Ala Ser Thr Lys Gly Pro Ser Val Phe Pro Leu Ala
                340                 345                 350
Pro Cys Ser Arg Ser Thr Ser Glu Ser Thr Ala Ala Leu Gly Cys Leu
            355                 360                 365
Val Lys Asp Tyr Phe Pro Glu Pro Val Thr Val Ser Trp Asn Ser Gly
        370                 375                 380
Ala Leu Thr Ser Gly Val His Thr Phe Pro Ala Val Leu Gln Ser Ser
385                 390                 395                 400
Gly Leu Tyr Ser Leu Ser Ser Val Val Thr Val Pro Ser Ser Ser Leu
                    405                 410                 415
Gly Thr Lys Thr Tyr Thr Cys Asn Val Asp His Lys Pro Ser Asn Thr
                420                 425                 430
Lys Val Asp Lys Arg Val Glu Ser Lys Tyr Gly Pro Pro Cys Pro Pro
            435                 440                 445
Cys Pro Ala Pro Glu Phe Leu Gly Gly Pro Ser Val Phe Leu Phe Pro
        450                 455                 460
Pro Lys Pro Lys Asp Thr Leu Met Ile Ser Arg Thr Pro Glu Val Thr
465                 470                 475                 480
Cys Val Val Val Asp Val Ser Gln Glu Asp Pro Glu Val Gln Phe Asn
                    485                 490                 495
Trp Tyr Val Asp Gly Val Glu Val His Asn Ala Lys Thr Lys Pro Arg
                500                 505                 510
Glu Glu Gln Phe Asn Ser Thr Tyr Arg Val Val Ser Val Leu Thr Val
            515                 520                 525
Leu His Gln Asp Trp Leu Asn Gly Lys Glu Tyr Lys Cys Lys Val Ser
        530                 535                 540
Asn Lys Gly Leu Pro Ser Ser Ile Glu Lys Thr Ile Ser Lys Ala Lys
545                 550                 555                 560
Gly Gln Pro Arg Glu Pro Gln Val Tyr Thr Leu Pro Pro Ser Gln Glu
                    565                 570                 575
Glu Met Thr Lys Asn Gln Val Ser Leu Thr Cys Leu Val Lys Gly Phe
                580                 585                 590
Tyr Pro Ser Asp Ile Ala Val Glu Trp Glu Ser Asn Gly Gln Pro Glu
            595                 600                 605
Asn Asn Tyr Lys Thr Thr Pro Pro Val Leu Asp Ser Asp Gly Ser Phe
        610                 615                 620
Phe Leu Tyr Ser Arg Leu Thr Val Asp Lys Ser Arg Trp Gln Glu Gly
625                 630                 635                 640
Asn Val Phe Ser Cys Ser Val Met His Glu Ala Leu His Asn His Tyr
                    645                 650                 655
Thr Gln Lys Ser Leu Ser Leu Ser Leu Gly Lys Gly Gly Gly Gly Gly
                660                 665                 670
Ala Gln Gln Glu Glu Cys Glu Trp Asp Pro Trp Thr Cys Glu His Met
            675                 680                 685
Gly Ser Gly Ser Ala Thr Gly Gly Ser Gly Ser Thr Ala Ser Ser Gly
        690                 695                 700
```

Ser Gly Ser Ala Thr His Gln Glu Glu Cys Glu Trp Asp Pro Trp Thr
705                 710                 715                 720

Cys Glu His Met Leu Glu
            725

<210> SEQ ID NO 237
<211> LENGTH: 438
<212> TYPE: PRT
<213> ORGANISM: Artificial Sequence
<220> FEATURE:
<223> OTHER INFORMATION: Synthetic

<400> SEQUENCE: 237

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
    115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
    195                 200                 205

Gly Ser Gly Gly Gly Gly Ser Gly Gly Gly Gly Ser Asp Ile Val Leu
210                 215                 220

Thr Gln Ser Pro Ala Ser Leu Ala Val Ser Pro Gly Gln Arg Ala Thr
225                 230                 235                 240

Ile Thr Cys Arg Ala Ser Lys Ser Val Ser Thr Ser Gly Phe Ser Tyr
                245                 250                 255

Ile His Trp Tyr Gln Gln Lys Pro Gly Gln Pro Pro Lys Leu Leu Ile
            260                 265                 270

Tyr Leu Ala Ser Asn Leu Glu Ser Gly Val Pro Ala Arg Phe Ser Gly
    275                 280                 285

Ser Gly Ser Gly Thr Asp Phe Thr Leu Thr Ile Asn Pro Val Glu Ala
290                 295                 300

Asn Asp Thr Ala Asn Tyr Tyr Cys Gln His Thr Trp Glu Leu Pro Asn
305                 310                 315                 320

Thr Phe Gly Gly Gly Thr Lys Val Glu Ile Lys Arg Thr Val Ala Ala
                325                 330                 335

Pro Ser Val Phe Ile Phe Pro Pro Ser Asp Glu Gln Leu Lys Ser Gly
            340                 345                 350

Thr Ala Ser Val Val Cys Leu Leu Asn Asn Phe Tyr Pro Arg Glu Ala
        355                 360                 365

Lys Val Gln Trp Lys Val Asp Asn Ala Leu Gln Ser Gly Asn Ser Gln
    370                 375                 380

Glu Ser Val Thr Glu Gln Asp Ser Lys Asp Ser Thr Tyr Ser Leu Ser
385                 390                 395                 400

Ser Thr Leu Thr Leu Ser Lys Ala Asp Tyr Glu Lys His Lys Val Tyr
                405                 410                 415

Ala Cys Glu Val Thr His Gln Gly Leu Ser Ser Pro Val Thr Lys Ser
            420                 425                 430

Phe Asn Arg Gly Glu Cys
            435

<210> SEQ ID NO 238
<211> LENGTH: 726
<212> TYPE: PRT
<213> ORGANISM: Artificial Sequence
<220> FEATURE:
<223> OTHER INFORMATION: Synthetic

<400> SEQUENCE: 238

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Gly Gly Gly Gly Ser Gln Val Gln Leu
    210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Thr Tyr Tyr Ile Tyr Trp
                245                 250                 255

```
Val Arg Gln Ala Pro Gly Gln Gly Leu Glu Trp Met Gly Gly Ile Asn
            260                 265                 270

Pro Gly Asn Gly Gly Thr Asn Phe Asn Glu Lys Phe Lys Ile Arg Val
            275                 280                 285

Thr Met Thr Arg Asp Thr Ser Ile Ser Thr Ala Tyr Met Glu Leu Ser
290                 295                 300

Ser Leu Arg Ser Glu Asp Thr Ala Val Tyr Tyr Cys Ala Arg Arg Tyr
305                 310                 315                 320

His Gly Tyr Asp Gly Gly Leu Asp Tyr Trp Gly Gln Gly Thr Leu Val
                325                 330                 335

Thr Val Ser Ser Ala Ser Thr Lys Gly Pro Ser Val Phe Pro Leu Ala
            340                 345                 350

Pro Cys Ser Arg Ser Thr Ser Glu Ser Thr Ala Ala Leu Gly Cys Leu
            355                 360                 365

Val Lys Asp Tyr Phe Pro Glu Pro Val Thr Val Ser Trp Asn Ser Gly
    370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
                405                 410                 415

Gly Thr Lys Thr Tyr Thr Cys Asn Val Asp His Lys Pro Ser Asn Thr
            420                 425                 430

Lys Val Asp Lys Arg Val Glu Ser Lys Tyr Gly Pro Pro Cys Pro Pro
            435                 440                 445

Cys Pro Ala Pro Glu Phe Leu Gly Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
            515                 520                 525

Leu His Gln Asp Trp Leu Asn Gly Lys Glu Tyr Lys Cys Lys Val Ser
    530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
                565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
    595                 600                 605

Asn Asn Tyr Lys Thr Thr Pro Pro Val Leu Asp Ser Asp Gly Ser Phe
            610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys Gly Gly Gly Gly Gly
            660                 665                 670
```

```
Ala Gln Gln Glu Glu Cys Glu Trp Asp Pro Trp Thr Cys Glu His Met
            675                 680                 685

Gly Ser Gly Ser Ala Thr Gly Gly Ser Gly Ser Thr Ala Ser Ser Gly
    690                 695                 700

Ser Gly Ser Ala Thr His Gln Glu Glu Cys Glu Trp Asp Pro Trp Thr
705                 710                 715                 720

Cys Glu His Met Leu Glu
                725
```

```
<210> SEQ ID NO 239
<211> LENGTH: 218
<212> TYPE: PRT
<213> ORGANISM: Artificial Sequence
<220> FEATURE:
<223> OTHER INFORMATION: Synthetic

<400> SEQUENCE: 239

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 240
<211> LENGTH: 506
<212> TYPE: PRT
<213> ORGANISM: Artificial Sequence
<220> FEATURE:
<223> OTHER INFORMATION: Synthetic

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30
```

Tyr Ile Tyr Trp Val Arg Gln Ala Pro Gly Gln Gly Leu Glu Trp Met
            35                  40                  45

Gly Gly Ile Asn Pro Gly Asn Gly Gly Thr Asn Phe Asn Glu Lys Phe
        50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Leu Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
            435                 440                 445

```
Gly Gly Gly Gly Ala Gln Gln Glu Glu Cys Glu Trp Asp Pro Trp Thr
            450                 455                 460
Cys Glu His Met Gly Ser Gly Ser Ala Thr Gly Gly Ser Gly Ser Thr
465                 470                 475                 480
Ala Ser Ser Gly Ser Gly Ser Ala Thr His Gln Glu Glu Cys Glu Trp
            485                 490                 495
Asp Pro Trp Thr Cys Glu His Met Leu Glu
            500                 505
```

<210> SEQ ID NO 241
<211> LENGTH: 438
<212> TYPE: PRT
<213> ORGANISM: Artificial Sequence
<220> FEATURE:
<223> OTHER INFORMATION: Synthetic

<400> SEQUENCE: 241

```
Ser Asp Thr Gly Arg Pro Phe Val Glu Met Tyr Ser Glu Ile Pro Glu
1               5                   10                  15
Ile Ile His Met Thr Glu Gly Arg Glu Leu Val Ile Pro Cys Arg Val
                20                  25                  30
Thr Ser Pro Asn Ile Thr Val Thr Leu Lys Lys Phe Pro Leu Asp Thr
            35                  40                  45
Leu Ile Pro Asp Gly Lys Arg Ile Ile Trp Asp Ser Arg Lys Gly Phe
50                  55                  60
Ile Ile Ser Asn Ala Thr Tyr Lys Glu Ile Gly Leu Leu Thr Cys Glu
65                  70                  75                  80
Ala Thr Val Asn Gly His Leu Tyr Lys Thr Asn Tyr Leu Thr His Arg
                85                  90                  95
Gln Thr Asn Thr Ile Ile Asp Val Val Leu Ser Pro Ser His Gly Ile
            100                 105                 110
Glu Leu Ser Val Gly Glu Lys Leu Val Leu Asn Cys Thr Ala Arg Thr
        115                 120                 125
Glu Leu Asn Val Gly Ile Asp Phe Asn Trp Glu Tyr Pro Ser Ser Lys
130                 135                 140
His Gln His Lys Lys Leu Val Asn Arg Asp Leu Lys Thr Gln Ser Gly
145                 150                 155                 160
Ser Glu Met Lys Lys Phe Leu Ser Thr Leu Thr Ile Asp Gly Val Thr
                165                 170                 175
Arg Ser Asp Gln Gly Leu Tyr Thr Cys Ala Ala Ser Ser Gly Leu Met
            180                 185                 190
Thr Lys Lys Asn Ser Thr Phe Val Arg Val His Glu Lys Gly Gly Gly
        195                 200                 205
Gly Ser Gly Gly Gly Gly Ser Gly Gly Gly Gly Ser Asp Ile Val Leu
210                 215                 220
Thr Gln Ser Pro Ala Ser Leu Ala Val Ser Pro Gly Gln Arg Ala Thr
225                 230                 235                 240
Ile Thr Cys Arg Ala Ser Lys Ser Val Ser Thr Ser Gly Phe Ser Tyr
                245                 250                 255
Ile His Trp Tyr Gln Gln Lys Pro Gly Gln Pro Pro Lys Leu Leu Ile
            260                 265                 270
Tyr Leu Ala Ser Asn Leu Glu Ser Gly Val Pro Ala Arg Phe Ser Gly
        275                 280                 285
Ser Gly Ser Gly Thr Asp Phe Thr Leu Thr Ile Asn Pro Val Glu Ala
290                 295                 300
```

Asn Asp Thr Ala Asn Tyr Tyr Cys Gln His Thr Trp Glu Leu Pro Asn
305                 310                 315                 320

Thr Phe Gly Gly Gly Thr Lys Val Glu Ile Lys Arg Thr Val Ala Ala
            325                 330                 335

Pro Ser Val Phe Ile Phe Pro Pro Ser Asp Glu Gln Leu Lys Ser Gly
            340                 345                 350

Thr Ala Ser Val Val Cys Leu Leu Asn Asn Phe Tyr Pro Arg Glu Ala
            355                 360                 365

Lys Val Gln Trp Lys Val Asp Asn Ala Leu Gln Ser Gly Asn Ser Gln
            370                 375                 380

Glu Ser Val Thr Glu Gln Asp Ser Lys Asp Ser Thr Tyr Ser Leu Ser
385                 390                 395                 400

Ser Thr Leu Thr Leu Ser Lys Ala Asp Tyr Glu Lys His Lys Val Tyr
            405                 410                 415

Ala Cys Glu Val Thr His Gln Gly Leu Ser Ser Pro Val Thr Lys Ser
            420                 425                 430

Phe Asn Arg Gly Glu Cys
            435

<210> SEQ ID NO 242
<211> LENGTH: 726
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
            35                  40                  45

Gly Gly Ile Asn Pro Gly Asn Gly Gly Thr Asn Phe Asn Glu Lys Phe
        50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Tyr His Gly Tyr Asp Gly Gly Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

-continued

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys Gly
    435                 440                 445

Gly Gly Gly Gly Ala Gln Gln Glu Glu Cys Glu Trp Asp Pro Trp Thr
450                 455                 460

Cys Glu His Met Gly Ser Gly Ser Ala Thr Gly Gly Ser Gly Ser Thr
465                 470                 475                 480

Ala Ser Ser Gly Ser Gly Ser Ala Thr His Gln Glu Glu Cys Glu Trp
            485                 490                 495

Asp Pro Trp Thr Cys Glu His Met Leu Glu Gly Gly Gly Gly Ser Gly
        500                 505                 510

Gly Gly Gly Ser Gly Gly Gly Ser Ser Asp Thr Gly Arg Pro Phe
    515                 520                 525

Val Glu Met Tyr Ser Glu Ile Pro Glu Ile Ile His Met Thr Glu Gly
530                 535                 540

Arg Glu Leu Val Ile Pro Cys Arg Val Thr Ser Pro Asn Ile Thr Val
545                 550                 555                 560

Thr Leu Lys Lys Phe Pro Leu Asp Thr Leu Ile Pro Asp Gly Lys Arg
            565                 570                 575

Ile Ile Trp Asp Ser Arg Lys Gly Phe Ile Ile Ser Asn Ala Thr Tyr
        580                 585                 590

Lys Glu Ile Gly Leu Leu Thr Cys Glu Ala Thr Val Asn Gly His Leu
    595                 600                 605

Tyr Lys Thr Asn Tyr Leu Thr His Arg Gln Thr Asn Thr Ile Ile Asp
    610                 615                 620

Val Val Leu Ser Pro Ser His Gly Ile Glu Leu Ser Val Gly Glu Lys
625                 630                 635                 640

Leu Val Leu Asn Cys Thr Ala Arg Thr Glu Leu Asn Val Gly Ile Asp

```
                        645                 650                 655

Phe Asn Trp Glu Tyr Pro Ser Ser Lys His Gln His Lys Lys Leu Val
                660                 665                 670

Asn Arg Asp Leu Lys Thr Gln Ser Gly Ser Glu Met Lys Lys Phe Leu
            675                 680                 685

Ser Thr Leu Thr Ile Asp Gly Val Thr Arg Ser Asp Gln Gly Leu Tyr
    690                 695                 700

Thr Cys Ala Ala Ser Ser Gly Leu Met Thr Lys Lys Asn Ser Thr Phe
705                 710                 715                 720

Val Arg Val His Glu Lys
                725

<210> SEQ ID NO 243
<211> LENGTH: 218
<212> TYPE: PRT
<213> ORGANISM: Artificial Sequence
<220> FEATURE:
<223> OTHER INFORMATION: Synthetic

<400> SEQUENCE: 243

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 244
<211> LENGTH: 218
<212> TYPE: PRT
<213> ORGANISM: Artificial Sequence
<220> FEATURE:
<223> OTHER INFORMATION: Synthetic

<400> SEQUENCE: 244
```

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 245
<211> LENGTH: 440
<212> TYPE: PRT
<213> ORGANISM: Artificial Sequence
<220> FEATURE:
<223> OTHER INFORMATION: Synthetic

<400> SEQUENCE: 245

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
    130                 135                 140
```

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 246
<211> LENGTH: 214
<212> TYPE: PRT
<213> ORGANISM: Artificial Sequence
<220> FEATURE:
<223> OTHER INFORMATION: Synthetic

<400> SEQUENCE: 246

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 247
<211> LENGTH: 622
<212> TYPE: PRT
<213> ORGANISM: Artificial Sequence
<220> FEATURE:
<223> OTHER INFORMATION: Synthetic

<400> SEQUENCE: 247

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Glu Val Gln Leu Val Glu Ser Gly Gly Leu Val Gln Pro Gly
            115                 120                 125

Gly Ser Leu Arg Leu Ser Cys Ala Ala Ser Gly Tyr Thr Phe Thr Asn
130                 135                 140

Tyr Gly Met Asn Trp Val Arg Gln Ala Pro Gly Lys Gly Leu Glu Trp
145                 150                 155                 160

Val Gly Trp Ile Asn Thr Tyr Thr Gly Glu Pro Thr Tyr Ala Ala Asp
                165                 170                 175

Phe Lys Arg Arg Phe Thr Phe Ser Leu Asp Thr Ser Lys Ser Thr Ala
            180                 185                 190

Tyr Leu Gln Met Asn Ser Leu Arg Ala Glu Asp Thr Ala Val Tyr Tyr
            195                 200                 205
```

```
Cys Ala Lys Tyr Pro His Tyr Tyr Gly Ser Ser His Trp Tyr Phe Asp
    210                 215                 220

Val Trp Gly Gln Gly Thr Leu Val Thr Val Ser Ser Ala Ser Thr Lys
225                 230                 235                 240

Gly Pro Ser Val Phe Pro Leu Ala Pro Cys Ser Arg Ser Thr Ser Glu
                245                 250                 255

Ser Thr Ala Ala Leu Gly Cys Leu Val Lys Asp Tyr Phe Pro Glu Pro
            260                 265                 270

Val Thr Val Ser Trp Asn Ser Gly Ala Leu Thr Ser Gly Val His Thr
                275                 280                 285

Phe Pro Ala Val Leu Gln Ser Ser Gly Leu Tyr Ser Leu Ser Ser Val
290                 295                 300

Val Thr Val Pro Ser Ser Ser Leu Gly Thr Lys Thr Tyr Thr Cys Asn
305                 310                 315                 320

Val Asp His Lys Pro Ser Asn Thr Lys Val Asp Lys Arg Val Glu Ser
                325                 330                 335

Lys Tyr Gly Pro Pro Cys Pro Pro Cys Pro Ala Pro Glu Phe Leu Gly
                340                 345                 350

Gly Pro Ser Val Phe Leu Phe Pro Pro Lys Pro Lys Asp Thr Leu Met
                355                 360                 365

Ile Ser Arg Thr Pro Glu Val Thr Cys Val Val Val Asp Val Ser Gln
370                 375                 380

Glu Asp Pro Glu Val Gln Phe Asn Trp Tyr Val Asp Gly Val Glu Val
385                 390                 395                 400

His Asn Ala Lys Thr Lys Pro Arg Glu Glu Gln Phe Asn Ser Thr Tyr
                405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Gly Leu Pro Ser Ser Ile
                435                 440                 445

Glu Lys Thr Ile Ser Lys Ala Lys Gly Gln Pro Arg Glu Pro Gln Val
                450                 455                 460

Tyr Thr Leu Pro Pro Ser Gln Glu Glu Met Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
                500                 505                 510

Val Leu Asp Ser Asp Gly Ser Phe Phe Leu Tyr Ser Arg Leu Thr Val
                515                 520                 525

Asp Lys Ser Arg Trp Gln Glu Gly Asn Val Phe Ser Cys Ser Val Met
                530                 535                 540

His Glu Ala Leu His Asn His Tyr Thr Gln Lys Ser Leu Ser Leu Ser
545                 550                 555                 560

Leu Gly Lys Gly Gly Gly Gly Ala Gln Gln Glu Glu Cys Glu Trp
                565                 570                 575

Asp Pro Trp Thr Cys Glu His Met Gly Ser Gly Ser Ala Thr Gly Gly
                580                 585                 590

Ser Gly Ser Thr Ala Ser Ser Gly Ser Gly Ser Ala Thr His Gln Glu
                595                 600                 605

Glu Cys Glu Trp Asp Pro Trp Thr Cys Glu His Met Leu Glu
                610                 615                 620
```

-continued

<210> SEQ ID NO 248
<211> LENGTH: 333
<212> TYPE: PRT
<213> ORGANISM: Artificial Sequence
<220> FEATURE:
<223> OTHER INFORMATION: Synthetic

<400> SEQUENCE: 248

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Asp Ile Gln Met Thr Gln Ser Pro Ser
        115                 120                 125

Ser Leu Ser Ala Ser Val Gly Asp Arg Val Thr Ile Thr Cys Ser Ala
    130                 135                 140

Ser Gln Asp Ile Ser Asn Tyr Leu Asn Trp Tyr Gln Gln Lys Pro Gly
145                 150                 155                 160

Lys Ala Pro Lys Val Leu Ile Tyr Phe Thr Ser Ser Leu His Ser Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Phe Ala Thr Tyr Tyr Cys Gln
        195                 200                 205

Gln Tyr Ser Thr Val Pro Trp Thr Phe Gly Gln Gly Thr Lys Val Glu
    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 249
<211> LENGTH: 633
<212> TYPE: PRT
<213> ORGANISM: Artificial Sequence
<220> FEATURE:
<223> OTHER INFORMATION: Synthetic

<400> SEQUENCE: 249

| | | | | | | | | | | | | | | |
|---|---|---|---|---|---|---|---|---|---|---|---|---|---|---|
|Asp|Ile|Val|Leu|Thr|Gln|Ser|Pro|Ala|Ser|Leu|Ala|Val|Ser|Pro|Gly
1| | | |5| | | | |10| | | | |15|

Gln Arg Ala Thr Ile Thr Cys Arg Ala Ser Lys Ser Val Ser Thr Ser
                  20                   25                 30

Gly Phe Ser Tyr Ile His Trp Tyr Gln Gln Lys Pro Gly Gln Pro Pro
        35                   40                45

Lys Leu Leu Ile Tyr Leu Ala Ser Asn Leu Glu Ser Gly Val Pro Ala
50                  55                   60

Arg Phe Ser Gly Ser Gly Ser Gly Thr Asp Phe Thr Leu Thr Ile Asn
65                  70              75              80

Pro Val Glu Ala Asn Asp Thr Ala Asn Tyr Tyr Cys Gln His Thr Trp
               85                90              95

Glu Leu Pro Asn Thr Phe Gly Gly Thr Lys Val Glu Ile Lys Arg
             100               105          110

Thr Val Ala Ala Pro Ser Val Phe Ile Phe Pro Pro Glu Val Gln Leu
             115               120              125

Val Glu Ser Gly Gly Gly Leu Val Gln Pro Gly Gly Ser Leu Arg Leu
130                 135              140

Ser Cys Ala Ala Ser Gly Tyr Thr Phe Thr Asn Tyr Gly Met Asn Trp
145                 150              155           160

Val Arg Gln Ala Pro Gly Lys Gly Leu Glu Trp Val Gly Trp Ile Asn
             165               170          175

Thr Tyr Thr Gly Glu Pro Thr Tyr Ala Ala Asp Phe Lys Arg Arg Phe
             180               185          190

Thr Phe Ser Leu Asp Thr Ser Lys Ser Thr Ala Tyr Leu Gln Met Asn
             195               200          205

Ser Leu Arg Ala Glu Asp Thr Ala Val Tyr Tyr Cys Ala Lys Tyr Pro
210                 215              220

His Tyr Tyr Gly Ser Ser His Trp Tyr Phe Asp Val Trp Gly Gln Gly
225                 230              235          240

Thr Leu Val Thr Val Ser Ser Ala Ser Thr Lys Gly Pro Ser Val Phe
             245               250          255

Pro Leu Ala Pro Cys Ser Arg Ser Thr Ser Glu Ser Thr Ala Ala Leu
             260               265          270

Gly Cys Leu Val Lys Asp Tyr Phe Pro Glu Pro Val Thr Val Ser Trp
             275               280          285

Asn Ser Gly Ala Leu Thr Ser Gly Val His Thr Phe Pro Ala Val Leu
290                 295              300

Gln Ser Ser Gly Leu Tyr Ser Leu Ser Ser Val Val Thr Val Pro Ser
305                 310              315          320

Ser Ser Leu Gly Thr Lys Thr Tyr Thr Cys Asn Val Asp His Lys Pro
             325               330          335

Ser Asn Thr Lys Val Asp Lys Arg Val Glu Ser Lys Tyr Gly Pro Pro
             340               345          350

Cys Pro Pro Cys Pro Ala Pro Glu Phe Leu Gly Gly Pro Ser Val Phe
             355               360          365

Leu Phe Pro Pro Lys Pro Lys Asp Thr Leu Met Ile Ser Arg Thr Pro
        370                 375                380

Glu Val Thr Cys Val Val Val Asp Val Ser Gln Glu Asp Pro Glu Val
385                 390              395          400

Gln Phe Asn Trp Tyr Val Asp Gly Val Glu Val His Asn Ala Lys Thr

```
            405                 410                 415
Lys Pro Arg Glu Glu Gln Phe Asn Ser Thr Tyr Arg Val Val Ser Val
                420                 425                 430

Leu Thr Val Leu His Gln Asp Trp Leu Asn Gly Lys Glu Tyr Lys Cys
            435                 440                 445

Lys Val Ser Asn Lys Gly Leu Pro Ser Ser Ile Glu Lys Thr Ile Ser
        450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Arg Leu Thr Val Asp Lys Ser Arg Trp
    530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly Lys Gly Gly
                565                 570                 575

Gly Gly Gly Ala Gln Gln Glu Glu Cys Glu Trp Asp Pro Trp Thr Cys
            580                 585                 590

Glu His Met Gly Ser Gly Ser Ala Thr Gly Gly Ser Gly Ser Thr Ala
        595                 600                 605

Ser Ser Gly Ser Gly Ser Ala Thr His Gln Glu Glu Cys Glu Trp Asp
    610                 615                 620

Pro Trp Thr Cys Glu His Met Leu Glu
625                 630

<210> SEQ ID NO 250
<211> LENGTH: 347
<212> TYPE: PRT
<213> ORGANISM: Artificial Sequence
<220> FEATURE:
<223> OTHER INFORMATION: Synthetic

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45

Gly Gly Ile Asn Pro Gly Asn Gly Gly Thr Asn Phe Asn Glu Lys Phe
    50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Asp Ile Gln Met Thr Gln Ser Pro Ser Ser Leu
```

```
            130                 135                 140
Ser Ala Ser Val Gly Asp Arg Val Thr Ile Thr Cys Ser Ala Ser Gln
145                 150                 155                 160

Asp Ile Ser Asn Tyr Leu Asn Trp Tyr Gln Gln Lys Pro Gly Lys Ala
                165                 170                 175

Pro Lys Val Leu Ile Tyr Phe Thr Ser Ser Leu His Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Tyr
    210                 215                 220

Ser Thr Val Pro Trp Thr Phe Gly Gln Gly Thr Lys Val Glu Ile Lys
225                 230                 235                 240

Arg Thr Val Ala Ala Pro Ser Val Phe Ile Phe Pro Pro Ser Asp Glu
                245                 250                 255

Gln Leu Lys Ser Gly Thr Ala Ser Val Val Cys Leu Leu Asn Asn Phe
            260                 265                 270

Tyr Pro Arg Glu Ala Lys Val Gln Trp Lys Val Asp Asn Ala Leu Gln
        275                 280                 285

Ser Gly Asn Ser Gln Glu Ser Val Thr Glu Gln Asp Ser Lys Asp Ser
    290                 295                 300

Thr Tyr Ser Leu Ser Ser Thr Leu Thr Leu Ser Lys Ala Asp Tyr Glu
305                 310                 315                 320

Lys His Lys Val Tyr Ala Cys Glu Val Thr His Gln Gly Leu Ser Ser
                325                 330                 335

Pro Val Thr Lys Ser Phe Asn Arg Gly Glu Cys
            340                 345

<210> SEQ ID NO 251
<211> LENGTH: 629
<212> TYPE: PRT
<213> ORGANISM: Artificial Sequence
<220> FEATURE:
<223> OTHER INFORMATION: Synthetic

<400> SEQUENCE: 251

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Tyr Thr Phe Thr Asn Tyr Gly Met Asn Trp Val Arg Gln Ala
```

```
145                 150                 155                 160
Pro Gly Lys Gly Leu Glu Trp Val Gly Trp Ile Asn Thr Tyr Thr Gly
                165                 170                 175

Glu Pro Thr Tyr Ala Ala Asp Phe Lys Arg Arg Phe Thr Phe Ser Leu
                180                 185                 190

Asp Thr Ser Lys Ser Thr Ala Tyr Leu Gln Met Asn Ser Leu Arg Ala
                195                 200                 205

Glu Asp Thr Ala Val Tyr Tyr Cys Ala Lys Tyr Pro His Tyr Tyr Gly
210                 215                 220

Ser Ser His Trp Tyr Phe Asp Val Trp Gly Gln Gly Thr Leu Val Thr
225                 230                 235                 240

Val Ser Ser Ala Ser Thr Lys Gly Pro Ser Val Phe Pro Leu Ala Pro
                245                 250                 255

Cys Ser Arg Ser Thr Ser Glu Ser Thr Ala Ala Leu Gly Cys Leu Val
                260                 265                 270

Lys Asp Tyr Phe Pro Glu Pro Val Thr Val Ser Trp Asn Ser Gly Ala
                275                 280                 285

Leu Thr Ser Gly Val His Thr Phe Pro Ala Val Leu Gln Ser Ser Gly
                290                 295                 300

Leu Tyr Ser Leu Ser Ser Val Val Thr Val Pro Ser Ser Ser Leu Gly
305                 310                 315                 320

Thr Lys Thr Tyr Thr Cys Asn Val Asp His Lys Pro Ser Asn Thr Lys
                325                 330                 335

Val Asp Lys Arg Val Glu Ser Lys Tyr Gly Pro Pro Cys Pro Pro Cys
                340                 345                 350

Pro Ala Pro Glu Phe Leu Gly Gly Pro Ser Val Phe Leu Phe Pro Pro
                355                 360                 365

Lys Pro Lys Asp Thr Leu Met Ile Ser Arg Thr Pro Glu Val Thr Cys
                370                 375                 380

Val Val Val Asp Val Ser Gln Glu Asp Pro Glu Val Gln Phe Asn Trp
385                 390                 395                 400

Tyr Val Asp Gly Val Glu Val His Asn Ala Lys Thr Lys Pro Arg Glu
                405                 410                 415

Glu Gln Phe Asn Ser Thr Tyr Arg Val Val Ser Val Leu Thr Val Leu
                420                 425                 430

His Gln Asp Trp Leu Asn Gly Lys Glu Tyr Lys Cys Lys Val Ser Asn
                435                 440                 445

Lys Gly Leu Pro Ser Ser Ile Glu Lys Thr Ile Ser Lys Ala Lys Gly
                450                 455                 460

Gln Pro Arg Glu Pro Gln Val Tyr Thr Leu Pro Pro Ser Gln Glu Glu
465                 470                 475                 480

Met Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
                500                 505                 510

Asn Tyr Lys Thr Thr Pro Pro Val Leu Asp Ser Asp Gly Ser Phe Phe
                515                 520                 525

Leu Tyr Ser Arg Leu Thr Val Asp Lys Ser Arg Trp Gln Glu Gly Asn
                530                 535                 540

Val Phe Ser Cys Ser Val Met His Glu Ala Leu His Asn His Tyr Thr
545                 550                 555                 560

Gln Lys Ser Leu Ser Leu Ser Leu Gly Lys Gly Gly Gly Gly Gly Ala
                565                 570                 575
```

```
Gln Gln Glu Glu Cys Glu Trp Asp Pro Trp Thr Cys Glu His Met Gly
            580                 585                 590

Ser Gly Ser Ala Thr Gly Gly Ser Gly Ser Thr Ala Ser Ser Gly Ser
            595                 600                 605

Gly Ser Ala Thr His Gln Glu Glu Cys Glu Trp Asp Pro Trp Thr Cys
            610                 615                 620

Glu His Met Leu Glu
625

<210> SEQ ID NO 252
<211> LENGTH: 344
<212> TYPE: PRT
<213> ORGANISM: Artificial Sequence
<220> FEATURE:
<223> OTHER INFORMATION: Synthetic

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Phe Pro Gly Ser Gly Asn Ser Lys Tyr Asn Glu Asn Phe
    50                  55                  60

Lys Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Glu Thr Tyr Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Asp Ile Gln Met Thr Gln Ser Pro Ser Ser Leu Ser Ala Ser
    130                 135                 140

Val Gly Asp Arg Val Thr Ile Thr Cys Ser Ala Ser Gln Asp Ile Ser
145                 150                 155                 160

Asn Tyr Leu Asn Trp Tyr Gln Gln Lys Pro Gly Lys Ala Pro Lys Val
                165                 170                 175

Leu Ile Tyr Phe Thr Ser Ser Leu His Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Tyr Ser Thr Val
    210                 215                 220

Pro Trp Thr Phe Gly Gln Gly Thr Lys Val Glu Ile Lys Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300
```

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340

<210> SEQ ID NO 253
<211> LENGTH: 612
<212> TYPE: PRT
<213> ORGANISM: Artificial Sequence
<220> FEATURE:
<223> OTHER INFORMATION: Synthetic

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Gln Val Gln Leu Val Glu Ser Gly Gly Val Val Gln Pro Gly
        115                 120                 125

Arg Ser Leu Arg Leu Asp Cys Lys Ala Ser Gly Ile Thr Phe Ser Asn
130                 135                 140

Ser Gly Met His Trp Val Arg Gln Ala Pro Gly Lys Gly Leu Glu Trp
145                 150                 155                 160

Val Ala Val Ile Trp Tyr Asp Gly Ser Lys Arg Tyr Tyr Ala Asp Ser
                165                 170                 175

Val Lys Gly Arg Phe Thr Ile Ser Arg Asp Asn Ser Lys Asn Thr Leu
            180                 185                 190

Phe Leu Gln Met Asn Ser Leu Arg Ala Glu Asp Thr Ala Val Tyr Tyr
        195                 200                 205

Cys Ala Thr Asn Asp Asp Tyr Trp Gly Gln Gly Thr Leu Val Thr Val
    210                 215                 220

Ser Ser Ala Ser Thr Lys Gly Pro Ser Val Phe Pro Leu Ala Pro Cys
225                 230                 235                 240

Ser Arg Ser Thr Ser Glu Ser Thr Ala Ala Leu Gly Cys Leu Val Lys
                245                 250                 255

Asp Tyr Phe Pro Glu Pro Val Thr Val Ser Trp Asn Ser Gly Ala Leu
            260                 265                 270

Thr Ser Gly Val His Thr Phe Pro Ala Val Leu Gln Ser Ser Gly Leu
        275                 280                 285

Tyr Ser Leu Ser Ser Val Val Thr Val Pro Ser Ser Ser Leu Gly Thr
    290                 295                 300

Lys Thr Tyr Thr Cys Asn Val Asp His Lys Pro Ser Asn Thr Lys Val
305                 310                 315                 320

```
Asp Lys Arg Val Glu Ser Lys Tyr Gly Pro Pro Cys Pro Cys Pro
            325                 330                 335

Ala Pro Glu Phe Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
            355                 360                 365

Val Val Asp Val Ser Gln Glu Asp Pro Glu Val Gln Phe Asn Trp Tyr
370                 375                 380

Val Asp Gly Val Glu Val His Asn Ala Lys Thr Lys Pro Arg Glu Glu
385                 390                 395                 400

Gln Phe Asn Ser Thr Tyr Arg Val Val Ser Val Leu Thr Val Leu His
            405                 410                 415

Gln Asp Trp Leu Asn Gly Lys Glu Tyr Lys Cys Lys Val Ser Asn Lys
            420                 425                 430

Gly Leu Pro Ser Ser Ile Glu Lys Thr Ile Ser Lys Ala Lys Gly Gln
            435                 440                 445

Pro Arg Glu Pro Gln Val Tyr Thr Leu Pro Pro Ser Gln Glu Glu Met
    450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Arg Leu Thr Val Asp Lys Ser Arg Trp Gln Glu Gly Asn Val
            515                 520                 525

Phe Ser Cys Ser Val Met His Glu Ala Leu His Asn His Tyr Thr Gln
            530                 535                 540

Lys Ser Leu Ser Leu Ser Leu Gly Lys Gly Gly Gly Gly Ala Gln
545                 550                 555                 560

Gln Glu Glu Cys Glu Trp Asp Pro Trp Thr Cys Glu His Met Gly Ser
                565                 570                 575

Gly Ser Ala Thr Gly Gly Ser Gly Ser Thr Ala Ser Ser Gly Ser Gly
            580                 585                 590

Ser Ala Thr His Gln Glu Glu Cys Glu Trp Asp Pro Trp Thr Cys Glu
            595                 600                 605

His Met Leu Glu
    610

<210> SEQ ID NO 254
<211> LENGTH: 343
<212> TYPE: PRT
<213> ORGANISM: Artificial Sequence
<220> FEATURE:
<223> OTHER INFORMATION: Synthetic

<400> SEQUENCE: 254

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60
```

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Glu Ile Val Leu Thr Gln Ser Pro Ala Thr Leu Ser Leu Ser Pro
    130                 135                 140

Gly Glu Arg Ala Thr Leu Ser Cys Arg Ala Ser Gln Ser Val Ser Ser
145                 150                 155                 160

Tyr Leu Ala Trp Tyr Gln Gln Lys Pro Gly Gln Ala Pro Arg Leu Leu
                165                 170                 175

Ile Tyr Asp Ala Ser Asn Arg Ala Thr Gly Ile Pro Ala Arg Phe Ser
            180                 185                 190

Gly Ser Gly Ser Gly Thr Asp Phe Thr Leu Thr Ile Ser Ser Leu Glu
        195                 200                 205

Pro Glu Asp Phe Ala Val Tyr Tyr Cys Gln Gln Ser Ser Asn Trp Pro
    210                 215                 220

Arg Thr Phe Gly Gln Gly Thr Lys Val Glu Ile Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
    290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
            340

<210> SEQ ID NO 255
<211> LENGTH: 694
<212> TYPE: PRT
<213> ORGANISM: Artificial Sequence
<220> FEATURE:
<223> OTHER INFORMATION: Synthetic

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45

Gly Gly Ile Asn Pro Gly Asn Gly Gly Thr Asn Phe Asn Glu Lys Phe
    50                  55                  60

Lys Ile Arg Val Thr Met Thr Arg Asp Thr Ser Ile Ser Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Arg Arg Tyr His Gly Tyr Asp Gly Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Gly Gly Gln Glu Glu Cys Glu Trp Asp Pro
            355                 360                 365

Trp Thr Cys Glu His Met Gly Gly Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
450                 455                 460

Lys Gly Gly Gly Gly Ser Gly Gly Gly Gly Ser Gly Gly Gly Gly Ser
465                 470                 475                 480

Asp Ile Gln Leu Thr Gln Ser Pro Ser Ser Leu Ser Ala Ser Val Gly
                485                 490                 495
```

Asp Arg Val Thr Ile Thr Cys Ser Ala Ser Gln Asp Ile Ser Asn Tyr
              500                 505                 510

Leu Asn Trp Tyr Gln Gln Lys Pro Gly Lys Ala Pro Lys Val Leu Ile
              515                 520                 525

Tyr Phe Thr Ser Ser Leu His Ser Gly Val Pro Ser Arg Phe Ser Gly
              530                 535                 540

Ser Gly Ser Gly Thr Asp Phe Thr Leu Thr Ile Ser Ser Leu Gln Pro
545                 550                 555                 560

Glu Asp Phe Ala Thr Tyr Tyr Cys Gln Gln Tyr Ser Thr Val Pro Trp
              565                 570                 575

Thr Phe Gly Gln Gly Thr Lys Val Glu Ile Lys Arg Thr Val Ala Ala
              580                 585                 590

Pro Ser Val Phe Ile Phe Pro Pro Ser Asp Glu Gln Leu Lys Ser Gly
              595                 600                 605

Thr Ala Ser Val Val Cys Leu Leu Asn Asn Phe Tyr Pro Arg Glu Ala
              610                 615                 620

Lys Val Gln Trp Lys Val Asp Asn Ala Leu Gln Ser Gly Asn Ser Gln
625                 630                 635                 640

Glu Ser Val Thr Glu Gln Asp Ser Lys Asp Ser Thr Tyr Ser Leu Ser
              645                 650                 655

Ser Thr Leu Thr Leu Ser Lys Ala Asp Tyr Glu Lys His Lys Val Tyr
              660                 665                 670

Ala Cys Glu Val Thr His Gln Gly Leu Ser Ser Pro Val Thr Lys Ser
              675                 680                 685

Phe Asn Arg Gly Glu Cys
              690

<210> SEQ ID NO 256
<211> LENGTH: 218
<212> TYPE: PRT
<213> ORGANISM: Artificial Sequence
<220> FEATURE:
<223> OTHER INFORMATION: Synthetic

<400> SEQUENCE: 256

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
              20                  25                  30

Gly Phe Ser Tyr Ile His Trp Tyr Gln Gln Lys Pro Gly Gln Pro Pro
          35                  40                  45

Lys Leu Leu Ile Tyr Leu Ala Ser Asn Leu Glu Ser Gly Val Pro Ala
      50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
              85                  90                  95

Glu Leu Pro Asn Thr Phe Gly Gly Gly Thr Lys Val Glu Ile Lys Arg
              100                 105                 110

Thr Val Ala Ala Pro Ser Val Phe Ile Phe Pro Pro Ser Asp Glu Gln
              115                 120                 125

Leu Lys Ser Gly Thr Ala Ser Val Val Cys Leu Leu Asn Asn Phe Tyr
          130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 257
<211> LENGTH: 231
<212> TYPE: PRT
<213> ORGANISM: Artificial Sequence
<220> FEATURE:
<223> OTHER INFORMATION: Synthetic

<400> SEQUENCE: 257

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230
```

<210> SEQ ID NO 258
<211> LENGTH: 676
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Thr Tyr
            20                  25                  30
Tyr Ile Tyr Trp Val Arg Gln Ala Pro Gly Gln Cys Leu Glu Trp Met
            35                  40                  45
Gly Gly Ile Asn Pro Asn Gly Gly Thr Asn Phe Asn Glu Lys Phe
50                  55                  60
Lys Ile Arg Val Thr Met Thr Arg Asp Thr Ser Ile Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Arg Tyr His Gly Tyr Asp Gly Gly Leu Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
            405                 410                 415
Trp Gln Glu Gly Asn Val Phe Ser Cys Ser Val Met His Glu Ala Leu
            420                 425                 430
```

His Asn His Tyr Thr Gln Lys Ser Leu Ser Leu Ser Leu Gly Lys Gly
            435                 440                 445

Gly Gly Gly Ser Gly Gly Gly Ser Gly Gly Gly Ser Asp Ile
450                 455                 460

Gln Leu Thr Gln Ser Pro Ser Leu Ser Ala Ser Val Gly Asp Arg
465                 470                 475                 480

Val Thr Ile Thr Cys Ser Ala Ser Gln Asp Ile Ser Asn Tyr Leu Asn
                485                 490                 495

Trp Tyr Gln Gln Lys Pro Gly Lys Ala Pro Lys Val Leu Ile Tyr Phe
            500                 505                 510

Thr Ser Ser Leu His Ser Gly Val Pro Ser Arg Phe Ser Gly Ser Gly
            515                 520                 525

Ser Gly Thr Asp Phe Thr Leu Thr Ile Ser Ser Leu Gln Pro Glu Asp
530                 535                 540

Phe Ala Thr Tyr Tyr Cys Gln Gln Tyr Ser Thr Val Pro Trp Thr Phe
545                 550                 555                 560

Gly Gln Gly Thr Lys Val Glu Ile Lys Arg Thr Val Ala Ala Pro Ser
                565                 570                 575

Val Phe Ile Phe Pro Pro Ser Asp Glu Gln Leu Lys Ser Gly Thr Ala
            580                 585                 590

Ser Val Val Cys Leu Leu Asn Asn Phe Tyr Pro Arg Glu Ala Lys Val
            595                 600                 605

Gln Trp Lys Val Asp Asn Ala Leu Gln Ser Gly Asn Ser Gln Glu Ser
            610                 615                 620

Val Thr Glu Gln Asp Ser Lys Asp Ser Thr Tyr Ser Leu Ser Ser Thr
625                 630                 635                 640

Leu Thr Leu Ser Lys Ala Asp Tyr Glu Lys His Lys Val Tyr Ala Cys
                645                 650                 655

Glu Val Thr His Gln Gly Leu Ser Ser Pro Val Thr Lys Ser Phe Asn
            660                 665                 670

Arg Gly Glu Cys
        675

<210> SEQ ID NO 259
<211> LENGTH: 277
<212> TYPE: PRT
<213> ORGANISM: Artificial Sequence
<220> FEATURE:
<223> OTHER INFORMATION: Synthetic

<400> SEQUENCE: 259

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Cys Gly Thr Lys Val Glu Ile Lys Arg
            100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys Gly Gly Gly Gly Gly Ala
    210                 215                 220

Gln Gln Glu Glu Cys Glu Trp Asp Pro Trp Thr Cys Glu His Met Gly
225                 230                 235                 240

Ser Gly Ser Ala Thr Gly Gly Ser Gly Ser Thr Ala Ser Ser Gly Ser
                245                 250                 255

Gly Ser Ala Thr His Gln Glu Glu Cys Glu Trp Asp Pro Trp Thr Cys
                260                 265                 270

Glu His Met Leu Glu
        275

<210> SEQ ID NO 260
<211> LENGTH: 231
<212> TYPE: PRT
<213> ORGANISM: Artificial Sequence
<220> FEATURE:
<223> OTHER INFORMATION: Synthetic

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Leu
225                 230

<210> SEQ ID NO 261
<211> LENGTH: 676
<212> TYPE: PRT
<213> ORGANISM: Artificial Sequence
<220> FEATURE:
<223> OTHER INFORMATION: Synthetic

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45

Gly Gly Ile Asn Pro Gly Asn Gly Gly Thr Asn Phe Asn Glu Lys Phe
    50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
        435                 440                 445

Gly Gly Gly Ser Gly Gly Gly Ser Gly Gly Gly Ser Asp Ile
450                 455                 460

Gln Leu Thr Gln Ser Pro Ser Ser Leu Ser Ala Ser Val Gly Asp Arg
465                 470                 475                 480

Val Thr Ile Thr Cys Ser Ala Ser Gln Asp Ile Ser Asn Tyr Leu Asn
                485                 490                 495

Trp Tyr Gln Gln Lys Pro Gly Lys Ala Pro Lys Val Leu Ile Tyr Phe
            500                 505                 510

Thr Ser Ser Leu His Ser Gly Val Pro Ser Arg Phe Ser Gly Ser Gly
        515                 520                 525

Ser Gly Thr Asp Phe Thr Leu Thr Ile Ser Ser Leu Gln Pro Glu Asp
530                 535                 540

Phe Ala Thr Tyr Tyr Cys Gln Gln Tyr Ser Thr Val Pro Trp Thr Phe
545                 550                 555                 560

Gly Gln Gly Thr Lys Val Glu Ile Lys Arg Thr Val Ala Ala Pro Ser
                565                 570                 575

Val Phe Ile Phe Pro Pro Ser Asp Glu Gln Leu Lys Ser Gly Thr Ala
            580                 585                 590

Ser Val Val Cys Leu Leu Asn Asn Phe Tyr Pro Arg Glu Ala Lys Val
        595                 600                 605

Gln Trp Lys Val Asp Asn Ala Leu Gln Ser Gly Asn Ser Gln Glu Ser
610                 615                 620

Val Thr Glu Gln Asp Ser Lys Asp Ser Thr Tyr Ser Leu Ser Ser Thr
625                 630                 635                 640

Leu Thr Leu Ser Lys Ala Asp Tyr Glu Lys His Lys Val Tyr Ala Cys
                645                 650                 655

Glu Val Thr His Gln Gly Leu Ser Ser Pro Val Thr Lys Ser Phe Asn
            660                 665                 670

Arg Gly Glu Cys
        675

<210> SEQ ID NO 262
<211> LENGTH: 218
<212> TYPE: PRT
<213> ORGANISM: Artificial Sequence
<220> FEATURE:
<223> OTHER INFORMATION: Synthetic

<400> SEQUENCE: 262
```

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 263
<211> LENGTH: 290
<212> TYPE: PRT
<213> ORGANISM: Artificial Sequence
<220> FEATURE:
<223> OTHER INFORMATION: Synthetic

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Leu Gly Gly Gly Gly Ala Gln Gln Glu
225                 230                 235                 240

Glu Cys Glu Trp Asp Pro Trp Thr Cys Glu His Met Gly Ser Gly Ser
                245                 250                 255

Ala Thr Gly Gly Ser Gly Ser Thr Ala Ser Ser Gly Ser Gly Ser Ala
            260                 265                 270

Thr His Gln Glu Glu Cys Glu Trp Asp Pro Trp Thr Cys Glu His Met
        275                 280                 285

Leu Glu
    290

<210> SEQ ID NO 264
<211> LENGTH: 735
<212> TYPE: PRT
<213> ORGANISM: Artificial Sequence
<220> FEATURE:
<223> OTHER INFORMATION: Synthetic

<400> SEQUENCE: 264

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile Tyr Trp Val Arg Gln Ala Pro Gly Gln Gly Leu Glu Trp Met
        35                  40                  45

Gly Gly Ile Asn Pro Gly Asn Gly Gly Thr Asn Phe Asn Glu Lys Phe
    50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
        435                 440                 445

Gly Gly Gly Ser Gly Gly Gly Ser Gly Gly Gly Ser Asp Ile
450                 455                 460

Gln Leu Thr Gln Ser Pro Ser Ser Leu Ser Ala Ser Val Gly Asp Arg
465                 470                 475                 480

Val Thr Ile Thr Cys Ser Ala Ser Gln Asp Ile Ser Asn Tyr Leu Asn
                485                 490                 495

Trp Tyr Gln Gln Lys Pro Gly Lys Ala Pro Lys Val Leu Ile Tyr Phe
            500                 505                 510

Thr Ser Ser Leu His Ser Gly Val Pro Ser Arg Phe Ser Gly Ser Gly
            515                 520                 525

Ser Gly Thr Asp Phe Thr Leu Thr Ile Ser Ser Leu Gln Pro Glu Asp
530                 535                 540

Phe Ala Thr Tyr Tyr Cys Gln Gln Tyr Ser Thr Val Pro Trp Thr Phe
545                 550                 555                 560

Gly Gln Gly Thr Lys Val Glu Ile Lys Arg Thr Val Ala Ala Pro Ser
                565                 570                 575

Val Phe Ile Phe Pro Pro Ser Asp Glu Gln Leu Lys Ser Gly Thr Ala
            580                 585                 590

Ser Val Val Cys Leu Leu Asn Asn Phe Tyr Pro Arg Glu Ala Lys Val
            595                 600                 605

Gln Trp Lys Val Asp Asn Ala Leu Gln Ser Gly Asn Ser Gln Glu Ser
610                 615                 620

Val Thr Glu Gln Asp Ser Lys Asp Ser Thr Tyr Ser Leu Ser Ser Thr
```

```
                    625                 630                 635                 640
Leu Thr Leu Ser Lys Ala Asp Tyr Glu Lys His Lys Val Tyr Ala Cys
                645                 650                 655

Glu Val Thr His Gln Gly Leu Ser Ser Pro Val Thr Lys Ser Phe Asn
                660                 665                 670

Arg Gly Glu Cys Gly Gly Gly Gly Ala Gln Gln Glu Glu Cys Glu
                675                 680                 685

Trp Asp Pro Trp Thr Cys Glu His Met Gly Ser Gly Ser Ala Thr Gly
            690                 695                 700

Gly Ser Gly Ser Thr Ala Ser Ser Gly Ser Gly Ser Ala Thr His Gln
705                 710                 715                 720

Glu Glu Cys Glu Trp Asp Pro Trp Thr Cys Glu His Met Leu Glu
                725                 730                 735

<210> SEQ ID NO 265
<211> LENGTH: 231
<212> TYPE: PRT
<213> ORGANISM: Artificial Sequence
<220> FEATURE:
<223> OTHER INFORMATION: Synthetic

<400> SEQUENCE: 265

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Leu
225                 230

<210> SEQ ID NO 266
<211> LENGTH: 218
<212> TYPE: PRT
```

```
<213> ORGANISM: Artificial Sequence
<220> FEATURE:
<223> OTHER INFORMATION: Synthetic

<400> SEQUENCE: 266

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
                20                  25                  30

Gly Phe Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 267
<211> LENGTH: 735
<212> TYPE: PRT
<213> ORGANISM: Artificial Sequence
<220> FEATURE:
<223> OTHER INFORMATION: Synthetic

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Tyr Ile Tyr Trp Val Arg Gln Ala Pro Gly Gln Gly Leu Glu Trp Met
            35                  40                  45

Gly Gly Ile Asn Pro Gly Asn Gly Gly Thr Asn Phe Asn Glu Lys Phe
        50                  55                  60

Lys Ile Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr His Gly Tyr Asp Gly Gly Leu Asp Tyr Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
        435                 440                 445

Gly Gly Gly Ser Gly Gly Gly Gly Ser Gly Gly Gly Gly Ser Asp Ile
    450                 455                 460

Gln Leu Thr Gln Ser Pro Ser Ser Leu Ser Ala Ser Val Gly Asp Arg
465                 470                 475                 480

Val Thr Ile Thr Cys Ser Ala Ser Gln Asp Ile Ser Asn Tyr Leu Asn
                485                 490                 495

Trp Tyr Gln Gln Lys Pro Gly Lys Ala Pro Lys Val Leu Ile Tyr Phe
            500                 505                 510

Thr Ser Ser Leu His Ser Gly Val Pro Ser Arg Phe Ser Gly Ser Gly
        515                 520                 525

Ser Gly Thr Asp Phe Thr Leu Thr Ile Ser Ser Leu Gln Pro Glu Asp
```

```
                530             535             540
Phe Ala Thr Tyr Tyr Cys Gln Gln Tyr Ser Thr Val Pro Trp Thr Phe
545                 550             555                 560

Gly Gln Gly Thr Lys Val Glu Ile Lys Arg Thr Val Ala Ala Pro Ser
                565             570             575

Val Phe Ile Phe Pro Pro Ser Asp Glu Gln Leu Lys Ser Gly Thr Ala
            580             585             590

Ser Val Val Cys Leu Leu Asn Asn Phe Tyr Pro Arg Glu Ala Lys Val
        595             600             605

Gln Trp Lys Val Asp Asn Ala Leu Gln Ser Gly Asn Ser Gln Glu Ser
610             615             620

Val Thr Glu Gln Asp Ser Lys Asp Ser Thr Tyr Ser Leu Ser Ser Thr
625             630             635             640

Leu Thr Leu Ser Lys Ala Asp Tyr Glu Lys His Lys Val Tyr Ala Cys
                645             650             655

Glu Val Thr His Gln Gly Leu Ser Ser Pro Val Thr Lys Ser Phe Asn
            660             665             670

Arg Gly Glu Cys Gly Gly Gly Gly Ala Gln Gln Glu Glu Cys Glu
        675             680             685

Trp Asp Pro Trp Thr Cys Glu His Met Gly Ser Gly Ser Ala Thr Gly
        690             695             700

Gly Ser Gly Ser Thr Ala Ser Ser Gly Ser Gly Ser Ala Thr His Gln
705             710             715             720

Glu Glu Cys Glu Trp Asp Pro Trp Thr Cys Glu His Met Leu Glu
            725             730             735
```

<210> SEQ ID NO 268
<211> LENGTH: 218
<212> TYPE: PRT
<213> ORGANISM: Artificial Sequence
<220> FEATURE:
<223> OTHER INFORMATION: Synthetic

<400> SEQUENCE: 268

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Gly Phe Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                    165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 269
<211> LENGTH: 290
<212> TYPE: PRT
<213> ORGANISM: Artificial Sequence
<220> FEATURE:
<223> OTHER INFORMATION: Synthetic

<400> SEQUENCE: 269

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Asp Phe Thr His Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro Tyr Tyr Tyr Gly Thr Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Leu Gly Gly Gly Gly Ala Gln Gln Glu
225                 230                 235                 240
Glu Cys Glu Trp Asp Pro Trp Thr Cys Glu His Met Gly Ser Gly Ser
                245                 250                 255
Ala Thr Gly Gly Ser Gly Ser Thr Ala Ser Ser Gly Ser Gly Ser Ala
            260                 265                 270
Thr His Gln Glu Glu Cys Glu Trp Asp Pro Trp Thr Cys Glu His Met
        275                 280                 285
Leu Glu
    290
```

<210> SEQ ID NO 270
<211> LENGTH: 815
<212> TYPE: PRT
<213> ORGANISM: Artificial Sequence
<220> FEATURE:
<223> OTHER INFORMATION: Synthetic

<400> SEQUENCE: 270

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Gly Gly Gly Gly Ser Gln Val Gln Leu
    210                 215                 220

Val Gln Ser Gly Ala Glu Val Lys Lys Pro Gly Ala Ser Val Lys Val
225                 230                 235                 240

Ser Cys Lys Ala Ser Gly Tyr Thr Phe Thr Ser Tyr Tyr Ile His Trp
                245                 250                 255

Val Arg Gln Ala Pro Gly Gln Gly Leu Glu Trp Met Gly Trp Ile Phe
            260                 265                 270

Pro Gly Ser Gly Asn Ser Lys Tyr Asn Glu Asn Phe Lys Gly Arg Val
        275                 280                 285

Thr Leu Thr Ala Asp Thr Ser Thr Ser Thr Val Tyr Met Glu Leu Ser
    290                 295                 300

Ser Leu Arg Ser Glu Asp Thr Ala Val Tyr Tyr Cys Ala Ser Glu Thr
305                 310                 315                 320

Tyr Asp Tyr Gly Asp Tyr Trp Gly Gln Gly Thr Leu Val Thr Val Ser
                325                 330                 335

Ser Ala Ser Thr Lys Gly Pro Ser Val Phe Pro Leu Ala Pro Cys Ser
            340                 345                 350

Arg Ser Thr Ser Glu Ser Thr Ala Ala Leu Gly Cys Leu Val Lys Asp
        355                 360                 365

Tyr Phe Pro Glu Pro Val Thr Val Ser Trp Asn Ser Gly Ala Leu Thr
```

```
            370                 375                 380
Ser Gly Val His Thr Phe Pro Ala Val Leu Gln Ser Ser Gly Leu Tyr
385                 390                 395                 400

Ser Leu Ser Ser Val Val Thr Val Pro Ser Ser Leu Gly Thr Lys
                405                 410                 415

Thr Tyr Thr Cys Asn Val Asp His Lys Pro Ser Asn Thr Lys Val Asp
                420                 425                 430

Lys Arg Val Glu Ser Lys Tyr Gly Pro Pro Cys Pro Pro Cys Pro Ala
            435                 440                 445

Pro Glu Phe Leu Gly Gly Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser Gln Glu Asp Pro Glu Val Gln Phe Asn Trp Tyr Val
                485                 490                 495

Asp Gly Val Glu Val His Asn Ala Lys Thr Lys Pro Arg Glu Glu Gln
                500                 505                 510

Phe Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Gly
530                 535                 540

Leu Pro Ser Ser Ile Glu Lys Thr Ile Ser Lys Ala Lys Gly Gln Pro
545                 550                 555                 560

Arg Glu Pro Gln Val Tyr Thr Leu Pro Pro Ser Gln Glu Glu Met Thr
                565                 570                 575

Lys Asn Gln Val Ser Leu Thr Cys Leu Val Lys Gly Phe Tyr Pro Ser
                580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Arg Leu Thr Val Asp Lys Ser Arg Trp Gln Glu Gly Asn Val Phe
625                 630                 635                 640

Ser Cys Ser Val Met His Glu Ala Leu His Asn His Tyr Thr Gln Lys
                645                 650                 655

Ser Leu Ser Leu Ser Leu Gly Lys Gly Gly Gly Gly Ser Gly Gly Gly
            660                 665                 670

Gly Ser Gly Gly Gly Gly Ser Ile Pro Pro His Val Gln Lys Ser Val
            675                 680                 685

Asn Asn Asp Met Ile Val Thr Asp Asn Asn Gly Ala Val Lys Phe Pro
690                 695                 700

Gln Leu Cys Lys Phe Cys Asp Val Arg Phe Ser Thr Cys Asp Asn Gln
705                 710                 715                 720

Lys Ser Cys Met Ser Asn Cys Ser Ile Thr Ser Ile Cys Glu Lys Pro
                725                 730                 735

Gln Glu Val Cys Val Ala Val Trp Arg Lys Asn Asp Glu Asn Ile Thr
            740                 745                 750

Leu Glu Thr Val Cys His Asp Pro Lys Leu Pro Tyr His Asp Phe Ile
            755                 760                 765

Leu Glu Asp Ala Ala Ser Pro Lys Cys Ile Met Lys Glu Lys Lys
        770                 775                 780

Pro Gly Glu Thr Phe Phe Met Cys Ser Cys Ser Ser Asp Glu Cys Asn
785                 790                 795                 800
```

Asp Asn Ile Ile Phe Ser Glu Glu Tyr Asn Thr Ser Asn Pro Asp
            805                 810                 815

<210> SEQ ID NO 271
<211> LENGTH: 214
<212> TYPE: PRT
<213> ORGANISM: Artificial Sequence
<220> FEATURE:
<223> OTHER INFORMATION: Synthetic

<400> SEQUENCE: 271

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 272
<211> LENGTH: 815
<212> TYPE: PRT
<213> ORGANISM: Artificial Sequence
<220> FEATURE:
<223> OTHER INFORMATION: Synthetic

<400> SEQUENCE: 272

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp

```
                65                  70                  75                  80
Pro Lys Leu Pro Tyr His Asp Phe Ile Leu Glu Asp Ala Ala Ser Pro
                    85                  90                  95
Lys Cys Ile Met Lys Glu Lys Lys Pro Gly Glu Thr Phe Phe Met
            100                 105                 110
Cys Ser Cys Ser Ser Asp Glu Cys Asn Asp Asn Ile Ile Phe Ser Glu
        115                 120                 125
Glu Tyr Asn Thr Ser Asn Pro Asp Gly Gly Gly Ser Gly Gly Gly
    130                 135                 140
Gly Ser Gly Gly Gly Ser Gln Val Gln Leu Val Gln Ser Gly Ala
145                 150                 155                 160
Glu Val Lys Lys Pro Gly Ala Ser Val Lys Val Ser Cys Lys Ala Ser
                165                 170                 175
Gly Tyr Thr Phe Thr Ser Tyr Tyr Ile His Trp Val Arg Gln Ala Pro
            180                 185                 190
Gly Gln Gly Leu Glu Trp Met Gly Trp Ile Phe Pro Gly Ser Gly Asn
        195                 200                 205
Ser Lys Tyr Asn Glu Asn Phe Lys Gly Arg Val Thr Leu Thr Ala Asp
    210                 215                 220
Thr Ser Thr Ser Thr Val Tyr Met Glu Leu Ser Ser Leu Arg Ser Glu
225                 230                 235                 240
Asp Thr Ala Val Tyr Tyr Cys Ala Ser Glu Thr Tyr Asp Tyr Gly Asp
                245                 250                 255
Tyr Trp Gly Gln Gly Thr Leu Val Thr Val Ser Ser Ala Ser Thr Lys
            260                 265                 270
Gly Pro Ser Val Phe Pro Leu Ala Pro Cys Ser Arg Ser Thr Ser Glu
        275                 280                 285
Ser Thr Ala Ala Leu Gly Cys Leu Val Lys Asp Tyr Phe Pro Glu Pro
    290                 295                 300
Val Thr Val Ser Trp Asn Ser Gly Ala Leu Thr Ser Gly Val His Thr
305                 310                 315                 320
Phe Pro Ala Val Leu Gln Ser Ser Gly Leu Tyr Ser Leu Ser Ser Val
                325                 330                 335
Val Thr Val Pro Ser Ser Ser Leu Gly Thr Lys Thr Tyr Thr Cys Asn
            340                 345                 350
Val Asp His Lys Pro Ser Asn Thr Lys Val Asp Lys Arg Val Glu Ser
        355                 360                 365
Lys Tyr Gly Pro Pro Cys Pro Pro Cys Pro Ala Pro Glu Phe Leu Gly
    370                 375                 380
Gly Pro Ser Val Phe Leu Phe Pro Pro Lys Pro Lys Asp Thr Leu Met
385                 390                 395                 400
Ile Ser Arg Thr Pro Glu Val Thr Cys Val Val Val Asp Val Ser Gln
                405                 410                 415
Glu Asp Pro Glu Val Gln Phe Asn Trp Tyr Val Asp Gly Val Glu Val
                420                 425                 430
His Asn Ala Lys Thr Lys Pro Arg Glu Glu Gln Phe Asn Ser Thr Tyr
            435                 440                 445
Arg Val Val Ser Val Leu Thr Val Leu His Gln Asp Trp Leu Asn Gly
        450                 455                 460
Lys Glu Tyr Lys Cys Lys Val Ser Asn Lys Gly Leu Pro Ser Ser Ile
465                 470                 475                 480
Glu Lys Thr Ile Ser Lys Ala Lys Gly Gln Pro Arg Glu Pro Gln Val
                485                 490                 495
```

Tyr Thr Leu Pro Pro Ser Gln Glu Met Thr Lys Asn Gln Val Ser
            500                 505                 510

Leu Thr Cys Leu Val Lys Gly Phe Tyr Pro Ser Asp Ile Ala Val Glu
        515                 520                 525

Trp Glu Ser Asn Gly Gln Pro Glu Asn Asn Tyr Lys Thr Thr Pro Pro
530                 535                 540

Val Leu Asp Ser Asp Gly Ser Phe Phe Leu Tyr Ser Arg Leu Thr Val
545                 550                 555                 560

Asp Lys Ser Arg Trp Gln Glu Gly Asn Val Phe Ser Cys Ser Val Met
                565                 570                 575

His Glu Ala Leu His Asn His Tyr Thr Gln Lys Ser Leu Ser Leu Ser
            580                 585                 590

Leu Gly Lys Gly Gly Gly Gly Ser Gly Gly Gly Gly Ser Gly Gly Gly
        595                 600                 605

Gly Ser Ser Asp Thr Gly Arg Pro Phe Val Glu Met Tyr Ser Glu Ile
    610                 615                 620

Pro Glu Ile Ile His Met Thr Glu Gly Arg Glu Leu Val Ile Pro Cys
625                 630                 635                 640

Arg Val Thr Ser Pro Asn Ile Thr Val Thr Leu Lys Lys Phe Pro Leu
                645                 650                 655

Asp Thr Leu Ile Pro Asp Gly Lys Arg Ile Ile Trp Asp Ser Arg Lys
            660                 665                 670

Gly Phe Ile Ile Ser Asn Ala Thr Tyr Lys Glu Ile Gly Leu Leu Thr
        675                 680                 685

Cys Glu Ala Thr Val Asn Gly His Leu Tyr Lys Thr Asn Tyr Leu Thr
690                 695                 700

His Arg Gln Thr Asn Thr Ile Ile Asp Val Val Leu Ser Pro Ser His
705                 710                 715                 720

Gly Ile Glu Leu Ser Val Gly Glu Lys Leu Val Leu Asn Cys Thr Ala
                725                 730                 735

Arg Thr Glu Leu Asn Val Gly Ile Asp Phe Asn Trp Glu Tyr Pro Ser
            740                 745                 750

Ser Lys His Gln His Lys Lys Leu Val Asn Arg Asp Leu Lys Thr Gln
        755                 760                 765

Ser Gly Ser Glu Met Lys Lys Phe Leu Ser Thr Leu Thr Ile Asp Gly
770                 775                 780

Val Thr Arg Ser Asp Gln Gly Leu Tyr Thr Cys Ala Ala Ser Ser Gly
785                 790                 795                 800

Leu Met Thr Lys Lys Asn Ser Thr Phe Val Arg Val His Glu Lys
                805                 810                 815

<210> SEQ ID NO 273
<211> LENGTH: 214
<212> TYPE: PRT
<213> ORGANISM: Artificial Sequence
<220> FEATURE:
<223> OTHER INFORMATION: Synthetic

<400> SEQUENCE: 273

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

```
Tyr Ser Ala Ser Tyr Arg Tyr Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 274
<211> LENGTH: 330
<212> TYPE: PRT
<213> ORGANISM: Artificial Sequence
<220> FEATURE:
<223> OTHER INFORMATION: Synthetic

<400> SEQUENCE: 274

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 275
<211> LENGTH: 330
<212> TYPE: PRT
<213> ORGANISM: Artificial Sequence
<220> FEATURE:
<223> OTHER INFORMATION: Synthetic

<400> SEQUENCE: 275

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
            325                 330
```

<210> SEQ ID NO 276
<211> LENGTH: 330
<212> TYPE: PRT
<213> ORGANISM: Artificial Sequence
<220> FEATURE:
<223> OTHER INFORMATION: Synthetic

<400> SEQUENCE: 276

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 277
<211> LENGTH: 329
<212> TYPE: PRT
<213> ORGANISM: Artificial Sequence
<220> FEATURE:
<223> OTHER INFORMATION: Synthetic

<400> SEQUENCE: 277

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 278
<211> LENGTH: 326
<212> TYPE: PRT
<213> ORGANISM: Artificial Sequence
<220> FEATURE:
<223> OTHER INFORMATION: Synthetic

<400> SEQUENCE: 278

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50              55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 279
<211> LENGTH: 325
<212> TYPE: PRT
<213> ORGANISM: Artificial Sequence
<220> FEATURE:
<223> OTHER INFORMATION: Synthetic

<400> SEQUENCE: 279

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 280

<211> LENGTH: 327
<212> TYPE: PRT
<213> ORGANISM: Artificial Sequence
<220> FEATURE:
<223> OTHER INFORMATION: Synthetic

<400> SEQUENCE: 280

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 281
<211> LENGTH: 327
<212> TYPE: PRT
<213> ORGANISM: Artificial Sequence
<220> FEATURE:
<223> OTHER INFORMATION: Synthetic -continued

```
<400> SEQUENCE: 281

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Ala
                325

<210> SEQ ID NO 282
<211> LENGTH: 326
<212> TYPE: PRT
<213> ORGANISM: Artificial Sequence
<220> FEATURE:
<223> OTHER INFORMATION: Synthetic

<400> SEQUENCE: 282

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 283
<211> LENGTH: 3
<212> TYPE: PRT
<213> ORGANISM: Artificial Sequence
<220> FEATURE:
<223> OTHER INFORMATION: Synthetic

<400> SEQUENCE: 283

Gly Gly Gly
1

<210> SEQ ID NO 284
<211> LENGTH: 5
<212> TYPE: PRT
<213> ORGANISM: Artificial Sequence
<220> FEATURE:
<223> OTHER INFORMATION: Synthetic
```

<400> SEQUENCE: 284

Gly Gly Gly Gly Ser
1               5

<210> SEQ ID NO 285
<211> LENGTH: 10
<212> TYPE: PRT
<213> ORGANISM: Artificial Sequence
<220> FEATURE:
<223> OTHER INFORMATION: Synthetic

<400> SEQUENCE: 285

Gly Gly Gly Gly Ser Gly Gly Gly Gly Ser
1               5                   10

<210> SEQ ID NO 286
<211> LENGTH: 15
<212> TYPE: PRT
<213> ORGANISM: Artificial Sequence
<220> FEATURE:
<223> OTHER INFORMATION: Synthetic

<400> SEQUENCE: 286

Gly Gly Gly Gly Ser Gly Gly Gly Gly Ser Gly Gly Gly Gly Ser
1               5                   10                  15

<210> SEQ ID NO 287
<211> LENGTH: 20
<212> TYPE: PRT
<213> ORGANISM: Artificial Sequence
<220> FEATURE:
<223> OTHER INFORMATION: Synthetic

<400> SEQUENCE: 287

Gly Gly Gly Gly Ser Gly Gly Gly Gly Ser Gly Gly Gly Gly Ser Gly
1               5                   10                  15

Gly Gly Gly Ser
            20

<210> SEQ ID NO 288
<211> LENGTH: 25
<212> TYPE: PRT
<213> ORGANISM: Artificial Sequence
<220> FEATURE:
<223> OTHER INFORMATION: Synthetic

<400> SEQUENCE: 288

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 289
<211> LENGTH: 30
<212> TYPE: PRT
<213> ORGANISM: Artificial Sequence
<220> FEATURE:
<223> OTHER INFORMATION: Synthetic

<400> SEQUENCE: 289

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 290
<211> LENGTH: 103
<212> TYPE: PRT
<213> ORGANISM: Artificial Sequence
<220> FEATURE:
<223> OTHER INFORMATION: Synthetic

<400> SEQUENCE: 290

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 291
<211> LENGTH: 102
<212> TYPE: PRT
<213> ORGANISM: Artificial Sequence
<220> FEATURE:
<223> OTHER INFORMATION: Synthetic

<400> SEQUENCE: 291

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr
            100

<210> SEQ ID NO 292
<211> LENGTH: 107
<212> TYPE: PRT
<213> ORGANISM: Artificial Sequence
<220> FEATURE:
<223> OTHER INFORMATION: Synthetic

<400> SEQUENCE: 292

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 293
<211> LENGTH: 530
<212> TYPE: PRT
<213> ORGANISM: Artificial Sequence
<220> FEATURE:
<223> OTHER INFORMATION: Synthetic

<400> SEQUENCE: 293

```
Met Trp Glu Ala Gln Phe Leu Gly Leu Leu Phe Leu Gln Pro Leu Trp
 1               5                  10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
 50                  55                  60

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285
```

Gly Thr Arg Ser Phe Leu Thr Ala Lys Trp Thr Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Pro Ala Gly His Leu Leu Phe Leu Ile Leu Gly Val Leu
450                 455                 460

Ser Leu Leu Leu Leu Val Thr Gly Ala Phe Gly Phe His Leu Trp Arg
465                 470                 475                 480

Arg Gln Trp Arg Pro Arg Arg Phe Ser Ala Leu Glu Gln Gly Ile His
                485                 490                 495

Pro Pro Gln Ala Gln Ser Lys Ile Glu Glu Leu Glu Gln Glu Pro Glu
            500                 505                 510

Pro Glu Pro Glu Pro Glu Pro Glu Pro Glu Pro Glu Pro Glu Pro Glu
        515                 520                 525

Gln Leu
    530

<210> SEQ ID NO 294
<211> LENGTH: 123
<212> TYPE: PRT
<213> ORGANISM: Artificial Sequence
<220> FEATURE:
<223> OTHER INFORMATION: Synthetic

<400> SEQUENCE: 294

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

```
Trp Gly Gln Gly Thr Leu Val Thr Val Ser Ser
            115                 120
```

<210> SEQ ID NO 295
<211> LENGTH: 107
<212> TYPE: PRT
<213> ORGANISM: Artificial Sequence
<220> FEATURE:
<223> OTHER INFORMATION: Synthetic

<400> SEQUENCE: 295

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 296
<211> LENGTH: 676
<212> TYPE: PRT
<213> ORGANISM: Artificial Sequence
<220> FEATURE:
<223> OTHER INFORMATION: Synthetic

<400> SEQUENCE: 296

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Gly Asn Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Ala Gly Gly Gly Ser Gly Gly Gly Ser Gly Gly Gly
        450                 455                 460
Gly Ser Gly Gly Gly Ser Ser Asp Thr Gly Arg Pro Phe Val Glu
465                 470                 475                 480
Met Pro Ser Glu Ile Pro Glu Ile Ile His Met Thr Glu Gly Arg Glu
                485                 490                 495
Leu Val Ile Pro Cys Arg Val Thr Ser Pro Glu Ile Thr Val Thr Leu
                500                 505                 510
Lys Lys Phe Pro Leu Asp Thr Leu Ile Pro Asp Gly Lys Arg Ile Ile
            515                 520                 525
Trp Asp Ser Arg Lys Gly Phe Ile Ile Ser Glu Ala Thr Tyr Lys Glu
        530                 535                 540
Ile Gly Leu Leu Thr Cys Glu Ala Thr Val Asn Gly His Leu Tyr Lys
545                 550                 555                 560
Thr Asn Tyr Leu Thr His Arg Gln Thr Asn Thr Ile Ile Asp Val Val
                565                 570                 575
Leu Ser Pro Ser His Gly Ile Glu Leu Ser Val Gly Glu Lys Leu Val
                580                 585                 590
Leu Glu Cys Thr Ala Arg Thr Glu Leu Asn Val Gly Ile Asp Phe Asn
            595                 600                 605
```

Trp Glu Tyr Pro Ser Ser Lys His Gln His Lys Lys Leu Val Asn Arg
610                 615                 620

Asp Leu Lys Thr Gln Ser Gly Ser Glu Met Lys Lys Phe Leu Ser Thr
625                 630                 635                 640

Leu Thr Ile Asp Gly Val Thr Arg Ser Asp Gln Gly Leu Tyr Thr Cys
            645                 650                 655

Ala Ala Ser Ser Gly Leu Met Thr Lys Lys Glu Ser Thr Phe Val Arg
            660                 665                 670

Val His Glu Lys
        675

<210> SEQ ID NO 297
<211> LENGTH: 214
<212> TYPE: PRT
<213> ORGANISM: Artificial Sequence
<220> FEATURE:
<223> OTHER INFORMATION: Synthetic

<400> SEQUENCE: 297

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Lys Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 298
<211> LENGTH: 218
<212> TYPE: PRT
<213> ORGANISM: Artificial Sequence
<220> FEATURE:
<223> OTHER INFORMATION: Synthetic

<400> SEQUENCE: 298

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
                20                  25                  30

Gly Phe Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Thr Trp
                85                  90                  95

Glu Leu Pro Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 299
<211> LENGTH: 30
<212> TYPE: PRT
<213> ORGANISM: Artificial Sequence
<220> FEATURE:
<223> OTHER INFORMATION: Synthetic

<400> SEQUENCE: 299

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr
            20                  25                  30

<210> SEQ ID NO 300
<211> LENGTH: 14
<212> TYPE: PRT
<213> ORGANISM: Artificial Sequence
<220> FEATURE:
<223> OTHER INFORMATION: Synthetic

<400> SEQUENCE: 300

Trp Ile Arg Gln Pro Pro Gly Lys Gly Leu Glu Trp Ile Gly
1               5                   10

<210> SEQ ID NO 301
<211> LENGTH: 32
<212> TYPE: PRT
<213> ORGANISM: Artificial Sequence
<220> FEATURE:
<223> OTHER INFORMATION: Synthetic

<400> SEQUENCE: 301

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 302
<211> LENGTH: 11
<212> TYPE: PRT
<213> ORGANISM: Artificial Sequence
<220> FEATURE:
<223> OTHER INFORMATION: Synthetic

<400> SEQUENCE: 302

```
Trp Gly Gln Gly Thr Ser Val Thr Val Ser Ser
1               5                   10
```

<210> SEQ ID NO 303
<211> LENGTH: 23
<212> TYPE: PRT
<213> ORGANISM: Artificial Sequence
<220> FEATURE:
<223> OTHER INFORMATION: Synthetic

<400> SEQUENCE: 303

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 304
<211> LENGTH: 15
<212> TYPE: PRT
<213> ORGANISM: Artificial Sequence
<220> FEATURE:
<223> OTHER INFORMATION: Synthetic

<400> SEQUENCE: 304

```
Trp His Gln Gln Lys Pro Gly Lys Ala Pro Lys Leu Leu Ile Tyr
1               5                   10                  15
```

<210> SEQ ID NO 305
<211> LENGTH: 39
<212> TYPE: PRT
<213> ORGANISM: Artificial Sequence
<220> FEATURE:
<223> OTHER INFORMATION: Synthetic

<400> SEQUENCE: 305

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

Gln Gln Ser Tyr Ser Thr Pro
        35
```

<210> SEQ ID NO 306
<211> LENGTH: 11
<212> TYPE: PRT
<213> ORGANISM: Artificial Sequence
<220> FEATURE:
<223> OTHER INFORMATION: Synthetic

<400> SEQUENCE: 306

```
Phe Gly Gly Gly Thr Lys Leu Glu Ile Lys Arg
1               5                   10
```

```
<210> SEQ ID NO 307
<211> LENGTH: 30
<212> TYPE: PRT
<213> ORGANISM: Artificial Sequence
<220> FEATURE:
<223> OTHER INFORMATION: Synthetic

<400> SEQUENCE: 307

Gln Val Lys Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Synthetic

<400> SEQUENCE: 308

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Ser Cys Ala Arg
            20                  25                  30

<210> SEQ ID NO 309
<211> LENGTH: 11
<212> TYPE: PRT
<213> ORGANISM: Artificial Sequence
<220> FEATURE:
<223> OTHER INFORMATION: Synthetic

<400> SEQUENCE: 309

Trp Gly Gln Gly Thr Leu Val Thr Val Ser Ala
1               5                   10

<210> SEQ ID NO 310
<211> LENGTH: 23
<212> TYPE: PRT
<213> ORGANISM: Artificial Sequence
<220> FEATURE:
<223> OTHER INFORMATION: Synthetic

<400> SEQUENCE: 310

Asp Ile Gln Met Thr Gln Ser Pro Ser Ser Leu Ser Ala Ser Val Gly
1               5                   10                  15

Asp Arg Val Thr Ile Pro Cys
            20

<210> SEQ ID NO 311
<211> LENGTH: 15
<212> TYPE: PRT
<213> ORGANISM: Artificial Sequence
<220> FEATURE:
<223> OTHER INFORMATION: Synthetic

<400> SEQUENCE: 311

Trp Tyr Gln Gln Lys Pro Gly Lys Ala Pro Lys Leu Leu Ile Tyr
1               5                   10                  15

<210> SEQ ID NO 312
<211> LENGTH: 10
<212> TYPE: PRT
```

<213> ORGANISM: Artificial Sequence
<220> FEATURE:
<223> OTHER INFORMATION: Synthetic

<400> SEQUENCE: 312

Phe Gly Glu Gly Thr Lys Leu Glu Ile Lys
1               5                   10

<210> SEQ ID NO 313
<211> LENGTH: 30
<212> TYPE: PRT
<213> ORGANISM: Artificial Sequence
<220> FEATURE:
<223> OTHER INFORMATION: Synthetic

<400> SEQUENCE: 313

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 314
<211> LENGTH: 14
<212> TYPE: PRT
<213> ORGANISM: Artificial Sequence
<220> FEATURE:
<223> OTHER INFORMATION: Synthetic

<400> SEQUENCE: 314

Trp Val Gln Gln Ala Pro Gly Lys Gly Leu Glu Trp Met Gly
1               5                   10

<210> SEQ ID NO 315
<211> LENGTH: 32
<212> TYPE: PRT
<213> ORGANISM: Artificial Sequence
<220> FEATURE:
<223> OTHER INFORMATION: Synthetic

<400> SEQUENCE: 315

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 316
<211> LENGTH: 12
<212> TYPE: PRT
<213> ORGANISM: Artificial Sequence
<220> FEATURE:
<223> OTHER INFORMATION: Synthetic

<400> SEQUENCE: 316

Trp Gly Gln Gly Thr Leu Ile Thr Val Ser Val Ala
1               5                   10

<210> SEQ ID NO 317
<211> LENGTH: 32
<212> TYPE: PRT
<213> ORGANISM: Artificial Sequence
<220> FEATURE:
<223> OTHER INFORMATION: Synthetic

<400> SEQUENCE: 317

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 318
<211> LENGTH: 10
<212> TYPE: PRT
<213> ORGANISM: Artificial Sequence
<220> FEATURE:
<223> OTHER INFORMATION: Synthetic

<400> SEQUENCE: 318

Phe Gly Ala Gly Thr Lys Leu Glu Leu Lys
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Synthetic

<400> SEQUENCE: 319

Trp Gly Gln Gly Thr Leu Val Thr Val Ser Ser
1               5                   10

<210> SEQ ID NO 320
<211> LENGTH: 32
<212> TYPE: PRT
<213> ORGANISM: Artificial Sequence
<220> FEATURE:
<223> OTHER INFORMATION: Synthetic

<400> SEQUENCE: 320

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 321
<211> LENGTH: 10
<212> TYPE: PRT
<213> ORGANISM: Artificial Sequence
<220> FEATURE:
<223> OTHER INFORMATION: Synthetic

<400> SEQUENCE: 321

Phe Gly Ala Gly Thr Lys Leu Glu Ile Lys
1               5                   10

<210> SEQ ID NO 322
<211> LENGTH: 30
<212> TYPE: PRT
<213> ORGANISM: Artificial Sequence
<220> FEATURE:
<223> OTHER INFORMATION: Synthetic

<400> SEQUENCE: 322

Glu Val Gln Leu Lys Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 323
<211> LENGTH: 32
<212> TYPE: PRT

<213> ORGANISM: Artificial Sequence
<220> FEATURE:
<223> OTHER INFORMATION: Synthetic

<400> SEQUENCE: 323

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 324
<211> LENGTH: 30
<212> TYPE: PRT
<213> ORGANISM: Artificial Sequence
<220> FEATURE:
<223> OTHER INFORMATION: Synthetic

<400> SEQUENCE: 324

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 325
<211> LENGTH: 30
<212> TYPE: PRT
<213> ORGANISM: Artificial Sequence
<220> FEATURE:
<223> OTHER INFORMATION: Synthetic

<400> SEQUENCE: 325

Glu Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Synthetic

<400> SEQUENCE: 326

Arg Val Thr Met Ser Val Asp Thr Ser Lys Asn Gln Phe Ser Leu Lys
1               5                   10                  15

Leu Ser Ser Val Thr Ala Val Asp Thr Ala Val Tyr Tyr Cys Thr Arg
            20                  25                  30

<210> SEQ ID NO 327
<211> LENGTH: 32
<212> TYPE: PRT
<213> ORGANISM: Artificial Sequence
<220> FEATURE:
<223> OTHER INFORMATION: Synthetic

<400> SEQUENCE: 327

Gly Ala Pro Ser Arg Phe Ser Gly Ser Gly Ser Gly Thr Asp Phe Thr
1               5                   10                  15

Leu Thr Ile Ser Ser Leu Gln Pro Glu Asp Phe Gly Ile Tyr Tyr Cys
            20                  25                  30

<210> SEQ ID NO 328
<211> LENGTH: 10

```
<212> TYPE: PRT
<213> ORGANISM: Artificial Sequence
<220> FEATURE:
<223> OTHER INFORMATION: Synthetic

<400> SEQUENCE: 328

Phe Gly Gly Gly Thr Lys Leu Glu Phe Lys
1               5                   10

<210> SEQ ID NO 329
<211> LENGTH: 30
<212> TYPE: PRT
<213> ORGANISM: Artificial Sequence
<220> FEATURE:
<223> OTHER INFORMATION: Synthetic

<400> SEQUENCE: 329

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 330
<211> LENGTH: 14
<212> TYPE: PRT
<213> ORGANISM: Artificial Sequence
<220> FEATURE:
<223> OTHER INFORMATION: Synthetic

<400> SEQUENCE: 330

Trp Val Arg Gln Ala Pro Gly Gln Gly Leu Glu Trp Met Gly
1               5                   10

<210> SEQ ID NO 331
<211> LENGTH: 32
<212> TYPE: PRT
<213> ORGANISM: Artificial Sequence
<220> FEATURE:
<223> OTHER INFORMATION: Synthetic

<400> SEQUENCE: 331

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 332
<211> LENGTH: 23
<212> TYPE: PRT
<213> ORGANISM: Artificial Sequence
<220> FEATURE:
<223> OTHER INFORMATION: Synthetic

<400> SEQUENCE: 332

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 333
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 333

Trp Phe Gln Gln Arg Pro Gly Gln Ser Pro Arg Val Leu Ile Tyr
1               5                   10                  15

<210> SEQ ID NO 334
<211> LENGTH: 32
<212> TYPE: PRT
<213> ORGANISM: Artificial Sequence
<220> FEATURE:
<223> OTHER INFORMATION: Synthetic

<400> SEQUENCE: 334

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 335
<211> LENGTH: 10
<212> TYPE: PRT
<213> ORGANISM: Artificial Sequence
<220> FEATURE:
<223> OTHER INFORMATION: Synthetic

<400> SEQUENCE: 335

Phe Gly Arg Gly Thr Lys Leu Glu Ile Lys
1               5                   10

<210> SEQ ID NO 336
<211> LENGTH: 30
<212> TYPE: PRT
<213> ORGANISM: Artificial Sequence
<220> FEATURE:
<223> OTHER INFORMATION: Synthetic

<400> SEQUENCE: 336

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 337
<211> LENGTH: 14
<212> TYPE: PRT
<213> ORGANISM: Artificial Sequence
<220> FEATURE:
<223> OTHER INFORMATION: Synthetic

<400> SEQUENCE: 337

Trp Ile Arg Gln Pro Pro Gly Lys Ala Leu Glu Trp Leu Ala
1               5                   10

<210> SEQ ID NO 338
<211> LENGTH: 32
<212> TYPE: PRT
<213> ORGANISM: Artificial Sequence
<220> FEATURE:
<223> OTHER INFORMATION: Synthetic

<400> SEQUENCE: 338

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30
```

<210> SEQ ID NO 339
<211> LENGTH: 22
<212> TYPE: PRT
<213> ORGANISM: Artificial Sequence
<220> FEATURE:
<223> OTHER INFORMATION: Synthetic

<400> SEQUENCE: 339

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 340
<211> LENGTH: 15
<212> TYPE: PRT
<213> ORGANISM: Artificial Sequence
<220> FEATURE:
<223> OTHER INFORMATION: Synthetic

<400> SEQUENCE: 340

Trp Val Gln Gln Lys Pro Gly Gln Leu Phe Arg Gly Leu Ile Gly
1               5                   10                  15

<210> SEQ ID NO 341
<211> LENGTH: 32
<212> TYPE: PRT
<213> ORGANISM: Artificial Sequence
<220> FEATURE:
<223> OTHER INFORMATION: Synthetic

<400> SEQUENCE: 341

Trp Val Pro Ala Arg Phe Ser Gly Ser Leu Ile Gly Asp Lys Ala Ala
1               5                   10                  15

Leu Thr Leu Ser Gly Val Gln Pro Glu Asp Glu Ala Glu Tyr Phe Cys
            20                  25                  30

<210> SEQ ID NO 342
<211> LENGTH: 10
<212> TYPE: PRT
<213> ORGANISM: Artificial Sequence
<220> FEATURE:
<223> OTHER INFORMATION: Synthetic

<400> SEQUENCE: 342

Phe Gly Gly Gly Thr Lys Leu Thr Val Leu
1               5                   10

<210> SEQ ID NO 343
<211> LENGTH: 30
<212> TYPE: PRT
<213> ORGANISM: Artificial Sequence
<220> FEATURE:
<223> OTHER INFORMATION: Synthetic

<400> SEQUENCE: 343

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 344
<211> LENGTH: 32
<212> TYPE: PRT
<213> ORGANISM: Artificial Sequence

```
<220> FEATURE:
<223> OTHER INFORMATION: Synthetic

<400> SEQUENCE: 344

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 345
<211> LENGTH: 10
<212> TYPE: PRT
<213> ORGANISM: Artificial Sequence
<220> FEATURE:
<223> OTHER INFORMATION: Synthetic

<400> SEQUENCE: 345

Phe Gly Gln Gly Thr Lys Val Glu Ile Lys
1               5                   10

<210> SEQ ID NO 346
<211> LENGTH: 30
<212> TYPE: PRT
<213> ORGANISM: Artificial Sequence
<220> FEATURE:
<223> OTHER INFORMATION: Synthetic

<400> SEQUENCE: 346

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 347
<211> LENGTH: 14
<212> TYPE: PRT
<213> ORGANISM: Artificial Sequence
<220> FEATURE:
<223> OTHER INFORMATION: Synthetic

<400> SEQUENCE: 347

Trp Val Arg Gln Ala Pro Gly Lys Gly Leu Glu Trp Val Ser
1               5                   10

<210> SEQ ID NO 348
<211> LENGTH: 32
<212> TYPE: PRT
<213> ORGANISM: Artificial Sequence
<220> FEATURE:
<223> OTHER INFORMATION: Synthetic

<400> SEQUENCE: 348

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 349
<211> LENGTH: 11
<212> TYPE: PRT
<213> ORGANISM: Artificial Sequence
<220> FEATURE:
<223> OTHER INFORMATION: Synthetic

<400> SEQUENCE: 349
```

```
Trp Gly Gln Gly Thr Ser Val Thr Val Ser Ser
1               5                   10
```

<210> SEQ ID NO 350
<211> LENGTH: 23
<212> TYPE: PRT
<213> ORGANISM: Artificial Sequence
<220> FEATURE:
<223> OTHER INFORMATION: Synthetic

<400> SEQUENCE: 350

```
Asp Ile Gln Met Thr Gln Ser Pro Ser Ser Val Ser Ala Ser Val Gly
1               5                   10                  15

Asp Arg Val Thr Ile Thr Cys
            20
```

<210> SEQ ID NO 351
<211> LENGTH: 15
<212> TYPE: PRT
<213> ORGANISM: Artificial Sequence
<220> FEATURE:
<223> OTHER INFORMATION: Synthetic

<400> SEQUENCE: 351

```
Trp Tyr Gln Gln Lys Pro Gly Lys Ala Pro Lys Leu Leu Ile Tyr
1               5                   10                  15
```

<210> SEQ ID NO 352
<211> LENGTH: 32
<212> TYPE: PRT
<213> ORGANISM: Artificial Sequence
<220> FEATURE:
<223> OTHER INFORMATION: Synthetic

<400> SEQUENCE: 352

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 353
<211> LENGTH: 10
<212> TYPE: PRT
<213> ORGANISM: Artificial Sequence
<220> FEATURE:
<223> OTHER INFORMATION: Synthetic

<400> SEQUENCE: 353

```
Phe Gly Gly Gly Thr Lys Leu Glu Ile Lys
1               5                   10
```

<210> SEQ ID NO 354
<211> LENGTH: 30
<212> TYPE: PRT
<213> ORGANISM: Artificial Sequence
<220> FEATURE:
<223> OTHER INFORMATION: Synthetic

<400> SEQUENCE: 354

```
Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr
            20                  25                  30
```

<210> SEQ ID NO 355

```
<211> LENGTH: 14
<212> TYPE: PRT
<213> ORGANISM: Artificial Sequence
<220> FEATURE:
<223> OTHER INFORMATION: Synthetic

<400> SEQUENCE: 355

Trp Leu Arg Gln Ala Pro Gly Gln Gly Leu Glu Trp Met Gly
1               5                   10

<210> SEQ ID NO 356
<211> LENGTH: 32
<212> TYPE: PRT
<213> ORGANISM: Artificial Sequence
<220> FEATURE:
<223> OTHER INFORMATION: Synthetic

<400> SEQUENCE: 356

Arg Thr Thr Ser Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Thr Arg
            20                  25                  30

<210> SEQ ID NO 357
<211> LENGTH: 11
<212> TYPE: PRT
<213> ORGANISM: Artificial Sequence
<220> FEATURE:
<223> OTHER INFORMATION: Synthetic

<400> SEQUENCE: 357

Trp Gly Gln Gly Thr Leu Val Thr Val Ser Ser
1               5                   10

<210> SEQ ID NO 358
<211> LENGTH: 23
<212> TYPE: PRT
<213> ORGANISM: Artificial Sequence
<220> FEATURE:
<223> OTHER INFORMATION: Synthetic

<400> SEQUENCE: 358

Asp Ile Gln Met Thr Gln Ser Pro Ser Ser Leu Ser Ala Ser Val Gly
1               5                   10                  15

Asp Arg Val Thr Phe Thr Cys
            20

<210> SEQ ID NO 359
<211> LENGTH: 10
<212> TYPE: PRT
<213> ORGANISM: Artificial Sequence
<220> FEATURE:
<223> OTHER INFORMATION: Synthetic

<400> SEQUENCE: 359

Phe Gly Gly Gly Thr Lys Val Glu Ile Lys
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Synthetic

<400> SEQUENCE: 360
```

Trp Val Arg Gln Ala Pro Gly Gln Gly Leu Glu Trp Met Gly
1               5                   10

<210> SEQ ID NO 361
<211> LENGTH: 31
<212> TYPE: PRT
<213> ORGANISM: Artificial Sequence
<220> FEATURE:
<223> OTHER INFORMATION: Synthetic

<400> SEQUENCE: 361

Arg Val Thr Ser Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Ala
            20                  25                  30

<210> SEQ ID NO 362
<211> LENGTH: 11
<212> TYPE: PRT
<213> ORGANISM: Artificial Sequence
<220> FEATURE:
<223> OTHER INFORMATION: Synthetic

<400> SEQUENCE: 362

Trp Gly Gln Gly Thr Thr Leu Thr Val Ser Ser
1               5                   10

<210> SEQ ID NO 363
<211> LENGTH: 23
<212> TYPE: PRT
<213> ORGANISM: Artificial Sequence
<220> FEATURE:
<223> OTHER INFORMATION: Synthetic

<400> SEQUENCE: 363

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 364
<211> LENGTH: 10
<212> TYPE: PRT
<213> ORGANISM: Artificial Sequence
<220> FEATURE:
<223> OTHER INFORMATION: Synthetic

<400> SEQUENCE: 364

Phe Gly Ala Gly Thr Lys Leu Asp Leu Lys
1               5                   10

<210> SEQ ID NO 365
<211> LENGTH: 10
<212> TYPE: PRT
<213> ORGANISM: Artificial Sequence
<220> FEATURE:
<223> OTHER INFORMATION: Synthetic

<400> SEQUENCE: 365

Phe Gly Gly Gly Thr Lys Val Glu Ile Lys
1               5                   10

<210> SEQ ID NO 366
<211> LENGTH: 30
<212> TYPE: PRT
<213> ORGANISM: Artificial Sequence
<220> FEATURE:
<223> OTHER INFORMATION: Synthetic

<400> SEQUENCE: 366

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr
                20                  25                  30

<210> SEQ ID NO 367
<211> LENGTH: 32
<212> TYPE: PRT
<213> ORGANISM: Artificial Sequence
<220> FEATURE:
<223> OTHER INFORMATION: Synthetic

<400> SEQUENCE: 367

Arg Val Thr Met Thr Arg Asp Thr Ser Ile Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 368
<211> LENGTH: 23
<212> TYPE: PRT
<213> ORGANISM: Artificial Sequence
<220> FEATURE:
<223> OTHER INFORMATION: Synthetic

<400> SEQUENCE: 368

Asp Ile Val Leu Thr Gln Ser Pro Ala Ser Leu Ala Val Ser Pro Gly
1               5                   10                  15

Gln Arg Ala Thr Ile Thr Cys
                20

<210> SEQ ID NO 369
<211> LENGTH: 15
<212> TYPE: PRT
<213> ORGANISM: Artificial Sequence
<220> FEATURE:
<223> OTHER INFORMATION: Synthetic

<400> SEQUENCE: 369

Trp Tyr Gln Gln Lys Pro Gly Gln Pro Pro Lys Leu Leu Ile Tyr
1               5                   10                  15

<210> SEQ ID NO 370
<211> LENGTH: 32
<212> TYPE: PRT
<213> ORGANISM: Artificial Sequence
<220> FEATURE:
<223> OTHER INFORMATION: Synthetic

<400> SEQUENCE: 370

Gly Val Pro Ala Arg Phe Ser Gly Ser Gly Ser Gly Thr Asp Phe Thr
1               5                   10                  15

Leu Thr Ile Asn Pro Val Glu Ala Asn Asp Thr Ala Asn Tyr Tyr Cys
                20                  25                  30

<210> SEQ ID NO 371
<211> LENGTH: 31
<212> TYPE: PRT
<213> ORGANISM: Artificial Sequence
<220> FEATURE:
<223> OTHER INFORMATION: Synthetic

```
<400> SEQUENCE: 371

Arg Val Thr Leu Thr Ala Asp Thr Ser Thr Ser Thr Val Tyr Met Glu
1               5                   10                  15

Leu Ser Ser Leu Arg Ser Glu Asp Thr Ala Val Tyr Tyr Cys Ala
            20                  25                  30

<210> SEQ ID NO 372
<211> LENGTH: 23
<212> TYPE: PRT
<213> ORGANISM: Artificial Sequence
<220> FEATURE:
<223> OTHER INFORMATION: Synthetic

<400> SEQUENCE: 372

Asp Ile Gln Met Thr Gln Ser Pro Ser Phe Leu Ser Ala Ser Val Gly
1               5                   10                  15

Asp Arg Val Thr Ile Thr Cys
            20

<210> SEQ ID NO 373
<211> LENGTH: 15
<212> TYPE: PRT
<213> ORGANISM: Artificial Sequence
<220> FEATURE:
<223> OTHER INFORMATION: Synthetic

<400> SEQUENCE: 373

Trp Tyr Gln Gln Lys Pro Gly Lys Ala Pro Lys Ala Leu Ile Tyr
1               5                   10                  15

<210> SEQ ID NO 374
<211> LENGTH: 32
<212> TYPE: PRT
<213> ORGANISM: Artificial Sequence
<220> FEATURE:
<223> OTHER INFORMATION: Synthetic

<400> SEQUENCE: 374

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 375
<211> LENGTH: 10
<212> TYPE: PRT
<213> ORGANISM: Artificial Sequence
<220> FEATURE:
<223> OTHER INFORMATION: Synthetic

<400> SEQUENCE: 375

Phe Gly Gln Gly Thr Lys Leu Glu Ile Lys
1               5                   10

<210> SEQ ID NO 376
<211> LENGTH: 14
<212> TYPE: PRT
<213> ORGANISM: Artificial Sequence
<220> FEATURE:
<223> OTHER INFORMATION: Synthetic

<400> SEQUENCE: 376

Trp Met Lys Gln Ala Pro Gly Gln Gly Leu Glu Trp Met Gly
1               5                   10
```

<210> SEQ ID NO 377
<211> LENGTH: 23
<212> TYPE: PRT
<213> ORGANISM: Artificial Sequence
<220> FEATURE:
<223> OTHER INFORMATION: Synthetic

<400> SEQUENCE: 377

Asp Ile Gln Met Thr Gln Ser Pro Ser Ser Leu Ser Ala Ser Val Gly
1               5                   10                  15

Asp Arg Val Thr Ile Ser Cys
            20

<210> SEQ ID NO 378
<211> LENGTH: 15
<212> TYPE: PRT
<213> ORGANISM: Artificial Sequence
<220> FEATURE:
<223> OTHER INFORMATION: Synthetic

<400> SEQUENCE: 378

Trp Tyr Gln Gln Lys Pro Gly Lys Ala Pro Lys Leu Leu Ile Lys
1               5                   10                  15

<210> SEQ ID NO 379
<211> LENGTH: 32
<212> TYPE: PRT
<213> ORGANISM: Artificial Sequence
<220> FEATURE:
<223> OTHER INFORMATION: Synthetic

<400> SEQUENCE: 379

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 380
<211> LENGTH: 32
<212> TYPE: PRT
<213> ORGANISM: Artificial Sequence
<220> FEATURE:
<223> OTHER INFORMATION: Synthetic

<400> SEQUENCE: 380

Lys Ala Thr Met Thr Arg Asp Lys Ser Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 381
<211> LENGTH: 32
<212> TYPE: PRT
<213> ORGANISM: Artificial Sequence
<220> FEATURE:
<223> OTHER INFORMATION: Synthetic

<400> SEQUENCE: 381

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Phe Cys
            20                  25                  30

```
<210> SEQ ID NO 382
<211> LENGTH: 10
<212> TYPE: PRT
<213> ORGANISM: Artificial Sequence
<220> FEATURE:
<223> OTHER INFORMATION: Synthetic

<400> SEQUENCE: 382

Phe Gly Gln Gly Thr Lys Val Glu Ile Lys
1               5                   10

<210> SEQ ID NO 383
<211> LENGTH: 32
<212> TYPE: PRT
<213> ORGANISM: Artificial Sequence
<220> FEATURE:
<223> OTHER INFORMATION: Synthetic

<400> SEQUENCE: 383

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 384
<211> LENGTH: 32
<212> TYPE: PRT
<213> ORGANISM: Artificial Sequence
<220> FEATURE:
<223> OTHER INFORMATION: Synthetic

<400> SEQUENCE: 384

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 385
<211> LENGTH: 30
<212> TYPE: PRT
<213> ORGANISM: Artificial Sequence
<220> FEATURE:
<223> OTHER INFORMATION: Synthetic

<400> SEQUENCE: 385

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr
            20                  25                  30

<210> SEQ ID NO 386
<211> LENGTH: 14
<212> TYPE: PRT
<213> ORGANISM: Artificial Sequence
<220> FEATURE:
<223> OTHER INFORMATION: Synthetic

<400> SEQUENCE: 386

Trp Ile Arg Gln Phe Pro Gly Asn Lys Leu Glu Trp Met Gly
1               5                   10

<210> SEQ ID NO 387
<211> LENGTH: 32
<212> TYPE: PRT
<213> ORGANISM: Artificial Sequence
<220> FEATURE:
```

```
<223> OTHER INFORMATION: Synthetic

<400> SEQUENCE: 387

Arg Ile Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Ala Asn
            20                  25                  30

<210> SEQ ID NO 388
<211> LENGTH: 23
<212> TYPE: PRT
<213> ORGANISM: Artificial Sequence
<220> FEATURE:
<223> OTHER INFORMATION: Synthetic

<400> SEQUENCE: 388

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 389
<211> LENGTH: 15
<212> TYPE: PRT
<213> ORGANISM: Artificial Sequence
<220> FEATURE:
<223> OTHER INFORMATION: Synthetic

<400> SEQUENCE: 389

Trp Tyr Gln Gln Lys Pro Gly Gln Ser Pro Lys Leu Leu Ile Phe
1               5                   10                  15

<210> SEQ ID NO 390
<211> LENGTH: 32
<212> TYPE: PRT
<213> ORGANISM: Artificial Sequence
<220> FEATURE:
<223> OTHER INFORMATION: Synthetic

<400> SEQUENCE: 390

Gly Val Pro Asp Arg Phe Thr Gly Ser Gly Ser Gly Thr Asp Tyr Thr
1               5                   10                  15

Leu Thr Ile Ser Ser Val Gln Ala Glu Asp Leu Ala Leu Tyr Tyr Cys
            20                  25                  30

<210> SEQ ID NO 391
<211> LENGTH: 15
<212> TYPE: PRT
<213> ORGANISM: Artificial Sequence
<220> FEATURE:
<223> OTHER INFORMATION: Synthetic

<400> SEQUENCE: 391

Trp Val Arg Gln Ala Pro Gly Gln Arg Leu Glu Trp Met Gly Trp
1               5                   10                  15

<210> SEQ ID NO 392
<211> LENGTH: 32
<212> TYPE: PRT
<213> ORGANISM: Artificial Sequence
<220> FEATURE:
<223> OTHER INFORMATION: Synthetic

<400> SEQUENCE: 392

Arg Val Thr Ile Thr Arg Asp Thr Ser Ala Ser Thr Ala Tyr Met Glu
```

```
1               5                   10                  15
Leu Ser Ser Leu Arg Ser Glu Asp Thr Ala Val Tyr Tyr Cys Ala Arg
            20                  25                  30
```

<210> SEQ ID NO 393
<211> LENGTH: 23
<212> TYPE: PRT
<213> ORGANISM: Artificial Sequence
<220> FEATURE:
<223> OTHER INFORMATION: Synthetic

<400> SEQUENCE: 393

```
Asp Ile Gln Met Thr Gln Ser Pro Ser Ser Leu Ser Ala Phe Val Gly
1               5                   10                  15
Asp Arg Val Thr Ile Thr Cys
            20
```

<210> SEQ ID NO 394
<211> LENGTH: 15
<212> TYPE: PRT
<213> ORGANISM: Artificial Sequence
<220> FEATURE:
<223> OTHER INFORMATION: Synthetic

<400> SEQUENCE: 394

```
Trp Tyr Gln Gln Lys Pro Gly Lys Ala Pro Lys Leu Leu Ile His
1               5                   10                  15
```

<210> SEQ ID NO 395
<211> LENGTH: 32
<212> TYPE: PRT
<213> ORGANISM: Artificial Sequence
<220> FEATURE:
<223> OTHER INFORMATION: Synthetic

<400> SEQUENCE: 395

```
Gly Val Pro Ser Arg Phe Ser Gly Ser Gly Ser Gly Arg Asp Phe Thr
1               5                   10                  15
Phe Thr Ile Ser Ser Leu Gln Pro Glu Asp Ile Ala Thr Tyr Tyr Cys
            20                  25                  30
```

<210> SEQ ID NO 396
<211> LENGTH: 23
<212> TYPE: PRT
<213> ORGANISM: Artificial Sequence
<220> FEATURE:
<223> OTHER INFORMATION: Synthetic

<400> SEQUENCE: 396

```
Glu Ile Val Leu Thr Gln Ser Pro Val Thr Leu Ser Leu Ser Pro Gly
1               5                   10                  15
Glu Arg Ala Thr Leu Ser Cys
            20
```

<210> SEQ ID NO 397
<211> LENGTH: 15
<212> TYPE: PRT
<213> ORGANISM: Artificial Sequence
<220> FEATURE:
<223> OTHER INFORMATION: Synthetic

<400> SEQUENCE: 397

```
Trp Tyr Leu Gln Lys Pro Gly Gln Ala Pro Arg Leu Leu Ile Lys
1               5                   10                  15
```

<210> SEQ ID NO 398
<211> LENGTH: 31
<212> TYPE: PRT
<213> ORGANISM: Artificial Sequence
<220> FEATURE:
<223> OTHER INFORMATION: Synthetic

<400> SEQUENCE: 398

Ile Pro Ala Arg Phe Ser Gly Ser Gly Ser Gly Ser Asp Phe Thr Leu
1               5                   10                  15

Thr Ile Ser Ser Leu Glu Pro Glu Asp Phe Ala Val Tyr Tyr Cys
            20                  25                  30

<210> SEQ ID NO 399
<211> LENGTH: 30
<212> TYPE: PRT
<213> ORGANISM: Artificial Sequence
<220> FEATURE:
<223> OTHER INFORMATION: Synthetic

<400> SEQUENCE: 399

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr
            20                  25                  30

<210> SEQ ID NO 400
<211> LENGTH: 14
<212> TYPE: PRT
<213> ORGANISM: Artificial Sequence
<220> FEATURE:
<223> OTHER INFORMATION: Synthetic

<400> SEQUENCE: 400

Trp Met Arg Gln Ala Pro Gly Gln Gly Leu Glu Trp Met Gly
1               5                   10

<210> SEQ ID NO 401
<211> LENGTH: 32
<212> TYPE: PRT
<213> ORGANISM: Artificial Sequence
<220> FEATURE:
<223> OTHER INFORMATION: Synthetic

<400> SEQUENCE: 401

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Val Arg
            20                  25                  30

<210> SEQ ID NO 402
<211> LENGTH: 11
<212> TYPE: PRT
<213> ORGANISM: Artificial Sequence
<220> FEATURE:
<223> OTHER INFORMATION: Synthetic

<400> SEQUENCE: 402

Trp Gly Gln Gly Thr Leu Val Thr Val Ser Ser
1               5                   10

<210> SEQ ID NO 403
<211> LENGTH: 23
<212> TYPE: PRT
<213> ORGANISM: Artificial Sequence

```
<220> FEATURE:
<223> OTHER INFORMATION: Synthetic

<400> SEQUENCE: 403

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 404
<211> LENGTH: 15
<212> TYPE: PRT
<213> ORGANISM: Artificial Sequence
<220> FEATURE:
<223> OTHER INFORMATION: Synthetic

<400> SEQUENCE: 404

Trp Leu Gln Gln Lys Pro Glu Lys Ala Pro Lys Arg Leu Ile Tyr
1               5                   10                  15

<210> SEQ ID NO 405
<211> LENGTH: 32
<212> TYPE: PRT
<213> ORGANISM: Artificial Sequence
<220> FEATURE:
<223> OTHER INFORMATION: Synthetic

<400> SEQUENCE: 405

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 406
<211> LENGTH: 10
<212> TYPE: PRT
<213> ORGANISM: Artificial Sequence
<220> FEATURE:
<223> OTHER INFORMATION: Synthetic

<400> SEQUENCE: 406

Phe Gly Gly Gly Thr Lys Val Glu Ile Lys
1               5                   10

<210> SEQ ID NO 407
<211> LENGTH: 30
<212> TYPE: PRT
<213> ORGANISM: Artificial Sequence
<220> FEATURE:
<223> OTHER INFORMATION: Synthetic

<400> SEQUENCE: 407

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 408
<211> LENGTH: 14
<212> TYPE: PRT
<213> ORGANISM: Artificial Sequence
<220> FEATURE:
<223> OTHER INFORMATION: Synthetic

<400> SEQUENCE: 408
```

Trp Val Arg Gln Ala Pro Gly Gln Gly Leu Glu Trp Met Gly
1               5                   10

<210> SEQ ID NO 409
<211> LENGTH: 32
<212> TYPE: PRT
<213> ORGANISM: Artificial Sequence
<220> FEATURE:
<223> OTHER INFORMATION: Synthetic

<400> SEQUENCE: 409

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 410
<211> LENGTH: 15
<212> TYPE: PRT
<213> ORGANISM: Artificial Sequence
<220> FEATURE:
<223> OTHER INFORMATION: Synthetic

<400> SEQUENCE: 410

Trp Leu Gln Gln Lys Pro Gly Lys Ala Pro Lys Arg Leu Ile Tyr
1               5                   10                  15

<210> SEQ ID NO 411
<211> LENGTH: 30
<212> TYPE: PRT
<213> ORGANISM: Artificial Sequence
<220> FEATURE:
<223> OTHER INFORMATION: Synthetic

<400> SEQUENCE: 411

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser
            20                  25                  30

<210> SEQ ID NO 412
<211> LENGTH: 15
<212> TYPE: PRT
<213> ORGANISM: Artificial Sequence
<220> FEATURE:
<223> OTHER INFORMATION: Synthetic

<400> SEQUENCE: 412

Trp Val Arg Gln Ala Pro Gly Gln Gly Leu Glu Trp Met Gly Leu
1               5                   10                  15

<210> SEQ ID NO 413
<211> LENGTH: 30
<212> TYPE: PRT
<213> ORGANISM: Artificial Sequence
<220> FEATURE:
<223> OTHER INFORMATION: Synthetic

<400> SEQUENCE: 413

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Phe Cys
            20                  25                  30

<210> SEQ ID NO 414

```
<211> LENGTH: 26
<212> TYPE: PRT
<213> ORGANISM: Artificial Sequence
<220> FEATURE:
<223> OTHER INFORMATION: Synthetic

<400> SEQUENCE: 414

Phe Asp Tyr Trp Asp Asp Gly Tyr Tyr Val Glu His Phe Asp Tyr Trp
1               5                   10                  15

Gly Gln Gly Thr Leu Val Thr Val Ser Ser
            20                  25

<210> SEQ ID NO 415
<211> LENGTH: 15
<212> TYPE: PRT
<213> ORGANISM: Artificial Sequence
<220> FEATURE:
<223> OTHER INFORMATION: Synthetic

<400> SEQUENCE: 415

Trp Tyr Gln Gln Lys Pro Gly Lys Ala Pro Lys Arg Leu Ile Tyr
1               5                   10                  15

<210> SEQ ID NO 416
<211> LENGTH: 29
<212> TYPE: PRT
<213> ORGANISM: Artificial Sequence
<220> FEATURE:
<223> OTHER INFORMATION: Synthetic

<400> SEQUENCE: 416

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe
            20                  25

<210> SEQ ID NO 417
<211> LENGTH: 23
<212> TYPE: PRT
<213> ORGANISM: Artificial Sequence
<220> FEATURE:
<223> OTHER INFORMATION: Synthetic

<400> SEQUENCE: 417

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 418
<211> LENGTH: 18
<212> TYPE: PRT
<213> ORGANISM: Artificial Sequence
<220> FEATURE:
<223> OTHER INFORMATION: Synthetic

<400> SEQUENCE: 418

Trp Leu Ala Trp Tyr Gln Gln Lys Pro Gly Lys Ala Pro Lys Leu Leu
1               5                   10                  15

Ile Tyr

<210> SEQ ID NO 419
<211> LENGTH: 32
<212> TYPE: PRT
<213> ORGANISM: Artificial Sequence
```

```
<220> FEATURE:
<223> OTHER INFORMATION: Synthetic

<400> SEQUENCE: 419

Gly Val Pro Ser Arg Phe Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 420
<211> LENGTH: 10
<212> TYPE: PRT
<213> ORGANISM: Artificial Sequence
<220> FEATURE:
<223> OTHER INFORMATION: Synthetic

<400> SEQUENCE: 420

Phe Gly Gln Gly Thr Lys Leu Glu Ile Lys
1               5                   10
```